(12) United States Patent
Atkinson et al.

(10) Patent No.: US 10,966,961 B2
(45) Date of Patent: Apr. 6, 2021

(54) PYRAZOLE DERIVATIVES AS BROMODOMAIN INHIBITORS

(71) Applicant: GLAXOSMITHKLINE INTELLECTUAL PROPERTY (NO.2) LIMITED, Brentford (GB)

(72) Inventors: Stephen John Atkinson, Stevenage (GB); Emmanuel Hubert Demont, Stevenage (GB); Lee Andrew Harrison, Stevenage (GB); Gemma Michele Liwicki, Stevenage (GB); Simon Christopher Cranko Lucas, Stevenage (GB); Alexander G. Preston, Stevenage (GB); Jonathan Thomas Seal, Stevenage (GB); Ian David Wall, Stevenage (GB); Robert J. Watson, Stevenage (GB)

(73) Assignee: GLAXOSMITHKLINE INTELLECTUAL PROPERTY (NO.2) LIMITED, Middlesex (GB)

( * ) Notice: Subject to any disclaimer, the term of this patent is extended or adjusted under 35 U.S.C. 154(b) by 0 days.

(21) Appl. No.: 16/489,859

(22) PCT Filed: Feb. 27, 2018

(86) PCT No.: PCT/EP2018/054733
§ 371 (c)(1),
(2) Date: Aug. 29, 2019

(87) PCT Pub. No.: WO2018/158212
PCT Pub. Date: Sep. 7, 2018

(65) Prior Publication Data
US 2019/0381010 A1 Dec. 19, 2019

(30) Foreign Application Priority Data

Mar. 1, 2017 (GB) .................... 1703283
Oct. 6, 2017 (GB) .................... 1716374

(51) Int. Cl.

| | | |
|---|---|---|
| A61K 31/4155 | (2006.01) |
| C07D 405/12 | (2006.01) |
| A61K 31/415 | (2006.01) |
| C07D 231/14 | (2006.01) |
| C07D 403/12 | (2006.01) |
| C07D 471/04 | (2006.01) |
| A61K 31/437 | (2006.01) |
| A61K 31/4439 | (2006.01) |
| C07D 401/12 | (2006.01) |
| A61K 31/422 | (2006.01) |
| C07D 413/12 | (2006.01) |
| A61K 31/5377 | (2006.01) |
| C07D 405/14 | (2006.01) |
| C07D 417/12 | (2006.01) |
| A61K 31/4192 | (2006.01) |
| A61K 31/4184 | (2006.01) |
| A61K 31/4245 | (2006.01) |
| A61K 31/433 | (2006.01) |

(52) U.S. Cl.
CPC ........ *A61K 31/4155* (2013.01); *A61K 31/415* (2013.01); *A61K 31/4184* (2013.01); *A61K 31/4192* (2013.01); *A61K 31/422* (2013.01); *A61K 31/4245* (2013.01); *A61K 31/433* (2013.01); *A61K 31/437* (2013.01); *A61K 31/4439* (2013.01); *A61K 31/5377* (2013.01); *C07D 231/14* (2013.01); *C07D 401/12* (2013.01); *C07D 403/12* (2013.01); *C07D 405/12* (2013.01); *C07D 405/14* (2013.01); *C07D 413/12* (2013.01); *C07D 417/12* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 7,910,606 B2* | 3/2011 | Nazare | C07D 417/14 514/326 |
| 2012/0208814 A1 | 8/2012 | Demont et al. | |
| 2014/0179648 A1 | 6/2014 | Liu et al. | |

FOREIGN PATENT DOCUMENTS

| | | |
|---|---|---|
| EP | 1 357 111 A1 | 10/2003 |
| EP | 1 433 788 A1 | 6/2004 |
| EP | 1 477 186 A1 | 11/2004 |
| WO | WO 2004/033446 A1 | 4/2004 |
| WO | WO 2014/074675 A1 | 5/2014 |
| WO | WO 2014/096965 A2 | 6/2014 |
| WO | WO 2015/015318 A2 | 2/2015 |
| WO | WO 2017/037116 A1 | 3/2017 |
| WO | WO 2017/060180 A1 | 4/2017 |

(Continued)

OTHER PUBLICATIONS

Dittmer et al., "Models for the Pyridine Nucleotide Coenzymes. Synthesis and Properties of Bridged Dinicotinamide Derivatives[1-3]", *J. Org. Chem.*, vol. 38, No. 16, pp. 2873-2882 (1973).

(Continued)

*Primary Examiner* — Kamal A Saeed
(74) *Attorney, Agent, or Firm* — Robert H. Brink; Duke M. Fitch; Edward R. Gimmi

(57) ABSTRACT

The present invention is directed to pyrazole derivatives, pharmaceutical compositions comprising the compounds and the use of the compounds or the compositions in the treatment of various diseases.

17 Claims, No Drawings

(56) References Cited

FOREIGN PATENT DOCUMENTS

| WO | WO 2017/174621 A1 | 10/2017 |
|----|-------------------|---------|
| WO | WO 2017/202742 A1 | 11/2017 |

OTHER PUBLICATIONS

Gallenkamp et al., "Bromodomains and Their Pharmacological Inhibitors", *ChemMedChem*, vol. 9, No. 3, pp. 438-464 (2014).
Gamier et al., "BET bromodomain inhibitors: a patent review", *Expert Opinion on Therapeutic Patents*, vol. 24, No. 2, pp. 185-199 (2014).
International Search Report for International application No. PCT/EP2016/070519, dated Oct. 20, 2016, 4 pages.
International Search Report for International application No. PCT/EP2016/072216, International filing date: Sep. 20, 2016, 3 pages.
International Search Report for International application No. PCT/EP2016/073532, dated Nov. 30, 2016, 5 pages.
International Search Report for International application No. PCT/EP2017/058050, dated May 24, 2017, 5 pages.
International Search Report for International application No. PCT/EP2017/062208, dated Jul. 6, 2017, 5 pages.
International Search Report for International application No. PCT/EP2018/054730, dated May 4, 2018, 5 pages.
International Search Report for International application No. PCT/EP2018/054733, dated Jun. 11, 2018, 5 pages.
Non-Final Office Action for U.S. Appl. No. 15/766,222, USPTO, notification dated Oct. 4, 2018, 9 pages.
Notice of Allowance for U.S. Appl. No. 15/762,229, USPTO, dated Dec. 11, 2018, 9 pages.
Notice of Allowance for U.S. Appl. No. 15/766,222, USPTO, dated Jan. 17, 2019, 6 pages.
Notice of Allowance for U.S. Appl. No. 15/762,229, USPTO, dated Mar. 20, 2019, 9 pages.
Restriction Requirement for U.S. Appl. No. 15/757,199, USPTO, notification dated Feb. 11, 2019, 9 pages.

\* cited by examiner

PYRAZOLE DERIVATIVES AS BROMODOMAIN INHIBITORS

This application is a § 371 of International Application No. PCT/EP2018/054733, filed 27 Feb. 2018, which claims the priority of GB 1716374.2, filed 6 Oct. 2017, and GB 1703283.0, filed 1 Mar. 2017.

FIELD OF THE INVENTION

The present invention is directed to pyrazole derivatives which are bromodomain inhibitors, pharmaceutical compositions comprising the compounds and the use of the compounds or the compositions in the treatment of various diseases or conditions, for example acute or chronic autoimmune and/or inflammatory conditions, viral infections and cancer.

BACKGROUND TO THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation and SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al., *J Med. Chem.*, 2011, 54, 3827-3838).

Chan et al. report that BET bromodomain inhibition suppresses transcriptional responses to cytokine-Jak-STAT signalling in a gene-specific maner in human monocytes, which suggests that BET inhibition reduces inflammation partially through suppression of cytokine activity. (Chan et al., *Eur. J. Immunol.*, 2015, 45: 287-297).

Klein et al. report that the bromodomain protein inhibitor I-BET151 suppresses expression of inflammatory genes and matrix degrading enzymes in rheumatoid arthritis synovial fibroblasts, which suggests a therapeutic potential in the targeting of epigenetic reader proteins in rheumatoid arthritis. (Klein et al., *Ann. Rheum. Dis.*, 2014, 0:1-8).

Park-Min et al. report that I-BET151 that targets bromo and extra-terminal (BET) proteins that 'read' chromatin states by binding to acetylated histones, strongly suppresses osteoclastogenesis. (Park-Min et al. *Nature Communications*, 2014, 5, 5418).

PCT patent applications PCT/EP2016/070519, PCT/EP2016/072216 and PCT/EP2016/073532 each describe a series of pyridone derivatives as bromodomain inhibitors.

SUMMARY OF THE INVENTION

The invention is directed to compounds of formula (I)

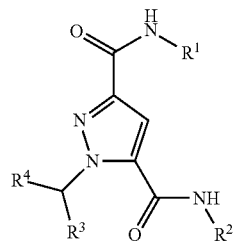

(I)

or a salt thereof
wherein:

$R^1$ is —$C_{1-3}$alkyl or cyclopropyl;

$R^2$ is —$C_{0-3}$alkyl-cycloalkyl, wherein the cycloalkyl group is optionally substituted with one, two or three $R^5$ groups which may be the same or different; or $R^2$ is —$C_{0-4}$alkyl-heterocyclyl or —$(CH_2)_p$O-heterocyclyl wherein each heterocyclyl is optionally substituted by one or two $R^9$ groups which may be the same or different; or $R^2$ is H, —$CH_3$, —$C_{2-6}$alkyl optionally substituted by one, two, three, four or five fluoro, —$C_{2-6}$alkyl $OR^6$, —$C_{2-6}$alkylNR$^{10a}$R$^{11a}$, —$(CH_2)_m$SO$_2$C$_{1-3}$alkyl, —$(CH_2)_m$SO$_2$NR$^{10}$R$^{11}$, —$(CH_2)_m$C(O)NR$^{10}$R$^{11}$, —$(CH_2)_m$CN, —$(CH_2)_m$CO$_2$R$^6$, —$(CH_2)_m$NHCO$_2$C$_{1-4}$alkyl, —$(CH_2)_m$NHC(O)C$_{1-4}$alkyl or —$(CH_2)_n$heteroaryl wherein the heteroaryl is optionally substituted by one or two $R^7$ groups which may be the same or different;

$R^3$ is H, —$C_{1-4}$alkyl, cyclopropyl, —$CH_2F$, —$C_{1-3}$alkylOR$^6$ or —$C_{1-3}$alkylCN;

$R^4$ is phenyl or a heteroaryl group wherein each are optionally substituted by one, two or three $R^7$ groups which may be the same or different;

each $R^5$ is independently halo, —$C_{0-6}$alkyl-$R^8$, —O—$C_{2-6}$alkyl-$R^8$, —OCH$_2$phenyl, —CN or —SO$_2$C$_1$-3alkyl;

$R^6$ is H or —$C_{1-4}$alkyl;

each $R^7$ is independently oxo, halo, —$C_{1-4}$alkyl optionally substituted by one, two or three fluoro, —$C_{0-3}$alkylOR$^6$, —OC$_{2-3}$alkylOR$^6$, —$C_{0-3}$alkylNR$^{19}$R$^{11}$, —$C_{0-3}$alkyl- CONR$^{10}$R$^{11}$, —CN, —SO$_2$—C$_{1-3}$alkyl, —SO$_2$NR$^{19}$R$^{11}$ or —SO$_2$phenyl optionally substituted by —C$_{1-4}$alkyl;

R$^8$ is H, —OR$^6$, —NR$^{10}$R$^{11}$ or heteroaryl;

each R$^9$ is independently halo, —C$_{1-4}$alkyl, cyclopropyl, cyclobutyl, —CH$_2$CF$_3$, —CH$_2$CHF$_2$, —CH$_2$CH$_2$F, —OCH$_2$CH$_2$OR$^6$, —C$_{0-3}$alkylOR$^6$, —C$_{0-3}$alkylNR$^{10}$R$^{11}$, —NHCH$_2$CH$_2$OR$^6$, —NHCO$_2$C$_{1-4}$alkyl, oxo, —C(O)R$^6$, —C(O)OR$^6$ or —C(O)NR$^{19}$R$^{11}$;

R$^{10}$ and R$^{11}$ are each independently selected from H and —C$_{1-3}$alkyl; or R$^{10}$ and R$^{11}$ may join together with the nitrogen to which they are attached, to form a 4 to 7-membered heterocyclyl optionally substituted by one or two substituents independently selected from —C$_{1-3}$alkyl optionally substituted with one, two or three fluorine atoms, —C$_{2-4}$alkylOH, —OH and F;

R$^{10a}$ and R$^{11a}$ are each independently selected from H and —C$_{1-3}$alkyl;

m is an integer selected from 2, 3 or 4;

n is an integer selected from 0, 1, 2, 3 or 4; and p is an integer selected from 2, 3 or 4.

Compounds of the invention have been shown to be bromodomain inhibitors, in particular BD2 selective and may be useful in the treatment of various diseases or conditions, for example acute or chronic auto-immune and/or inflammatory conditions, for example rheumatoid arthritis and cancer. Accordingly, the invention is further directed to pharmaceutical compositions comprising a compound of formula (I), or a pharmaceutically acceptable salt thereof. The invention is still further directed to methods of treatment of diseases or conditions associated with bromodomains using a compound of formula (I) or a pharmaceutically acceptable salt thereof, or a pharmaceutical composition comprising a compound of formula (I) or a pharmaceutically acceptable salt thereof.

DETAILED DESCRIPTION OF THE INVENTION

Compounds of formula (I) and salts thereof are referred to herein as "compounds of the invention".

"BD2" refers to Binding Domain 2 of any of the the BET family of proteins BRD2, BRD3, BRD4 or BRDT.

"Alkyl" refers to a saturated hydrocarbon chain having the specified number of carbon atoms. For example, the term "C$_{1-3}$alkyl" and "C$_{1-4}$alkyl" as used herein refers to a straight or branched alkyl group having from 1 to 3 or 1 to 4 carbon atoms respectively. Further, the term "C$_{0-3}$alkyl" refers to a straight or branched alkyl group having from 0 (i.e. a bond) to 3 carbon atoms. Representative branched alkyl groups have one, two or three branches. An alkyl group may form part of a chain, for example, —C$_{0-3}$alkylOR$^6$ refers to a straight or branched alkyl chain having from 0 (i.e. a bond) to 3 carbon atoms linked to a group R$^6$. "Alkyl" includes, but is not limited to, methyl, ethyl, n-propyl, iso-propyl, n-butyl, iso-butyl, t-butyl, pentyl and hexyl.

"Cycloalkyl" refers to a saturated hydrocarbon mono or bicyclic ring or a saturated spiro-linked bicyclic hydrocarbon ring, having 3, 4, 5, 6, 7, 8, 9 or 10 member atoms in the ring. Suitable examples of cycloalkyl include, but are not limited to, cyclopropyl, cyclobutyl, cyclopentyl, cyclohexyl, cycloheptanyl, spiro[3.3]heptanyl, bicyclo[2.2.1]heptanyl, adamantyl, bicyclo[3.1.0]hexanyl and bicyclo[2.2.2]octanyl. "C$_{3-7}$cycloalkyl" refers to a saturated hydrocarbon mono or bicyclic ring or a saturated spiro-linked bicyclic hydrocarbon ring, having 3, 4, 5, 6 or 7 member atoms in the ring. Examples of C$_{3-7}$cycloalkyl groups include, but are not limited to, cyclopropyl, cyclobutyl, cyclopentyl, cyclohexyl, cycloheptanyl and bicyclo[3.1.0]hexanyl.

"Halo" refers to a halogen radical, for example, fluoro, chloro, bromo, or iodo.

"Heteroaryl" refers to a monocyclic or bicyclic group having 5, 6, 8, 9, 10 or 11 member atoms, including one, two or three heteroatoms independently selected from nitrogen, sulphur and oxygen, wherein at least a portion of the group is aromatic. The point of attachment to the rest of the molecule may be by any suitable carbon or nitrogen atom. Examples of "heteroaryl" groups include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, benzazepinyl, 2,3,4,5-tetrahydro-1H-benzo[d]azepinyl, indolizinyl, indolyl, indolinyl, isoindolyl, dihydroindolyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, imidazopyridinyl, pyrazolopyridinyl, pyrrolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

"C$_{5-6}$ heteroaryl" refers to a monocyclic aromatic group having 5 or 6 member atoms, including 1, 2, 3 or 4 heteroatoms independently selected from nitrogen, sulphur and oxygen. The point of attachment to the rest of the molecule may be by any suitable carbon or nitrogen atom. Examples of "C$_{5-6}$ heteroaryl" groups include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl and triazinyl.

"Heteroatom" refers to a nitrogen, sulfur, or oxygen atom.

"Heterocyclyl" refers to a non-aromatic heterocyclic monocyclic or bicyclic ring system containing 4, 5, 6, 7, 8, 9 or 10 ring member atoms, including one heteroatom and optionally containing a further heteroatom selected from nitrogen, oxygen or sulphur. Examples of "heterocyclyl" groups include, but are not limited to, azetidinyl, oxetanyl, thietanyl, pyrrolidinyl, pyrrolinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, homopiperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, thiomorpholinyl, hexahydro-1H-1,4-diazepinyl, azabicyclo[3.2.1]octyl, azabicyclo[3.3.1]nonyl, azabicylco[4.3.0]nonyl, oxa bicyclo[2.2.1]heptyl, 1,1-dioxidotetrahydro-2H-thiopyranyl, 1,5,9-triazacyclododecyl, 3-oxabicyclo[3.1.0]hexanyl, 3-azabicyclo[3.1.0]hexanyl, (1r,5s)-3-oxabicyclo[3.1.0]hexanyl and (1r,5s)-3-azabicyclo[3.1.0]hexanyl.

"4 to 7-membered heterocyclyl" refers to a non-aromatic heterocyclic ring system containing 4, 5, 6 or 7 ring member atoms, including one heteroatom and optionally containing a further heteroatom selected from nitrogen, oxygen or sulphur. Examples of "4 to 7-membered heterocyclyl" groups include, but are not limited to, azetidinyl, pyrrolidinyl, piperidinyl, piperazinyl and morpholinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group attached to a chain or a ring are not member atoms in the chain or ring.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient are avoided. In addition, each excipient must of course be pharmaceutically acceptable e.g. of sufficiently high purity.

"rac" refers to the racemic mixture of the compounds of formula (I).

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds according to formula (I) may contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic mixtures, enantiomerically-enriched mixtures, or as enantiomerically-pure individual stereoisomers. Accordingly, the present invention encompasses all isomers of the compounds of formula (I) whether as individual isomers isolated such as to be substantially free of the other isomer (i.e. pure) or as mixtures (i.e. racemic mixtures). An individual isomer isolated such as to be substantially free of the other isomer (i.e. pure) may be isolated such that less than 10%, particularly less than about 1%, for example less than about 0.1% of the other isomer is present.

Racemic compounds with a single stereocentre are denoted with either no stereochemistry (single bond) or have the annotation (+/−) or rac. Racemic compounds with two or more stereocentres where relative stereochemistry is known are denoted cis or transas drawn in the structure. Resolved single enantiomers with unknown absolute stereochemistry but known relative stereochemistry are referred to with (R* or S*) with the appropriate relative stereochemistry depicted.

Where diastereoisomers are represented and only the relative stereochemistry is referred to, the bold or hashed solid bond symbols (━ /⁙⁙⁙ ) are used. Where the absolute stereochemistry is known and the compound is a single enantiomer, the bold or hashed wedges symbols (━ /⁙⁙⁙ ) are used as appropriate.

Individual stereoisomers of a compound according to formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It will be appreciated that, for compounds of formula (I) tautomers may be observed. Any comment relating to the biological activity of a tautomer should be taken to include both tautomers. It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

Because of their potential use in medicine, salts of the compounds of formula (I) are desirably pharmaceutically acceptable. Suitable pharmaceutically acceptable salts can include acid addition salts or base addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated from the foregoing that included within the scope of the invention are solvates, isomers and polymorphic forms of the compounds of formula (I) and salts thereof.

Statement of the Invention

In a first aspect there are provided compounds of formula (I):

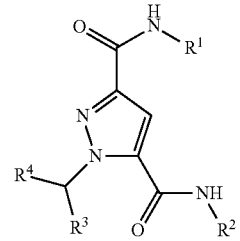

or a salt thereof
wherein:
$R^1$ is —$C_{1-3}$alkyl or cyclopropyl;
$R^2$ is —$C_{0-3}$alkyl-cycloalkyl, wherein the cycloalkyl group is optionally substituted with one, two or three $R^5$ groups which may be the same or different; or
$R^2$ is —$C_{0-4}$alkyl-heterocyclyl or —$(CH_2)_p$O-heterocyclyl wherein each heterocyclyl is optionally substituted by one or two $R^9$ groups which may be the same or different; or
$R^2$ is H, —$CH_3$, —$C_{2-6}$alkyl optionally substituted by one, two, three, four or five fluoro, —$C_{2-6}$alkyl $OR^6$, —$C_{2-6}$alkyl $NR^{10a}R^{11a}$, —$(CH_2)_mSO_2C_{1-3}$alkyl, —$(CH_2)_mSO_2NR^{10}R^{11}$, —$(CH_2)_mC(O)NR^{10}R^{11}$, —$(CH_2)_mCN$, —$(CH_2)_mCO_2R^6$, —$(CH_2)_mNHCO_2C_{1-4}$alkyl, —$(CH_2)_mNHC(O)C_{1-4}$alkyl or —$(CH_2)_n$heteroaryl wherein the heteroaryl is optionally substituted by one or two $R^7$ groups which may be the same or different;
$R^3$ is H, —$C_{1-4}$alkyl, cyclopropyl, —$CH_2F$, —$C_{1-3}$alkylOR^6$ or —$C_{1-3}$alkylCN;
$R^4$ is phenyl or a heteroaryl group wherein each are optionally substituted by one, two or three $R^7$ groups which may be the same or different;
each $R^5$ is independently halo, —$C_{0-6}$alkyl-$R^8$, —O—$C_{2-6}$alkyl-$R^8$, —O—$CH_2$phenyl, —CN or —$SO_2C_1$-3alkyl;
$R^6$ is H or —$C_{1-4}$alkyl;
each $R^7$ is independently oxo, halo, —$C_{1-4}$alkyl optionally substituted by one, two or three fluoro, —$C_{0-3}$alkylOR^6$, —$OC_{2-3}$alkylOR^6$, —$C_{0-3}$alkylNR$^{10}R^{11}$, —$C_{0-3}$alkylCONR$^{10}R^{11}$, —CN, —$SO_2$—$C_{1-3}$alkyl, —$SO_2NR^{10}R^{11}$ or —$SO_2$phenyl optionally substituted by —$C_{1-4}$alkyl
$R^8$ is H, —$OR^6$, —$NR^{10}R^{11}$ or heteroaryl;
each $R^9$ is independently halo, —$C_{1-4}$alkyl, cyclopropyl, cyclobutyl, —$CH_2CF_3$, —$CH_2CHF_2$, —$CH_2CH_2F$, —$OCH_2CH_2OR^6$, —$C_{0-3}$alkylOR^6$, —$C_{0-3}$alkylNR$^{10}R^{11}$, —$NHCH_2CH_2OR^6$, —$NHCO_2C_{1-4}$alkyl, oxo, —$C(O)R^6$, —$C(O)OR^6$ or —$C(O)NR^{10}R^{11}$;
$R^{10}$ and $R^{11}$ are each independently selected from H and —$C_{1-3}$alkyl; or $R^{10}$ and $R^{11}$ may join together with the nitrogen to which they are attached, to form a 4 to 7-membered heterocyclyl optionally substituted by one or two substituents independently selected from —$C_{1-3}$alkyl optionally substituted with one, two or three fluorine atoms, —$C_{2-4}$alkylOH, —OH and F;
$R^{10a}$ and $R^{11a}$ are each independently selected from H and —$C_{1-3}$alkyl;
m is an integer selected from 2, 3 or 4;
n is an integer selected from 0, 1, 2, 3 or 4; and
p is an integer selected from 2, 3 or 4.
In one embodiment there is provided a compound of formula (I) or a salt thereof wherein:
$R^1$ is —$C_{1-3}$alkyl or cyclopropyl;
$R^2$ is —$C_{0-3}$alkyl-cycloalkyl, wherein the cycloalkyl group is optionally substituted with one, two or three $R^5$ groups which may be the same or different; or $R^2$ is —$C_{0-4}$alkyl-heterocyclyl or —$(CH_2)_p$O-heterocyclyl wherein each heterocyclyl is optionally substituted by one or two $R^9$ groups which may be the same or different; or $R^2$ is H, —$CH_3$, —$C_{2-6}$alkyl optionally substituted by up to five fluoro, —$C_{2-6}$alkylOR$^6$, —$C_{2-6}$alkylNR$^{10a}$R$^{11a}$, —$(CH_2)_mSO_2C_{1-3}$alkyl, —$(CH_2)_mSO_2NR^{10}R^{11}$, —$(CH_2)_mC(O)NR^{10}R^{11}$, —$(CH_2)_mCN$, —$(CH_2)_mCO_2R^6$, —$(CH_2)_mNHCO_2C_{1-4}$alkyl, —$(CH_2)_mNHC(O)C_{1-4}$alkyl or —$(CH_2)_n$heteroaryl wherein the heteroaryl is optionally substituted by one or two $R^7$ groups which may be the same or different;

$R^3$ is —H, —$C_{1-4}$alkyl, cyclopropyl, —$CH_2F$, —$C_{1-3}$alkylOR$^6$ or —$C_{1-3}$alkylCN;

$R^4$ is phenyl or a heteroaryl group wherein each are optionally substituted by one, two or three $R^7$ groups which may be the same or different;

each $R^5$ is independently halo, —$C_{0-6}$alkyl-$R^8$, —O—$C_{2-6}$alkyl-$R^8$, —CN or —$SO_2C_{1-3}$alkyl; $R^6$ is H or —$C_{1-4}$alkyl;

each $R^7$ is independently oxo, halo, —$C_{1-4}$alkyl optionally substituted by 1, 2 or 3 fluoro, —$C_{0-3}$alkylOR$^6$, —$OC_{0-3}$alkylOR$^6$, —$C_{0-3}$alkylNR$^{10}R^{11}$, —$C_{0-3}$alkylCONR$^{10}R^{11}$, —CN, —$SO_2$—$C_{1-3}$alkyl or —$SO_2NR^{10}R^{11}$;

$R^8$ is H, —OR$^6$, —NR$^{10}R^{11}$ or heteroaryl;

each $R^9$ is independently halo, —$C_{1-4}$alkyl, cyclopropyl, cyclobutyl, —$CH_2CF_3$, —$CH_2CHF_2$, —$CH_2CH_2F$, —$OCH_2CH_2OR^6$, —$C_{0-3}$alkylOR$^6$, —$C_{0-3}$alkylNR$^{10}R^{11}$, —$NHCH_2CH_2OR^6$, —$NHCO_2R^6$, oxo, —$C(O)R^6$, —$C(O)OR^6$ or —$C(O)NR^{10}R^{11}$;

$R^{10}$ and $R^{11}$ are each independently selected from —H and —$C_{1-3}$alkyl; or $R^{10}$ and $R^{11}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH and F;

$R^{10a}$ and $R^{11a}$ are each independently selected from —H and —$C_{1-3}$alkyl;

m is an integer selected from 2, 3 or 4;
n is an integer selected from 0, 1, 2, 3 or 4; and
p is an integer selected from 2, 3 or 4.

In one embodiment $R^1$ is methyl.

In one embodiment $R^2$ is —$C_{0-3}$alkyl-cycloalkyl, wherein the cycloalkyl group is optionally substituted with one, two or three $R^5$ groups which may be the same or different. In one embodiment $R^2$ is a —$C_{0-3}$alkyl-$C_{3-7}$cycloalkyl group, wherein the $C_{3-7}$cycloalkyl group is selected from the group consisting of cyclopropyl, cyclobutyl, cyclohexyl or bicyclo[3.1.0]hexanyl, said groups being optionally substituted with one, two or three $R^5$ groups which may be the same or different. In another embodiment $R^2$ is cyclopropyl, cyclobutyl, cyclohexyl or bicyclo[3.1.0]hexanyl optionally substituted with one, two or three $R^5$ groups which may be the same or different. In another embodiment $R^2$ is cyclopropyl, cyclobutyl, cyclohexyl or bicyclo[3.1.0]hexanyl optionally substituted with one $R^5$ group selected from methyl, fluoro and —OH. In a particular embodiment $R^2$ is a cyclopropyl optionally substituted by one methyl group. In another particular embodiment $R^2$ is a cyclohexyl group optionally substituted with a OH group. In another embodiment $R^2$ is a cyclohexyl group optionally substituted with a methoxy group.

In one embodiment $R^2$ is —$C_{0-4}$alkyl-heterocyclyl or —$(CH_2)_p$O-heterocyclyl wherein each heterocyclyl is optionally substituted by one or two $R^9$ groups which may be the same or different. In another embodiment $R^2$ is —$C_{0-4}$alkyl-heterocyclyl wherein the heterocyclyl is optionally substituted by one or two $R^9$ groups which may be the same or different. In another embodiment $R^2$ is —$C_{0-4}$alkyl-heterocyclyl which is -heterocyclyl, —$CH_2CH_2$-heterocyclyl or —$CH_2CH_2CH_2$-heterocyclyl. In another embodiment $R^2$ is —$C_{0-4}$alkyl-heterocyclyl wherein the heterocyclyl is selected from oxetanyl, tetrahydrofuranyl, tetrahydro-2/pyranyl, morpholinyl, piperidinyl, piperazinyl, (1 r,5s)-3-oxa bicyclo[3.1.0]hexanyl and (1r,5S)-3-azabicyclo[3.1.0]hexanyl said groups being optionally substituted by one or two $R^9$ groups which may be the same or different. In another embodiment $R^2$ is —$C_{0-4}$alkyl-heterocyclyl wherein the heterocyclyl is selected from oxetanyl, tetrahydrofuranyl, tetrahydro-2/pyranyl, morpholinyl, piperidinyl, piperazinyl, (1r,5S)-3-oxabicyclo[3.1.0]hexanyl and (1r,5s)-3-azabicyclo[3.1.0]hexanyl optionally substituted by one or two $R^9$ groups selected from methyl, —$C(O)CH_3$ and fluoro. In a further embodiment $R^2$ is —$C_{0-4}$alkyl-heterocyclyl wherein the heterocyclyl optionally substituted by one or two $R^9$ groups, is selected from:

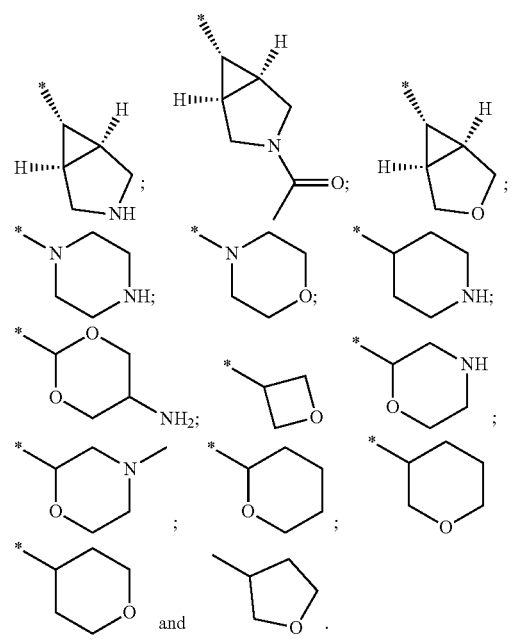

* denotes point of attachment

In another embodiment $R^2$ is H, —$CH_3$, $C_{2-6}$alkyl optionally substituted by one, two, three, four or five fluoro, —$C_{2-6}$alkylOR$^6$, —$C_{2-6}$alkylNR$^{19}R^{11}$, —$(CH_2)_mSO_2C_{1-3}$alkyl, —$(CH_2)_mSO_2NR^{19}R^{11}$, —$(CH_2)_mC(O)NR^{19}R^{11}$, —$(CH_2)_mCN$, —$(CH_2)_mCO_2R^6$, —$(CH_2)_mNHCO_2C_{1-4}$alkyl —$(CH_2)_mNHC(O)C_{1-4}$alkyl or —$(CH_2)_n$heteroaryl wherein the heteroaryl is optionally substituted by one or two $R^7$ groups which may be the same or different.

In another embodiment $R^2$ is selected from methyl, ethyl, propyl, iso-propyl, butyl, —$CH_2CH_2CH(CH_3)_2$, —$CH_2CH(CH_3)_2$, —$CH_2CH_2OR^6$, —$CH_2CH_2CH_2OR^6$, —$CH_2CH(CH_3)OR^6$, —$CH_2CH_2CH(CH_3)OR^6$—$CH_2CH_2CH(CH_3)NR^{10}R^{11}$, —$CH_2CH_2CH_2NR^{10}R^{11}$, —$(CH_2)_mSO_2CH_3$, —$(CH_2)_mC(O)NHCH_3$, —$(CH_2)_mCN$, —$(CH_2)_mCO_2R^6$, —$(CH_2)_mCF_3$ and —$(CH_2)_mNHCO_2C(CH_3)_3$.

In another embodiment $R^2$ is —$C_{1-6}$alkyl selected from methyl, ethyl, propyl, iso-propyl, butyl, —$CH_2CH_2CH(CH_3)_2$ and —$CH_2CH(CH_3)_2$. In another embodiment $R^2$ is —$C_{1-6}$alkylOR$^6$ selected from —$CH_2CH_2OR^6$, —$CH_2CH_2CH_2OR^6$, —$CH_2CH(CH_3)OR^6$ and —CH$_2$CH$_2$CH(CH$_3$)OR$^6$. In another embodiment R$^2$ is —C$_{1-6}$alkylNR$^{10}$R$^{11}$ selected from —CH$_2$CH$_2$CH(CH$_3$)NR$^{10}$R$^{11}$ and —CH$_2$CH$_2$CH$_2$NR$^{10}$R$^{11}$. In another embodiment R$^2$ is —(CH$_2$)$_m$SO$_2$CH$_3$. In another embodiment R$^2$ is —(CH$_2$)$_m$C(O)NHCH$_3$. In another embodiment R$^2$ is —(CH$_2$)$_m$CN. In another embodiment R$^2$ is —(CH$_2$)$_m$CO$_2$R$^6$. In another embodiment R$^2$ is —(CH$_2$)$_m$CF$_3$. In another embodiment R$^2$ is —(CH$_2$)$_m$NHCO$_2$C(CH$_3$)$_3$.

In one embodiment R$^2$ is —(CH$_2$)$_n$heteroaryl wherein the heteroaryl is optionally substituted by one or two R$^7$ groups which may be the same or different. In a further embodiment R$^2$ is —(CH$_2$)$_n$C$_{5-6}$heteroaryl wherein the C$_{5-6}$heteroaryl is selected from furanyl, thienyl, pyrrolyl, triazolyl, thiazolyl, oxazolyl, isoxazolyl, oxadiazolyl, imidazolyl, pyrazolyl, triazolyl, tetrazolyl, isoxazolyl, pyridinyl, pyridazinyl, pyrazinyl and pyrimidinyl said groups being optionally substituted by one or two R' substituents independently selected from halo, C$_{1-4}$alkyl (such as methyl) and —C$_{0-3}$alkylOR$^6$. In another embodiment there is provided compounds of formula (I) in which R$^2$ is —(CH$_2$)$_n$C$_{5-6}$heteroaryl wherein the C$_{5-6}$heteroaryl is pyrazolyl optionally substituted by C$_{1-4}$alkyl or —C$_{0-3}$alkylOR$^6$. In a particular embodiment there is provided compounds of formula (I) in which R$^2$ is —(CH$_2$)$_n$C$_{5-6}$heteroaryl wherein the optionally substituted C$_{5-6}$heteroaryl group is selected from the group consisting of

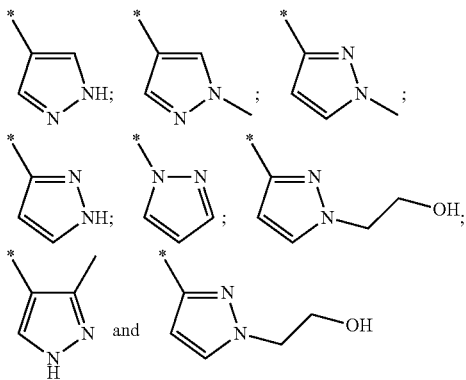

wherein * denotes the point of attachment.

In one embodiment R$^3$ is H, methyl, ethyl, —CH$_2$F, —CH$_2$OH, —CH(OH)CH$_3$, —CH$_2$OMe or —CH$_2$CN. In one embodiment R$^3$ is H, methyl, ethyl or CH$_2$OH.

In one embodiment R$^4$ is phenyl optionally substituted by one, two or three R$^7$ groups which may be the same or different. In another embodiment R$^4$ is unsubstituted phenyl. In another embodiment R$^4$ is phenyl substituted by one or two R$^7$ groups which may be the same or different selected from halo, —C$_{1-4}$alkyl optionally substituted one, two or three fluoro, —C$_{0-3}$alkylOR$^6$, —OC$_2$-3alkylOR$^6$ and CN. In another embodiment R$^4$ is phenyl substituted by one or two R$^7$ groups which may be the same or different selected from halo, —C$_{1-4}$alkyl, —C$_{0-3}$alkylOR$^6$ and CN. In another embodiment R$^4$ is phenyl substituted by one R$^7$ groups selected from the group consisting of fluoro, chloro, methyl, cyano and methoxy.

In another embodiment R$^4$ is a heteroaryl group which is pyridyl optionally substituted by one, two or three R$^7$ groups which may be the same or different. In another embodiment R$^4$ is a heteroaryl group which is unsubstituted pyridyl.

In another embodiment R$^4$ is a heteroaryl group which is indolyl (e.g 1H-indol-4-yl or 1H-indol-5-yl) optionally substituted by one, two or three R$^7$ groups which may be the same or different. In another embodiment R$^4$ is a heteroaryl group which is 1H-indol-4-yl.

In another embodiment R$^4$ is a heteroaryl group which is a pyrrolopyridinyl (e.g. 1H-pyrrolo[2,3,b]pyridinyl or 1H-pyrrolo[2,3,c]pyridinyl)) optionally substituted by one, two or three R$^7$ groups which may be the same or different. In another embodiment R$^4$ is a heteroaryl group which is unsubstituted pyrrolopyridinyl.

In one embodiment each R$^5$ is independently halo or —C$_{0-6}$alkyl-R$^8$ wherein R$^8$ is H, OR$^6$ (such as OH) or NR$^{10}$R$^{11}$ (such as NH$_2$).

In one embodiment R$^6$ is H, methyl, ethyl or t-butyl.

In one embodiment each R$^7$ is independently oxo, halo, —C$_{1-4}$alkyl optionally substituted by one, two or three fluoro, —C$_{0-3}$alkylOR$^6$, —C$_{0-3}$alkylNR$^{10}$R$^{11}$, —C$_{0-3}$alkylCONR$^{10}$R$^{11}$, —CN, —SO$_2$—C$_{1-3}$alkyl or —SO$_2$NR$^{10}$R$^{11}$. In another embodiment each R$^7$ is independently halo, —C$_{1-4}$alkyl optionally substituted by one, two or three fluoro, —C$_{0-3}$alkylOR$^6$ or CN.

In one embodiment each R$^7$ is independently halo, —C$_{1-4}$alkyl, —C$_{0-3}$alkylOR$^6$ or CN; In one embodiment R$^8$ is H, —OH or methoxy.

In one embodiment each R$^9$ is independently halo, C$_{1-4}$alkyl (such as methyl), —C$_{0-3}$alkylOR$^6$, —C$_{0-3}$alkylNR$^{10}$R$^{11}$, oxo, or —C(O)R$^6$ (such as C(O)CH$_3$).

In one embodiment m is 2 or 3.

In one embodiment n is 0, 1 or 2. In a further embodiment n is 0. In a yet further embodiment n is 2.

In one embodiment p is 2 or 3.

It is to be understood that the present invention covers all combinations of substituent groups described hereinabove.

Compounds of the invention include the compounds of Examples 1 to 261 and salts thereof.

Compounds of the invention include the compounds of Examples 1 to 138 and salts thereof.

In one embodiment the compound of formula (I) is selected from:

N$^5$-((1R,5S,6r)-3-oxabicyclo[3.1.0]hexan-6-yl)-N$^3$-methyl-1-((S)-1-phenylethyl)-1H-pyrazole-3,5-dicarboxamide;

N$^5$-((1r,4S)-4-hydroxycyclohexyl)-N$^3$-methyl-1-((S)-1-phenylethyl)-1H-pyrazole-3,5-dicarboxamide; and N$^5$-((1R,3R,5S,6r)-3-hydroxybicyclo[3.1.0]hexan-6-yl)-N$^3$-methyl-1-((S)-1-phenylethyl)-1H-pyrazole-3,5-dicarboxamide or a salt thereof.

In one embodiment there is provided

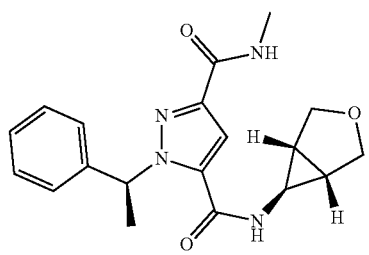 [SMILES: CNC(=O)c1cc(C(=O)N[C@H]2[C@@H]3COC[C@@H]32)n([C@@H](C)c2ccccc2)n1]

or a pharmaceutically acceptable salt thereof.

In one embodiment there is provided

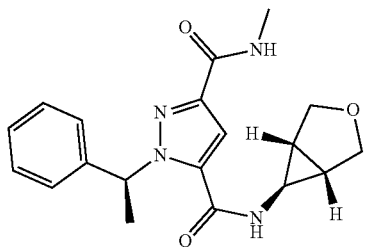 [SMILES: CNC(=O)c1cc(C(=O)N[C@H]2[C@@H]3COC[C@@H]32)n([C@@H](C)c2ccccc2)n1]

In one embodiment there is provided

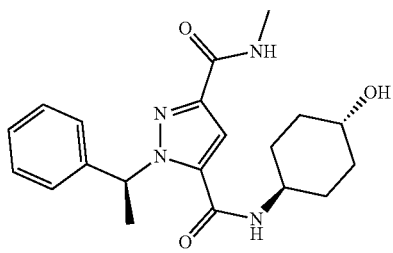 [SMILES: CNC(=O)c1cc(C(=O)N[C@H]2CC[C@H](O)CC2)n([C@@H](C)c2ccccc2)n1]

or a pharmaceutically acceptable salt thereof.

In one embodiment there is provided

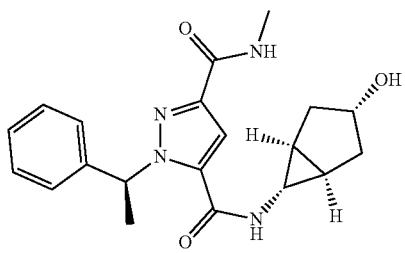 [SMILES: CNC(=O)c1cc(C(=O)N[C@H]2[C@@H]3C[C@@H](O)C[C@@H]32)n([C@@H](C)c2ccccc2)n1]

In another embodiment the compound of formula (I) is selected from:

$N^5$-((1R,5S,6r)-3-oxabicyclo[3.1.0]hexan-6-yl)-1-((S)-1-(4-chlorophenyl)ethyl)-$N^3$-methyl-1H-pyrazole-3,5-dicarboxamide;

(S)—$N^5$-methyl-1-(1-phenylethyl)-$N^5$-(1H-pyrazol-4-yl)-1H-pyrazole-3,5-dicarboxamide;

1-((S)-1-(4-chlorophenyl)ethyl)-$N^5$-((1R,3R,5S,6r)-3-hydroxybicyclo[3.1.0]hexan-6-yl)-$N^3$-methyl-1H-pyrazole-3,5-dicarboxamide;

1-((S)-1-(3-chlorophenyl)ethyl)-$N^5$-((1R,3R,5S,6r)-3-hydroxybicyclo[3.1.0]hexan-6-yl)-$N^3$-methyl-1H-pyrazole-3,5-dicarboxamide; and $N^5$-((1R,3R,5S,6r)-3-hydroxybicyclo[3.1.0]hexan-6-yl)-$N^3$-methyl-1-((S)-1-phenylpropyl)-1H pyrazole-3,5-dicarboxamide or a salt thereof.

In a second aspect of the present invention, there is provided a pharmaceutical composition comprising a compound of formula (I) or a pharmaceutically acceptable salt thereof and one or more pharmaceutically acceptable excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

The compounds of the invention may possess an improved profile over known BET inhibitors (including properties such as potency, selectivity and/or developability). Certain compounds of the invention may have an advantageous combination of such properties.

Statement of Use

The compounds of formula (I) and salts thereof are bromodomain inhibitors, and thus are believed to have potential utility in the treatment of diseases or conditions for which a bromodomain inhibitor is indicated.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, psoriatic arthritis, ankylosing spondylitis, osteoarthritis, acute gout, psoriasis, systemic lupus erythematosus, multiple sclerosis, inflammatory bowel disease (Crohn's disease and ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolennia, atherosclerosis, Alzheimer's disease, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, acute alcoholic hepatitis, chronic alcoholic hepatitis, alcoholic steato-hepatitis, non-alcoholic steato-hepatitis (NASH), cirrhosis, Childs-Pugh cirrhosis, autoimmune hepatitis, fulminant hepatitis, chronic viral hepatitis, alcoholic liver disease, systemic sclerosis, systemic sclerosis with associated interstitial lung disease, sarcoidosis, neurosarcoidosis, Addison's disease, hypophysitis, thyroiditis, Type I diabetes, Type II diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement, acute rejection of transplanted organs and systemic sclerosis.

In one embodiment the acute or chronic autoimmune and/or inflammatory condition is a disorder of lipid metabolism mediated via the regulation of APO-A1 such as hypercholesterolemia, atherosclerosis or Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease or Ulcerative colitis).

In another embodiment, the acute or chronic autoimmune and/or inflammatory condition is multiple sclerosis.

In another embodiment, the acute or chronic autoimmune and/or inflammatory condition is Type I diabetes.

In another embodiment, the acute or chronic autoimmune and/or inflammatory condition is rheumatoid arthritis.

Bromodomain inhibitors may be useful in the treatment of depression.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of cardiovascular diseases such as coronary artery diseases (for example, angina or myocardial infarction), pulmonary arterial hypertension, cerebro-vascular ischaemia (stroke), hypertensive heart disease, rheumatic heart disease, cardiomyopathy, atrial fibrillation, congenital heart disease, endocarditis, aortic aneurysms or peripheral artery disease.

Bromodomain inhibitors may be useful in the treatment of fibrotic conditions such as idiopathic pulmonary fibrosis, pulmonary fibrosis, cystic fibrosis, progressive massive fibrosis, renal fibrosis, liver fibrosis, liver cirrhosis, non-alcoholic steatohepatitis (NASH), non-alcoholic fatty liver disease (NAFLD), post-operative stricture, keloid scar formation, scleroderma (including morphea and systemic sclerosis), cardiac fibrosis, atrial fibrosis, endomyocardial fibrosis, old myocardial infarction, arthrofibrosis, Dupuytren's contracture, mediastinal, myelofibrosis, Peyronie's disease, nephrogenic systemic fibrosis, retroperitoneal fibrosis and adhesive capsulitis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox or smallpox, or African swine fever virus. In one embodiment the viral infection is a HPV infection of skin or cervical epithelia. In another embodiment the viral infection is a latent HIV infection.

Bromodomain inhibitors may be useful in the treatment of a wide variety of bone disorders such as osteoporosis, osteopenia, osteoarthritis and ankylosing spondylitis.

Bromodomain inhibitors may be useful in the treatment of cancer, including hematological cancers (such as leukaemia, lymphoma and multiple myeloma), epithelial cancers (including lung, breast or colon carcinomas), midline carcinomas, or mesenchymal, hepatic, renal or neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colorectal cancer. In another embodiment the cancer is prostate cancer. In another embodiment the cancer is castration resistant prostate cancer.

Bromodomain inhibitors may be useful in the treatment of diseases associated with systemic inflammatory response syndrome, such as sepsis, burns, pancreatitis, major trauma, haemorrhage and ischaemia. In this embodiment, the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

The present invention thus provides a compound of formula (I) or a pharmaceutically acceptable salt thereof for use in therapy. In one embodiment there is provided $N^5$-((1R,5S,6r)-3-oxabicyclo[3.1.0]hexan-6-yl)-$N^3$-methyl-1-((S)-1-phenylethyl)-1H-pyrazole-3,5-dicarboxamide, or a pharmaceutically salt thereof for use in therapy.

The compound of formula (I) or a pharmaceutically salt thereof can be used in the treatment of diseases or conditions for which a bromodomain inhibitor is indicated. The present invention thus provides a compound of formula (I) or a pharmaceutically acceptable salt thereof for use in the treatment of a disease or condition for which a bromodomain inhibitor is indicated. In one embodiment there is provided a compound of formula (I) or a pharmaceutically acceptable salt thereof for use in the treatment of acute or chronic auto-immune and/or inflammatory conditions. In one embodiment there is provided a compound of formula (I) or a pharmaceutically acceptable salt thereof for use in the treatment of rheumatoid arthritis. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of conditions associated with ischaemia-reperfusion injury. In another embodiment there is provided a compound of formula (I) or a pharmaceutically acceptable salt thereof for use in the treatment of cardiovascular diseases. In another embodiment there is provided a compound of formula (I) or a pharmaceutically acceptable salt thereof for use in the treatment of fibrotic conditions. In another embodiment there is provided a compound of formula (I) or a pharmaceutically acceptable salt thereof for use in the treatment of viral infections. In another embodiment there is provided a compound of formula (I) or a pharmaceutically acceptable salt thereof for use in the treatment of bone disorders. In another embodiment there is provided a compound of formula (I) or a pharmaceutically acceptable salt thereof for use in the treatment of cancer. In a further embodiment there is provided a compound of formula (I) or a pharmaceutically acceptable salt thereof for use in the treatment of diseases associated with systemic inflammatory response syndrome.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In one embodiment there is provided the use of a compound of formula (I) or a pharmaceutically acceptable salt thereof in the manufacture of a medicament for the treatment of rheumatoid arthritis. In another embodiment there is provided the use of a compound of formula (I) or a pharmaceutically acceptable salt thereof in the manufacture of a medicament for the treatment of diseases or conditions which involve inflammatory responses to infections with bacteria, viruses, fungi, parasites or their toxins. In another embodiment there is provided the use of a compound of formula (I) or a pharmaceutically acceptable salt thereof in the manufacture of a medicament for the treatment of conditions associated with ischaemia-reperfusion injury. In another embodiment there is provided the use of a compound of formula (I) or a pharmaceutically acceptable salt thereof in the manufacture of a medicament for the treatment of cardiovascular diseases. In another embodiment there is provided the use of a compound of formula (I) or a pharmaceutically acceptable salt thereof in the manufacture of a medicament for the treatment of fibrotic conditions. In another embodiment there is provided the use of a compound of formula (I) or a pharmaceutically acceptable salt thereof in the manufacture of a medicament for the treatment of viral infections. In another embodiment there is provided the use of a compound of formula (I) or a pharmaceutically acceptable salt thereof in the manufacture of a medicament for the treatment of cancer. In a further embodiment there is provided the use of a compound of formula (I) or a pharmaceutically acceptable salt thereof in the manufacture of a medicament for the treatment of diseases associated with systemic inflammatory response syndrome.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In one embodiment there is provided a method of treating rheumatoid arthritis in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating conditions associated with ischaemia-reperfusion injury in a subject in need thereof which comprises administering a therapeutically effective amount of a compound of formula (I) or a pharmaceutically acceptable salt thereof. In another embodiment there is provided a method of treating cardiovascular diseases in a subject in need thereof which comprises administering a therapeutically effective amount of a compound of formula (I) or a pharmaceutically acceptable salt thereof. In another embodiment there is provided a method of treating fibrotic conditions in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In another embodiment there is provided a method of treating cancer in a subject in need thereof which comprises administering a therapeutically effective amount of a compound of formula (I) or a pharmaceutically acceptable salt thereof. In a further embodiment there is provided a method of treating diseases associated with systemic inflammatory response syndrome in a subject in need thereof which comprises administering a therapeutically effective amount of a compound of formula (I) or a pharmaceutically acceptable salt thereof.

Suitably the subject in need thereof is a mammal, particularly a human.

The invention further provides for a method for inhibiting a bromodomain containing protein which comprises contacting the bromodomain containing protein with a compound of formula (I) or a pharmaceutically acceptable salt thereof.

As used herein the reference to the "treatment" of a particular disease or condition includes the prevention or prophylaxis of such a disease or condition.

Pharmaceutical Compositions/Routes of Administration/Dosages

Compositions

While it is possible that for use in therapy, a compound of formula (I) as well as pharmaceutically acceptable salts thereof may be administered as the raw chemical, it is common to present the active ingredient as a pharmaceutical composition. The compounds of formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of formula (I), or a pharmaceutically acceptable salt thereof, and one or more (e.g. two, three, four, five or six) pharmaceutically acceptable excipients. In one embodiment there is provided $N^5$-(1R,5S,6r)-3-oxabicyclo[3.1.0]hexan-6-yl)-$N^3$-methyl-1-((S)-1-phenylethyl)-1H-pyrazole-3,5-dicarboxamide, or a pharmaceutically acceptable salt thereof, and one or more pharmaceutically acceptable excipients. The compounds of formula (I) and pharmaceutically acceptable salts are as described above. The excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable excipients. A pharmaceutical composition comprising a compound of formula (I) or a pharmaceutically acceptable salt thereof may be prepared by, for example, admixture at ambient temperature and atmospheric pressure. The pharmaceutical composition can be used in the treatment of any of the conditions described herein.

In a further aspect the invention is directed to pharmaceutical compositions for the treatment of a disease or condition for which a bromodomain inhibitor is indicated comprising a compound of formula (I) or a pharmaceutically acceptable salt thereof.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.25 mg to 1 g, or from 0.5 mg to 500 mg, or from 1 mg to 100 mg, of a compound of formula (I) or a pharmaceutically acceptable salt thereof.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the subject from one organ, or portion of the body, to another organ, or portion of the body. Certain pharmaceutically acceptable excipients may be chosen for their ability to enhance subject compliance.

Suitable pharmaceutically-acceptable excipients include the following types of excipients: carriers, diluents, fillers, binders, disintegrants, lubricants, glidants, granulating agents, coating agents, wetting agents, solvents, co-solvents, suspending agents, emulsifiers, sweeteners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (*Gower Publishing Limited*), and *The Handbook of Pharmaceutical Excipients* (*the American Pharmaceutical Association and the Pharmaceutical Press*).

The pharmaceutical compositions of the invention are prepared using techniques and methods known to those skilled in the art. Some of the methods commonly used in the art are described in *Remington's Pharmaceutical Sciences* (*Mack Publishing Company*).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions (which may contain anti-oxidants, buffers, bacteriostats and solutes which render the composition isotonic with the blood of the intended recipient) and aqueous and non-aqueous sterile suspensions (which may include suspending agents and thickening agents). The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents (disintegrants) and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrants include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

For compositions suitable and/or adapted for oral administration, the compound of formula (I) or a pharmaceutically acceptable salt thereof, may be in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situgellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent.

Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser.

Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in International Patent Application Publication No. WO 2005/044354 A1.

A therapeutically effective amount of a compound of formula (I) or a pharmaceutically acceptable salt thereof, will depend upon a number of factors including, for example, the age and weight of the patient, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 mg to 3000 mg, more preferably 0.5 mg to 1000 mg, of a compound of formula (I) or a pharmaceutically acceptable salt thereof, calculated as the free base. Each dosage unit for nasal or inhaled administration preferably contains from 0.001 mg to 50 mg, more preferably 0.01 mg to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 mg to 1000 mg per day or 100 mg to 2500 mg per day, or a nasal or inhaled dose of 0.001 mg to 50 mg per day or 0.01 mg to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists, beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are described in Cancer Principles and Practice of Oncology by V. T. Devita and S. Hellman (editors), $6^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents (such as PD-1 inhibitors, including nivolumab and pembrolizumab, and CTLA-4 inhibitors, including ipilimumab); proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

It will be clear to a person skilled in the art that, where appropriate, the other therapeutic agent(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic agent. It will be clear also that, where appropriate, the therapeutic agents may be used in optically pure form.

The combinations referred to above may conveniently be presented for use in the form of a pharmaceutical composition and thus pharmaceutical compositions comprising a combination as defined above together with a pharmaceutically acceptable excipient represent a further aspect of the invention.

General Synthetic Routes

The compounds of the invention may be made by a variety of methods. Any previously defined variable will continue to have the previously defined meaning unless otherwise indicated. Illustrative general synthetic methods are set out in the following schemes, and can be readily adapted to prepare other compounds of the invention. Specific compounds of the invention are prepared in the Examples section.

Compounds of formula (I) may be prepared as described in any of the Schemes below:

Step 4: is a base-mediated ester hydrolysis and may be carried out using any suitable base, such as lithium hydroxide, optionally in a suitable solvent or mixture of solvents, such as 1,4-dioxane and water, at a suitable temperature, such as room temperature.

Step 5: is an amide coupling reaction and may be carried out using an amine reagent, $R^2$—$NH_2$, in the presence of a suitable tertiary amine, such as triethylamine or DIPEA, in the presence of a suitable amide coupling reactant, such as HATU, in a suitable solvent, such as DCM or DMF, at a suitable temperature, such as room temperature.

Step 6: is an acid-mediated ester cleavage and may be carried out using any suitable acid, such as sulfuric acid, optionally in a suitable solvent or mixture of solvents, such as 1,4 dioxane and water, at a suitable temperature, such as heating at reflux.

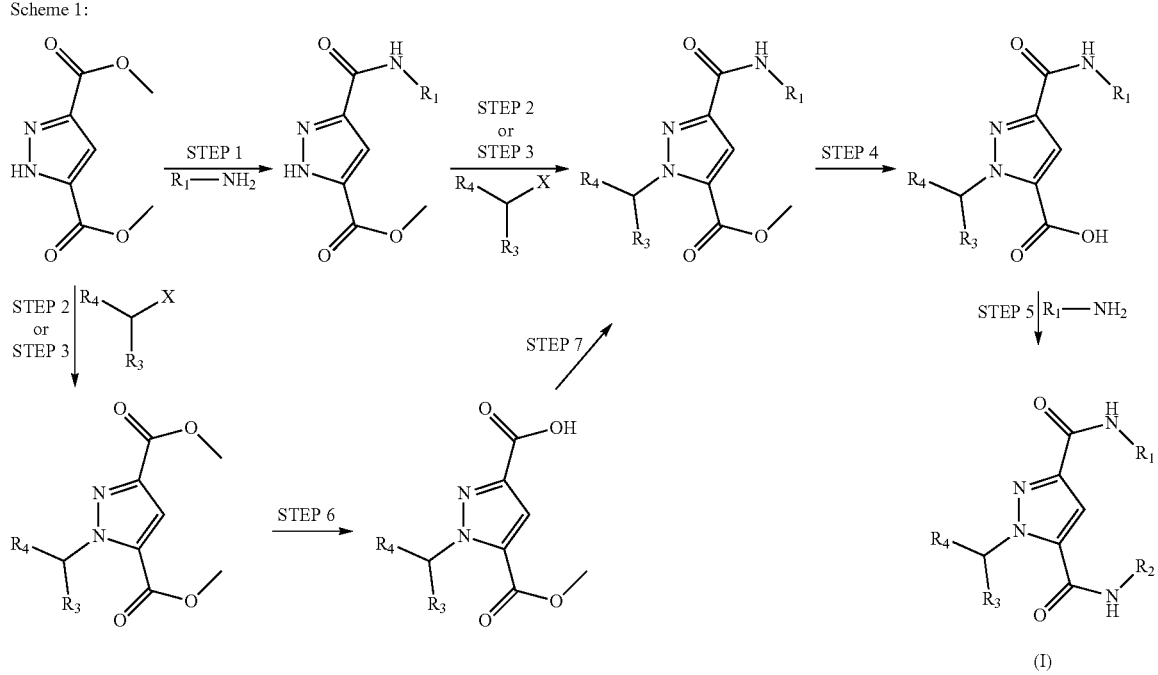

Scheme 1:

wherein $R^1$, $R^2$, $R^3$ and $R^4$ are as described above and X is either Br, Cl or OH.

In respect of the steps shown in Scheme 1 above the following reaction conditions may be utilised:

Step 1: is an amidation of an ester and may be carried out using an appropriate amine of formula $R_1$—$NH_2$, optionally in the presence of a suitable solvent, such as THF, at a suitable temperature, such as 0° C. to r.t.

Step 2: is a Mitsunobu coupling reaction where X=OH and may be carried out using any suitable alcohol, in the presence of a Mitsunobu coupling reagent, such as either DEAD or DIAD with a suitable phosphine, such as $Ph_3P$; or alternately with a suitable phosphorane reagent such as CMBP in a suitable solvent, such as THF or acetonitrile, at a suitable temperature, such as room temperature or at 120° C.

Step 3: is an alkylation reaction where X=Br or Cl and may be carried out using a suitable base, such as potassium carbonate in a suitable solvent, such as acetone, at a suitable temperature, such as room temperature.

Step 7: is an amide coupling reaction and may be carried out using an amine reagent, $R^1$—$NH_2$, in the presence of a suitable tertiary amine, such as triethylamine or DIPEA, in the presence of a suitable amide coupling reactant, such as HATU, in a suitable solvent, such as DCM or DMF, at a suitable temperature, such as room temperature.

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006), incorporated herein by reference as it relates to such procedures.

Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by acid mediated cleavage (e.g. using an acid such as hydrochloric acid in 1,4-dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—C(O)CF₃) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above form a yet further aspect of the invention.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used.

Conventional methods of drying organic solvents, solutions, or extracts, such as shaking with anhydrous magnesium sulfate, or anhydrous sodium sulfate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times and temperatures may typically be determined by reaction-monitoring techniques, for example thin-layer chromatography and LC-MS.

General Experimental Details

All temperatures referred to are in ° C.

As used herein the symbols and conventions used in these processes, schemes and examples are consistent with those used in the contemporary scientific literature, for example, the *Journal of the American Chemical Society*. Unless otherwise noted, all starting materials were obtained from commercial suppliers and used without further purification. Specifically, the following abbreviations may be used in the examples and throughout the specification:

General Methods

General Experimental Details

As used herein the symbols and conventions used in these processes, schemes and examples are consistent with those used in the contemporary scientific literature, for example, the *Journal of the American Chemical Society*. Unless otherwise noted, all starting materials were obtained from commercial suppliers and used without further purification. Specifically, the following abbreviations may be used in the examples and throughout the specification:

Abbreviations

AcOH acetic acid
AMU atomic mass units
Aq aqueous
BOC/Boc tert-butyloxycarbonyl
Cs₂CO₃ cesium carbonate
CHCl₃ chloroform
CMBP (cyanomethylene)tributylphosphorane
CPME cyclopentyl methyl ether
CV column volume
DCM dichloromethane
DIAD diisopropyl azodicarboxylate
DIBAL-H diisobutylaluminium hydride
DIPEA diisopropylethylamine
DMAP 4-dimethylaminopyridine
DMF dimethylformamide
DMSO dimethylsulfoxide
DMSO-d₆ deuterated dimethylsulfoxide
DPPA diphenylphosphoryl azide
Et₃N triethylamine
EtOAc ethyl acetate
EtOH ethanol
h hour(s)
HATU O-(7-azabenzotriazol-1-yl)-N,N,N',N'-tramethyluronium hexafluorophosphate
HBr hydrogen bromide
HCl hydrochloric acid
HPLC high performance (quid chromatography
Isolera Biotage® Flash purification system
K₂CO₃ potassium carbonate
LiCl lithium chloride
LCMS liquid chromatography-mass spectrometry
LiOH lithium hydroxide
M molar (concentration)
MDAP mass directed autopreparative chromatography
MeCN acetonitrile
MeOH methanol
2-MeTHF 2-methyltetrahydrofuran
minutes(s)
MS mass spectrometry
Ms-Cl methanesulfonyl chloride
N normal (concentration)
N₂ nitrogen gas
NaBH₄ sodium borohydride
Na₂CO₃ sodium carbonate
NaH sodium hydride
NaHCO₃ sodium bicarbonate
NaOH sodium hydroxide
Na₂SO₄ sodium sulphate
NH₃ ammonia
NH₄Cl ammonium chloride
NUT nuclear protein in testis
obs obscured
Ph₃P triphenylphosphine
RBF round bottomed flask
Rt retention time
rt room temperature
sat saturated
SCX Isolute strong cation exchange sorbent SPE
SFC supercritical fluid chromatography
SiO₂ silicon dioxide
SNAP Biotage® (silica) flash chromatography cartridge
SP4 Biotage® Flash purification system
SPE solid phase extraction
T₃P propylphosphonic anhydride solution
TFA trifluoroacetic acid
THF tetrahydrofuran
TBDMS-Cl tert-butyldimethylsilyl chloride
TLC Thin layer chromatography
Ts tosyl
pTsCl tosyl chloride
UPLC ultra performance liquid chromatograpy
UV ultraviolet
XantPhos 1,1'-(9,9-dimethyl-9H-xanthene-4,5-diyl)bis[1,1-diphenylphosphine The names of the following compounds have been obtained using the compound naming programme "ACD Name Pro 6.02" or using the naming functionality of ChemDraw Ultra 12.0.

LCMS Methodology
Formic Method
LC Conditions

The UPLC analysis was conducted on an Acquity UPLC CSH C18 column (50 mm×2.1 mm, i.d. 1.7 µm packing diameter) at 40° C.

The solvents employed were:
A=0.1% v/v solution of formic acid in water
B=0.1% v/v solution of formic acid in acetonitrile The gradient employed was:

| Time (min) | Flow rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

MS conditions
MS Waters ZQ
Ionisation mode Alternate-scan positive and negative electrospray
Scan range 100 to 1000 AMU
Scan time 0.27 sec
Inter scan delay 0.10 sec High pH Method
LC Conditions The UPLC analysis was conducted on an Acquity UPLC CSH C18 column (50 mm×2.1 mm, i.d. 1.7 µm packing diameter) at 40° C.

The solvents employed were:
A=10 mM ammonium hydrogen carbonate in water adjusted to pH10 with ammonia solution
B=acetonitrile The gradient employed was:

| Time (min) | Flow rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

MS Conditions
MS Waters ZQ
Ionisation mode Alternate-scan positive and negative electrospray
Scan range 100 to 1000 AMU
Scan time 0.27 sec
Inter scan delay 0.10 sec TFA Method
LC conditions The UPLC analysis was conducted on an Acquity UPLC CSH $C_{18}$ column (50 mm×2.1 mm, i.d. 1.7 µm packing diameter) at 40° C.

The solvents employed were:
A=0.1% v/v solution of trifluoroacetic acid in water
B=0.1% v/v solution of trifluoroacetic acid in acetonitrile The gradient employed was:

| Time (min) | Flow rate (mL/min) | % A | % B |
|---|---|---|---|
| 0 | 1 | 95 | 5 |
| 1.5 | 1 | 5 | 95 |
| 1.9 | 1 | 5 | 95 |
| 2.0 | 1 | 95 | 5 |

The UV detection was a summed signal from wavelength of 210 nm to 350 nm.

MS conditions
MS Waters ZQ
Ionisation mode Alternate-scan positive and negative electrospray
Scan range 100 to 1000 AMU
Scan time 0.27 sec
Inter scan delay 0.10 sec Method A
LC conditions The UPLC analysis was conducted on an Acquity BEH C18 column (50 mm×2.1 mm, i.d. 1.7 µm packing diameter) at 35° C.

The solvents employed were:
A=0.1% v/v solution of formic acid in water
B=0.1% v/v solution of formic acid in acetonitrile The gradient employed was:

| Time (min) | Flow rate (mL/min) | % A | % B |
|---|---|---|---|
| 0 | 0.6 | 97 | 3 |
| 0.4 | 0.6 | 97 | 3 |
| 3.2 | 0.6 | 2 | 98 |
| 3.8 | 0.6 | 2 | 98 |
| 4.2 | 0.6 | 97 | 3 |
| 4.5 | 0.6 | 97 | 3 |

Method B
LC Conditions

The UPLC analysis was conducted on an Acquity BEH C18 column (50 mm×2.1 mm, i.d. 1.7 µm packing diameter) at 35° C.

The solvents employed were:
A=0.05% v/v solution of formic acid in water
B=0.05% v/v solution of formic acid in acetonitrile The gradient employed was:

| Time (min) | Flow rate (mL/min) | % A | % B |
|---|---|---|---|
| 0 | 0.6 | 97 | 3 |
| 0.4 | 0.6 | 97 | 3 |
| 3.2 | 0.6 | 2 | 98 |
| 3.8 | 0.6 | 2 | 98 |
| 4.2 | 0.6 | 97 | 3 |
| 4.5 | 0.6 | 97 | 3 |

Method C
LC Conditions

The UPLC analysis was conducted on a Xbridge C18 column (150 mm×4.6 mm, i.d. 3.5 µm packing diameter) at 35° C.

The solvents employed were:
A=0.05% v/v solution of trifluoroacetic acid in water
B=acetonitrile
The gradient employed was:

| Time (min) | Flow rate (mL/min) | % A | % B |
|---|---|---|---|
| 0 | 1.0 | 95 | 5 |
| 0.5 | 1.0 | 95 | 5 |
| 7 | 1.0 | 5 | 95 |
| 14 | 1.0 | 5 | 95 |
| 14.5 | 1.0 | 95 | 5 |
| 15 | 1.0 | 95 | 5 |

Method D
LC Conditions

The UPLC analysis was conducted on an Acquity BEH $C_{18}$ column (100 mm×2.1 mm, i.d. 1.7 μm packing diameter) at 35° C.

The solvents employed were:
A=0.05% v/v solution of formic acid in acetonitrile
B=0.05% v/v solution of formic acid in water
The gradient employed was:

| Time (min) | Flow rate (mL/min) | % A | % B |
|---|---|---|---|
| 0 | 0.45 | 3 | 97 |
| 0.4 | 0.45 | 3 | 97 |
| 7.5 | 0.45 | 98 | 2 |
| 9.5 | 0.45 | 98 | 2 |
| 9.6 | 0.45 | 3 | 97 |
| 10 | 0.45 | 3 | 97 |

Method E
LC Conditions

The UPLC analysis was conducted on an Acquity BEH $C_{18}$ column (50 mm×2.1 mm, i.d. 1.7 μm packing diameter) at 35° C.

The solvents employed were:
A=0.05% v/v solution of formic acid in acetonitrile
B=0.05% v/v solution of formic acid in water
The gradient employed was:

| Time (min) | Flow rate (mL/min) | % A | % B |
|---|---|---|---|
| 0 | 0.45 | 3 | 97 |
| 0.4 | 0.45 | 3 | 97 |
| 4.0 | 0.45 | 98 | 2 |
| 4.5 | 0.45 | 97.5 | 2.5 |
| 5.0 | 0.45 | 3 | 97 |
| 5.5 | 0.45 | 3 | 97 |

General MDAP Purification Methods

Listed below are examples of mass-directed autopreparative chromatography (MDAP) methods that have been used or may be used in compound purification.

MDAP (High pH). The HPLC analysis was conducted on an Xselect CSH C18 column (150 mm×30 mm i.d. 5 μm packing diameter) at ambient temperature, eluting with 10 mM ammonium bicarbonate in water adjusted to pH 10 with ammonia solution (Solvent A) and acetonitrile (Solvent B) using an elution gradient of between 0 and 100% Solvent B over 15 or 25 min.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (Formic). The HPLC analysis was conducted on an Xselect CSH C18 column (150 mm×30 mm i.d. 5 μm packing diameter) at ambient temperature, eluting with 0.1% formic acid in water (Solvent A) and 0.1% formic acid in acetonitrile (Solvent B) using an elution gradient of between 0 and 100% solvent B over 15 or 25 min.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (TFA). The HPLC analysis was conducted on an Xselect CSH C18 column (150 mm×30 mm i.d. 5 μm packing diameter) at ambient temperature, eluting with 0.1% v/v solution of trifluoroacetic acid in water (Solvent A) and 0.1% v/v solution of trifluoroacetic acid in acetonitrile (Solvent B) using an elution gradient of between 0 and 100% solvent B over 15 or 25 min.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

NMR

Spectra were run on either a 400 MHz or 600 MHz NMR machine at 302 K.

Intermediate 1: Methyl 3-(methylcarbamoyl)-1H-pyrazole-5-carboxylate

A solution of dimethyl 1H-pyrazole-3,5-dicarboxylate (10 g, 54.3 mmol, commercially available from, for example, Fluorochem) in methanamine (5% wt solution in water) (67.5 g, 109 mmol, commercially available from, for example, Spectrochem) was stirred under nitrogen at 0° C. The reaction mixture was stirred at 0° C. for 30 min. After 16 h the reaction mixture was neutralized with 1N HCl, extracted with EtOAc (500 mL) and washed with brine (100 mL). The organic layer was dried over $Na_2SO_4$, filtered and the filtrate was concentrated to afford methyl 5-(methylcarbamoyl)-1H-pyrazole-3-carboxylate (4 g, 14.19 mmol, 26% yield) of the crude compound. The reaction was repeated again on the same scale to afford a further 3.8 g of crude compound and again using a solution of dimethyl 1H-pyrazole-3,5-dicarboxylate (20 g, 54.3 mmol) in methanamine (5% wt solution in water) (67.5 g, 109 mmol) stirred under nitrogen at 0° C. using the same work-up as above to afford a further 7 g of crude compound. The combined crude batches were purified by column chromatography (100-200 silica gel) eluting with 0-10% MeOH in DCM. The desired fractions were collected and dried under reduced pressure to afford the crude compound (10 g). This was diluted with anhydrous methanol (100 mL) and kept at rt for 24 h. After 24 h the solid was filtered through a Buchner funnel, washed with cooled anhydrous methanol (20 mL) and the residue was then washed with pentane and dried to afford methyl 5-(methylcarbamoyl)-1H-pyrazole-3-carboxylate (8 g, 43.6 mmol, 20% yield) as a off white solid.

$^1$H NMR (400 MHz, DMSO-$d_6$) δ ppm 14.27 (br. s., 1H) 8.42 (br. s., 1H) 7.22 (br. s., 1H) 3.83 (s, 3H) 2.76 (d, J=4.6 Hz, 3H)

LCMS (2 min Formic): Rt=0.44 min, [MH]$^+$=184.1.

Intermediate 2: Methyl (S)-dimethyl 1-(1-phenyl-ethyl)-1H-pyrazole-3,5-dicarboxylate

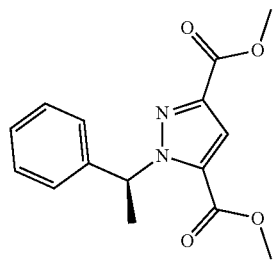 [SMILES: COC(=O)c1cc(C(=O)OC)n([C@@H](C)c2ccccc2)n1]

Diisopropyl (E)-diazene-1,2-dicarboxylate (8.24 g, 40.7 mmol) was added dropwise to a suspension of dimethyl 1H-pyrazole-3,5-dicarboxylate (5 g, 27.2 mmol, commercially available from, for example, Fluorochem), (R)-1-phenylethan-1-ol (3.98 g, 32.6 mmol, commercially available from, for example, Sigma Aldrich) and triphenylphosphine polymer bound 3 mmol/g (13.70 g, 40.7 mmol, commercially available from, for example, Sigma Aldrich) in 2-MeTHF (50 mL) at 0° C. under nitrogen. The mixture was stirred overnight, allowing it to warm to rt. In a separate reaction, dimethyl 1H-pyrazole-3,5-dicarboxylate (2 g, 10.86 mmol), (R)-1-phenylethan-1-ol (1.592 g, 13.03 mmol) and triphenylphosphine polymer bound 3 mmol/g (5.48 g, 16.29 mmol) were combined in a RBF, 2-MeTHF (50 mL) was added and the mixture was stirred under nitrogen, cooling in an ice bath for 30 min, then diisopropyl (E)-diazene-1,2-dicarboxylate (3.29 g, 16.29 mmol) was added dropwise over 30 min and the resulting mixture stirred overnight, allowing it to warm to rt. The reaction mixtures were combined and the combined suspension was filtered and the solid polymer bound triphenylphosphine (oxide) was washed with EtOAc (100 mL). Then the combined organics were washed with water (200 mL), dried and evaporated in vacuo and the residue purified by chromatography on a 340 g silica column eluting with 0-25% EtOAc/cyclohexane. The product-containing fractions were evaporated in vacuo to give dimethyl (S)-1-(1-phenylethyl)-1H-pyrazole-3,5-dicarboxylate (7.2 g, 24.97 mmol, 66% yield) as a colourless oil.

$^1$H NMR (400 MHz, CHLOROFORM-d) δ ppm 7.39 (s, 1H) 7.29-7.33 (m, 4H) 7.22-7.28 (m, 1H) 6.63 (q, J=7.1 Hz, 1H) 3.96 (s, 3H) 3.86 (s, 3H) 1.99 (d, J=7.1 Hz, 3H) LCMS (2 min High pH): Rt=1.13 min, [MH]$^+$=289.2.

Intermediate 3: (S)-5-(Methoxycarbonyl)-1-(1-phenylethyl)-1H-pyrazole-3-carboxylic acid

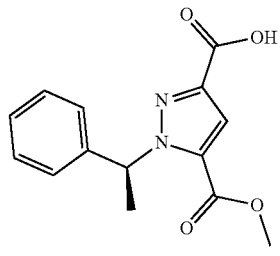 [SMILES: COC(=O)c1cc(C(=O)O)nn1[C@@H](C)c1ccccc1]

Dimethyl (S)-1-(1-phenylethyl)-1H-pyrazole-3,5-dicarboxylate (15 g, 52.0 mmol) was dissolved in 1,4-dioxane (60 mL), then water (120 mL) was added followed by dropwise addition of $H_2SO_4$ (1.664 mL, 31.2 mmol). The mixture was heated at reflux for 3 days, then cooled to rt and extracted with EtOAc (2×100 mL). The combined organics were dried and evaporated in vacuo to give a colourless gum, which was dissolved in DCM and loaded onto a 340 g silica column, then eluted with 0-50% (1% AcOH/EtOAc)/cyclohexane and the product-containing fractions were evaporated in vacuo to give (S)-5-(methoxycarbonyl)-1-(1-phenylethyl)-1H-pyrazole-3-carboxylic acid (6.7 g, 24.43 mmol, 47% yield) as a colourless solid.

$^1$H NMR (400 MHz, CHLOROFORM-d) δ ppm 7.46 (s, 1H) 7.24-7.37 (m, 5H) 6.66 (q, J=7.1 Hz, 1H) 3.88 (s, 3H) 2.00 (d, J=7.1 Hz, 3H). 1 exchangeable proton not observed.

LCMS (2 min Formic): Rt=0.96 min, [MH]$^+$=275.3.

Intermediate 4: (S)-Methyl 3-(methylcarbamoyl)-1-(1-phenylethyl)-1H-pyrazole-5-carboxylate

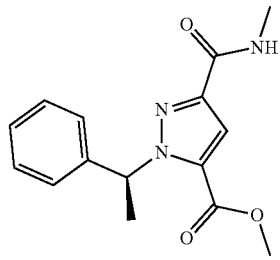 [SMILES: CNC(=O)c1cc(C(=O)OC)n([C@@H](C)c2ccccc2)n1]

(S)-5-(Methoxycarbonyl)-1-(1-phenylethyl)-1H-pyrazole-3-carboxylic acid (2 g, 7.29 mmol) was dissolved in DCM (20 mL) and Et$_3$N (1.525 mL, 10.94 mmol) and HATU (3.33 g, 8.75 mmol) were added, followed by methanamine (2M in THF) (3.65 mL, 7.29 mmol) and the mixture was stirred for 2 h at rt, then washed with water (20 mL) and 0.5M HCl (20 mL). The organic layer was dried and evaporated in vacuo and the residue purified by chromatography on a 50 g silica column to give methyl (S)-3-(methylcarbamoyl)-1-(1-phenylethyl)-1H-pyrazole-5-carboxylate (2.1 g, 7.31 mmol, 100% yield) as a colourless gum.

$^1$H NMR (400 MHz, CHLOROFORM-d) δ ppm 7.38 (s, 1H) 7.23-7.35 (m, 5H) 6.96 (d, J=3.7 Hz, 1H) 6.63 (q, J=7.1 Hz, 1H) 3.86 (s, 3H) 3.03 (s, 3H) 1.92 (d, J=7.1 Hz, 3H)

LCMS (2 min Formic): Rt=0.99 min, [MH]$^+$=288.2.

Intermediate 5: (S)-3-(Methylcarbamoyl)-1-(1-phenylethyl)-1H-pyrazole-5-carboxylic acid

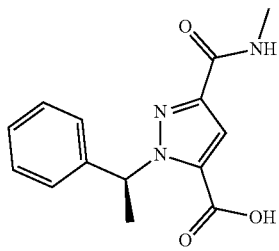 [SMILES: CNC(=O)c1cc(C(=O)O)n([C@@H](C)c2ccccc2)n1]

Methyl (S)-3-(methylcarbamoyl)-1-(1-phenylethyl)-1H-pyrazole-5-carboxylate (4.2 g, 14.62 mmol) was dissolved in a mixture of methanol (10 mL) and THF (10 mL), then NaOH (2M aqueous solution, 14.62 mL, 29.2 mmol) was added and the mixture was stirred for 3 h at rt. The solvent was evaporated in vacuo, the residue dissolved in water (30 mL) and washed with ether, then the aqueous layer acidified with 2M HCl to pH 4 and the resulting mixture stirred for 20 min while cooling in an ice bath. The resulting solid was collected by filtration to give (S)-3-(methylcarbamoyl)-1-(1-phenylethyl)-1/pyrazole-5-carboxylic acid (3.3 g, 12.07 mmol, 83% yield) as a colourless solid.

$^1$H NMR (400 MHz, DMSO-$d_6$) δ ppm 13.62 (br. s., 1H) 8.26 (d, J=4.6 Hz, 1H) 7.18-7.37 (m, 5H) 7.14 (s, 1H) 6.61 (q, J=6.8 Hz, 1H) 2.77 (d, J=4.6 Hz, 3H) 1.80-1.91 (m, 3H) LCMS (2 min Formic): Rt=0.86 min, [MH]$^+$=274.2.

Intermediate 6: Dimethyl 1-benzyl-1H-pyrazole-3,5-dicarboxylate

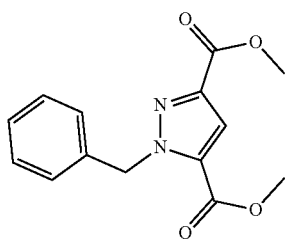 [SMILES: COC(=O)c1cc(C(=O)OC)n(Cc2ccccc2)n1]

To a solution of dimethyl 1H-pyrazole-3,5-dicarboxylate (10 g, 54.3 mmol) in acetone (100 mL) stirred under nitrogen at 0° C. was added $K_2CO_3$ (15.01 g, 109 mmol), followed by the addition of benzyl bromide (7.10 mL, 59.7 mmol) dropwise over 1 min. The reaction mixture was stirred at rt for 5 h. The reaction was filtered and the filtrate was concentrated under vaccum to afford the crude product. The crude product was triturated with n-pentane (3×10 mL), then dried under vaccum to afford pure dimethyl 1-benzyl-1H-pyrazole-3,5-dicarboxylate (8.5 g, 31.0 mmol, 57% yield) as a white solid.

LCMS (10 min Method D): Rt=4.87 min, [MH]$^+$=275.0.

Intermediate 7: 1-Benzyl-5-(methoxycarbonyl)-1H-pyrazole-3-carboxylic acid

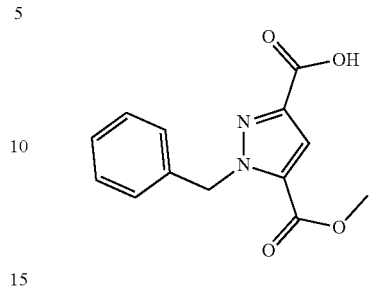

To a solution of dimethyl 1-benzyl-1H-pyrazole-3,5-dicarboxylate (30 g, 109 mmol) in 1,4-dioxane (140 mL) and water (280 mL) stirred under nitrogen at rt was added conc. $H_2SO_4$ (2.92 mL, 54.7 mmol, 18.4M) in one charge. The reaction mixture was stirred at reflux for 72 h. The reaction was then cooled to Rt and extracted with EtOAc (3×125 mL). The combined organic layer was washed with brine solution, dried over sodium sulphate, filtered and the filtrate was concentrated under vaccum to afford the crude product. The crude product was added to a silica gel 60-120 column and was eluted with 15% EtOAc in n-hexane and collected starting material fractions were concentrated under reduced pressure to get recovered starting material (15 g) as an off-white solid. The column was then eluted with 60% EtOAc in hexane and collected pure fractions were concentrated under vacuum to provide pure 1-benzyl-5-(methoxycarbonyl)-1H-pyrazole-3-carboxylic acid (6 g) as a white solid. Impure fractions were also isolated to give a further 10 g of crude mixture which was added to a silica gel 60-120 column and was eluted with 60% EtOAc in hexane to provide further pure fractions. These were concentrated under vacuum to get a second batch of pure required product (5.5 g) which was combined to give 1-benzyl-5-(methoxycarbonyl)-1H-pyrazole-3-carboxylic acid (11.5 g, 44.0 mmol, 40% yield) as an off-white solid. Then the column was flushed with EtOAc to give a further batch of impure product (3.4 g).

LCMS (10 min Method D): Rt=4.89 min, [MH]$^+$=261.0.

Intermediate 8: Methyl 1-benzyl-3-(methylcarbamoyl)-1H-pyrazole-5-carboxylate

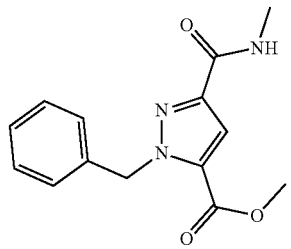 [SMILES: CNC(=O)c1cc(C(=O)OC)n(Cc2ccccc2)n1]

To a solution of 1-benzyl-5-(methoxycarbonyl)-1H-pyrazole-3-carboxylic acid (13.6 g, 50.7 mmol) and DIPEA (26.6 mL, 152 mmol) in DMF (100 mL) stirred under nitrogen at rt was added HATU (28.9 g, 76 mmol), followed by the addition of methanamine hydrochloride (4.11 g, 60.8 mmol) in one charge over 1 min. The reaction mixture was stirred at rt for 16 h. The reaction was poured into ice water, then extracted with EtOAc (3×100 mL). The combined organic layer was washed with water (3×50 mL), brine solution, then dried over sodium sulphate, filtered and the filtrate was concentrated under vacuum to afford the crude product. The crude product was added to a silica gel 60-120 column and was eluted with 65% EtOAc in n-hexane and the collected pure fractions were concentrated under reduced pressure to get methyl 1-benzyl-3-(methylcarbamoyl)-1H-pyrazole-5-carboxylate (12.1 g, 42.7 mmol, 84% yield) as an off-white solid.

LCMS (5.5 min Method E): Rt=2.32 min, [MH]$^+$=274.1.

Intermediate 9: 1-Benzyl-3-(methylcarbamoyl)-1H-pyrazole-5-carboxylic acid

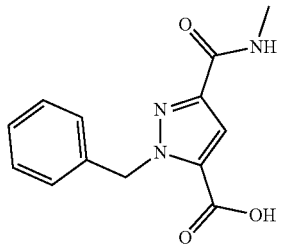 [SMILES: CNC(=O)c1cc(C(=O)O)n(Cc2ccccc2)n1]

To a solution of methyl 1-benzyl-3-(methylcarbamoyl)-1H-pyrazole-5-carboxylate (12.1 g, 42.7 mmol) in THF (70 mL) and water (70 mL) stirred under nitrogen at rt was added LiOH (5.11 g, 213 mmol) in one charge over 1 min. The reaction mixture was stirred at rt for 2 h. The reaction was then diluted with water (20 mL), then the aqueous layer was washed with EtOAc (3×15 mL). Then the aqueous layer pH was adjusted with 2NHCl to pH 1, then this was extracted with EtoAc (3×100 mL). The combined organic layer was washed with brine solution, dried over sodium sulphate, filtered and the filtrate was concentrated under vacuum to afford the crude product. The crude product was added to a silica gel 60-120 column and was eluted with 85% EtOAc in n-hexane and collected pure fractions were concentrated under reduced pressure to afford the desired product, 1-benzyl-3-(methylcarbamoyl)-1H-pyrazole-5-carboxylic acid (8.5 g, 32.8 mmol, 77% yield) as an off-white solid.

LCMS (10 min Method D): Rt=3.25 min, [MH]$^+$=260.1.

Intermediate 10: N$^3$-Cyclopropyl-N$^3$-methyl-1H-pyrazole-3,5-dicarboxamide

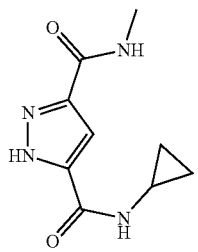

To a solution of 1-benzyl-N$^5$-cyclopropyl-N$^3$-methyl-1H-pyrazole-3,5-dicarboxamide (500 mg, 1.525 mmol, for a preparation, see example 92) in ethanol (1 mL) stirred under nitrogen at rt was added palladium hydroxide on carbon (100 mg, 0.712 mmol) in one charge. The reaction mixture was stirred at rt for 16 h. The reaction was filtered through the Celite bed, then washed with ethanol (25 mL) and the filtrate was concentrated under vacuum to afford the crude product. The crude product was triturated with diethyl ether (3×1 mL), to afford crystalline solid, filtered and the solid was dried under vacuum to get N$^5$-cyclopropyl-N$^3$-methyl-1H-pyrazole-3,5-dicarboxamide (250 mg, 1.045 mmol, 68.5% yield) as a white solid.

LCMS (5.5 min Method E): Rt=1.29 min, [MH]$^+$=209.3.

Intermediate 11: N$^5$-Cyclopropyl-N$^3$-methyl-1-(1-phenylethyl)-1H-pyrazole-3,5-dicarboxamide

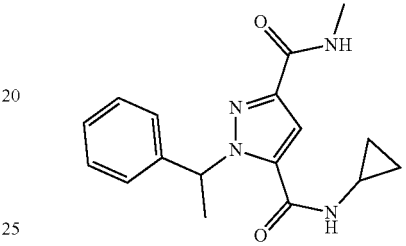

To a solution of N$^5$-cyclopropyl-N$^3$-methylpyrazole-3,5-dicarboxamide (250 mg, 1.045 mmol) in DMF (2 mL) stirred under nitrogen at rt was added K$_2$CO$_3$ (433 mg, 3.13 mmol) followed by the addition of (1-bromoethyl)benzene (232 mg, 1.253 mmol) in one charge. The reaction mixture was stirred at rt for 16 h. The reaction mass was poured into ice water, then extracted with EtOAc (3×20 mL). The combined organic layer was washed with water (3×15 mL), brine solution, dried over sodium sulphate, filtered and the filtrate was concentrated under vacuum to afford the crude product. This showed two regioisomers.

Regio-isomer 1
LCMS (10 min Method D): Rt=3.40 min, [MH]$^+$=313.1.
Regio-isomer 2
LCMS (10 min Method D): Rt=3.48 min, [MH]$^+$=313.1.

Intermediate 12: Methyl 1-tosyl-1H-indole-5-carboxylate

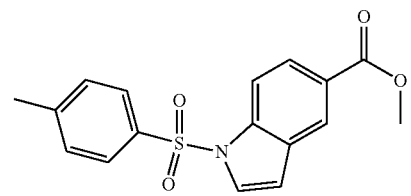

To a solution of methyl 1H-indole-5-carboxylate (2 g, 11.42 mmol) in DMF (15 mL) stirred under nitrogen at 0° C. was added NaH (0.548 g, 13.70 mmol, 60% dispersion in mineral oil) portion wise, then the reaction mixture was stirred for 10 min at the same temperature, then at rt for 30 min, after which was added pTsCl (2.61 g, 13.70 mmol) portionwise over 1 min. The reaction mixture was stirred at rt for 2 h. The reaction was poured into ice water, then extracted with EtOAc (3×25 mL). The combined organic layer was washed with cold water (3×15 mL), brine solution, dried over sodium sulphate, filtered and the filtrate was concentrated under vacuum to afford the crude product. The crude product was added to a silica gel 60-120 column and was eluted with 15% EtOAc in n-hexane and the collected pure fractions were concentrated under reduced pressure to afford methyl 1-tosyl-1H-indole-5-carboxylate (1.9 g, 5.59 mmol, 49.0% yield) as an off-white solid.

LCMS (5.5 min Method E): Rt=3.27 min, [MH]$^+$=330.0.

Intermediate 13: (1-Tosyl-1H-indol-5-yl)methanol

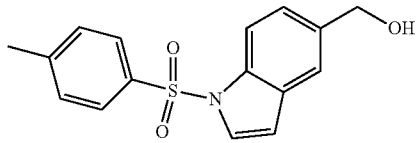 [SMILES: Cc1ccc(S(=O)(=O)n2ccc3cc(CO)ccc32)cc1]

To a solution of methyl 1-tosyl-1H-indole-5-carboxylate (1.9 g, 5.59 mmol) in DCM (20 mL) stirred under nitrogen at rt was added a solution of DIBAL-H (25.2 mL, 25.2 mmol, 1M solution in Toluene) dropwise over 1 min. The reaction mixture was stirred at −78° C. for 2.5 h. The reaction was then quenched with methanol (0.226 mL, 5.59 mmol) at −78° C. and then allowed to warm up to ambient temperature. The reaction mass was diluted with saturated Rochelle's salt solution (120 mL) and stirred for 16 h, then the layers were separated, and the aqueous phase was extracted with DCM (2×100 mL). The combined organic layer was washed with brine solution, dried over sodium sulphate, filtered and the filtrate was concentrated under vaccum to afford the crude product. The crude product was triturated with n-pentane (3×2 mL) then dried under vaccum to afford (1-tosyl-1H-indol-5-yl)methanol (1.70 g, 5.41 mmol, 97% yield) as an off-white solid.

LCMS (5.5 min Method E): Rt=2.72 min, [MH]$^+$=300.0.

Intermediate 14: 5-(Bromomethyl)-1-tosyl-1H-indole

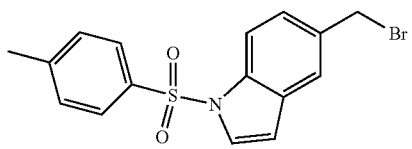 [SMILES: Cc1ccc(S(=O)(=O)n2ccc3cc(CBr)ccc32)cc1]

To a solution of (1-tosyl-1H-indol-5-yl)methanol (1.70 g, 5.41 mmol) in DCM (20 mL) stirred under nitrogen at rt was added a solution of HBr (0.294 mL, 5.41 mmol) dropwise during 1 min. The reaction mixture was stirred at rt for 4 h. The reaction was poured into ice water, then stirred for 10 min at rt, then filtered and the solid product was dried under vacuum to give 5-(bromomethyl)-1-tosyl-1H-indole (1.48 g, 3.49 mmol, 65% yield) as an off-white solid.

LCMS (5.5 min Method E): Rt=3.47 min, [MH]$^+$=365.9.

Intermediate 15: N$^5$-Cyclopropyl-N$^3$-methyl-1-((1-tosyl-1H-indol-5-yl)methyl)-1H-pyrazole-3,5-dicarboxamide

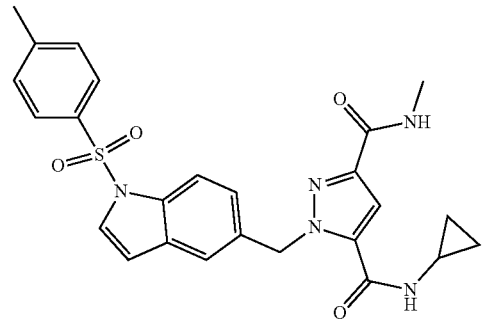 [SMILES: CNC(=O)c1cc(C(=O)NC2CC2)n(Cc2ccc3c(ccn3S(=O)(=O)c3ccc(C)cc3)c2)n1]

To a solution of N$^5$-cyclopropyl-N$^3$-methylpyrazole-3,5-dicarboxamide (300 mg, 1.366 mmol) in DMF (2 mL) stirred under nitrogen at rt was added K$_2$CO$_3$ (566 mg, 4.10 mmol), followed by the addition of 5-(bromomethyl)-1-tosyl-1H-indole (703 mg, 1.640 mmol) dropwise over 1 min. The reaction mixture was stirred at rt for 1 h. The reaction was poured into ice water, then extracted with EtOAc (3×15 mL). The combined organic layer was washed with brine solution, dried over sodium sulphate, filtered and the filtrate was concentrated under vacuum to give the crude product (420 mg) as a mixture of regioisomers which were used in the next step without purification.

LCMS (5.5 min Method E): Rt=2.82 min, [MH]$^+$=492.0. Regioisomer 1

LCMS (5.5 min Method E): Rt=2.85 min, [MH]$^+$=492.0. Regioisomer 2

Intermediate 16: N$^5$-Cyclopropyl-N$^3$-methyl-1-((1-tosyl-1H-indol-4-yl)methyl)-1H-pyrazole-3,5-dicarboxamide

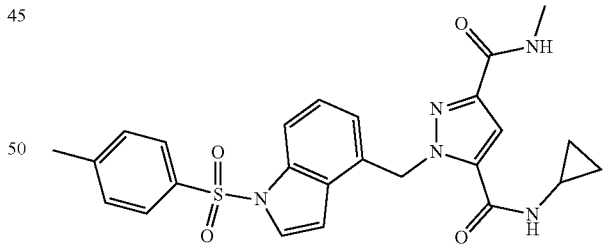

To a solution of N$^5$-cyclopropyl-N$^3$-methyl-1H-pyrazole-3,5-dicarboxamide (300 mg, 1.366 mmol) in acetone (1 mL) stirred under nitrogen at rt was added K$_2$CO$_3$ (566 mg, 4.10 mmol) followed by the addition of 4-(bromomethyl)-1-tosyl-1H-indole (597 mg, 1.640 mmol) in one charge. The reaction mixture was stirred at rt for 16 h. The reaction was poured into ice water, then extracted with EtOAc (3×25 mL). The combined organic layers were washed with water (3×15 mL), brine solution, dried over sodium sulpate, filtered and the filtrate was concentrated under vaccum to give the crude product as a mixture of regioisomers (550 mg) which were used in the next step without purification.

LCMS (10 min Method D): Rt=4.39 min, [MH]⁺=492.1. Regioisomer 1

LCMS (10 min Method D): Rt=4.44 min, [MH]⁺=492.1. Regioisomer 2

Intermediate 17: N³,N⁵-Dimethyl-1H-pyrazole-3,5-dicarboxamide

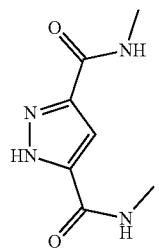

1H-Pyrazole-3,5-dicarboxylic acid (200 mg, 1.281 mmol), methanamine (2M in THF, 0.705 mL, 1.409 mmol) and HATU (536 mg, 1.409 mmol) were combined in DMF (2 mL). DIPEA (0.448 mL, 2.56 mmol) was added and reaction mixture stirred at rt. under N₂ for 2 h. The reaction mixture was concentrated to dryness and used crude for the next step.

LCMS (2 min Formic): Rt=0.37 min, [MH]⁺=183.1.

Intermediate 18: 4-Bromo-1-tosyl-1H-pyrrolo[2,3-c]pyridine

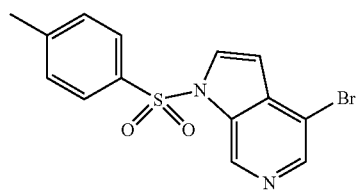 [SMILES: Cc1ccc(S(=O)(=O)n2ccc3c(Br)cncc32)cc1]

4-Bromo-1H-pyrrolo[2,3-c]pyridine (5 g, 25.4 mmol, commercially available from, for example, Fluorochem) was dissolved in DMF (50 mL) and cooled in an ice bath under nitrogen, then NaH (a 60% suspension in mineral oil, 1.319 g, 33.0 mmol) was added in small portions and the mixture was stirred for 20 min before addition of tosyl chloride (5.32 g, 27.9 mmol). The mixture was stirred overnight, allowing it to warm to rt, then the mixture was diluted with water (100 mL) and stirred for 30 min, giving a white suspension. This was filtered and the solid washed with water, then dried to give a colourless solid. The crude product was suspended in ether (20 mL) and stirred for 5 min, then diluted with cyclohexane (20 mL) and filtered to give the desired product (7.9 g, 22.49 mmol, 89% yield) as a colourless solid.

LCMS (2 min High pH): Rt=1.24 min, [MH]⁺=351/353

Intermediate 19: Methyl 1-tosyl-1H-pyrrolo[2,3-c]pyridine-4-carboxylate

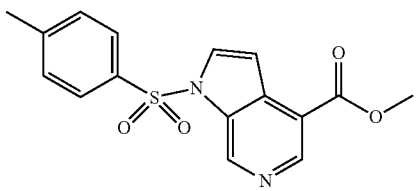

4-Bromo-1-tosyl-1H-pyrrolo[2,3-c]pyridine (7.8 g, 22.21 mmol) palladium(II) acetate (0.499 g, 2.221 mmol) and xantphos (1.285 g, 2.221 mmol) were combined in a round-bottomed flask, which was sealed with a suba seal and purged with nitrogen. DMF (20 mL), Et₃N (9.29 mL, 66.6 mmol) and methanol (17.97 mL, 444 mmol) were added, the vessel was purged with carbon monoxide from a balloon, then heated under a CO atmosphere overnight. The mixture was diluted with water (20 mL) and extracted with EtOAc (20 mL), the organic layer washed with 10% aq LiCl solution, dried and evaporated in vacuo and the residue purified by chromatography on a 50 g silica column eluting with 0-100% EtOAc/cyclohexane to give the desired product (4.4 g, 13.32 mmol, 60% yield)

LCMS (2 min High pH): Rt=1.12 min, [MH]⁺=331.1

Intermediate 20: (1-Tosyl-1H-pyrrolo[2,3-c]pyridin-4-yl)methanol

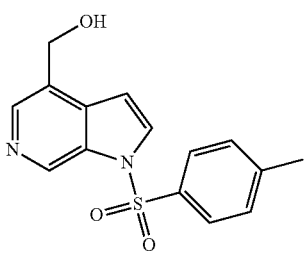 [SMILES: Cc1ccc(S(=O)(=O)n2ccc3c(CO)cncc32)cc1]

Methyl 1-tosyl-1H-pyrrolo[2,3-c]pyridine-4-carboxylate (510 mg, 1.544 mmol) was taken up in DCM (15 mL) under nitrogen and cooled to −78° C. DIBAL-H (1M in THF, 15.44 mL, 15.44 mmol) was added to the reaction dropwise and it was left to stir at −78° C. for 3 h. The reaction was quenched with methanol (15 mL added dropwise) at −78° C. and then allowed to warm to rt. Rochelle's salt (saturated in 25 mL of water) was added and the mixture was stirred for 45 min. The mixture was separated, and the organic layer was washed with brine (50 mL), filtered through a hydrophobic frit and concentrated in vacuo to yield a yellow solid. This solid was taken up in DCM (15 mL), put under nitrogen and cooled to −78° C. DIBAL-H (1M in THF, 15.44 mL, 15.44 mmol) was added dropwise, and then the reaction was allowed to warm up to −40° C. It was left to stir at this temperature for 5 h. The reaction was quenched with methanol (15 mL added dropwise) at −40° C. and then allowed to warm to rt. Rochelle's salt (saturated in 30 mL of water) was added and the mixture was stirred for 45 min. The mixture was separated, and the organic layer was washed with brine (2×25 mL), filtered through a hydrophobic frit and concentrated in vacuo to yield a yellow oil (486 mg). The crude product was purified by silica gel column chromatography, eluting with 5-50% (3:1 EtOAc:EtOH) in cyclohexane. The appropriate fractions were combined and concentrated in vacuo to yield the desired product (148 mg, 0.416 mmol, 27% yield) as a white solid LCMS (2 min Formic): Rt=0.57 min, [MH]$^+$=303.1

Intermediate 21: 1-(1-Tosyl-1H-pyrrolo[2,3-b]pyridin-4-yl)ethanone

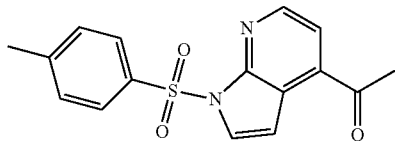 [SMILES: CC(=O)c1ccnc2c1ccn2S(=O)(=O)c1ccc(C)cc1]

1-(1H-Pyrrolo[2,3-b]pyridin-4-yl)-ethan-1-one (500 mg, 3.12 mmol, commercially available from, for example, Activate Scientific) was dissolved in DMF (5 mL) and cooled to 0° C. in an ice-bath under a nitrogen atmosphere. Sodium hydride (60% in mineral oil, 150 mg, 3.75 mmol) was added portionwise, and the reaction mixture was stirred at 0° C. for 30 min before warming to rt for 30 min. Tosyl chloride (714 mg, 3.75 mmol) was added giving an orange suspension (exothermic addition) and the reaction mixture stirred at rt for 15 min. The reaction mixture was cooled to 0° C. in an ice-bath and quenched with the dropwise addition of water (3 mL). This was then partitioned between ethyl acetate (20 mL) and sat. aq. LiCl solution (20 mL). The organic layer was separated and the aq. layer further extracted with ethyl acetate. The combined organic layers were dried (Na$_2$SO$_4$) and conc. to give ~1.5 g crude brown residue. This was purified by silica gel column chromatography eluting with 5-50% ethyl acetate/cyclohexane to give the desired product (438 mg, 1.254 mmol, 40% yield) as a pale yellow solid.

LCMS (2 min Formic): Rt=1.12 min, [MH]$^+$=315

Intermediate 22: 1-(1-Tosyl-1H-pyrrolo[2,3-b]pyridin-4-yl)-ethanol

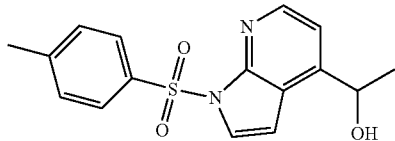 [SMILES: Cc1ccc(S(=O)(=O)n2ccc3c(C(C)O)ccnc32)cc1]

To a suspension of 1-(1-tosyl-1H-pyrrolo[2,3-b]pyridin-4-yl)-ethan-1-one (438 mg, 1.393 mmol) in ethanol (10 mL) was added THF (4 mL) to solubilise the reaction mixture, followed by sodium borohydride (58.0 mg, 1.533 mmol) in an ice-bath. The reaction mixture was stirred under a nitrogen atmosphere at rt for 1 h. 1M HCl solution (20 mL) was added and the aqueous layer extracted with DCM. The combined organic layers were dried (hydrophobic frit) and concentrated to give the desired product (493 mg, 1.325 mmol, 95% yield) as a pale yellow oil.

LCMS (2 min Formic): Rt=0.98 min, [MH]$^+$=317

Intermediate 23: Methyl 1-tosyl-1H-indole-5-carboxylate

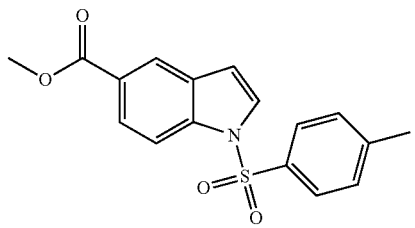

Methyl 1H-indole-5-carboxylate (4.31 g, 24.60 mmol, commercially available from, for example, Sigma Aldrich) was taken up in DMF (50 mL) and cooled to 0° C. NaH (60% suspension in mineral oil, 1.181 g, 29.5 mmol) was added in small portions, and the reaction was left to stir for 1 h. Tosyl chloride (5.63 g, 29.5 mmol) was added, and the reaction was allowed to warm to rt and stirred overnight. Additional NaH (0.480 g, 60% suspension in mineral oil) was added, and the reaction left to stir at rt for 1 h. The reaction was quenched with water (25 mL). Water (175 mL) was added, and the reaction was extracted with ethyl acetate (2×250 mL). The combined organics were washed with brine (200 mL), dried with Na$_2$SO$_4$, filtered and concentrated in vacuo to yield a brown solid. 1:1 MeOH:DCM (50 mL) was added to the crude product, and free flow silica added (5 g). The solvent was removed in vacuo and the silica loaded onto a 100 g silica gel column cartridge and eluted with 5-25% ethyl acetate in cyclohexane. The fractions were combined and concentrated in vacuo. The crude product was applied to a 340 g silica gel column cartridge in the minimum of DCM and eluted with 0-25% ethyl acetate in cyclohexane. The appropriate fractions were combined and concentrated in vacuo to yield the desired product (6.463 g, 18.64 mmol, 76% yield) as a white solid.

LCMS (2 min Formic): Rt=1.27 min, [MH]$^+$=330.4

Intermediate 24: 1-(1-Tosyl-1H-indol-5-yl)ethanone

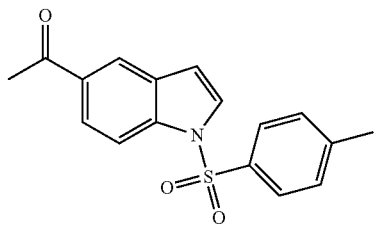 [SMILES: CC(=O)c1ccc2c(ccn2S(=O)(=O)c2ccc(C)cc2)c1]

1-(1H-Indol-5-yl)-ethan-1-one (1 g, 6.28 mmol, commercially available from, for example, Fluorochem) was taken up in DMF (10 mL) and cooled to 0° C. NaH (0.302 g, 7.54 mmol, 60% dispersion in mineral oil) was added in small portions and allowed to stir for 15 min. tosyl-Cl (1.437 g, 7.54 mmol) was added, and the reaction was allowed to warm to rt and left to stir for 1.5 h. Additional NaH (63 mg, 0.25 eq., 60% dispersion in mineral oil) was added, and the reaction was left to stir for 30 min. The reaction was quenched with water (40 mL). The reaction mixture was extracted with ethyl acetate (2×50 mL) and the combined organics were washed with brine (75 mL), dried with Na$_2$SO$_4$, filtered and concentrated in vacuo to yield a brown solid. The crude product was applied to a 100 g ULTRA SNAP cartridge in the minimum of DCM and eluted with 0-5% ethyl acetate in DCM. The appropriate fractions were combined and concentrated in vacuo to yield 1-(1-tosyl-1H-indol-5-yl)-ethan-1-one (1.408 g, 4.27 mmol, 68% yield) as a cream solid.

LCMS (2 min High pH): Rt=1.20 min, [MH]$^+$=314.3.

Intermediate 25: 1-(1-Tosyl-1H-indol-5-yl)-ethanol

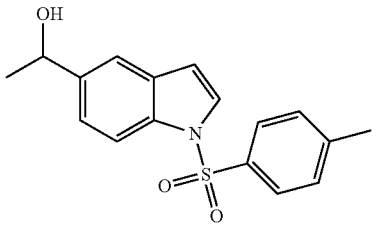 [SMILES: Cc1ccc(S(=O)(=O)n2ccc3cc(C(C)O)ccc32)cc1]

1-(1-Tosyl-1H-indol-5-yl)-ethan-1-one (1.394 g, 4.45 mmol) was taken up in THF (40 mL), cooled to 0° C. in an ice bath, and put under nitrogen. sodium borohydride (0.337 g, 8.90 mmol) was added, and the reaction left to stir at rt overnight. Additional sodium borohydride (0.169 g) was added, and the reaction left to stir for 2.5 h. The reaction was cooled to 0° C. and slowly quenched with 1N HCl (20 mL). It was then extracted with DCM (2×25 mL), and the combined organics were filtered through a hydrophobic frit and concentrated in vacuo to yield 1-(1-tosyl-1H-indol-5-yl)-ethan-1-ol (1.398 g, 4.21 mmol, 95% yield) as a colourless gum.

LCMS (2 min High pH): Rt=1.11 min, [M−H]$^−$=314.3.

Intermediate 26: (1-Tosyl-1H-indol-5-yl)methanol

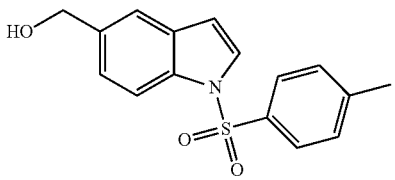 [SMILES: Cc1ccc(S(=O)(=O)n2ccc3cc(CO)ccc32)cc1]

Methyl 1-tosyl-1H-indole-5-carboxylate (1.027 g, 3.12 mmol) was taken up in THF (25 mL) under nitrogen, and cooled to −78° C. DIBAL-H (1M in THF, 8 mL, 8.00 mmol) was added dropwise over 10 min and the reaction was left to stir at −78° C. for 4 h. The reaction was allowed to warm to rt and was left to stir overnight. The reaction was cooled to −78° C. and DIBAL-H (1M in THF, 6.5 mL, 6.50 mmol) was added dropwise over 10 min. The reaction was then allowed to warm to rt and was left to stir for 1.5 h. The reaction was cooled to 0° C. and quenched with MeOH (10 mL added dropwise). Saturated Rochelle's salts (50 mL) was added, and the reaction allowed to warm to rt. Water (50 mL) and DCM (50 mL) were added to the reaction mixture, and the layers were separated. The organic layer was washed with brine (50 mL), eluted through a hydrophobic frit and concentrated in vacuo to yield a colourless oil. The crude product was applied to a silica gel column in the minimum of DCM and eluted with 5-50% ethyl acetate in cyclohexane. The appropriate fractions were combined and concentrated in vacuo to yield the desired product (876 mg, 2.76 mmol, 89% yield) as a colourless gum.

LCMS (2 min Formic): Rt=0.98 min, [MH]$^+$=317

Intermediate 27: 1-(1-Tosyl-1H-indol-4-yl)ethanone

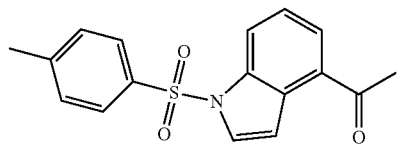 [SMILES: CC(=O)c1cccc2c1ccn2S(=O)(=O)c1ccc(C)cc1]

1-(1H-Indol-4-yl)-ethan-1-one (500 mg, 3.14 mmol, commercially available from, for example, Activate Scientific) was dissolved in DMF (5 mL) and cooled to 0° C. in an ice-bath under a nitrogen atmosphere. Sodium hydride (151 mg, 3.77 mmol, 60% dispersion in mineral oil) was added portionwise, and the reaction mixture was stirred at 0° C. for 30 min before warming to rt for 30 min. Tosyl chloride (719 mg, 3.77 mmol) was added giving an orange suspension (exothermic addition) and reaction mixture stirred at rt for 15 min. The reaction mixture was cooled to 0° C. in an ice-bath and quenched by the dropwise addition of water (3 mL). This was then partitioned between ethyl acetate (20 mL) and sat. aq. LiCl solution (20 mL). The organic layer was separated and aq. layer further extracted with ethyl acetate. The combined organic layers were dried (Na$_2$SO$_4$) and conc. to give 1.11 g of crude brown residue. This was purified by chromatography on silica gel, eluting with 5-30% ethyl acetate/cyclohexane to give the desired product (809 mg, 2.323 mmol, 74% yield) as a white solid.

LCMS (2 min Formic): Rt=1.24 min, [MH]$^+$=314

Intermediate 28: 1-(1-Tosyl-1H-indol-4-1)ethanol

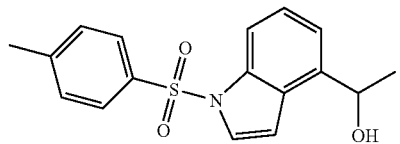 [SMILES: Cc1ccc(S(=O)(=O)n2ccc3c(C(C)O)cccc32)cc1]

To a suspension of 1-(1-tosyl-1H-indol-4-yl)-ethan-1-one (803 mg, 2.56 mmol) in ethanol (20 mL) was added sodium borohydride (107 mg, 2.82 mmol) in an ice-bath. The reaction mixture was stirred under a nitrogen atmosphere at rt for 1.5 h. THF (17 mL) was added to solubilise the reaction mixture which was stirred at rt for a further 2 h. A further portion of sodium borohydride (107 mg, 2.82 mmol) was added and reaction mixture stirred at rt overnight. 1M HCl solution (20 mL) was added and the aqueous layer extracted with DCM. The combined organic layers were dried (hydrophobic frit) and concentrated to give the desired product (797 mg, 2.274 mmol, 89% yield) as a pink solid.

LCMS (2 min Formic): Rt=1.12 min, [MH]$^−$=314.2

Intermediate 29: Methyl 1-tosyl-1H-indole-4-carboxylate

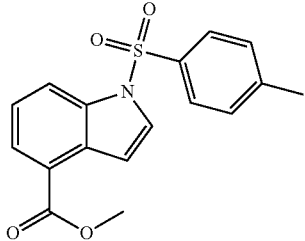 [SMILES: COC(=O)c1cccc2c1ccn2S(=O)(=O)c1ccc(C)cc1]

Methyl 1H-indole-4-carboxylate (5 g, 28.5 mmol, commercially available from, for example, Alfa Aesar) was taken up in DMF (50 mL) and cooled in an ice-bath. NaH (60% suspension in mineral oil, 1.370 g, 34.2 mmol) was added portionwise and the reaction left to stir for 30 min. Tosyl chloride (6.53 g, 34.2 mmol) was added and the reaction left to stir and warm up overnight. The reaction was cooled in an ice-bath and carefully quenched with water (200 mL). The mixture was extracted with EtOAc (2×250 mL). The combined organics were washed with brine (200 mL) and eluted through a hydrophobic frit then concentrated in vacuo to give a brown solid. The crude product was applied to a 100 g silica gel cartridge in the minimum of DCM and eluted with 5-25% ethyl acetate in cyclohexane. The appropriate fractions were concentrated in vacuo to give the desired product (6.554 g, 18.90 mmol, 66% yield) as a white solid.

LCMS (2 min High pH): Rt=1.32 min, [MH]$^+$=330.2

Intermediate 30: (1-Tosyl-1H-indo-4-yl)methanol

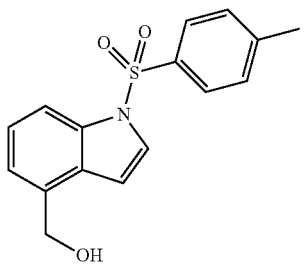 [SMILES: Cc1ccc(S(=O)(=O)n2ccc3c(CO)cccc32)cc1]

Methyl 1-tosyl-1H-indole-4-carboxylate (6.248 g, 18.97 mmol) was taken up in DCM (200 mL) under nitrogen and cooled to −78° C. DIBAL-H (1M, 83 mL, 83 mmol) was added slowly over ~30 min and the reaction left to stir at −78° C. for 90 min before being left to stir and warm to rt over the weekend. The reaction was cooled in an ice-bath and slowly quenched with MeOH (2 mL in 0.1 mL aliquots). Saturated Rochelle's salt solution (200 mL) was added and the mixture stirred and allowed to warm to rt for 3 h. The layers were separated and the organic layer eluted through a hydrophobic frit then concentrated in vacuo to give a yellow oil. The crude product was applied to a 100 g silica gel cartridge in the minimum of DCM and eluted with 5-50% ethyl acetate in cyclohexane. The appropriate fractions were concentrated in vacuo to give the desired product (5.172 g, 16.30 mmol, 86% yield) as a white solid.

LCMS (2 min High pH): Rt=1.07 min, [MH]$^+$=301.2

Intermediate 31: Ethyl 1-tosyl-1H-pyrrolo[2,3-b]pyridine-4-carboxylate

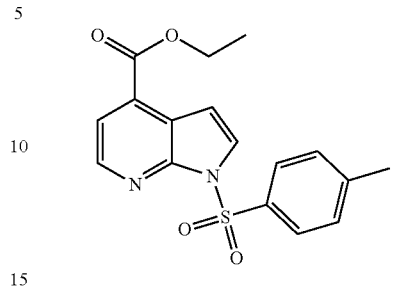

Ethyl 1H-pyrrolo[2,3-b]pyridine-4-carboxylate (1.00 g, 5.26 mmol, commercially available from, for example, Alfa Aesar) was taken up in DMF (10 mL) and cooled in an ice bath. NaH (60% suspension in mineral oil, 0.252 g, 6.31 mmol) was added, and the reaction left to stir for 15 min. Tosyl chloride (1.203 g, 6.31 mmol) was added and the reaction was left to warm up to rt, and stirred for 1 h. The reaction was cooled in an ice bath, and quenched with water (5 mL). The reaction was concentrated in vacuo, brine (50 mL) was added to the residue and it was extracted with ethyl acetate (2×50 mL). This organic layer was dried with Na$_2$SO$_4$, filtered and concentrated in vacuo to yield a brown solid. The crude product was applied to a 50 g silica gel cartridge in the minimum of DCM and eluted with 5-25% (3:1 EtOAc:EtOH) in cyclohexane. The appropriate fractions were combined and concentrated in vacuo to yield a cream solid. This crude product was taken up in 1:2 MeOH:DCM (15 mL) and free flow silica added (10 g). The solvent was removed in vacuo and the silica loaded onto a 100 g ULTRA SNAP cartridge and eluted with 5-25% (3:1 EtOAc:EtOH) in cyclohexane. The appropriate fractions were concentrated in vacuo to yield the desired product (1.084 g, 2.52 mmol, 48% yield) as a cream solid.

LCMS (2 min Formic): Rt=1.27 min, [MH]$^+$=345.1

Intermediate 32: (1-Tosyl-1H-pyrrolo[2,3-b]pyridin-4-yl)methanol

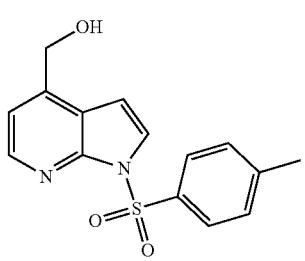 [SMILES: Cc1ccc(S(=O)(=O)n2ccc3c(CO)ccnc32)cc1]

Ethyl 1-tosyl-1H-pyrrolo[2,3-b]pyridine-4-carboxylate (936 mg, 2.72 mmol) was taken up in DCM (25 mL) under nitrogen and cooled to −78° C. DIBAL-H (1M in THF, 27.2 mL, 27.2 mmol) was added to the reaction dropwise and the reaction was left to stir at −78° C. overnight. The reaction was quenched with MeOH (1 mL added in small portions), and then allowed to warm to rt. Rochelle's salt (saturated in 50 mL of water) was added and the mixture was stirred for 15 min. The layers were separated and the organic layer was washed with brine (2×25 mL), dried with Na$_2$SO$_4$, filtered and concentrated in vacuo to yield an orange solid. The aqueous layers were extracted with 10% MeOH in DCM (50 mL). The two resulting organic layers were combined, dried with Na₂SO₄, filtered and concentrated in vacuo to yield an orange oil. The crude products were combined and applied to a 25 g silica gel cartridge in the minimum of DCM and eluted with 5-40% (3:1 EtOAc:EtOH) in cyclohexane. The appropriate fractions were concentrated in vacuo to yield the desired product as a white solid (659 mg, 2.07 mmol, 76% yield).

LCMS (2 min Formic): Rt=0.92 min, [MH]⁺=303.1

Intermediate 33: (S)-Methyl 1-(1-(4-chlorophenyl)ethyl)-3-(methylcarbamoyl)-1H-pyrazole-5-carboxylate

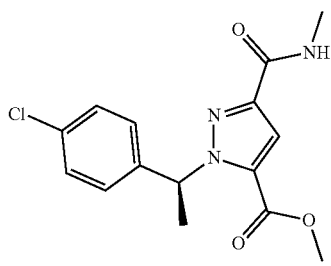 [SMILES: CNC(=O)c1cc(C(=O)OC)n([C@@H](C)c2ccc(Cl)cc2)n1]

Methyl 3-(methylcarbamoyl)-1H-pyrazole-5-carboxylate (0.5 g, 2.73 mmol) was taken up in THF (20 mL) and acetonitrile (5 mL). (R)-1-(4-Chlorophenyl)ethan-1-ol (0.4 mL, 2.96 mmol, commercially available from, for example, Sigma Aldrich) and Ph₃P (1.078 g, 4.11 mmol) were added, and the reaction was put under nitrogen and cooled to 0° C. DIAD (0.8 mL, 4.11 mmol) was added dropwise and the reaction was allowed to warm to rt and left to stir for 90 min. EtOAc (25 mL) was added to the reaction mixture, followed by water (50 mL). The layers were separated and the organic layer washed with brine (50 mL), dried with Na₂SO₄, filtered and concentrated in vacuo to yield a yellow oil. The crude product was applied to a 100 g ULTRA SNAP cartridge in the minimum of DCM and eluted with 5-50% ethyl acetate in cyclohexane. The desired fractions were combined and concentrated in vacuo to yield methyl (S)-1-(1-(4-chlorophenyl)ethyl)-3-(methylcarbamoyl)-1H-pyrazole-5-carboxylate (415 mg, 1.225 mmol, 45% yield) as a colourless gum.

LCMS (2 min Formic): Rt=1.08 min, [MH]⁺=322.4.

The following intermediates were prepared in a similar manner to Intermediate 33.

| Intermediate | | LCMS: (System, t_RET, MH⁺) |
|---|---|---|
| 34 | ![structure] (S)-Methyl 3-(methylcarbamoyl)-1-(1-(m-tolyl)ethyl)-1H-pyrazole-5-carboxylate | Formic, 1.04 min, 302.3 |
| 35 | ![structure] (S)-Methyl 3-(methylcarbamoyl)-1-(1-phenylpropyl)-1H-pyrazole-5-carboxylate | Formic, 1.07 min, 302.2 |

| Intermediate | | LCMS: (System, $t_{RET}$, MH$^+$) |
|---|---|---|
| 36 | (S)-Methyl 1-(1-(4-fluorophenyl)ethyl)-3-(methylcarbamoyl)-1H-pyrazole-5-carboxylate | Formic, 1.00 min, 306.1 |
| 37 | (S)-Methyl 1-(1-(3-fluorophenyl)ethyl)-3-(methylcarbamoyl)-1H-pyrazole-5-carboxylate | Formic, 0.99 min, 306.4 |
| 38 | (S)-Methyl 1-(1-(2-fluorophenyl)ethyl)-3-(methylcarbamoyl)-1H-pyrazole-5-carboxylate | Formic, 0.99 min, 306.4 |
| 39 | Methyl 3-(methylcarbamoyl)-1-((1-tosyl-1H-indol-4-yl)methyl)-1H-pyrazole-5-carboxylate | Formic, 1.18 min, 467.3 |

| Intermediate | | LCMS: (System, $t_{RET}$, MH+) |
|---|---|---|
| 40 | 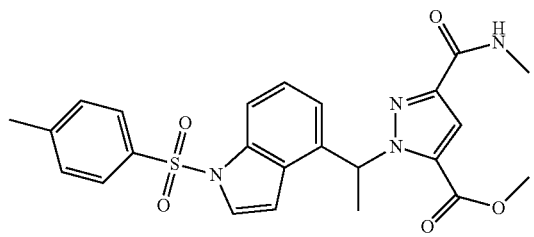 Methyl 3-(methylcarbamoyl)-1-(1-(1-tosyl-1H-indol-4-yl)ethyl)-1H-pyrazole-5-carboxylate | Formic, 1.22 min, MH− 479 |
| 41 | 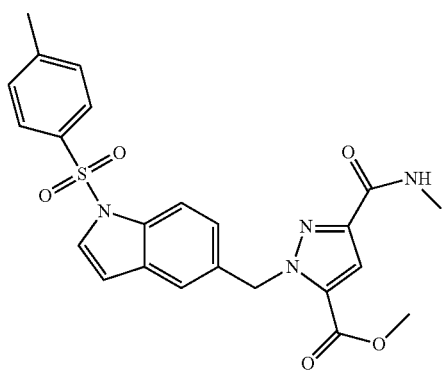 [SMILES: CNC(=O)c1cc(C(=O)OC)n(Cc2ccc3c(ccn3S(=O)(=O)c3ccc(C)cc3)c2)n1] Methyl 3-(methylcarbamoyl)-1-((1-tosyl-1H-indol-5-yl)methyl)-1H-pyrazole-5-carboxylate | Formic, 1.16 min, 467.5 |
| 42 | 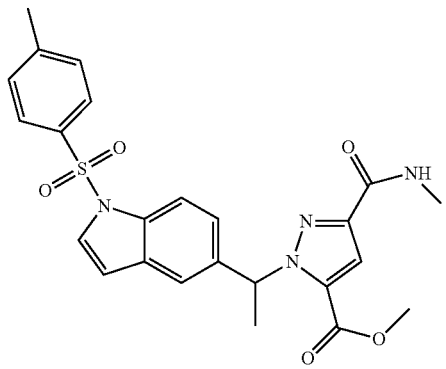 [SMILES: CNC(=O)c1cc(C(=O)OC)n(C(C)c2ccc3c(ccn3S(=O)(=O)c3ccc(C)cc3)c2)n1] Methyl 3-(methylcarbamoyl)-1-(1-(1-tosyl-1H-indol-5-yl)ethyl)-1H-pyrazole-5-carboxylate | Formic, 1.23 min, [M − H]− at 479.5 |

Intermediate 43: (S)-Methyl 1-(1-(3-chlorophenyl)ethyl)-3-(methylcarbamoyl)-1H-pyrazole-5-carboxylate

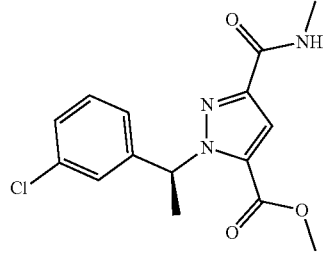 [SMILES: CNC(=O)c1cc(C(=O)OC)n([C@@H](C)c2cccc(Cl)c2)n1]

Methyl 3-(methylcarbamoyl)-1H-pyrazole-5-carboxylate (0.5 g, 2.73 mmol), (R)-1-(3-chlorophenyl)ethan-1-ol (0.513 g, 3.28 mmol), cyanomethylenetributylphosphorane (CMBP) (1.432 mL, 5.46 mmol, commercially available from, for example, TCI) and toluene (10 mL) were added to the reaction vessel. The reaction vessel was sealed and heated in a Biotage Initiator microwave to 150° C. for 30 min. After cooling the reaction, it was concentrated in vacuo to yield a brown oil. The crude product was applied to a 100 g ULTRA SNAP cartridge in the minimum of DCM and eluted with 5-60% ethyl acetate in cyclohexane. The appropriate fractions were combined and concentrated in vacuo to yield methyl (S)-1-(1-(3-chlorophenyl)ethyl)-3-(methylcarbamoyl)-1H-pyrazole-5-carboxylate (462 mg, 1.364 mmol, 50% yield) as an orange solid.

LCMS (2 min Formic): Rt=1.09 min, [MH]$^+$=322.2.

The following intermediates were prepared in a similar manner to Intermediate 43.

| Intermediate | | LCMS: (System, $t_{RET}$, MH$^+$) |
|---|---|---|
| 44 | Methyl 3-(methylcarbamoyl)-1-((1-tosyl-1H-pyrrolo[2,3-c]pyridin-4-yl)methyl)-1H-pyrazole-5-carboxylate | Formic, 0.83 min, 468.3 |
| 45 | Methyl 3-(methylcarbamoyl)-1-(1-(1-tosyl-1H-pyrrolo[2,3-b]pyridin-4-yl)ethyl)-1H-pyrazole-5-carboxylate | Formic, 1.11 min, 482.3 |
| 46 | Methyl 3-(methylcarbamoyl)-1-((1-tosyl-1H-pyrrolo[2,3-b]pyridin-4-yl)methyl)-1H-pyrazole-5-carboxylate | Formic, 1.06 min, 468.2 |

| Intermediate | | LCMS: (System, $t_{RET}$, MH+) |
|---|---|---|
| 47 | 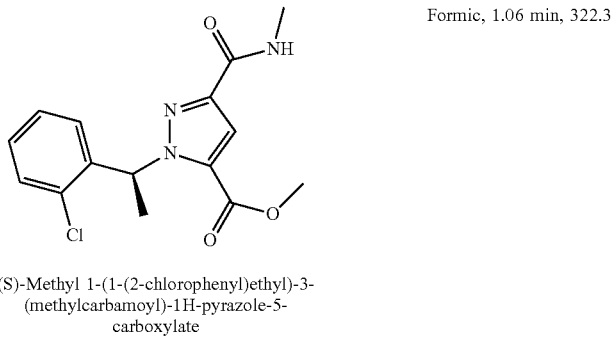 (S)-Methyl 1-(1-(2-chlorophenyl)ethyl)-3-(methylcarbamoyl)-1H-pyrazole-5-carboxylate | Formic, 1.06 min, 322.3 |
| 48 | 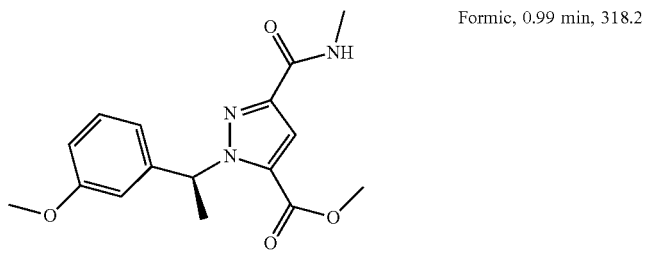 (S)-Methyl 1-(1-(3-methoxyphenyl)ethyl)-3-(methylcarbamoyl)-1H-pyrazole-5-carboxylate | Formic, 0.99 min, 318.2 |

Intermediate 49: 3-(Methylcarbamoyl)-1-((1-tosyl-1H-indol-4-yl)methyl)-1H-pyrazole-5-carboxylic acid

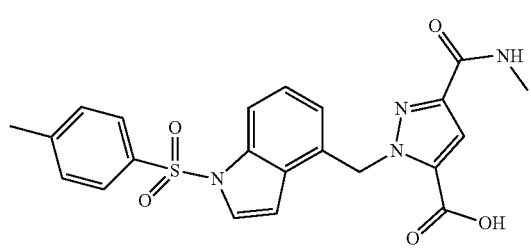

Methyl 3-(methylcarbamoyl)-1-((1-tosyl-1H-indol-4-yl)methyl)-1H-pyrazole-5-carboxylate (265 mg, 0.426 mmol) was taken up in methanol (2.5 mL) and THF (2.5 mL). 1M LiOH in water (0.852 mL, 0.852 mmol) was added and the mixture stirred at 50° C. for 90 min. The reaction was concentrated in vacuo. The residue was partitioned between ethyl acetate and water (10 mL each). The aqueous layer was acidified with 2M HCl, and then extracted with ethyl acetate (2×10 mL), dried with $Na_2SO_4$, filtered and concentrated in vacuo to yield the desired product (173.5 mg, 0.326 mmol, 77% yield) as a white solid LCMS (2 min Formic): Rt=1.13 min, [MH]+=453.3

The following intermediates were prepared in a similar manner to intermediate 49.

| Intermediate | Intermediate used | | LC MS: (System, $t_{RET}$, MH+) |
|---|---|---|---|
| 50 | (S)-3-(Methylcarbamoyl)-1-(1-(m-tolyl)ethyl)-1H-pyrazole-5-carboxylic acid | Intermediate 34 | Formic, 0.86 min, 274.2 |
| 51 | (S)-3-(Methylcarbamoyl)-1-(1-phenylpropyl)-1H-pyrazole-5-carboxylic acid | Intermediate 35 | Formic, 0.96 min, 288.2 |
| 52 | (S)-1-(1-(4-Fluorophenyl)ethyl)-3-(methylcarbamoyl)-1H-pyrazole-5-carboxylic acid | Intermediate 36 | Formic, 0.88 min, 292.1 |
| 53 | (S)-1-(1-(3-Fluorophenyl)ethyl)-3-(methylcarbamoyl)-1H-pyrazole-5-carboxylic acid | Intermediate 37 | Formic, 0.90 min, 292.4 |

-continued

| Intermediate | | Intermediate used | LC MS: (System, $t_{RET}$, MH+) |
|---|---|---|---|
| 54 | 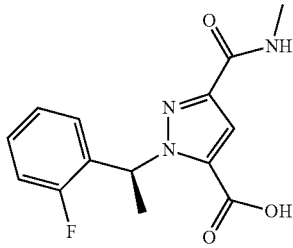(S)-1-(1-(2-Fluorophenyl)ethyl)-3-(methylcarbamoyl)-1H-pyrazole-5-carboxylic acid | Intermediate 38 | Formic, 0.89 min, 292.4 |
| 55 | 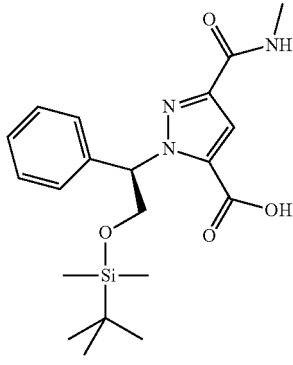 [SMILES: CNC(=O)c1cc(C(=O)O)n([C@@H](CO[Si](C)(C)C(C)(C)C)c2ccccc2)n1](R)-1-(2-((tert-Butyldimethylsilyl)oxy)-1-phenylethyl)-3-(methylcarbamoyl)-1H-pyrazole-5-carboxylic acid | Intermediate 90 | High pH, 0.90 min, 404.6 |
| 56 | 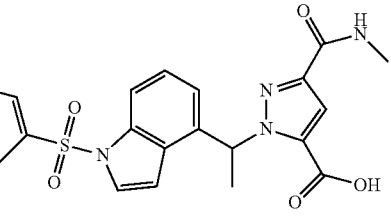3-(Methylcarbamoyl)-1-(1-(1-tosyl-1H-indol-4-yl)ethyl)-1H-pyrazole-5-carboxylic acid | Intermediate 40 | Formic, 1.16 min, MH− 465 |
| 57 | 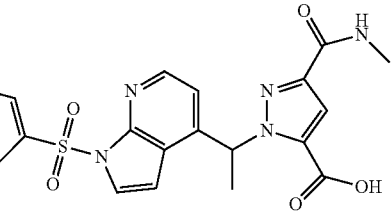3-(Methylcarbamoyl)-1-(1-(1-tosyl-1H-pyrrolo[2,3-b]pyridin-4-yl)ethyl)-1H-pyrazole-5-carboxylic acid | Intermediate 45 | Formic, 1.06 min, MH− 468 |

| Intermediate | Intermediate used | | LC MS: (System, $t_{RET}$, MH+) |
|---|---|---|---|
| 58 | 3-(Methylcarbamoyl)-1-((1-tosyl-1H-indol-5-yl)methyl)-1H-pyrazole-5-carboxylic acid | Intermediate 41 | Formic, 1.11 min, 453.6 |
| 59 | 3-(Methylcarbamoyl)-1-(1-(1-tosyl-1H-indol-5-yl)ethyl)-1H-pyrazole-5-carboxylic acid | Intermediate 42 | Formic, 1.17 min, [M − H]− at 465.5 |
| 60 | 1-((1H-Pyrrolo[2,3-b]pyridin-4-yl)methyl)-3-(methylcarbamoyl)-1H-pyrazole-5-carboxylic acid | Intermediate 46 | Formic, 0.44 min, 300.1 |

-continued

| Intermediate | | Intermediate used | LC MS: (System, $t_{RET}$, MH+) |
|---|---|---|---|
| 61 | 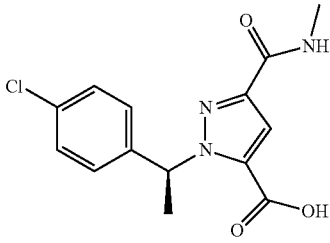 [SMILES: CNC(=O)c1cc(C(=O)O)n([C@@H](C)c2ccc(Cl)cc2)n1]<br>(S)-1-(1-(4-Chlorophenyl)ethyl)-3-(methylcarbamoyl)-1H-pyrazole-5-carboxylic acid | Intermediate 33 | Formic, 0.99 min, 308.2 |
| 62 | 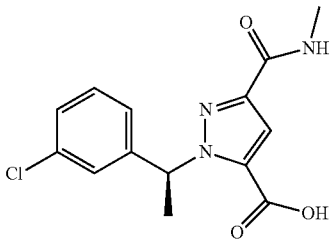 [SMILES: CNC(=O)c1cc(C(=O)O)n([C@@H](C)c2cccc(Cl)c2)n1]<br>(S)-1-(1-(3-Chlorophenyl)ethyl)-3-(methylcarbamoyl)-1H-pyrazole-5-carboxylic acid | Intermediate 43 | Formic, 0.99 min, 308.1 |
| 63 | 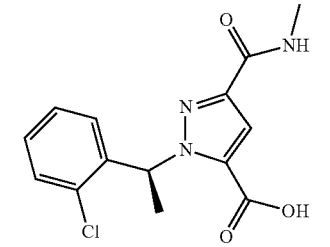 [SMILES: CNC(=O)c1cc(C(=O)O)n([C@@H](C)c2ccccc2Cl)n1]<br>(S)-1-(1-(2-Chlorophenyl)ethyl)-3-(methylcarbamoyl)-1H-pyrazole-5-carboxylic acid | Intermediate 47 | Formic, 0.95 min, 308.2 |
| 64 | 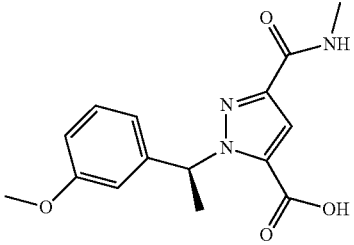<br>(S)-1-(1-(3-Methoxyphenyl)ethyl)-3-(methylcarbamoyl)-1H-pyrazole-5-carboxylic acid | Intermediate 48 | Formic, 0.88 min, 304.1 |

Intermediate 65: N⁵-((1R,5S,6r)-3-Oxabicyclo[3.1.0]hexan-6-yl)-N³-methyl-1-((1-tosyl-1H-indol-4-yl)methyl)-1H-pyrazole-3,5-dicarboxamide

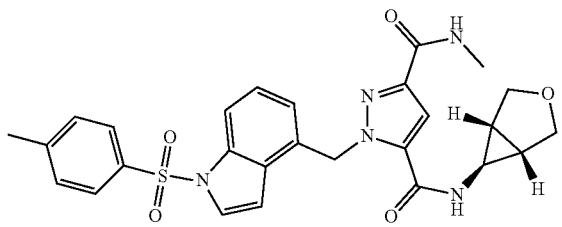 [SMILES: CNC(=O)c1cc(C(=O)N[C@H]2[C@@H]3COC[C@@H]32)n(Cc2cccc3c2ccn3S(=O)(=O)c2ccc(C)cc2)n1]

3-(Methylcarbamoyl)-1-((1-tosyl-1H-indol-4-yl)methyl)-1H-pyrazole-5-carboxylic acid (173 mg, 0.382 mmol) was taken up in DMF (5 mL). DIPEA (0.200 mL, 1.147 mmol), then HATU (218 mg, 0.573 mmol) were added and the reaction left to stir for 5 min, giving a brown solution. (1R,5S,6r)-3-Oxabicyclo[3.1.0]hexan-6-amine hydrochloride (For a preparation, see intermediate 94, 57.0 mg, 0.421 mmol) was then added, and the reaction was left to stir at rt overnight. The reaction mixture was partitioned between ethyl acetate and sodium bicarbonate (15 mL each). The organic layer was washed with 2M HCl (15 mL), brine (15 mL), and then dried with Na$_2$SO$_4$, filtered and concentrated in vacuo to give the crude product as a yellow oil. The crude product was purified by silica gel column chromatography, eluting with 10-60% (3:1 EtOAc:EtOH) in cyclohexane. The appropriate fractions were combined and concentrated in vacuo to give the desired product (99.7 mg, 0.178 mmol, 46% yield) as a cream solid.

LCMS (2 min Formic): Rt=1.09 min, [MH]⁺=534.3

Intermediate 66: 1-((1H-Indol-4-yl)methyl)-3-(methylcarbamoyl)-1H-pyrazole-5-carboxylic acid

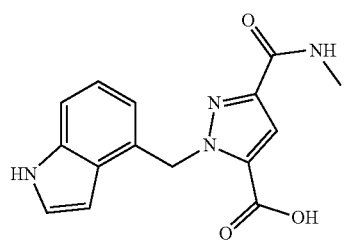 [SMILES: CNC(=O)c1cc(C(=O)O)n(Cc2cccc3[nH]ccc23)n1]

3-(Methylcarbamoyl)-1-((1-tosyl-1H-indol-4-yl)methyl)-1H-pyrazole-5-carboxylic acid (139 mg, 0.307 mmol) was taken up in THF (6 mL) and methanol (3 mL). Cesium carbonate (500 mg, 1.536 mmol) was added and the reaction was left to stir at 70° C. for 3.5 h. The reaction was concentrated in vacuo, water (10 mL) was added to the residue, which was then acidified with 2N HCl, and extracted with ethyl acetate (2×10 mL). This organic layer was dried with Na$_2$SO$_4$, filtered and concentrated in vacuo to yield the desired product (91.5 mg, 0.291 mmol, 95% yield) as a pink solid.

LCMS (2 min Formic): Rt=0.75 min, [MH]⁺=299.1

Intermediate 67: (1R,5S,6s)-tert-Butyl 6-(1-((1H-indol-4-yl)methyl)-3-(methylcarbamoyl)-1H-pyrazole-5-carboxamido)-3-azabicyclo[3.1.0]hexane-3-carboxylate

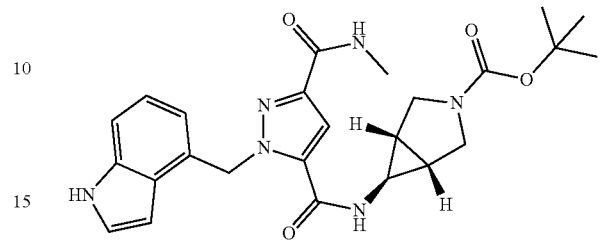

1-((1H-indol-4-yl)methyl)-3-(methylcarbamoyl)-1H-pyrazole-5-carboxylic acid (78.6 mg, 0.263 mmol) was taken up in DMF (5 mL). HATU (150 mg, 0.395 mmol), then DIPEA (0.138 mL, 0.790 mmol) were added and the reaction was left to stir for 5 min, giving a brown solution. tert-Butyl (1R,5S,6s)-6-amino-3-azabicyclo[3.1.0]hexane-3-carboxylate, hydrochloride (68.0 mg, 0.290 mmol, commercially available from, for example, Astatech) was added and the reaction was left to stir at rt for 1 h. The reaction was concentrated in vacuo. The residue was partitioned between ethyl acetate and sodium bicarbonate (10 mL each). The layers were separated and the organic layer was washed with 2N HCl (10 mL), brine (10 mL), and then dried with Na$_2$SO$_4$, filtered and concentrated in vacuo to yield the crude product as a brown solid. The crude product was applied to a 10 g ULTRA SNAP cartridge in the minimum of DCM (with a couple of drops of MeOH) and eluted with 5-50% (3:1 EtOAc:EtOH) in cyclohexane. The appropriate fractions were combined and concentrated in vacuo to yield the desired product (93.8 mg, 0.186 mmol, 71% yield) as a cream solid.

LCMS (2 min Formic): Rt=1.00 min, [MH]⁺=479

Intermediate 68: 3-Hydroxybicyclo[3.1.0]hexane-6-carboxylic acid

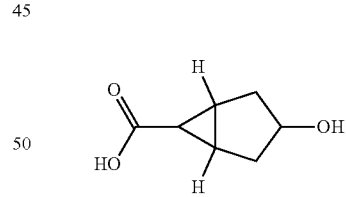

Sodium hydroxide (6 mL, 12.00 mmol, 2M aqueous solution) was added to a solution of ethyl 3-hydroxybicyclo[3.1.0]hexane-6-carboxylate (1 g, 5.88 mmol, commercially available from, for example, Fluorochem) in ethanol (10 mL) and the mixture was stirred for 2 h at rt, then evaporated in vacuo to half its original volume and acidified with 2M HCl to ~pH 2. The solution was saturated with sodium chloride (solid added and the mixture stirred for 1 h), then extracted first with 10% MeOH/DCM (5×10 mL) and then with EtOAc (5×10 mL). The combined organics were dried over sodium sulphate and evaporated in vacuo to give 3-hydroxybicyclo[3.1.0]hexane-6-carboxylic acid (0.65 g, 4.57 mmol, 78% yield) as a colourless gum. This was used crude in subsequent reactions.

Intermediate 69: 6-Aminobicyclo[3.1.0]hexan-3-ol

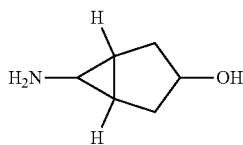

3-Hydroxybicyclo[3.1.0]hexane-6-carboxylic acid (650 mg, 4.57 mmol) was dissolved in toluene (10 mL) and tert-butanol (10 mL), then Et₃N (1.275 mL, 9.15 mmol) and diphenyl phosphorazidate (1.478 mL, 6.86 mmol) were added and the mixture was heated at 80° C. overnight. The mixture was diluted with EtOAc (20 mL) and washed with water (20 mL), the solvent was dried and evaporated to give a pale yellow gum. This was dissolved in DCM (10 mL) and loaded onto a 50 g silica column, then eluted with 0-100% EtOAc/cyclohexane and ninhydrin active fractions were evaporated in vacuo to give three batches of impure Boc-protected amine intermediates (each likely with a different diastereomer as the major component), batch A (105 mg), batch B (122 mg) and batch C (85 mg). Each of these was dissolved in DCM (3 mL) and TFA (1 mL) was added, the solutions were stirred for 1 h, then evaporated in vacuo and the residue dissolved in methanol and loaded onto 5 g SCX cartridges. These were washed with methanol and then eluted with 2M methanolic ammonia. The eluants were evaporated in vacuo to give three batches of product as pale yellow glasses (each likely with a different diastereomer as the major component), batch A (15 mg), batch B (12 mg) and batch C (14 mg). The products were used crude and coupled in subsequent reactions.

Intermediate 70:
tert-Butyl(cyclopent-3-en-1-yloxy)dimethylsilane

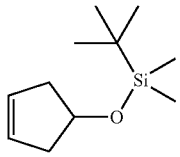

Cyclopent-3-en-1-ol (5 g, 59.4 mmol, commercially available from, for example, Astatech) was dissolved in DCM (100 mL) and TBDMS-Cl (8.96 g, 59.4 mmol) and imidazole (4.86 g, 71.3 mmol) were added, then the resulting suspension was stirred at rt over the weekend. The mixture was washed with water (2×100 mL), dried and evaporated in vacuo to give tert-butyl(cyclopent-3-en-1-yloxy)dimethylsilane (12.05 g, 60.7 mmol, 102% yield) as a pale yellow liquid.
¹H NMR (400 MHz, CDCl₃) δ ppm 5.68 (s, 2H) 4.50-4.62 (m, 1H) 2.59 (dd, J=14.9, 6.8 Hz, 2H) 2.23-2.37 (m, 2H) 0.91 (s, 9H) 0.09 (s, 6H).

Intermediate 71: (1R,5S,6r)-Ethyl 3-((tert-Butyldimethylsily)oxy)bicyclo[3.1.0]hexane-6-carboxylate, Mixture of Diastereomers

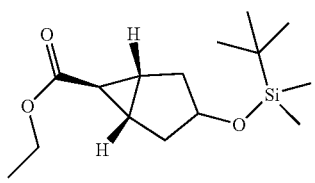 [SMILES: CCOC(=O)[C@H]1[C@@H]2CC(O[Si](C)(C)C(C)(C)C)C[C@@H]21]

Ethyl diazoacetate (6.90 mL, 66.5 mmol) was dissolved in DCM (150 mL) and added dropwise over 5 h to a mixture of rhodium(II) acetate dimer (1 g, 2.263 mmol) and tert-butyl(cyclopent-3-en-1-yloxy)dimethylsilane (12 g, 60.5 mmol) in DCM (150 mL) at rt. The resulting green solution was stirred overnight, then evaporated in vacuo to give a green liquid. This was loaded onto a 340 g silica column and eluted with 0-40% EtOAc/cyclohexane and TLC plates of the fractions were visualised using permanganate dip. Active fractions were evaporated in vacuo to give ethyl (1R,5S,6r)-3-((tert-butyldimethylsilyl)oxy)bicyclo[3.1.0]hexane-6-carboxylate (5.5 g, 19.33 mmol, 32.0% yield) as a colourless liquid, as a mixture of isomers at the silyl ether position (~3:1 ratio) and this was carried through crude to the next step.
LCMS (2 min High pH): Rt=0.96 min, [MI-1]±=not present.

Intermediate 72: (1R,5S,6r)-3-((tert-Butyldimethylsilyloxy)bicyclo[3.1.0]hexane-6-carboxylic acid, Mixture of Diastereomers

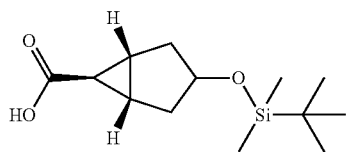 [SMILES: CC(C)(C)[Si](C)(C)OC1C[C@@H]2[C@H](C1)[C@H]2C(=O)O]

Sodium hydroxide (20 mL, 40.0 mmol, 2M aqueous solution) was added to a solution of ethyl (1R,5S,6r)-3-((tert-butyldimethylsilyloxy)bicyclo[3.1.0]hexane-6-carboxylate (5.0 g, 17.58 mmol) in ethanol (50 mL) at rt and the mixture was stirred for 3 h. TLC suggested that all the starting material had been consumed and the mixture was evaporated in vacuo to about 30 mL volume, then diluted with water (30 mL) and washed with ether (50 mL). The ether washings from the workup were dried and evaporated in vacuo to give recovered starting material:ethyl (1R,5S,6r)-3-((tert-butyldimethylsilyl)oxy)bicyclo[3.1.0]hexane-6-carboxylate (3.85 g). This was dissolved in ethanol (30 mL) and 2M aqueous NaOH solution (20 mL) was added, then the mixture was heated at 70° C. for 3 h, then evaporated in vacuo. The residue was dissolved in water (50 mL) and washed with ether (50 mL), then the aqueous layer was acidified with 2M HCl (20 mL) and extracted with EtOAc (2×50 mL). The combined organics were dried and evaporated in vacuo to give (1R,5S,6r)-3-((tert-butyldimethylsilyl)oxy)bicyclo[3.1.0]hexane-6-carboxylic acid (1.9 g, 7.41 mmol, 42.2% yield) as a pale yellow solid, the NMR is consistent with a mixture of isomers. The product was carried through to the next step without purification.

Intermediate 73: Benzyl ((1R,5S,6r)-3-((tert-butyldimethylsilyl)oxy)bicyclo[3.1.0]hexan-6-yl)carbamate, Mixture of Diastereomers

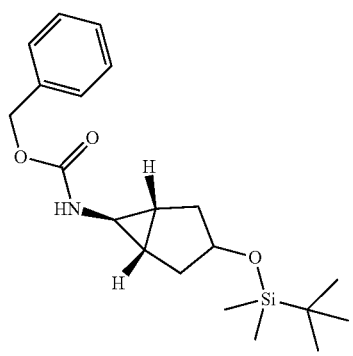 [SMILES: CC(C)(C)[Si](C)(C)OC1C[C@@H]2[C@H](C1)[C@H]2NC(=O)OCc1ccccc1]

(1R,5S,6r)-3-((tert-Butyldimethylsilyl)oxy)bicyclo[3.1.0]hexane-6-carboxylic acid (1.8 g, 7.02 mmol) was dissolved in a mixture of toluene (20 mL) and Et$_3$N (1.957 mL, 14.04 mmol), then DPPA (1.815 mL, 8.42 mmol) was added and the mixture was stirred for 30 min at rt. Benzyl alcohol (1.095 mL, 10.53 mmol) was added and the mixture heated at 100° C. for 4 h, then cooled to rt. Ethyl acetate (100 mL) was added and the solution was washed with water (2×100 mL), then dried over sodium sulphate, filtered and the filtrate evaporated in vacuo to give a pale yellow oil. This was dissolved in DCM (10 mL) and loaded onto a 50 g silica column, then eluted with 0-30% EtOAc/cyclohexane and product-containing fractions (detected by permanganate dip) were collected and evaporated in vacuo to give benzyl ((1R,5S,6r)-3-((tert-butyldimethylsilyl)oxy)bicyclo[3.1.0]hexan-6-yl)carbamate (1.90 g, 5.26 mmol, 75% yield) as a pale yellow oil, the NMR is consistent with desired product as a mixture of isomers in approximately 2:1 ratio. The compound was taken through to the next step without further purification.

LCMS (2 min Formic): Rt=1.56 min, [MH]+=362.6.

Intermediate 74: (1R,5S,6r)-3-((tert-Butyldimethylsilypoxy)bicyclo[3.1.0]hexan-6-amine, Mixture of Diastereomers

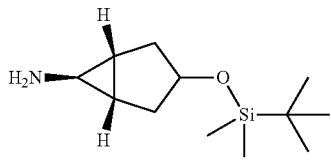

Benzyl ((1R,5S,6r)-3-((tert-butyldimethylsilyl)oxy)bicyclo[3.1.0]hexan-6-yl)carbamate (1.9 g, 5.26 mmol) was dissolved in ethanol (100 mL) and hydrogenated in the H-Cube at atmospheric pressure and 1 mL/min flow rate. The eluant was evaporated in vacuo to give (1R,5S,6r)-3-((tert-butyldimethylsilyl)oxy)bicyclo[3.1.0]hexan-6-amine (1.12 g, 4.92 mmol, 84% yield) as a pale yellow oil. Product is an unequal mixture of diastereomers at the silyl ether position with a ratio of approximately 65:35.

$^1$H NMR (400 MHz, CDCl$_3$) δ ppm 4.22 ppm, 1H [A](br.t, CH), 3.80 ppm 1H [B] (m, CH), 2.47 ppm, 1H [A] (t, CH), 2.05-1.93 ppm 2H [A]+3H [B] (m, 5×CH), 1.75-1.66 ppm NH2 [A]+—NH2 [B]+2×CH [B}, 1.62 ppm 2H, [A] (dd, 2×CH). Both diasteromers assigned. 1.20-1.15 ppm 2H [A]+2H [B] (M, 4×CH), 0.86 ppm, 9H [A] (s, 3×CH$_3$)+ 9H [B] (s, 3×CH$_3$), 0.00 ppm, 6H [A+B] (s, 2×CH$_3$)

Intermediate 75: N$^5$-((1r,4r)-4-Hydroxycyclohexyl)-N$^3$-methyl-1-(1-(1-tosyl-1H-indol-4-yl)ethyl)-1H-pyrazole-3,5-dicarboxamide

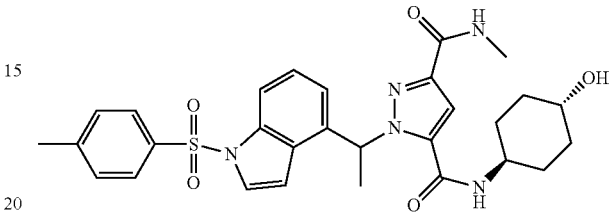

To a solution of 3-(methylcarbamoyl)-1-(1-(1-tosyl-1H-indol-4-yl)ethyl)-1H-pyrazole-5-carboxylic acid (255 mg, 0.547 mmol) in DMF (4 mL) was added HATU (312 mg, 0.820 mmol) followed by (1r,4r)-4-aminocyclohexan-1-ol (126 mg, 1.093 mmol, commercially available from, for example, Fluorochem) and DIPEA (0.477 mL, 2.73 mmol). The resulting reaction mixture was stirred at rt in air for 5 h. The reaction mixture was concentrated in vacuo to remove DMF and partitioned between ethyl acetate and saturated aq. LiCl solution. The organic layer was separated, washed with brine, dried (hydrophobic frit) and concentrated to give a crude orange oil. This was purified by chromatography on silica gel column, eluting with 0-50% (25% ethanol in ethyl acetate)/ethyl acetate to give the desired product (330 mg, 0.439 mmol, 80% yield) as a pale yellow oil.

LCMS (2 min Formic): Rt=1.07 min, [M+Na]+=586

The following intermediates were prepared in a similar manner to Intermediate 75:

| Intermediate | |
| --- | --- |
| 76 | 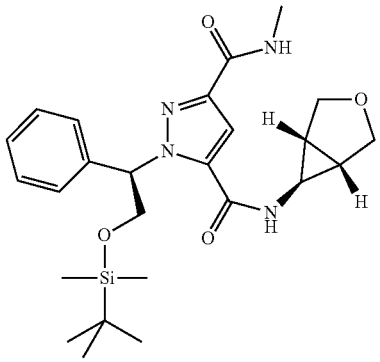 [SMILES: CNC(=O)c1cc(C(=O)N[C@H]2[C@@H]3COC[C@@H]32)n([C@@H](CO[Si](C)(C)C(C)(C)C)c2ccccc2)n1]<br>N$^5$-((1R,5S,6r)-3-Oxabicyclo[3.1.0]hexan-6-yl)-1-((R)-2-((tert-butyldimethylsilyl)oxy)-1-phenylethyl)-N$^3$-methyl-1H-pyrazole-3,5-dicarboxamide |

77 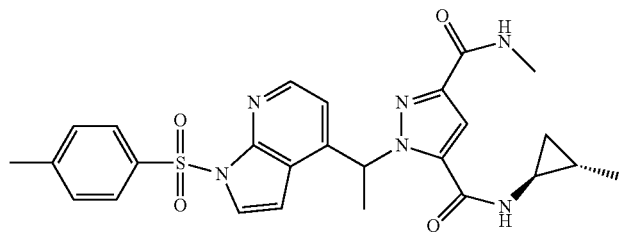
N³-Methyl-N⁵-((1S,2S)-2-methylcyclopropyl)-1-(1-(1-tosyl-1H-pyrrolo[2,3-b]pyridin-4-yl)ethyl)-1H-pyrazole-3,5-dicarboxamide
78 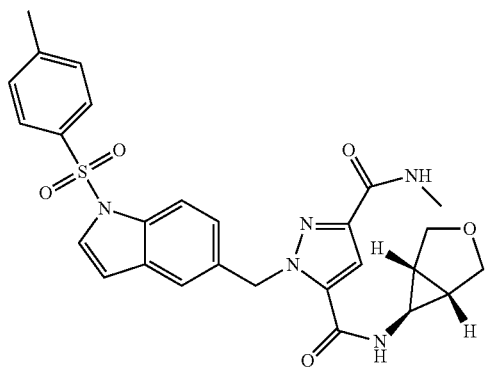
N⁵-((1R,5S,6r)-3-Oxabicyclo[3.1.0]hexan-6-yl)-N³-methyl-1-((1-tosyl-1H-indol-5-yl)methyl)-1H-pyrazole-3,5-dicarboxamide
79 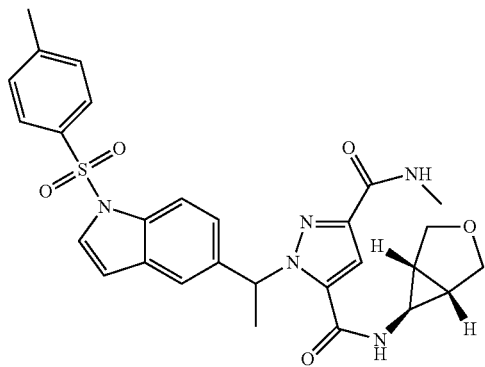 [SMILES: CNC(=O)c1cc(C(=O)N[C@H]2[C@@H]3COC[C@@H]32)n(Cc2ccc3c(ccn3S(=O)(=O)c3ccc(C)cc3)c2)n1]
N⁵-((1R,5S,6r)-3-Oxabicyclo[3.1.0]hexan-6-yl)-N³-methyl-1-(1-(1-tosyl-1H-indol-5-yl)ethyl)-1H-pyrazole-3,5-dicarboxamide

| | | |
|---|---|---|
| 80 | 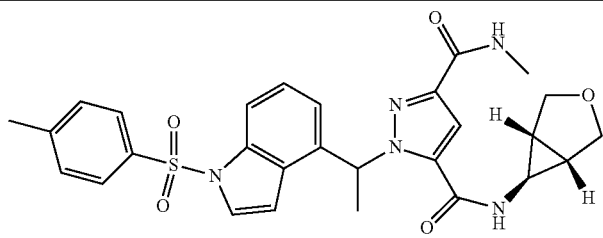

N⁵-((1R,5S,6r)-3-
Oxabicyclo[3.1.0]hexan-6-yl)-
N³-methyl-1-(1-(1-tosyl-1H-
indol-4-yl)ethyl)-1H-pyrazole-
3,5-dicarboxamide | |
| 81 | 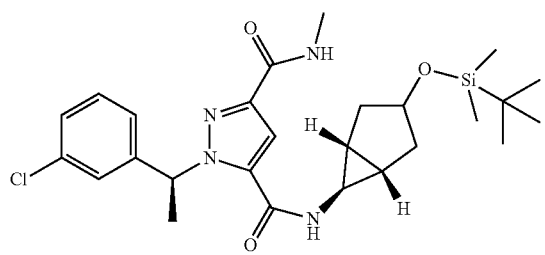 [SMILES: CNC(=O)c1cc(C(=O)N[C@H]2[C@@H]3CC(O[Si](C)(C)C(C)(C)C)C[C@@H]32)n([C@@H](C)c2cccc(Cl)c2)n1]

N⁵-((1R*,5S*,6r*)-3-((tert-
Butyldimethylsilyl)oxy)bicyclo
[3.1.0]hexan-6-yl)-1-((S)-1-(3-
chlorophenyl)ethyl)-N³-methyl-
1H-pyrazole-3,5-dicarboxamide | |
| 82 | 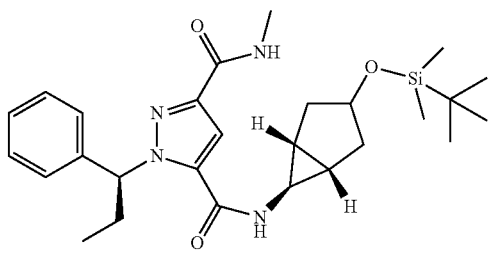 [SMILES: CC[C@@H](c1ccccc1)n1nc(C(=O)NC)cc1C(=O)N[C@H]1[C@@H]2CC(O[Si](C)(C)C(C)(C)C)C[C@@H]21]

N⁵-((1R,5S,6r)-3-((tert-
Butyldimethylsilyl)oxy)bicyclo
[3.1.0]hexan-6-yl)-N³-methyl-1-
((S)-1-phenylpropyl)-1H-
pyrazole-3,5-dicarboxamide | |

| Inter-mediate | Intermediate used | LCMS: (System, $t_{RET}$, MH⁺) |
|---|---|---|
| 76 | ![structure]

Intermediate 55 | High pH, 1.29 min, 485.7 |

| | | |
|---|---|---|
| 77 | 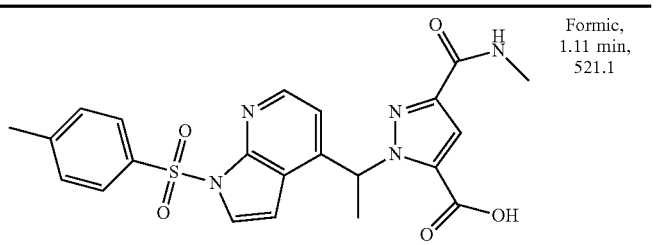<br>Intermediate 57 | Formic, 1.11 min, 521.1 |
| 78 | 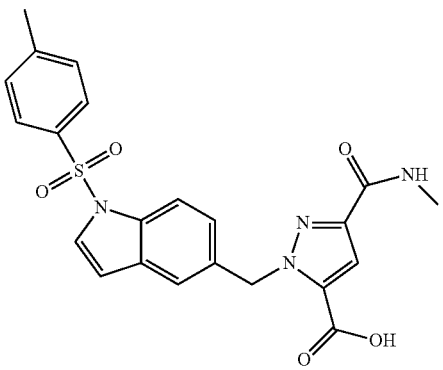 [SMILES: CNC(=O)c1cc(C(=O)O)n(Cc2ccc3c(ccn3S(=O)(=O)c3ccc(C)cc3)c2)n1]<br>Intermediate 58 | Formic, 1.06 min, 534.6 |
| 79 | 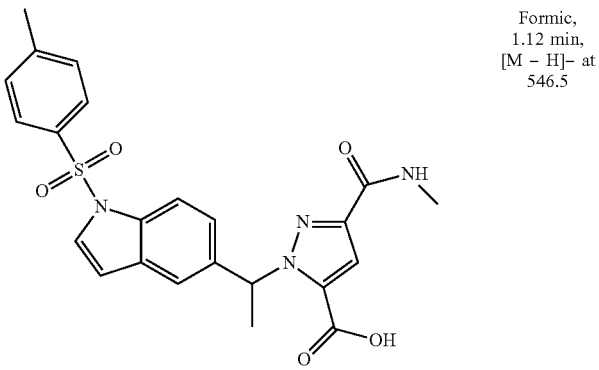<br>Intermediate 59 | Formic, 1.12 min, [M − H]− at 546.5 |
| 80 | 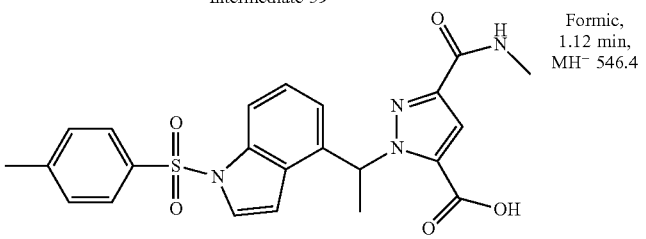<br>Intermediate 56 | Formic, 1.12 min, MH− 546.4 |
| 81 | 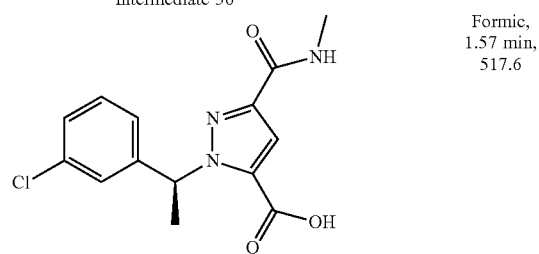<br>Intermediate 62 | Formic, 1.57 min, 517.6 |

82

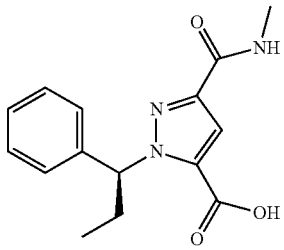 [SMILES: CC[C@@H](c1ccccc1)n1nc(C(=O)NC)cc1C(=O)O]

Intermediate 51

High pH, 1.55 min, 497.7

Intermediate 83: 1-((1H-Pyrrolo[2,3-c]pyridin-4-yl)methyl)-3-(methylcarbamoyl)-1H-pyrazole-5-carboxylic acid

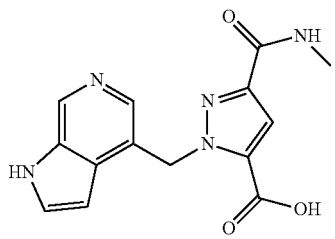 [SMILES: CNC(=O)c1cc(C(=O)O)n(Cc2cncc3[nH]ccc23)n1]

Methyl 3-(methylcarbamoyl)-1-((1-tosyl-1H-pyrrolo[2,3-c]pyridin-4-yl)methyl)-1H-pyrazole-5-carboxylate (106 mg, 0.227 mmol) was taken up in methanol (1.5 mL) and THF (1.5 mL). 1M LiOH in water (0.453 mL, 0.453 mmol) was added and the reaction left to stir at rt overnight. Additional 1M LiOH in water (0.453 mL) was added, and the reaction left to stir for 4 h. The residue was partitioned between water and ethyl acetate (10 mL of each). The aqueous layer was acidified with 2N HCl and extracted with ethyl acetate (2×15 mL). The aqueous layer was then extracted with 10% MeOH in DCM (2×15 mL), and the aqueous layer concentrated in vacuo to give the crude residue. The crude product was dissolved in 1:1 DMSO:MeCN (2 mL), filtered and then purified by MDAP (High pH). The appropriate fractions were concentrated in vacuo to yield the title compound (22 mg, 0.051 mmol, 23% yield) as a cream solid.

LCMS (2 min Formic): Rt=0.37 min, [MH]$^+$=300.2

Intermediate 84: (S)—N$^5$-(3,3-Diethoxypropyl)-N$^3$-methyl-1-(1-phenylethyl)-1H-pyrazole-3,5-dicarboxamide

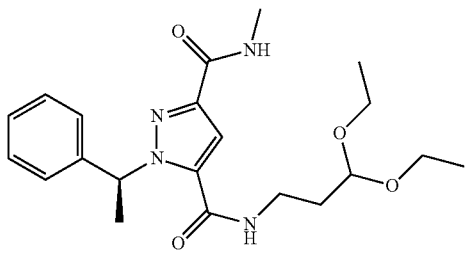 [SMILES: CCOC(CCNC(=O)c1cc(C(=O)NC)nn1[C@@H](C)c1ccccc1)OCC]

(S)-3-(Methylcarbamoyl)-1-(1-phenylethyl)-1H-pyrazole-5-carboxylic acid (121 mg, 0.443 mmol) was dissolved in DMF (2 mL). HATU (255 mg, 0.671 mmol) was added followed by 3,3-diethoxypropan-1-amine (0.12 mL, 0.742 mmol, commercially available from, for example, Acros) and then DIPEA (0.39 mL, 2.233 mmol). The reaction mixture was stirred under nitrogen for 3.25 h. The reaction mixture was partitioned between sat. aqueous LiCl (20 mL), Na$_2$CO$_3$ (~1 mL), and ethyl acetate (20 mL); the layers were separated. The aqueous layer was extracted with further ethyl acetate (2×20 mL). The organic layers were combined, back extracted with water (2×10 mL) and filtered through a cartridge fitted with a hydrophobic frit. The filtrate was evaporated in vacuo to give a colourless gum. This was redissolved in dichloromethane and directly applied to the top of a 10 g SNAP silica cartridge and purified by SP4 flash column chromatography (0-60% ethyl acetate/cyclohexane). The relevant fractions were combined to give (S)—N$^5$-(3,3-diethoxypropyl)-N$^3$-methyl-1-(1-phenylethyl)-1H-pyrazole-3,5-dicarboxamide (103 mg, 0.230 mmol, 52% yield)

LCMS (2 min High pH): Rt=1.05 min, [MH]$^+$=403.2.

Intermediate 85: 2-(1,3-Dihydroxypropan-2-yl)isoindoline-1,3-dione

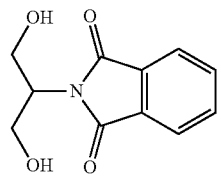 [SMILES: O=C1c2ccccc2C(=O)N1C(CO)CO]

To a solution of 2-aminopropane-1,3-diol (2.839 g, 31.2 mmol, commercially available from, for example, Sigma Aldrich) in DMF (60 mL) was added isobenzofuran-1,3-dione (4.62 g, 31.2 mmol, commercially available from, for example, Sigma Aldrich) dropwise at rt. The reaction was heated to 90° C. and stirred overnight. The reaction mixture was partitioned between EtOAc (200 mL) and water (250 mL) and the layers separated. The organic layer was analysed and shown to contain product. Therefore the aqueous layer was further extracted with EtOAc (2×100 mL) and then the combined organics were back extracted with water (2×50 mL) and sat. aq. LiCl solution (50 mL). The organics were then dried (Na$_2$SO$_4$) and concentrated in vacuo to afford 2-(1,3-dihydroxypropan-2-yl)isoindoline-1,3-dione (3.33 g, 15.05 mmol, 48% yield) as a cream solid.

LCMS (2 min High pH): Rt=0.52 min, [MH]$^+$=222.2.

Intermediate 86: N$^5$-(2-((2r,5S)-5-(1,3-Dioxoisoindolin-2-yl)-1,3-dioxan-2-yl)ethyl)-N$^3$-methyl-1-((S)-1-phenylethyl)-1H-pyrazole-3,5-dicarboxamide

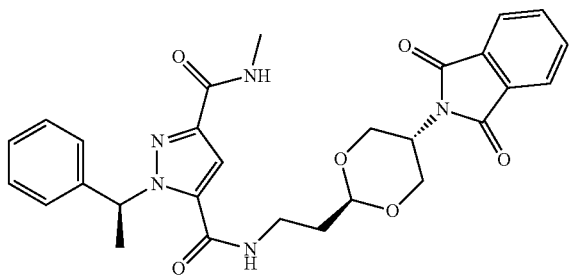 [SMILES: CNC(=O)c1cc(C(=O)NCC[C@H]2OC[C@H](N3C(=O)c4ccccc4C3=O)CO2)n([C@@H](C)c2ccccc2)n1]

A mixture of (S)—N$^3$-(3,3-diethoxypropyl)-N$^3$-methyl-1-(1-phenylethyl)-1H-pyrazole-3,5-dicarboxamide (113 mg, 0.280 mmol), 2-(1,3-dihydroxypropan-2-yl)isoindoline-1,3-dione (62 mg, 0.280 mmol) and p-toluenesulfonic acid monohydrate (12 mg, 0.063 mmol) in toluene (3 mL) was stirred at 110° C. under nitrogen for 2 h. The reaction mixture was then cooled to rt and the volatiles evaporated in vacuo to give a yellow solid. This was partitioned between 10% methanol in DCM (10 mL), water (5 mL) and sat. aqueous Na$_2$CO$_3$ (10 mL) and the layers separated. The aqueous phase was extracted with 10% methanol in DCM (3×10 mL) and ethyl acetate (5 mL). The organic layers were combined and filtered through a cartridge fitted with a hydrophobic frit. The organic layers were concentrated in vacuo to give 138 mg of crude product. The crude product was taken up in DCM and purified by flash chromatography (10 g SNAP silica cartridge) eluting with 0-100% EtOAc/cyclohexane. The relevant fractions were combined and concentrated in vacuo to give N$^5$-(2-((2r,5S)-5-(1,3-dioxoisoindolin-2-yl)-1,3-dioxan-2-yl)ethyl)-N$^3$-methyl-1-((S)-1-phenylethyl)-1H-pyrazole-3,5-dicarboxamide (102 mg, 0.154 mmol, 55% yield).

LCMS (2 min High pH): Rt=1.10 min, [MH]$^+$=532.2.

Intermediate 87: (S)—N$^5$-(4,4-Diethoxybutyl)-N$^3$-methyl-1-(1-phenylethyl)-1H-pyrazole-3,5-dicarboxamide

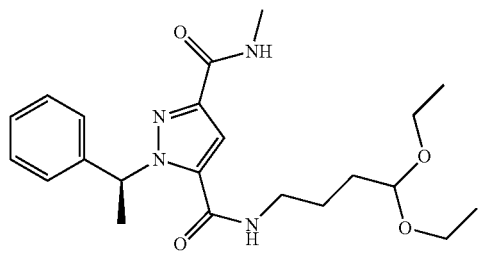 [SMILES: CCOC(CCCNC(=O)c1cc(C(=O)NC)nn1[C@@H](C)c1ccccc1)OCC]

(S)-3-(Methylcarbamoyl)-1-(1-phenylethyl)-1H-pyrazole-5-carboxylic acid (125 mg, 0.457 mmol) was dissolved in DMF (2 mL). HATU (272 mg, 0.715 mmol) was added followed by 4,4-diethoxybutan-1-amine (0.13 mL, 0.752 mmol, commercially available from, for example, Sigma Aldrich) and then DIPEA (0.4 mL, 2.290 mmol). The reaction mixture was stirred under nitrogen for 6 h. Further HATU (209 mg, 0.549 mmol), 4,4-diethoxybutan-1-amine (0.1 mL, 0.579 mmol) and then DIPEA (0.1 mL, 0.573 mmol) were added before stirring for a further 3 h. The reaction mixture was partitioned between sat. aqueous LiCl (20 mL) and ethyl acetate (20 mL) and the layers separated. The aqueous layer was extracted with further ethyl acetate (2×20 mL). The organic layers were combined, back extracted with water (2×10 mL) and filtered through a cartridge fitted with a hydrophobic frit. The filtrate was evaporated in vacuo to give a colourless gum. This was redissolved in dichloromethane and directly applied to the top of a 10 g SNAP silica cartridge and purified by SP4 flash column chromatography (0-70% ethyl acetate/cyclohexane). The relevant fractions were combined and concentrated in vacuo to give (S)—N$^5$-(4,4-diethoxybutyl)-N$^3$-methyl-1-(1-phenylethyl)-1H-pyrazole-3,5-dicarboxamide (190 mg, 0.411 mmol, 90% yield).

LCMS (2 min High pH): Rt=1.07 min, [M−H]$^-$=415.3.

Intermediate 88: N$^5$-(3-((2r,5S)-5-(1,3-Dioxoisoindolin-2-yl)-1,3-dioxan-2-yl)propyl)-M-methyl-1-((S)-1-phenylethyl)-1H-pyrazole-3,5-dicarboxamide

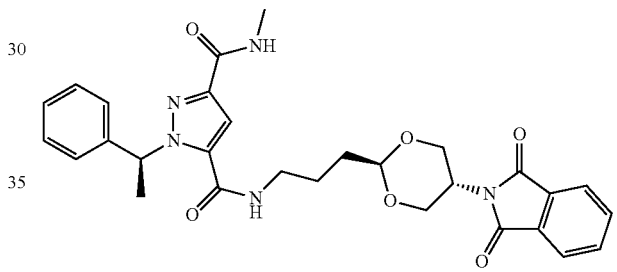

A mixture of (S)—N$^3$-(4,4-diethoxybutyl)-N$^3$-methyl-1-(1-phenylethyl)-1H-pyrazole-3,5-dicarboxamide (190 mg, 0.456 mmol), 2-(1,3-dihydroxypropan-2-yl)isoindoline-1,3-dione (112 mg, 0.506 mmol) and p-toluenesulfonic acid monohydrate (19 mg, 0.100 mmol) in toluene (4 mL) was stirred at 110° C. under nitrogen for 2 h. The reaction mixture was then cooled to rt and the volatiles evaporated in vacuo to give a yellow solid. This was partitioned between 10% methanol in DCM (10 mL), water (5 mL) and sat. aqueous Na$_2$CO$_3$ (10 mL) and the layers separated. The aqueous phase was extracted with 10% methanol in DCM (3×10 mL) and ethyl acetate (5 mL) and the organic layers were combined and filtered through a cartridge fitted with a hydrophobic frit. The organic layers were concentrated in vacuo to give 207 mg of crude product. The crude product was taken up in DCM and purified by flash chromatography (25 g SNAP silica cartridge) eluting with 0-100% EtOAc/cyclohexane. The relevant fractions were combined and concentrated in vacuo to give N$^5$-(3-((2r,5S)-5-(1,3-dioxoisoindolin-2-yl)-1,3-dioxan-2-yl)propyl)-N$^3$-methyl-1-((S)-1-phenylethyl)-1H-pyrazole-3,5-dicarboxamide (81 mg, 0.119 mmol, 26% yield).

LCMS (2 min High pH): Rt=1.12 min, [MH]$^+$=546.2.

Intermediate 89: (S)-2-((tert-Butyldimethylsilyloxy)-1-phenylethanol

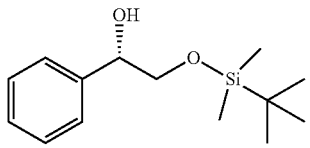 [SMILES: CC(C)(C)[Si](C)(C)OC[C@@H](O)c1ccccc1]

(S)-1-Phenylethane-1,2-diol (251 mg, 1.817 mmol, commercially available from, for example, Sigma Aldrich) was dissolved in DCM (7 mL) before the addition of DMAP (22 mg, 0.180 mmol). The solution was cooled to 0° C. before the addition of triethylamine (0.380 mL, 2.72 mmol) and, dropwise, TBDMS-Cl (411 mg, 2.72 mmol) in DCM (3 mL). The reaction mixture was then stirred at rt for 2 h. To the reaction mixture was added NH$_4$Cl (7 mL). The layers were separated and the aqueous was re-extracted with DCM (2×10 mL). The combined organic layers were dried and concentrated in vacuo to give 448 mg of crude product which was used directly in the next step.

LCMS (2 min High pH): Rt=1.41 min, [M−H]$^−$=251.1.

Intermediate 90: (R)-Methyl 1-(2-((tert-Butyldimethylsilyoxy)-1-phenylethyl)-3-(methylcarbamoyl)-1H-pyrazole-5-carboxylate

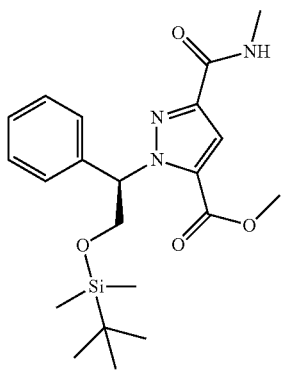 [SMILES: CNC(=O)c1cc(C(=O)OC)n([C@@H](CO[Si](C)(C)C(C)(C)C)c2ccccc2)n1]

Methyl 3-(methylcarbamoyl)-1H-pyrazole-5-carboxylate (216 mg, 1.179 mmol), (S)-2-((tert-butyldimethylsilyl)oxy)-1-phenylethan-1-ol (327 mg, 1.297 mmol) in toluene (2.5 mL), tri-n-butylphosphine (0.582 mL, 2.359 mmol) and 2-(tributylphosphoranylidene)acetonitrile (0.464 mL, 1.769 mmol) were combined. The reaction mixture was heated in a 5 mL microwave vial at 120° C. for 45 min. Further (S)-2-((tert-butyldimethylsilyl)oxy)-1-phenylethan-1-ol (119 mg, 0.471 mmol) was added to the reaction mixture before heating for 45 min at 120° C. in a microwave. The reaction mixture was concentrated in vacuo to give 1.574 g of crude product. The crude product was re-dissolved in DCM and purified by flash chromatography (100 g SNAP silica cartridge) eluting with 0-65% EtOAc:cyclohexane. The relevant fractions were combined and concentrated in vacuo to give methyl (R)-1-(2-((tert-butyldimethylsilyl)oxy)-1-phenylethyl)-3-(methylcarbamoyl)-1H-pyrazole-5-carboxylate (276 mg, 0.562 mmol, 48% yield).

LCMS (2 min Formic): Rt=1.42 min, [MH]$^+$=418.4.

Intermediate 91: (S)-3-(Methoxycarbonyl)-1-(1-phenylethyl)-1H-pyrazole-5-carboxylic acid

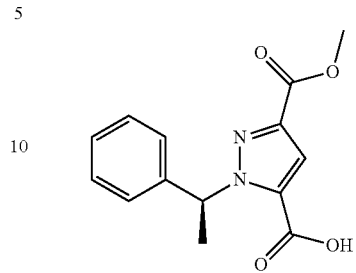

LiOH (0.888 g, 21.16 mmol) in water (20 mL) was added to a solution of dimethyl (S)-1-(1-phenylethyl)-1H-pyrazole-3,5-dicarboxylate (6.1 g, 21.16 mmol) in methanol (50 mL) and 2-MeTHF (50 mL) at 0° C. and the solution was stirred at 0° C. for 2 h, then acidified with 2M HCl (12 mL) and evaporated in vacuo to half the original volume. The mixture was further acidified to pH 2, then extracted with EtOAc (2×50 mL) and the combined organics dried and evaporated in vacuo to give a colourless gum. This was dissolved in DCM and loaded onto a 100 g silica column, then eluted with 0-50% (1% AcOH in EtOAc)/cyclohexane and the product-containing fractions were evaporated in vacuo to give (S)-3-(methoxycarbonyl)-1-(1-phenylethyl)-1H-pyrazole-5-carboxylic acid (4.2 g, 15.31 mmol, 72% yield)

LCMS (2 min Formic): Rt=1.00 min, [MH]$^+$=275.2.

Intermediate 92: (1R,5S,6r)-3-Oxabicyclo[3.1.0]hexane-6-carboxylic acid

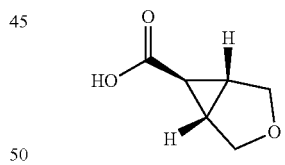

LiOH (751 mg, 31.4 mmol) was added to a solution of (1R,5S,6r)-ethyl 3-oxabicyclo[3.1.0]hexane-6-carboxylate (1000 mg, 6.27 mmol, commercially available from, for example, Pharmablock) in water (10 mL), THF (10 mL) and MeOH (10 mL) at rt. The resulting suspension was stirred for 3 h. For work-up, the mixture was evaporated, the remaining crude solid was dissolved in a minimum amount of water, and quenched with HCl (5 mL, 25% m/m), and extracted 4 times with MeOH/DCM solvent, the combined organic phases were dried over a hydrophobic frit, evaporated in vacuo, to yield the desired compound (1R,5S,6r)-3-oxabicyclo[3.1.0]hexane-6-carboxylic acid (750 mg, 5.85 mmol, 93% yield) $^1$H NMR (400 MHz, DMSO-d$_6$) δ ppm 12.13 (s, 1H) 3.80 (d, J=8.6 Hz, 2H) 3.62 (d, J=8.6 Hz, 2H) 2.00-2.15 (m, 2H) 1.32 (t, J=3.1 Hz, 1H)

Intermediate 93: Benzyl (1R,5S,6r)-3-oxabicyclo[3.1.0]hexan-6-ylcarbamate

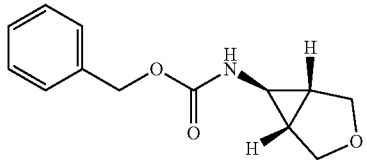 [SMILES: O=C(N[C@H]1[C@@H]2COC[C@@H]21)OCc1ccccc1]

(1R,5S,6r)-3-Oxabicyclo[3.1.0]hexane-6-carboxylic acid (340 mg, 2.65 mmol) was dissolved in toluene (12 mL), then Et$_3$N (1.110 mL, 7.96 mmol), diphenyl phosphorazidate (0.686 mL, 3.18 mmol) and benzyl alcohol (0.552 mL, 5.31 mmol) were added and the mixture was heated at reflux for 2 h. The solution was diluted with EtOAc (10 mL) and washed with water (10 mL) and NaHCO$_3$ solution (10 mL), the organic layer was dried and evaporated and the residue purified by chromatography on a 25 g silica column eluting with 0-50% EtOAc/cyclohexane and the product-containing fractions were evaporated in vacuo to give benzyl (1R,5S, 6r)-3-oxabicyclo[3.1.0]hexan-6-ylcarbamate (460 mg, 1.972 mmol, 74.3% yield) as a white solid.

LCMS (2 min Formic): Rt=0.83 min, [MH]$^+$=234.3.

$^1$H NMR (400 MHz, CDCl$_3$) δ ppm 7.29-7.41 (m, 5H) 5.11 (br. s., 2H) 4.86 (br. s., 1H) 3.98 (d, J=8.3 Hz, 2H) 3.72 (d, J=8.6 Hz, 2H) 2.45-2.52 (m, 1H) 1.80 (br. s, 2H)

Intermediate 94: (1R,5S,6r)-3-Oxabicyclo[3.1.0]hexan-6-amine, hydrochloride

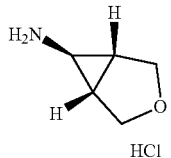

Benzyl (1R,5S,6r)-3-oxabicyclo[3.1.0]hexan-6-ylcarbamate (460 mg, 1.972 mmol) was dissolved in EtOH (20 mL) and the reaction was hydrogenated using an H-cube (settings: rt, 1 bar, 1 mL/min flow rate) and 10% Pd/C CatCart 30 as the catalyst. The reaction was cycled though the H-Cube for 1.5 h before acidifying the mixture with HCl (7M aqueous, 1.332 mL, 9.86 mmol) and evaporating in vacuo to yield an oily solid. The solid was dried in vacuo over 2 days to yield the desired product (1R,5S,6r)-3-oxabicyclo[3.1.0]hexan-6-amine, hydrochloride (262 mg, 1.836 mmol, 93% yield) as an off-white solid.

$^1$H NMR (400 MHz, DMSO-d$_6$) δ ppm 8.48 (br. s., 3H) 3.80 (d, J=8.8 Hz, 2H) 3.59 (d, J=8.6 Hz, 2H) 2.24 (t, J=2.3 Hz, 1H) 2.07 (t, J=2.6 Hz, 2H).

Intermediate 95: 4-Methoxycyclopent-1-ene

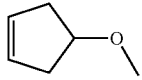

Cyclopent-3-en-1-ol (10 g, 119 mmol, commercially available from, for example, Fluorochem) was dissolved in a mixture of DMF (100 mL) and THF (50 mL) and cooled in an ice bath under nitrogen, then NaH (60% suspension in mineral oil, 5.71 g, 143 mmol) was added in small portions and the mixture stirred for 30 min, before addition of MeI (9.66 mL, 155 mmol). The resulting suspension was stirred at 0° C. for 2 h, then added to water (500 mL) and extracted with ether (500 mL). The organic layer was washed with water (2×200 mL) and brine (200 mL), dried and evaporated in vacuo to give the desired product as a pale yellow liquid, which was carried through to subsequent reactions without further purification.

$^1$H NMR (400 MHz, CDCl$_3$) δ ppm 5.61-5.82 (m, 2H) 4.13 (dt, J=6.72, 3.48 Hz, 1H) 3.35 (s, 3H) 2.59 (dd, J=15.77, 6.72 Hz, 2H) 2.32-2.47 (m, 2H)

Intermediate 96: Ethyl 3-methoxybicyclo[3.1.0]hexane-6-carboxylate

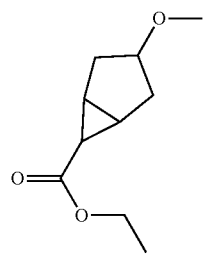

Ethyl diazoacetate (82 mL, 119 mmol) was dissolved in DCM (100 mL) and added dropwise to a mixture of 4-methoxycyclopent-1-ene (For a preparation, see Intermediate 95, 11.68 g, 119 mmol) and rhodium(II) acetate dimer (2.63 g, 5.95 mmol) in DCM (100 mL) at rt over 4 h, then the mixture was stirred for a further 2 h, then washed with water (300 mL) and the organic layer dried and evaporated in vacuo to give a crude pale green liquid. This was dissolved in cyclohexane and loaded onto a 100 g SNAP ultra silica column and purified by flash chromatography, eluting with 0-20% EtOAc/cyclohexane. The appropriate fractions were evaporated in vacuo to give ethyl 3-methoxybicyclo[3.1.0]hexane-6-carboxylate (1.4 g, 7.60 mmol, 6% yield) as a colourless oil as a mixture of isomers also containing some residual ethyl diazoacetate. This was taken on for subsequent reactions without any further purification.

$^1$H NMR (400 MHz, CDCl$_3$) δ ppm 4.26 (q, J=7.09 Hz, 2H) 3.51 (m, J=7.50, 7.50 Hz, 1H) 3.25 (s, 3H) 2.26 (dd, J=13.08, 6.97 Hz, 2H) 1.89 (td, J=2.93, 1.22 Hz, 2H) 1.74-1.83 (m, 2H) 1.27-1.34 (m, 4H)

Intermediate 97: 3-Methoxybicyclo[3.1.0]hexane-6-carboxylic acid

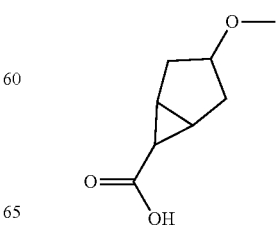

Ethyl 3-methoxybicyclo[3.1.0]hexane-6-carboxylate (For a preparation, see Intermediate 96, 1.4 g, 7.60 mmol) was dissolved in ethanol (10 mL) and an aqueous solution of 2M NaOH (10 mL, 20.00 mmol) was added, then the mixture was stirred at rt overnight. The solvent was evaporated in vacuo and the residue was acidified with 2M HCl(aq.) (11 mL), then extracted with EtOAc (2×20 mL). The combined organics were dried and evaporated in vacuo to give a pale yellow oil which was used directly in the next step.

$^1$H NMR (400 MHz, CDCl$_3$) δ ppm 3.54 (m, J=7.50, 7.50 Hz, 1H) 3.28 (s, 3H) 2.30 (dd, J=13.20, 7.09 Hz, 2H) 1.99 (td, J=2.93, 1.22 Hz, 2H) 1.74-1.89 (m, 2H) 1.31 (t, J=2.93 Hz, 1H). Exchangeable proton not observed Intermediate 98: tert-Butyl (3-methoxybicyclo[3.1.0]hexan-6-yl)carbamate

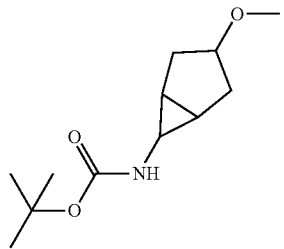 [SMILES: COC1CC2C(C1)C2NC(=O)OC(C)(C)C]

3-Methoxybicyclo[3.1.0]hexane-6-carboxylic acid (For a preparation, see Intermediate 97, 0.74 g, 4.74 mmol), diphenyl phosphoryl azide (1.956 g, 7.11 mmol) and Et$_3$N (1.321 mL, 9.48 mmol) were dissolved in toluene (20 mL) and the mixture was stirred for 30 min, then tert-butanol (6 mL) was added and the mixture was heated at reflux for 3 h, then allowed to stand at rt overnight. The mixture was diluted with EtOAc (50 mL), then washed with water and sodium bicarbonate aqueous solution and evaporated in vacuo. The resulting gum was dissolved in DCM and loaded onto a 25 g SNAP ultra silica column, then purified by flash chromoatography eluting with 0-30% EtOAc/cyclohexane. The product-containing fractions were evaporated in vacuo to give tert-butyl (3-methoxybicyclo[3.1.0]hexan-6-yl)carbamate (0.45 g, 1.980 mmol, 42% yield) as a colourless solid.

$^1$H NMR (400 MHz, CDCl$_3$) δ ppm 4.58 (br. s, 1H) 3.48 (quin, J=7.34 Hz, 1H) 3.26 (s, 3H) 2.24 (dd, J=12.84, 6.97 Hz, 2H) 2.16 (br. s., 1H) 1.71-1.80 (m, 2H) 1.39-1.49 (m, 11H)

Intermediate 99: 3-Methoxybicyclo[3.1.0]hexan-6-amine, hydrochloride

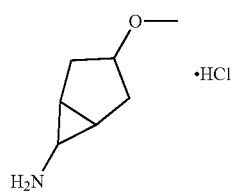

tert-Butyl (3-methoxybicyclo[3.1.0]hexan-6-yl)carbamate (For a preparation, see Intermediate 98, 380 mg, 1.672 mmol) was dissolved in HCl (4M in dioxane, 5 mL, 20.00 mmol) and the reaction mixture stirred at rt for 5 h. The reaction mixture was concentrated to give 3-methoxybicyclo[3.1.0]hexan-6-amine hydrochloride (270 mg, 1.402 mmol, 84% yield) as a light brown solid.

$^1$H NMR (400 MHz, DMSO-d$_6$) δ ppm 8.20 (br. s., 3H) 3.54 (m, J=7.30 Hz, 1H) 3.16 (s, 3H) 2.25 (br. s., 1H) 2.05-2.14 (m, 2H) 1.60-1.70 (m, 4H)

Intermediate 100: 7,7-Dimethyl-1,4-dioxaspiro[4.5]decan-8-one

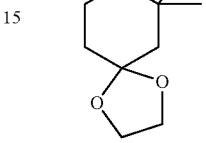

To a solution of 1,4-dioxaspiro[4.5]decan-8-one (5.45 g, 34.9 mmol, commercially available from, for example, Sigma Aldrich) in dry THF (20 mL) was added sodium hydride (60% in mineral oil, 2.79 g, 69.8 mmol) at 0° C. under nitrogen. The resulting reaction mixture was stirred at rt for 1 h followed by the addition of methyl iodide (5.45 mL, 87 mmol). The reaction mixture was stirred at 10° C. to rt over 1.5 h. The reaction mixture was quenched with saturated ammonium chloride solution (50 mL) and the aqueous layer was extracted with ethyl acetate (2×80 mL). The combined organic layers were washed with brine and dried through a hydrophobic frit. The organic layer was concentrated in vacuo to give ~6.8 g of crude yellow residue. This was purified by chromatography on SiO$_2$ (Biotage SNAP Ultra 100 g cartridge, eluting with 5-65% diethyl ether/cyclohexane) to give 7,7-dimethyl-1,4-dioxaspiro[4.5]decan-8-one (3.07 g, 14.16 mmol, 41% yield) as a colourless oil.

LCMS (2 min Formic): Rt=0.78 min, [MH]$^+$=185.0.

$^1$H NMR (400 MHz, CDCl$_3$) δ ppm 3.95-4.06 (m, 4H) 2.56-2.64 (m, 2H) 2.02 (d, J=1.26 Hz, 2H) 1.87-1.94 (m, 2H) 1.19 (s, 6H)

Intermediate 101: 7,7-Dimethyl-1,4-dioxaspiro[4.5]decan-8-ol

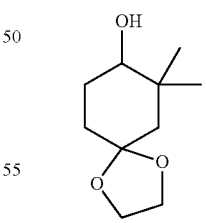

To a solution of 7,7-dimethyl-1,4-dioxaspiro[4.5]decan-8-one (For a preparation, see Intermediate 100, 3.04 g, 16.50 mmol) in methanol (10 mL) at 0° C. (ice-bath) was added sodium borohydride (0.624 g, 16.50 mmol) portionwise and the resulting reaction mixture was stirred at rt for 1 h. Water (10 mL) was added and the methanol removed in vacuo. The reaction mixture was partitioned between water and DCM. The organic layer was separated and the aqueous layer further extracted with DCM (2×20 mL). The combined organic layers were dried (hydrophobic frit) and concentrated under vacuum to give 7,7-dimethyl-1,4-dioxaspiro[4.5]decan-8-ol (2.87 g, 13.10 mmol, 79% yield) as a colourless oil.

LCMS (2 min Formic): Rt=0.62 min, [MH]⁺=187.1.

$^1$H NMR (400 MHz, CDCl$_3$) δ ppm 3.82-4.04 (m, 4H) 3.42 (ddd, J=8.31, 4.66, 3.40 Hz, 1H) 1.53-1.90 (m, 5H) 1.40-1.50 (m, 2H) 1.03 (br. s., 6H)

Intermediate 102:
4-Hydroxy-3,3-dimethylcyclohexanone

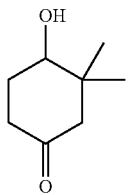

To a solution of 7,7-dimethyl-1,4-dioxaspiro[4.5]decan-8-ol (For a preparation, see Intermediate 101, 2.87 g, 15.41 mmol) in methanol (13 mL) was added HCl (2M aqueous solution, 30 mL, 60.0 mmol) and the reaction mixture stirred at rt overnight. The solvent was removed in vacuo and the residue neutralised (to ~pH 7) with sat. aqueous NaHCO$_3$ solution. The aqueous layer was extracted with ethyl acetate (2×40 mL) and the combined organic layers were dried (hydrophobic frit) and concentrated in vacuo to give 4-hydroxy-3,3-dimethylcyclohexan-1-one (2.18 g, 12.26 mmol, 80% yield) as a pale yellow oil.

LCMS (2 min Formic): Rt=0.54 min, [MH]⁺=143.0.

$^1$H NMR (400 MHz, CDCl$_3$) δ ppm 3.74 (dt, J=6.67, 3.46 Hz, 1H) 2.37-2.67 (m, 2H) 2.22-2.36 (m, 1H) 2.04-2.18 (m, 2H) 1.97 (dt, J=13.60, 6.80 Hz, 1H) 1.02 (br. s, 6H). Exchangeable proton not observed.

Intermediate 103:
4-(Benzylamino)-2,2-dimethylcyclohexanol, Mixture of Diastereomers

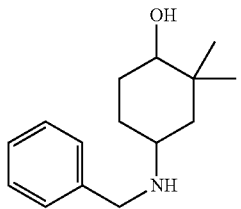 [SMILES: CC1(C)CC(NCc2ccccc2)CCC1O]

4-Hydroxy-3,3-dimethylcyclohexan-1-one (For a preparation, see Intermediate 102, 124 mg, 0.872 mmol) was dissolved in dichloromethane (2 mL). Phenylmethanamine (0.114 mL, 1.046 mmol) and acetic acid (0.050 mL, 0.872 mmol) were added and the reaction mixture was stirred under N$_2$ at rt After 3.5 h, sodium triacetoxyborohydride (222 mg, 1.046 mmol) was added and the reaction mixture stirred at rt overnight. The reaction mixture was quenched with sat. aqueous NaHCO$_3$ solution (5 mL) and the organic layer was separated. The aqueous layer was further extracted with DCM (2×10 mL) and the combined organic layers were dried (Na$_2$SO$_4$) and conc. to give 270 mg of crude yellow oil. This was purified by chromatography on SiO$_2$ (Biotage SNAP 25 g cartridge, eluting with 0-100% of (25% EtOH in ethyl acetate)/cyclohexane) to give a mixture of products. The desired fractions were concentrated to give 4-(benzylamino)-2,2-dimethylcyclohexanol (63 mg, 0.27 mmol, 26% yield) as a pale yellow oil.

LCMS (2 min Formic): Rt=0.38 min, [MH]⁺=234.2.

Intermediate 104:
(+/−)-4-Amino-2,2-dimethylcyclohexanol, Mixture of Diastereomers

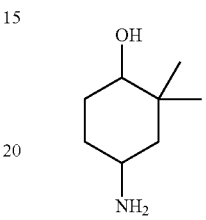

4-(Benzylamino)-2,2-dimethylcyclohexan-1-ol (For a preparation, see Intermediate 103, 63 mg, 0.270 mmol) was dissolved in ethyl acetate (6 mL), 10% palladium on carbon (40 mg) was added, and the mixture stirred under an atmosphere of hydrogen at rt for 21 h. The reaction mixture was filtered through celite to remove the catalyst and concentrated to give 4-amino-2,2-dimethylcyclohexan-1-ol (35 mg, 0.208 mmol, 77% yield) as a colourless oil as a racemic mixture of diastereomers. $^1$H NMR (400 MHz, CDCl$_3$) δ ppm 3.32 (dd, J=11.58, 4.53 Hz, 1H) 2.78-2.92 (m, 2H) 1.25-1.93 (m, 18H) 1.06-1.18 (m, 1H) 0.96-1.05 (m, 6H) 0.88-0.95 (m, 6H).

Intermediate 105: Methyl 1-tosyl-1H-indole-7-carboxylate

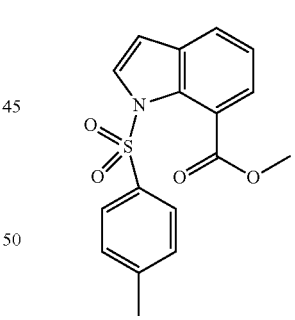

Methyl 1H-indole-7-carboxylate (1000 mg, 5.71 mmol, commercially available from, for example, Apollo Scientific) was taken up in DMF (18 mL) and cooled to 0° C. under nitrogen. Sodium hydride (60% suspension in mineral oil, 287 mg, 7.18 mmol) was added in small portions and the reaction was left to stir for 15 min. Tosyl-Cl (1308 mg, 6.86 mmol) was added, and the reaction was allowed to warm to rt and left to stir for 16 h. The reaction mixture was cooled to 0 degrees before the addition of further sodium hydride (60% suspension in mineral oil, 114 mg, 2.85 mmol). The reaction mixture was stirred for 15 min before being warmed to rt. The reaction mixture was stirred for a further 15 min before the addition of a further portion of tosyl-Cl (552 mg, 2.90 mmol). The resulting solution was stirred for 2 h. The reaction mixture was then heated to 60° C. for 1.5 h. The reaction mixture was quenched with water (~6 mL) before being partitioned between sat. aqueous LiCl (100 mL) and ethyl acetate (30 mL). The layers were separated and the aqueous was extracted twice more with ethyl acetate (2×30 mL). The combined organic layers were dried (hydrophobic frit) and concentrated in vacuo to give the crude product as a yellow oil. The crude product was redissolved in dichloromethane and directly applied to the top of a 100 g SNAP silica cartridge and purified by SP4 flash column chromatography (0-25% ethyl acetate/cyclohexane). The relevant fractions were combined and concentrated in vacuo to give methyl 1-tosyl-1H-indole-7-carboxylate (1025 mg, 2.80 mmol, 49% yield).

LCMS (2 min High pH): Rt=1.18 min, [MH]$^+$=330.1.

Intermediate 106: (1-Tosyl-1H-indol-7-yl)methanol

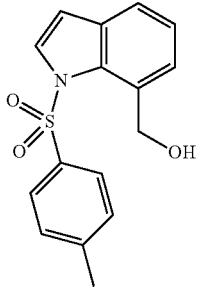 [SMILES: Cc1ccc(S(=O)(=O)n2ccc3cccc(CO)c32)cc1]

A solution of methyl 1-tosyl-1H-indole-7-carboxylate (For a preparation, see Intermediate 105, 1025 mg, 3.11 mmol) in dichloromethane (31 mL) under nitrogen, was cooled to −78° C. and DIBAL-H (1M solution in THF, 7.78 mL, 7.78 mmol) was added dropwise over 15 min and the reaction was stirred at −78° C. for 1.5 h. The reaction was left to stir for 18 h before the addition of further DIBAL-H (25% weight solution in toluene, 4.19 mL, 6.22 mmol). The reaction mixture was stirred for 20 h. The reaction was quenched with methanol when still at −78° C. and after allowed to warm to rt. The reaction was diluted with Rochelle's salt solution (10 mL) and stirred for 64 h. The layers were separated, and the aqueous phase was extracted with DCM (3×20 mL). The combined organic layers were dried through a hydrophobic frit, then concentrated in vacuo to yield the crude product (1-tosyl-1H-indol-7-yl)methanol (950 mg, 2.84 mmol, 91% yield) as an orange oil which was used as is for subsequent reactions.

LCMS (2 min High pH): Rt=1.18 min, [M-OH]+=284.1.

Intermediate 107: Methyl 1-tosyl-1H-indazole-4-carboxylate

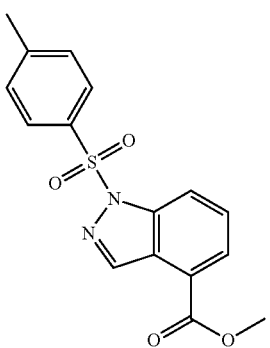 [SMILES: COC(=O)c1cccc2c1cnn2S(=O)(=O)c1ccc(C)cc1]

Methyl 1H-indazole-4-carboxylate (530 mg, 3.01 mmol, commercially available from, for example, Sigma Aldrich) was taken up in DMF (6.4 mL) and cooled to 0° C. under nitrogen. Sodium hydride (60% suspension in mineral oil, 241 mg, 6.02 mmol) was added in small portions and the reaction was left to stir for 10 min. Tosyl-Cl (775 mg, 4.07 mmol) was added before stirring for 30 min at 0° C. The reaction was allowed to warm to rt and left to stir for 1 h. The reaction mixture was poured onto 250 mL of water before filtering. The precipitate was dried in a vacuum oven overnight to give methyl 1-tosyl-1H-indazole-4-carboxylate (719 mg, 1.959 mmol, 65% yield).

LCMS (2 min High pH): Rt=1.22 min, [MH]$^+$=331.1.

Intermediate 108: (1-Tosyl-1H-indazol-4-yl)methanol

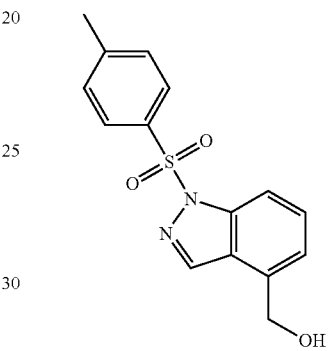

A solution of methyl 1-tosyl-1/indazole-4-carboxylate (For a preparation, see Intermediate 107, 804 mg, 2.434 mmol) in dichloromethane (24 mL) under nitrogen, was cooled to −78° C. and DIBAL-H (1.637 mL, 2.434 mmol, 25% wt in toluene) was added drop-wise over 15 min and the reaction was stirred at −78° C. for 62 h. Further DIBAL-H (3.27 mL, 4.87 mmol, 25% wt in toluene) was added to the reaction at −78° C. before stirring for 1 h. The reaction was quenched with methanol when still at −78° C. and after allowed to warm to rt. The reaction was diluted with Rochelle's salt solution (10 mL) and stirred for 16 h. The layers were separated, and the aqueous phase was extracted with DCM (3×20 mL). The combined organic layers were dried through a hydrophobic frit, then evaporated in vacuo to give (1-tosyl-1H-indazol-4-yl)methanol (686 mg, 2.042 mmol, 84% yield).

LCMS (2 min High pH): Rt=1.00 min, [MH]$^+$=303.1.

Intermediate 109: (+/−)-1-(3-Fluoro-2-methylphenyl)ethanol

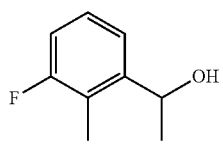

1-(3-Fluoro-2-methylphenyl)ethan-1-one (1000 mg, 6.57 mmol, commercially available from, for example, Alfa Aesar) was taken up in THF (10 mL) and ethanol (10 mL), cooled to 0° C., and put under nitrogen. Sodium borohydride (456 mg, 12.05 mmol) was added, and the reaction left to stir at rt for 1.5 h. The reaction was slowly quenched with 1M HCl until pH 3, before the addition of water. The layers were separated and the aqueous layer extracted twice more with DCM (2×20 mL). The organic layers were back extracted with sodium bicarbonate aq. solution, passed through a hydrophobic frit and concentrated in vacuo to yield a colourless oil as the crude product, 1-(3-fluoro-2-methylphenyl)ethan-1-ol (875 mg, 5.11 mmol, 78% yield).

LCMS (2 min Formic): Rt=0.85 min, No [MH]+

Intermediate 110: Ethyl 3-(benzyloxy)bicyclo[3.1.0]hexane-6-carboxylate, Mixture of Diastereomers

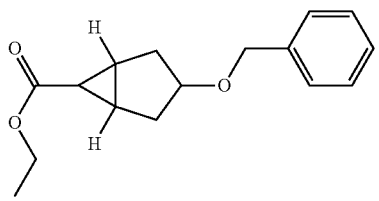 [SMILES: CCOC(=O)C1C2CC(OCc3ccccc3)CC21]

Ethyl diazoacetate (15 mL, 21.69 mmol) was dissolved in DCM (100 mL) and added dropwise to a mixture of ((cyclopent-3-en-1-yloxy)methyl)benzene (3.1 g, 17.79 mmol, commercially available from, for example, Fluorochem) and rhodium(II) acetate dimer (0.393 g, 0.890 mmol) in DCM (100 mL) at rt over 4 h, then the mixture was stirred for a further 2 h, then washed with water (300 mL) and the organic layer dried and evaporated in vacuo to give a pale green liquid. This was purified using silica gel column chromatography eluting with a gradient of 0-20% EtOAc/cyclohexane to give (+/−)-ethyl 3-(benzyloxy)bicyclo[3.1.0]hexane-6-carboxylate (0.91 g, 3.50 mmol, 20% yield) as a colourless liquid.

LCMS (2 min High pH): Rt=1.26 min, [MH]+=261.3

Intermediate 111: 3-(Benzyloxy)bicyclo[3.1.0]hexane-6-carboxylic acid, Mixture of Diastereomers

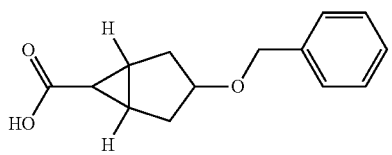 [SMILES: O=C(O)C1C2CC(OCc3ccccc3)CC21]

(+/−)-Ethyl 3-(benzyloxy)bicyclo[3.1.0]hexane-6-carboxylate (For a preparation, see Intermediate 110, 0.9 g, 3.46 mmol) was dissolved in EtOH (20 mL) and NaOH (5 mL, 10.00 mmol, 2M aqueous) was added, then the mixture was stirred at rt overnight. The solvent was evaporated in vacuo to about half its original volume, then acidified with 2M HCl (aq) to pH 4 and extracted with EtOAc (50 mL). The organic layer was dried and evaporated in vacuo to give (+/−)-3-(benzyloxy)bicyclo[3.1.0]hexane-6-carboxylic acid (0.74 g, 3.19 mmol, 92% yield) as a colourless solid and a mixture of diastereomers.

LCMS (2 min High pH): Rt=0.56 min, [MH]+=233.3

Intermediate 112: tert-Butyl (3-(benzyloxy)bicyclo[3.1.0]hexan-6-yl)carbamate, mixture of diastereomers

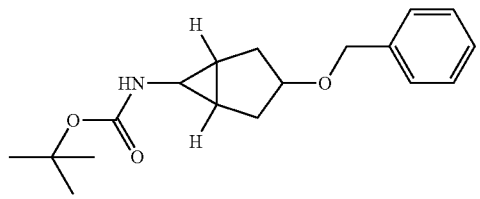 [SMILES: CC(C)(C)OC(=O)NC1C2CC(OCc3ccccc3)CC21]

3-(Benzyloxy)bicyclo[3.1.0]hexane-6-carboxylic acid (For a preparation, see Intermediate 111, 0.74 g, 3.19 mmol), diphenyl phosphoryl azide (1.140 g, 4.14 mmol) and Et₃N (0.888 mL, 6.37 mmol) were dissolved in toluene (20 mL) and the mixture was stirred for 30 min, then tert-butanol (6 mL) was added and the mixture was heated at reflux for 3 h, then allowed to stand at rt overnight. The mixture was diluted with EtOAc, then washed with water and sat NaHCO₃ (aq.) and evaporated in vacuo. The resulting gum was purified using silica gel column chromatography eluting with a gradient of 0-30% EtOAc:cyclohexane to give tert-butyl ((1R,3r,5S,6s)-3-(benzyloxy)bicyclo[3.1.0]hexan-6-yl)carbamate (0.35 g, 1.154 mmol, 36.2% yield) as a colourless solid and a mixture of diastereomers.

LCMS (2 min High pH): Rt=1.26 min, [MH]+=304.3.

Intermediate 113: 3-(Benzyloxy)bicyclo[3.1.0]hexan-6-amine, HCl, Mixture of Diastereomers

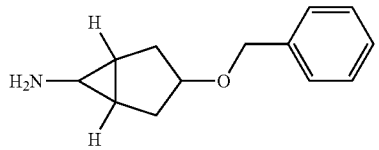 [SMILES: NC1C2CC(OCc3ccccc3)CC12]

tert-Butyl (3-(benzyloxy)bicyclo[3.1.0]hexan-6-yl)carbamate (For a preparation, see Intermediate 112, 350 mg, 1.154 mmol) was dissolved in HCl (4M in dioxane, 5 mL, 20.00 mmol) and reaction mixture stirred at rt for 4 h. The reaction mixture was concentrated to give 3-(benzyloxy)bicyclo[3.1.0]hexan-6-amine, hydrochloride (253 mg, 0.897 mmol, 78% yield) as a pale yellow solid and a mixture of diastereomers.

LCMS (2 min High pH): Rt=0.90 min, [MH]+=204.2.

Intermediate 114: (+/−)-7-Methyl-1,4-dioxaspiro[4.5]decan-8-one

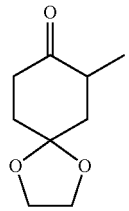

To a solution of 1,4-dioxaspiro[4.5]decan-8-one (1.04 g, 6.66 mmol, available from commercial suppliers such as Apollo Scientific) in THF (67 mL) under $N_2$ at −78° C. was added 1M LiHMDS in THF (7.32 mL, 7.32 mmol). The reaction was stirred for 1 h and MeI (0.547 mL, 8.66 mmol) was added dropwise. The reaction was stirred for 3 h at −78° C., and then left to warm up to rt overnight. It was then quenched with a sat. $NH_4Cl$ (aq) solution and extracted with EtOAc. The combined organics were filtered through a hydrophobic frit and concentrated in vacuo to a brown oil. This oil was purified by silica gel column chromatography eluting with a gradient of 0 to 32% EtOAc:cyclohexane to give (+/−)-7-methyl-1,4-dioxaspiro[4.5]decan-8-one (443 mg, 2.60 mmol, 39% yield) as a white solid.

$^1$H NMR (400 MHz, MeOH-$d_4$) δ ppm 3.95-4.16 (m, 4H) 2.58-2.88 (m, 2H) 2.24-2.41 (m, 1H) 2.04-2.17 (m, 2H) 1.90-2.01 (m, 1H) 1.71 (t, J=13.1 Hz, 1H) 0.94-1.07 (m, 3H)

Intermediate 115: (+/−)-(trans)-7-Methyl-1,4-dioxaspiro[4.5]decan-8-ol

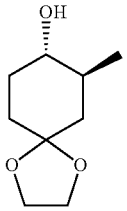

To a solution of 7-methyl-1,4-dioxaspiro[4.5]decan-8-one (For a preparation, see Intermediate 114, 438 mg, 2.57 mmol) in THF (10 mL) at −78° C. was added a 2M $LiAlH_4$ solution in THF (1.67 mL, 3.35 mmol). The mixture was stirred 1.5 h at −78° C. It was then allowed to warm to 0° C., the reaction mixture was carefully quenched with a Rochelle salt solution. EtOAc was added and the layers were separated, the aqueous layer was extracted with EtOAc and the combined organics were filtered through a hydrophobic frit and concentrated in vacuo to give (+/−)-(trans)-7-methyl-1,4-dioxaspiro[4.5]decan-8-ol (430 mg, 2.397 mmol, 93% yield) as a colourless oil.

$^1$H NMR (600 MHz, DMSO-$d_6$) δ=4.43 (d, J=5.5 Hz, 1H), 3.88-3.75 (m, 4H), 2.96 (ddt, J=4.8, 5.7, 10.1 Hz, 1H), 1.75-1.68 (m, 1H), 1.64-1.60 (m, 1H), 1.63-1.59 (m, 1H), 1.51-1.44 (m, 1H), 1.48-1.41 (m, 1H), 1.43-1.35 (m, 1H), 1.19 (t, J=12.9 Hz, 1H), 0.89 (d, J=6.6 Hz, 3H)

Intermediate 116: (+/−)-(trans)-4-Hydroxy-3-methylcyclohexanone

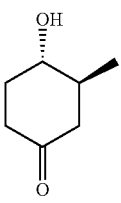

To a solution of (+/−)-(trans)-7-methyl-1,4-dioxaspiro[4.5]decan-8-ol (For a preparation, see Intermediate 115, 425 mg, 2.468 mmol) in acetone (7 mL) was added $H_2SO_4$ (18 mL, 9.00 mmol, 0.5M) and the solution was stirred for 20 h at rt. The reaction mixture was diluted with water and extracted with EtOAc. The combined organics were filtered through a hydrophobic frit and concentrated in vacuo to give (+/−)-(trans)-4-hydroxy-3-methylcyclohexan-1-one (290 mg, 2.265 mmol, 92% yield) as a yellow oil.

$^1$H NMR (400 MHz, MeOH-$d_4$) δ ppm 3.93 (d, J=2.3 Hz, 1H) 3.10 (td, J=10.2, 4.4 Hz, 1H) 1.90-2.13 (m, 2H) 1.73-1.86 (m, 1H) 1.25-1.59 (m, 2H) 1.09 (t, J=13.1 Hz, 1H) 0.97-1.03 (m, 3H).

Exchangeable Proton not Observed

Intermediate 117: (S)—N-((1S,3R,4R)-4-Hydroxy-3-methylcyclohexyl)-2-methylpropane-2-sulfinamide and (S)—N-((1S,3S,4S)-4-hydroxy-3-methylcyclohexyl)-2-methylpropane-2-sulfinamide (1:1 Diasteromeric Mixture)

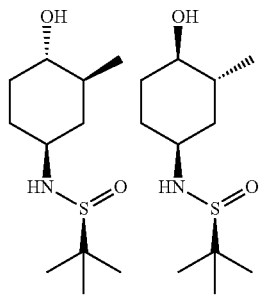

(+/−)-(trans)-4-hydroxy-3-methylcyclohexan-1-one (For a preparation, see Intermediate 116, 1.99 g, 15.53 mmol) was added to a solution of (R)-2-methylpropane-2-sulfinamide (2.304 g, 18.63 mmol) and tetraethoxytitanium (5.43 mL, 25.9 mmol) in THF (30 mL) and the reaction was stirred at 60° C. for 1.5 h and then at 70° C. for 1.5 h. The mixture was cooled to rt and then to −78° C. A 1M solution of L-selectride in THF (38.8 mL, 38.8 mmol) was added dropwise and the reaction mixture was allowed to warm slowly to rt with stirring overnight. The reaction mixture was then cooled to 0° C. and MeOH was added dropwise. The crude reaction mixture was poured onto brine. The resulting suspension was filtered through a plug of Celite, and the filter cake was washed with EtOAc. The filtrate was then concentrated in vacuo, diluted with water and extracted EtOAc. The combined organics were filtered through a hydrophobic frit and concentrated in vacuo to a yellow oil. This oil was purified using silica gel column chromatography eluting with a gradient of 10 to 42% of (25% EtOH in AcOEt):cyclohexane to give (S)—N-((1S,3R,4S)-4-hydroxy-3-methylcyclohexyl)-2-methylpropane-2-sulfinamide and (S)—N-((1S,3S,4S)-4-hydroxy-3-methylcyclohexyl)-2-methylpropane-2-sulfinamide (1:1 diasteromeric mixture) (303.5 mg, 1.301 mmol, 8% yield) as a yellow gum which was used directly in the next reaction.

Intermediate 118: (1R,2R,4S)-4-Amino-2-methylcyclohexanol and (1S,2S,4S)-4-amino-2-methylcyclohexanol (1:1 Diastereomeric Mixture)

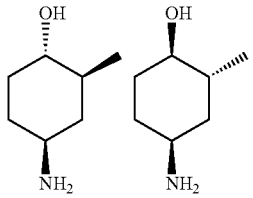

4M HCl in dioxane (1 mL, 4.00 mmol) was added to a solution of (S)—N-(1S,3R,4R)-4-hydroxy-3-methylcyclohexyl)-2-methylpropane-2-sulfinamide compound and (S)—N-((1S,3S,4S)-4-hydroxy-3-methylcyclohexyl)-2-methylpropane-2-sulfinamide (1:1 diasteromeric mixture, For a preparation, see Intermediate 117) (300 mg, 1.286 mmol) in DCM (5 mL) and the reaction was stirred overnight at rt. More 4M HCl in dioxane (1 mL, 4.00 mmol) was added and the reaction was stirred 6 h at rt. Further 4M HCl in dioxane (1 mL, 4.00 mmol) was added and the reaction was stirred 1 h at rt. The reaction was concentrated in vacuo, dissolved in MeOH and eluted through a 2 g SCX column (pre-conditioned with MeOH) washing with MeOH and 2M NH$_3$ in MeOH solution. The ammonia fractions were concentrated in vacuo to give (1R,2R,4S)-4-amino-2-methylcyclohexanol and (1S,2S,4S)-4-amino-2-methylcyclohexanol (1:1 diastereomeric mixture) (74.5 mg, 0.577 mmol, 45% yield) as a brown gum.

$^1$H NMR (400 MHz, DMSO-d$_6$) δ ppm 4.17-4.51 (m, 2H) 2.91-3.03 (m, 2H) 2.86 (td, J=10.2, 4.3 Hz, 2H) 1.61-1.82 (m, 4H) 1.35-1.58 (m, 4H) 1.09-1.28 (m, 4H) 0.95-1.07 (m, 2H) 0.90 (dd, J=9.4, 6.7 Hz, 6H) 0.61-0.84 (m, 2H)

Intermediate 119: (R)-1-(3-Fluoro-4-methylphenyl)ethanol

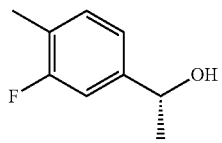

(+)-DIP-Cl (1.265 g, 3.94 mmol) was taken up in THF (20 mL) and was cooled to −25° C. under N$_2$. 1-(3-Fluoro-4-methylphenyl)ethan-1-one (0.5 g, 3.29 mmol, available from commercial suppliers such as Alfa Aesar) in THF (10 mL) was added and the reaction was left to stir overnight as it warmed from −25° C. to rt. The reaction was cooled to −35° C. and additional (+)-DIP-Cl (1.265 g, 3.94 mmol) in THF (5 mL) was added. The reaction was kept between −35 and −25° C. as it stirred for 6 h and then was allowed to warm to rt overnight. The reaction was quenched with acetaldehyde (0.5 mL, 8.85 mmol) and concentrated in vacuo. The residue was taken up in Et$_2$O (20 mL) and diethanolamine (1.036 g, 9.86 mmol) was added, this was left to stir for 2 h. The white precipitate was filtered off through Celite, and the filtrate was concentrated in vacuo to give a colourless oil. This oil was purified using silica gel column chromatography eluting with a gradient of 0-25% EtOAc:cyclohexane to give (R)-1-(3-fluoro-4-methylphenyl)ethan-1-ol (836 mg, 2.71 mmol, 83% yield) as a colourless liquid.

LCMS (2 min Formic): Rt=0.89 min, no [MH]$^+$

Intermediate 120: (+/−)-7-Chlorobicyclo[3.2.0]hept-2-en-6-one

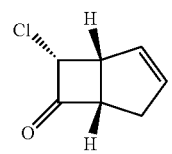

Zinc (8.42 g, 129 mmol) was added in small portions over 1 h to a solution of (+/−)-7,7-dichlorobicyclo[3.2.0]hept-2-en-6-one (24 g, 136 mmol, available from commercial suppliers such as Alfa Aesar) in AcOH (100 mL) at rt. The mixture was stirred for a further 1 h, then diluted with water and extracted with diethyl ether. The organic layer was washed with water and sat. sodium bicarbonate solution and brine, then dried and evaporated in vacuo to give (+/−)-7-chlorobicyclo[3.2.0]hept-2-en-6-one (20 g, 140 mmol, purity=70%) as a pale yellow liquid.

$^1$H NMR (400 MHz, CDCl$_3$) δ ppm 5.89-5.97 (m, 1H) 5.70-5.79 (m, 1H) 5.03-5.14 (m, 1H) 3.78-3.97 (m, 2H) 2.66-2.80 (m, 1H) 2.41-2.55 (m, 1H)

Intermediate 121: (+/−)-Bicyclo[3.1.0]hex-2-ene-6-carboxylic acid, Mixture of Diastereomers

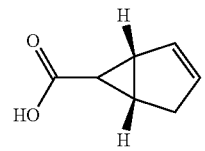

To a stirred mixture of KOH (2.16 g, 38.5 mmol) in 1,4-dioxane (24 mL) and water (10 mL) was added (+/−)-7-chlorobicyclo[3.2.0]hept-2-en-6-one (For a preparation, see Intermediate 120, 1.307 g, 5.50 mmol) dropwise. The flask containing the chloro-SM was then washed into the reaction vessel with further 1,4-dioxane (300 µL). The reaction was stirred for 30 min. The reaction was acidified with 2M HCl(aq.) to pH 2. The organics were extracted with DCM (3×40 mL) and the combined organics allowed to stand overnight. After 16 h, the combined organics were dried (Na$_2$SO$_4$), filtered and concentrated in vacuo to afford a brown oil. This was dried further in vacuo to afford the desired product as a brown waxy solid-(+/−)-bicyclo[3.1.0]hex-2-ene-6-carboxylic acid (581 mg, 4.68 mmol, 85% yield) which was a mixture of ~40%-endo/~60%-exo (desired).

LCMS (2 min Formic): (exo) Rt=0.65 min, no m/z; (endo) Rt=0.54 min, no m/z

Intermediate 122: (+/−)-Benzyl (cis)-bicyclo[3.1.0]hex-2-en-6-ylcarbamate

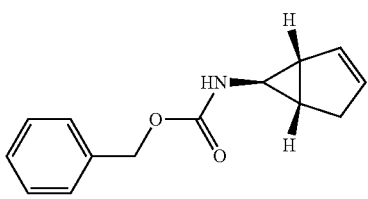 [SMILES: O=C(N[C@H]1[C@@H]2C=CC[C@@H]21)OCc1ccccc1]

DPPA (26.0 mL, 121 mmol) was added to a solution of (+/−)-bicyclo[3.1.0]hex-2-ene-6-carboxylic acid, mixture of diastereomers (For a preparation, see Intermediate 121, 10 g, 81 mmol) and Et$_3$N (22.46 mL, 161 mmol) in toluene (10 mL) at rt and the mixture was stirred for 30 min, then benzyl alcohol (16.75 mL, 161 mmol) was added and the mixture heated at reflux for 3 h. The solution was diluted with EtOAc and washed with water and sat. sodium bicarbonate solution (aq), then dried and evaporated in vacuo to give a brown oil. This oil was purified using silica gel column chromatography eluting with a gradient of 0-50% EtOAc: cyclohexane to give (+/−)-benzyl ((cis)-bicyclo[3.1.0]hex-2-en-6-yl)carbamate (3.7 g, 16.14 mmol, 20.03% yield) as a colourless solid.

LCMS (2 min Formic): Rt=1.08 min, [MH]$^+$=230.3

Intermediate 123: (+/−)-Benzyl ((cis)-2-hydroxybicyclo[3.1.0]hexan-6-yl)carbamate

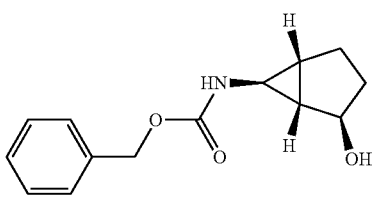 [SMILES: O=C(N[C@H]1[C@@H]2CC[C@@H](O)[C@@H]21)OCc1ccccc1]

Borane-methyl sulfide complex (2.299 mL, 24.21 mmol) was added to a solution of (+/−)-benzyl ((cis)-bicyclo[3.1.0]hex-2-en-6-yl)carbamate (For a preparation, see Intermediate 122, 3.7 g, 16.14 mmol) in THF (10 mL) at 0° C. and the mixture was stirred for 2 h, then allowed to warm to rt over 30 min. Water (2 mL) was added followed by aqueous solution of 2M NaOH (16.14 mL, 32.3 mmol). The mixture was cooled in an ice bath then H$_2$O$_2$ (30%, 3.30 mL, 32.3 mmol) was added and the mixture was stirred for a further 1 h. The mixture was diluted with EtOAc and water and the mixture stirred vigorously for 30 min, then the organic layer separated and the aqueous extracted with EtOAc. The combined organics were washed with 5% sodium thiosulphate solution (aq.) then dried and evaporated in vacuo to give a gum. This gum was triturated with ether and the resulting colourless solid collected by filtration. The filtrate was evaporated in vacuo to give a colourless gum which was purified by silica gel column chromatography eluting with a gradient of 0-50% EtOAc:cyclohexane. Later running fractions gave a colourless gum (0.53 g), which partially solidified on standing. This material was dissolved in EtOAc and allowed to stand overnight, giving a colourless solid, which was collected by filtration. The filtrate was evaporated in vacuo to give a colourless gum. This gum was purified using silica gel column chromatography eluting with a gradient of 0-50% EtOAc:cyclohexane to give (+/−) benzyl ((cis)-2-hydroxybicyclo[3.1.0]hexan-6-yl)carbamate (180 mg, 0.728 mmol, 5% yield) as a colourless gum.

$^1$H NMR (600 MHz, DMSO-d$_6$) δ ppm 7.19-7.44 (m, 6H) 4.96-5.04 (m, 2H) 4.53 (d, J=1.0 Hz, 1H) 4.07 (t, J=4.6 Hz, 1H) 2.09 (br. s., 1H) 1.83 (m, J=1.0, 1.0 Hz, 1H) 1.62 (dd, J=12.1, 8.4 Hz, 1H) 1.32-1.40 (m, 3H) 1.09-1.23 (m, 1H)

Intermediate 124: (+/−)-(cis)-6-Aminobicyclo[3.1.0]hexan-2-ol

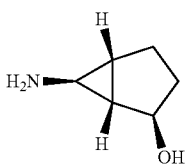

(+/−)-Benzyl ((cis)-2-hydroxybicyclo[3.1.0]hexan-6-yl)carbamate (For a preparation, see Intermediate 123, 180 mg, 0.728 mmol) was dissolved in EtOH (10 mL) and 10% Pd/C (35 mg, 0.329 mmol) was added. The reaction mixture was hydrogenated under atmospheric pressure for 6.5 h. The catalyst was filtered off and the reaction mixture concentrated to give (+/−)-(cis)-6-aminobicyclo[3.1.0]hexan-2-ol (82 mg, 0.728 mmol, purity=80%) as a pale yellow oil which was used crude directly in the next step.

Intermediate 125: (+/−)-(trans)-3-Methoxycyclopentanamine hydrochloride

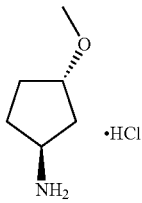

(+/−)-tert-butyl ((trans)-3-methoxycyclopentyl)carbamate (For a preparation, see Intermediate 126, 280 mg, 1.040 mmol) was taken up in a solution of 4M hydrochloric acid in dioxane (2.5 mL, 10.00 mmol) and was stirred for 2 h. The reaction mixture was concentrated in vacuo to give (+/−)-(trans)-3-methoxycyclopentan-1-amine hydrochloride (167 mg, 0.991 mmol, 95% yield).

$^1$H NMR (400 MHz, DMSO-d$_6$) δ ppm 8.05 (br s, 3H) 3.85-3.89 (m, 1H) 3.50-3.57 (m, 1H) 3.17 (s, 3H) 1.89-2.04 (m, 3H) 1.70-1.77 (m, 1H) 1.55-1.65 (m, 2H).

Intermediate 126: (+/−)-tert-Butyl ((trans)-3-methoxycyclopentyl)carbamate

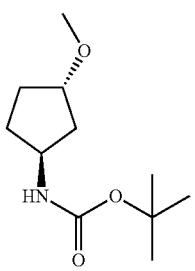

Crushed 3 Å molecular sieves were placed under vacuum in a 250 mL round-bottom flask and heated with a heat gun. The flask was allowed to cool, and (+/−)-tert-butyl ((trans)-3-hydroxycyclopentyl)carbamate (370 mg, 1.838 mmol, commercially available from, for example, Fluorochem) in anhydrous dichloromethane (13 mL) was added. N1,N1,N8,N8-Tetramethylnaphthalene-1,8-diamine (1.357 g, 6.33 mmol) was added, and the reaction was cooled to 0° C. and placed under an atmosphere of nitrogen. Trimethyloxonium tetrafluoroborate (680 mg, 4.60 mmol) was added, and the reaction allowed to warm to rt and stirred rapidly for 20 h. The reaction was diluted with dichloromethane (50 mL) and washed with water (50 mL). The aqueous layer was extracted with dichloromethane (2×25 mL), and the combined organics were washed with aqueous 0.5 M HCl solution (15 mL), saturated sodium bicarbonate solution (20 mL), and brine (30 mL). The organic phase was passed through a hydrophobic frit and concentrated in vacuo to yield a yellow oil. The crude product was redissolved in dichloromethane and directly applied to the top of a 25 g SNAP silica cartridge and purified by SP4 flash column chromatography eluting with a gradient of 0-100% ethyl acetate in cyclohexane. The relevant fractions were combined and concentrated in vacuo to give (+/−)-tert-butyl ((trans)-3-methoxycyclopentyl)carbamate (280 mg, 1.040 mmol, 57% yield).

$^1$H NMR (400 MHz, DMSO-$d_6$) δ ppm 6.80 (br d, 1H) 3.84 (q, 1H) 3.75-3.80 (m, 1H) 3.14 (s, 3H) 1.80-1.90 (m, 3H) 1.46-1.56 (m, 2H) 1.38 (s, 9H) 1.29-1.36 (m, 1H).

Intermediate 127:
1-(3-(2-Hydroxyethoxy)phenyl)ethanone

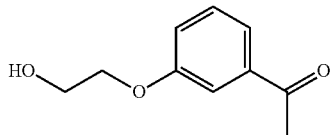

3-Hydroxyacetophenone (5.0 g, 36.7 mmol, commercially available from, for example, Sigma Aldrich), ethylene carbonate (4.85 g, 55.1 mmol) and potassium carbonate (5.08 g, 36.7 mmol) were mixed in DMF (50 mL) and heated at 120° C. overnight under nitrogen, then the mixture was diluted with water (200 mL) and extracted with EtOAc (2×100 mL). The combined organics were washed with water (200 mL) and brine (200 mL), dried and evaporated in vacuo to give a pale yellow oil. This was dissolved in DCM and loaded onto a 100 g SNAP Ultra column and eluted with 0-100% EtOAc/cyclohexane. The product-containing fractions were evaporated in vacuo to give 1-(3-(2-hydroxyethoxy)phenyl)ethan-1-one (5.5 g, 30.5 mmol, 83% yield), which was used directly in the next step.

LCMS (2 min High pH): Rt=0.67 min, [M−H]$^−$=179.1.

Intermediate 128: 1-(3-(2-((tert-Butyldimethylsilypoxy)ethoxy)phenyl)ethanone

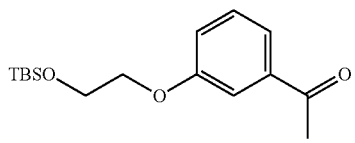 [SMILES: CC(=O)c1cccc(OCCO[Si](C)(C)C(C)(C)C)c1]

TBDMS-Cl (4.97 g, 33.0 mmol) was added to a mixture of 1-(3-(2-hydroxyethoxy)phenyl)ethan-1-one (For a preparation, see Intermediate 127, 5.4 g, 30.0 mmol) and imidazole (2.45 g, 36.0 mmol) in DCM (50 mL) and the mixture was stirred for 2 h, then allowed to stand over the weekend. The resulting suspension was washed with water (2×100 mL) and the organic layer dried and evaporated in vacuo to give a colourless oil. This was loaded onto a 100 g SNAP ultra silica column and purified by flash chromatography eluting with 0-30% EtOAc/cyclohexane. The product-containing fractions were evaporated in vacuo to give 1-(3-(2-((tert-butyldimethylsilyl)oxy)ethoxy)phenyl)ethan-1-one (6.6 g, 22.41 mmol, 75% yield) as a colourless liquid which was used directly in the next step.

LCMS (2 min Formic): Rt=1.46 min, [MH]$^+$=295.3.

Intermediate 129: (+/−)-1-(3-(2-((tert-Butyldimethylsilypoxy)ethoxy)phenyl)-ethanol

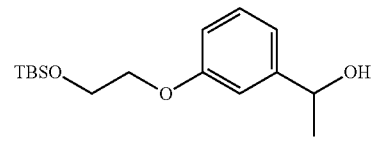 [SMILES: CC(O)c1cccc(OCCO[Si](C)(C)C(C)(C)C)c1]

Sodium borohydride (1.27 g, 33.6 mmol) was added to a solution of 1-(3-(2-((tert-butyldimethylsilyl)oxy)ethoxy)phenyl)ethan-1-one (For a preparation, see Intermediate 128, 6.6 g, 22.41 mmol) in ethanol (50 mL) at 0° C. and the mixture was stirred for 2 h, then quenched by very cautious addition of ammonium chloride solution (50 mL, initially slowly and dropwise-vigorous effervescence!). The resulting mixture was diluted with brine (50 mL) and extracted with EtOAc (2×100 mL), the combined organics dried and evaporated in vacuo to give 1-(3-(2-((tert-butyldimethylsilyl)oxy)ethoxy)phenyl)ethan-1-ol (5.61 g, 18.92 mmol, 84% yield) as a colourless oil which was used directly in the next step.

LCMS (2 min High pH): Rt=1.41 min, [MH]$^+$=296.3.

Intermediate 130: (+/−)-Methyl 1-(1-(3-(2-((tert-butyldimethylsilyl)oxy)ethoxy)phenyl)ethyl)-3-(methylcarbamoyl)-1H-pyrazole-5-carboxylate

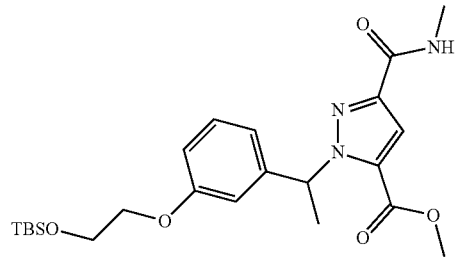 [SMILES: CNC(=O)c1cc(C(=O)OC)n(C(C)c2cccc(OCCO[Si](C)(C)C(C)(C)C)c2)n1]

DIAD (1.38 mL, 7.10 mmol) in DCM (10 mL) was added dropwise over 5 min to a solution of methyl 3-(methylcarbamoyl)-1H-pyrazole-5-carboxylate (For a preparation, see Intermediate 1, 1 g, 5.46 mmol), 1-(3-(2-((tert-butyldimethylsilyl)oxy)ethoxy)phenyl)-ethan-1-ol (For a preparation, see Intermediate 129, 1.942 g, 6.55 mmol) and triphenylphosphine (1.862 g, 7.10 mmol) in DCM (20 mL) at 0° C. and the mixture was stirred overnight, allowing it to warm to rt. The solution was washed with water (20 mL), dried and evaporated in vacuo to give a pale yellow gum. This was dissolved in DCM and loaded onto a 100 g SNAP ultra silica column, then eluted with 0-60% EtOAc/cyclohexane and the product-containing fractions were evaporated in vacuo to give (+/−)-methyl 1-(1-(3-(2-((tert-butyldimethylsilyl)oxy)ethoxy)phenyl)ethyl)-3-(methylcarbamoyl)-1H-pyrazole-5-carboxylate (2.61 g, 5.65 mmol, 104% yield) as a pale yellow gum, which was a 4:1 mixture of diastereomers (with alternate pyrazole alkylation product as minor component).

LCMS (2 min Formic): Rt=1.43 min, [MH]$^+$=462.3.

Intermediate 131: (+/−)-1-(1-(3-(2-((tert-Butyldimethylsilypoxy)ethoxy)phenyl)ethyl)-3-(methylcarbamoyl)-1H-pyrazole-5-carboxylic acid

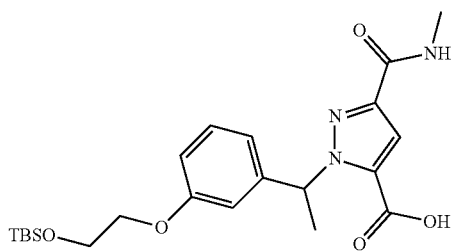 [SMILES: CNC(=O)c1cc(C(=O)O)n(C(C)c2cccc(OCCO[Si](C)(C)C(C)(C)C)c2)n1]

(+/−)-Methyl 1-(1-(3-(2-((tert-butyldimethylsilyl)oxy)ethoxy)phenyl)ethyl)-3-(methylcarbamoyl)-1H-pyrazole-5-carboxylate (For a preparation, see Intermediate 130, 2.6 g, 5.63 mmol) was dissolved in methanol (30 mL) and NaOH (10 mL, 20.00 mmol, 2M in water) was added, then the mixture was stirred at rt for 2 h. The solvent was then evaporated in vacuo. The resulting solid was dissolved in water (30 mL) and washed with ether (2×30 mL) then the aqueous layer was acidified with 2M HCl(aq.) (11 mL) and the resulting mixture was extracted with EtOAc (2×30 mL). The combined organics were washed with water, dried and evaporated in vacuo to give (+/−)-1-(1-(3-(2-((tert-butyldimethylsilyl)oxy)ethoxy)phenyl)ethyl)-3-(methylcarbamoyl)-1H-pyrazole-5-carboxylic acid (2.22 g, 4.96 mmol, 88% yield) as a colourless gum, as an approximately 4:1 ratio of regioisomers (with alternate pyrazole alkylation product as minor component from previous step), which appeared to be inseparable at this stage.

LCMS (2 min High pH): Rt=0.99 min, [MH]$^+$=448.4.

Intermediate 132: 1-(1-(3-(2-((tert-Butyldimethylsilypoxy)ethoxy)phenyl)ethyl)-N$^3$-methyl-N$^5$-((1S,2S)-2-methylcyclopropyl)-1H-pyrazole-3,5-dicarboxamide, Mixture of Diastereomers

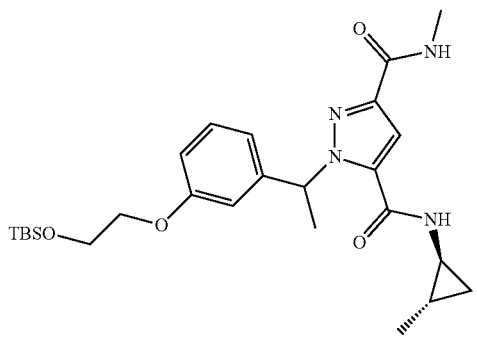 [SMILES: CNC(=O)c1cc(C(=O)N[C@H]2C[C@@H]2C)n(C(C)c2cccc(OCCO[Si](C)(C)C(C)(C)C)c2)n1]

(+/−)-1-(1-(3-(2-((tert-Butyldimethylsilypoxy)ethoxy)phenyl)ethyl)-3-(methylcarbamoyl)-1H-pyrazole-5-carboxylic acid (For a preparation, see Intermediate 131, 2 g, 4.47 mmol), (1S,2S)-2-methylcyclopropan-1-amine, hydrochloride (0.625 g, 5.81 mmol), HATU (2.209 g, 5.81 mmol) and Et$_3$N (1.868 mL, 13.40 mmol) were dissolved in DCM (20 mL) and the mixture was stirred for 2 h, then allowed to stand over the weekend at rt. The resulting mixture was stirred with water (50 mL) for 1 h, then the organic layer was separated, dried and evaporated in vacuo to give a pale yellow gum. This was dissolved in DCM and loaded onto a 100 g SNAP ultra silica column and purified by flash chromatography eluting with 0-100% EtOAc/cyclohexane. The product-containing fractions were evaporated in vacuo to give 1-(1-(3-(2-((tert-butyldimethylsilyl)oxy)ethoxy)phenyl)ethyl)-N$^3$-methyl-N$^5$-((1S,2S)-2-methylcyclopropyl)-1H-pyrazole-3,5-dicarboxamide (1.10 g, 2.197 mmol, 49% yield, mixture of diastereomers) as a colourless solid.

LCMS (2 min Formic): Rt=1.44 min, [MH]$^+$=501.4.

EXAMPLES

Example 1: N$^5$-((1R,5S,6r)-3-Oxabicyclo[3.1.0]hexan-6-yl)-N$^3$-methyl-1-((S)-1-phenylethyl)-1H-pyrazole-3,5-dicarboxamide

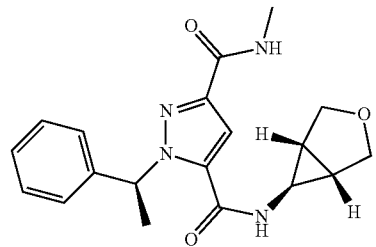 [SMILES: CNC(=O)c1cc(C(=O)N[C@H]2[C@@H]3COC[C@@H]32)n([C@@H](C)c2ccccc2)n1]

To a solution of (S)-3-(methylcarbamoyl)-1-(1-phenylethyl)-1H-pyrazole-5-carboxylic acid (98 mg, 0.359 mmol) in DMF (0.8 mL) was added HATU (205 mg, 0.538 mmol) followed by (1R,5S,6r)-3-oxabicyclo[3.1.0]hexan-6-amine, hydrochloride (107 mg, 0.789 mmol) and DIPEA (0.313 mL, 1.793 mmol). The resulting reaction mixture was stirred at rt in air for 18 h. The reaction mixture was purified by MDAP (Formic). The fractions containing desired product were partitioned between sat. NaHCO$_3$ solution and DCM. The organic layer was separated and aqueous layer further extracted with DCM (2×20 mL). Combined organic layers were dried (Na$_2$SO$_4$) and concentrated in vacuo to give N-((1R,5S,6r)-3-oxabicyclo[3.1.0]hexan-6-yl)-N$^3$-methyl-1-((S)-1-phenylethyl)-1H-pyrazole-3,5-dicarboxamide (25 mg, 0.063 mmol, 18% yield) as a white solid.

$^1$H NMR (400 MHz, MeOH-d$_4$) δ ppm 7.20-7.32 (m, 5H) 7.09 (s, 1H) 6.59 (d, J=7.1 Hz, 1H) 3.99 (dd, J=8.3, 2.7 Hz, 2H) 3.72 (dt, J=8.2, 3.5 Hz, 2H) 2.93 (s, 3H) 2.53 (t, J=2.4 Hz, 1H) 1.92 (d, J=7.1 Hz, 3H) 1.85-1.90 (m, 1H) 1.77-1.82 (m, 1H). 2 exchangeable protons not observed.

LCMS (2 min Formic): Rt=0.85 min, [MH]$^+$=355.3.

The crude product remaining after the first MDAP injection was also purified by MDAP (Formic) with fractions containing desired product partitioned between sat. NaHCO$_3$ solution and DCM. The organic layer was separated and aqueous layer further extracted with DCM (2×20 mL). Combined organic layers were dried (Na$_2$SO$_4$) and concentrated in vacuo to give a second batch of N$^5$-((1R, 5S,6r)-3-oxabicyclo[3.1.0]hexan-6-yl)-N³-methyl-1-((S)-1-phenylethyl)-1H-pyrazole-3,5-dicarboxamide (30 mg, 0.076 mmol, 21% yield) as a white solid.

LCMS (2 min Formic): Rt=0.85 min, [MH]⁺=355.3.

Example 2: N⁵-((1r,4.5)-4-Hydroxycyclohexyl)-N³-methyl-1-((S)-1-phenylethyl)-1H-pyrazole-3,5-dicarboxamide

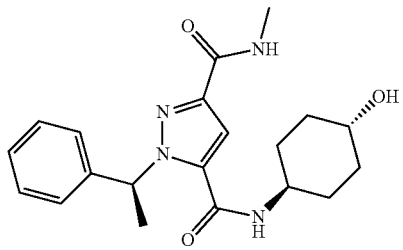 [SMILES: CNC(=O)c1cc(C(=O)N[C@H]2CC[C@H](O)CC2)n([C@@H](C)c2ccccc2)n1]

To a solution of (S)-3-(methylcarbamoyl)-1-(1-phenylethyl)-1H-pyrazole-5-carboxylic acid (451 mg, 1.650 mmol) in DMF (5 mL) was added HATU (941 mg, 2.475 mmol) followed by (1r,4r)-4-aminocyclohexanol (trans) (380 mg, 3.30 mmol) and DIPEA (1.441 mL, 8.25 mmol). The resulting reaction mixture was stirred at rt in air for 40 min. The reaction mixture was concentrated in vacuo to remove DMF and partitioned between ethyl acetate and saturated aq. LiCl solution. The organic layer was separated, washed with brine, dried (hydrophobic frit) and concentrated to give ~1.5 g of crude product as an orange oil (containing DMF). This was purified by chromatography on SiO₂ (Biotage SNAP 25 g cartridge, eluting with 20-100% ethyl acetate/cyclohexane, followed by 100% ethyl acetate to 12% ethanol/ethyl acetate) to give 447 mg of a colourless oil. This was further purified by MDAP (Formic). Fractions containing the desired product were partitioned between sat. NaHCO₃ solution and DCM. The organic layer was separated and aqueous layer further extracted with DCM (2×20 mL). Combined organic layers were dried (Na₂SO₄) and concentrated in vacuo to give N⁵-((1r,4S)-4-hydroxycyclohexyl)-N³-methyl-1-((S)-1-phenylethyl)-1H-pyrazole-3,5-dicarboxamide (163 mg, 0.396 mmol, 24% yield) as a white solid.

¹H NMR (600 MHz, DMSO-d₆) δ ppm 1.16-1.25 (m, 2H) 1.25-1.36 (m, 2H) 1.67-1.80 (m, 2H) 1.78-1.86 (m, 2H) 1.83 (d, J=6.0 Hz, 3H) 2.77 (d, J=4.8 Hz, 3H) 3.31-3.39 (m, 1H) 3.57-3.66 (m, 1H) 4.52 (d, J=4.5 Hz, 1H) 6.67 (q, J=7.0 Hz, 1H) 7.22-7.25 (m, 1H) 7.23-7.24 (m, 1H) 7.24-7.27 (m, 2H) 7.28-7.31 (m, 2H) 8.11 (q, J=4.5 Hz, 1H) 8.28 (d, J=7.8 Hz, 1H)

LCMS (2 min Formic): Rt=0.82 min, [MH]⁺=371.3.

Example 3: N⁵-((1R,3R,5S,6r)-3-Hydroxybicyclo[3.1.0]hexan-6-yl)-N³-methyl-1-((S)-1-phenylethyl)-1H-pyrazole-3,5-dicarboxamide

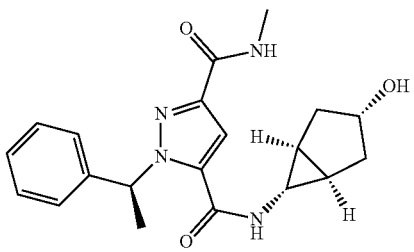 [SMILES: CNC(=O)c1cc(C(=O)N[C@H]2[C@@H]3C[C@@H](O)C[C@@H]32)n([C@@H](C)c2ccccc2)n1]

Crude tert-butyl (3-hydroxybicyclo[3.1.0]hexan-6-yl)carbamate (37 mg, 0.173 mmol) was dissolved in DCM (10 mL) and TFA (1 mL) was added, then the mixture was stirred for 2 h at rt. The solvent was evaporated in vacuo to give a pale yellow gum. The crude residue was dissolved in DCM (5 mL), then HATU (86 mg, 0.226 mmol), Et₃N (0.048 mL, 0.347 mmol) and (S)-3-(methylcarbamoyl)-1-(1-phenylethyl)-1H-pyrazole-5-carboxylic acid (47.4 mg, 0.173 mmol) were added and the mixture was stirred for 2 h at rt. The solvent was evaporated in vacuo and the residue purified by MDAP (high pH) to give N⁵-((1R,3R,5S,6s)-3-hydroxybicyclo[3.1.0]hexan-6-yl)-N³-methyl-1-((S)-1-phenylethyl)-1H-pyrazole-3,5-dicarboxamide (3 mg, 8.14 µmol, 5% yield).

¹H NMR (600 MHz, DMSO-d₆) δ ppm 1.36-1.40 (m, 2H) 1.58 (ddt, J=12.4, 8.3, 4.4, 4.4 Hz, 2H) 1.82 (d, J=7.0 Hz, 3H) 2.01 (dt, J=12.6, 7.1 Hz, 2H) 2.42 (dt, J=3.9, 2.0 Hz, 1H) 2.75 (d, J=4.6 Hz, 3H) 3.80 (br t, J=7.0 Hz, 1H) 4.59 (br d, J=3.3 Hz, 1H) 6.68 (q, J=7.0 Hz, 1H) 7.19 (s, 1H) 7.21-7.26 (m, 1H) 7.23-7.26 (m, 2H) 7.27-7.33 (m, 2H) 8.13 (q, J=4.6 Hz, 1H) 8.42 (d, J=4.0 Hz, 1H)

LCMS (2 min High pH): Rt=0.79 min, [MH]⁺=369.4.

The following examples were prepared in a similar manner to Example 3:

| Example | | Intermediate used | LCMS: (System, $t_{RET}$, MH⁺) |
|---|---|---|---|
| 4 | N⁵-((1r,4S)-4-Hydroxycyclohexyl)-N³-methyl-1-((S)-1-(m-tolyl)ethyl)-1H-pyrazole-3,5-dicarboxamide | Intermediate 50 | Formic, 0.88 min, 385.4 |

| Example | Intermediate used | LCMS: (System, $t_{RET}$, MH+) |
|---|---|---|
| 5 | N5-((1R,5S,6r)-3-Oxabicyclo[3.1.0]hexan-6-yl)-N3-methyl-1-((S)-1-phenylpropyl)-1H-pyrazole-3,5-dicarboxamide | Intermediate 51 — Formic, 0.94 min, 369.3 |
| 6 | N5-((1r,4S)-4-Hydroxycyclohexyl)-N3-methyl-1-((S)-1-phenylpropyl)-1H-pyrazole-3,5-dicarboxamide | Intermediate 51 — Formic, 0.89 min, 385.3 |
| 7 | N3-((1R,5S,6r)-3-Oxabicyclo[3.1.0]hexan-6-yl)-1-((S)-1-(4-fluorophenyl)ethyl)-N5-methyl-1H-pyrazole-3,5-dicarboxamide | Intermediate 52 — Formic, 0.87 min, 373.2 |
| 8 | N5-((1R,5S,6r)-3-Oxabicyclo[3.1.0]hexan-6-yl)-1-((S)-1-(3-fluorophenyl)ethyl)-N3-methyl-1H-pyrazole-3,5-dicarboxamide | Intermediate 53 — Formic, 0.87 min, 373.5 |

-continued

| Example | Intermediate used | | LCMS: (System, $t_{RET}$, MH+) |
|---|---|---|---|
| 9 | N⁵-((1R,5S,6r)-3-Oxabicyclo[3.1.0]hexan-6-yl)-1-((S)-1-(2-fluorophenyl)ethyl)-N³-methyl-1H-pyrazole-3,5-dicarboxamide | Intermediate 54 | Formic, 0.86 min, 373.6 |
| 10 | (S)-N⁵-Cyclopropyl-N³-methyl-1-(1-phenylethyl)-1H-pyrazole-3,5-dicarboxamide | Intermediate 5 | High pH, 0.91 min, 313.3 |
| 11 | N³-Methyl-N⁵-((1S,2S)-2-methylcyclopropyl)-1-((S)-1-phenylethyl)-1H-pyrazole-3,5-dicarboxamide | Intermediate 5 | Formic, 0.98 min, 327.3 |
| 12 | (1R,5S,6s)-tert-Butyl 6-(3-(methylcarbamoyl)-1-((S)-1-phenylethyl)-1H-pyrazole-5-carboxamido)-3-azabicyclo[3.1.0]hexane-3-carboxylate | Intermediate 5 | Formic, 1.11 min, 454 |

| Example | Intermediate used | | LCMS: (System, $t_{RET}$, MH+) |
|---|---|---|---|
| 13 | 1-((1H-Pyrrolo[2,3-c]pyridin-4-yl)methyl)-N³-methyl-N⁵-((1S,2S)-2-methylcyclopropyl)-1H-pyrazole-3,5-dicarboxamide | Intermediate 83 | High pH, 0.70 min, 353.5 |
| 14 | 1-((1H-Pyrrolo[2,3-b]pyridin-4-yl)methyl)-N³-methyl-N⁵-((1S,2S)-2-methylcyclopropyl)-1H-pyrazole-3,5-dicarboxamide | Intermediate 60 | Formic, 0.60 min, 353.2 |
| 15 | N⁵-((1R,5S,6r)-3-Oxabicyclo[3.1.0]hexan-6-yl)-1-((S)-1-(4-chlorophenyl)ethyl)-N³-methyl-1H-pyrazole-3,5-dicarboxamide | Intermediate 61 | Formic, 0.97 min, 389.3 |
| 16 | 1-((S)-1-(4-Chlorophenyl)ethyl)-N⁵-((1r,4S)-4-hydroxycyclohexyl)-N³-methyl-1H-pyrazole-3,5-dicarboxamide | Intermediate 61 | Formic, 0.92 min, 405.4 |

-continued

| Example | Intermediate used | | LCMS: (System, $t_{RET}$, MH+) |
|---|---|---|---|
| 17 | 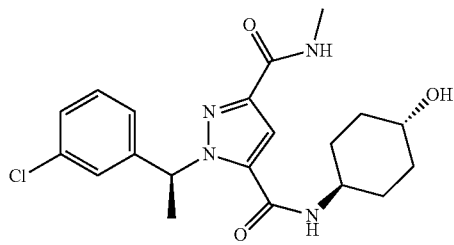 [SMILES: CNC(=O)c1cc(C(=O)N[C@H]2CC[C@H](O)CC2)n([C@@H](C)c2cccc(Cl)c2)n1]<br>1-((S)-1-(3-Chlorophenyl)ethyl)-N⁵-((1r,4S)-4-hydroxycyclohexyl)-N³-methyl-1H-pyrazole-3,5-dicarboxamide | 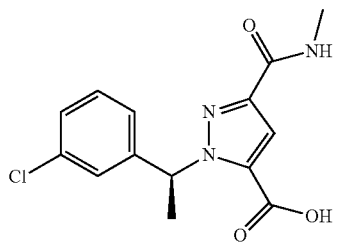 [SMILES: CNC(=O)c1cc(C(=O)O)n([C@@H](C)c2cccc(Cl)c2)n1]<br>Intermediate 62 | Formic, 0.89 min, 405.1 |
| 18 | 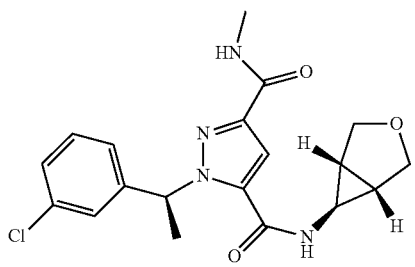 [SMILES: CNC(=O)c1cc(C(=O)N[C@H]2[C@@H]3COC[C@@H]32)n([C@@H](C)c2cccc(Cl)c2)n1]<br>N⁵-((1R,5S,6r)-3-Oxabicyclo[3.1.0]hexan-6-yl)-1-((S)-1-(3-chlorophenyl)ethyl)-N³-methyl-1H-pyrazole-3,5-dicarboxamide | 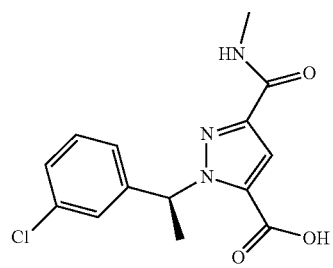 [SMILES: CNC(=O)c1cc(C(=O)O)n([C@@H](C)c2cccc(Cl)c2)n1]<br>Intermediate 62 | Formic, 0.94 min, 389.1 |
| 19 | 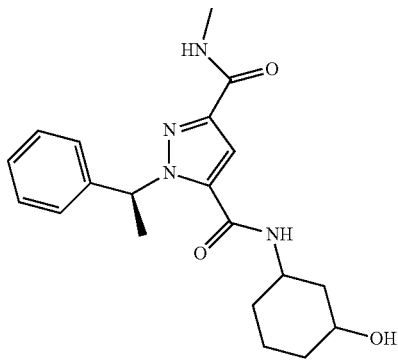 [SMILES: CNC(=O)c1cc(C(=O)NC2CCCC(O)C2)n([C@@H](C)c2ccccc2)n1]<br>N⁵-(3-Hydroxycyclohexyl)-N³-methyl-1-((S)-1-phenylethyl)-1H-pyrazole-3,5-dicarboxamide, mixture of diastereomers | 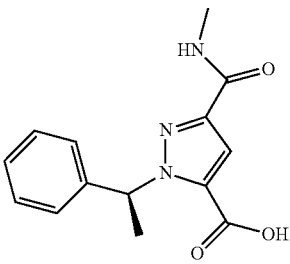 [SMILES: CNC(=O)c1cc(C(=O)O)n([C@@H](C)c2ccccc2)n1]<br>Intermediate 5 | Formic, 0.87 min, 371.1 |

| Example | | Intermediate used | LCMS: (System, $t_{RET}$, MH+) |
|---|---|---|---|
| 20 | 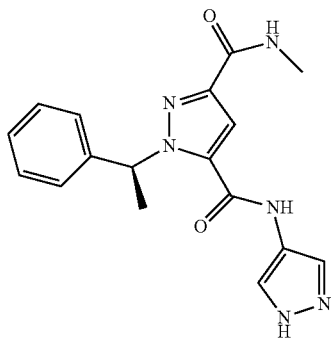 [SMILES: CNC(=O)c1cc(C(=O)Nc2cn[nH]c2)n([C@@H](C)c2ccccc2)n1]<br>(S)-N³-Methyl-1-(1-phenylethyl)-N⁵-(1H-pyrazol-4-yl)-1H-pyrazole-3,5-dicarboxamide | 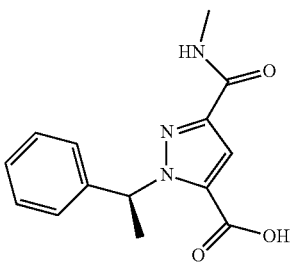 [SMILES: CNC(=O)c1cc(C(=O)O)n([C@@H](C)c2ccccc2)n1]<br>Intermediate 5 | Formic, 0.83 min, 339.0 |
| 21 | 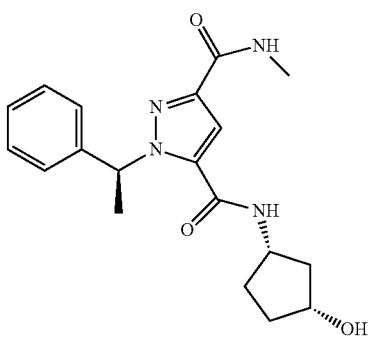 [SMILES: CNC(=O)c1cc(C(=O)N[C@H]2CC[C@@H](O)C2)n([C@@H](C)c2ccccc2)n1]<br>N⁵-((1S,3R)-3-Hydroxycyclopentyl)-N³-methyl-1-((S)-1-phenylethyl)-1H-pyrazole-3,5-dicarboxamide | 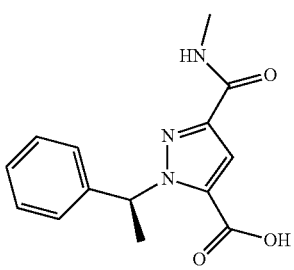 [SMILES: CNC(=O)c1cc(C(=O)O)n([C@@H](C)c2ccccc2)n1]<br>Intermediate 5 | Formic, 0.86 min, 357.1 |
| 22 | 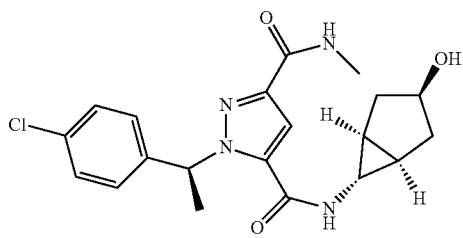 [SMILES: CNC(=O)c1cc(C(=O)N[C@H]2[C@@H]3C[C@H](O)C[C@@H]32)n([C@@H](C)c2ccc(Cl)cc2)n1]<br>1-((S)-1-(4-Chlorophenyl)ethyl)-N⁵-((1R,3S,5S,6r)-3-hydroxybicyclo[3.1.0]hexan-6-yl)-N³-methyl-1H-pyrazole-3,5-dicarboxamide | 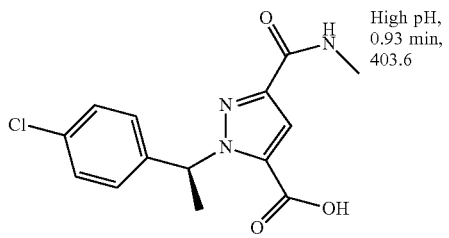<br>Intermediate 61 | High pH, 0.93 min, 403.6 |

| Example | Intermediate used | LCMS: (System, $t_{RET}$, MH⁺) |
|---|---|---|
| 23 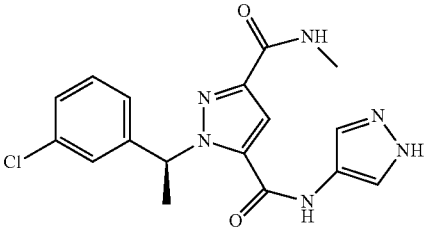 [SMILES: CNC(=O)c1cc(C(=O)Nc2cn[nH]c2)n([C@@H](C)c2cccc(Cl)c2)n1]<br>(S)-1-(1-(3-Chlorophenyl)ethyl)-N³-methyl-N⁵-(1H-pyrazol-4-yl)-1H-pyrazole-3,5-dicarboxamide | 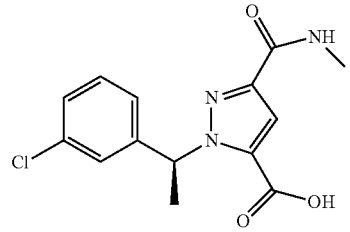 [SMILES: CNC(=O)c1cc(C(=O)O)n([C@@H](C)c2cccc(Cl)c2)n1]<br>Intermediate 62 | Formic, 0.90 min, 373.5 |
| 24 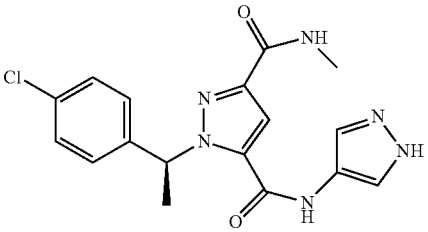 [SMILES: CNC(=O)c1cc(C(=O)Nc2cn[nH]c2)n([C@@H](C)c2ccc(Cl)cc2)n1]<br>(S)-1-(1-(4-Chlorophenyl)ethyl)-N³-methyl-N⁵-(1H-pyrazol-4-yl)-1H-pyrazole-3,5-dicarboxamide | 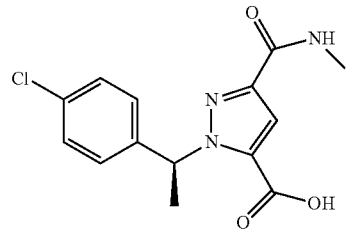 [SMILES: CNC(=O)c1cc(C(=O)O)n([C@@H](C)c2ccc(Cl)cc2)n1]<br>Intermediate 61 | Formic, 0.91 min, 373.5 |
| 25 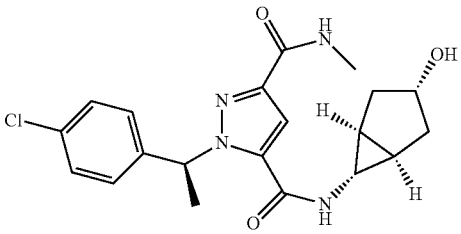 [SMILES: CNC(=O)c1cc(C(=O)N[C@H]2[C@@H]3C[C@@H](O)C[C@@H]32)n([C@@H](C)c2ccc(Cl)cc2)n1]<br>1-((S)-1-(4-Chlorophenyl)ethyl)-N⁵-((1R,3R,5S,6r)-3-hydroxybicyclo[3.1.0]hexan-6-yl)-N³-methyl-1H-pyrazole-3,5-dicarboxamide | 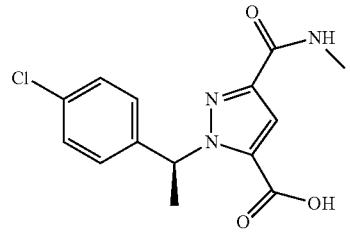 [SMILES: CNC(=O)c1cc(C(=O)O)n([C@@H](C)c2ccc(Cl)cc2)n1]<br>Intermediate 61 | High pH, 0.90 min, 403.6 |
| 26 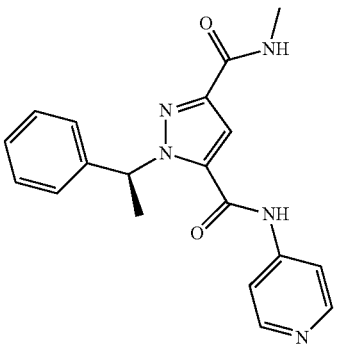 [SMILES: CNC(=O)c1cc(C(=O)Nc2ccncc2)n([C@@H](C)c2ccccc2)n1]<br>(S)-N³-Methyl-1-(1-phenylethyl)-N⁵-(pyridin-4-yl)-1H-pyrazole-3,5-dicarboxamide | 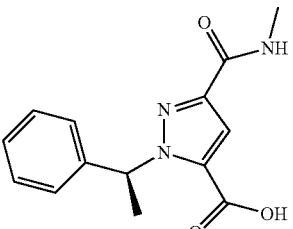<br>Intermediate 5 | Formic, 0.61 min, 350.1 |

| Example | Intermediate used | LCMS: (System, $t_{RET}$, MH+) |
|---|---|---|
| 27 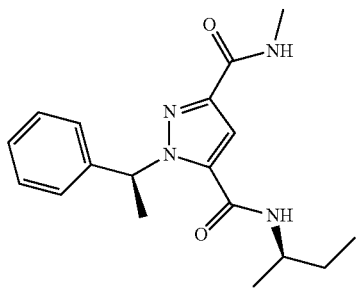 [SMILES: CC[C@@H](C)NC(=O)c1cc(C(=O)NC)nn1[C@@H](C)c1ccccc1] $N^5$-((R)-sec-Butyl)-$N^3$-methyl-1-((S)-1-phenylethyl)-1H-pyrazole-3,5-dicarboxamide | 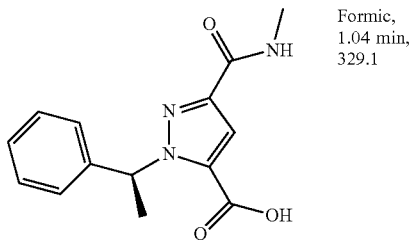 Intermediate 5 | Formic, 1.04 min, 329.1 |
| 28 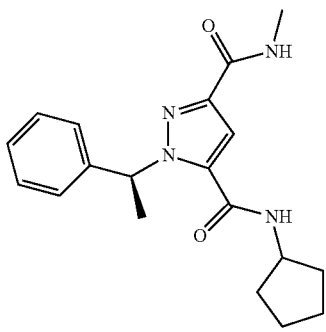 [SMILES: CNC(=O)c1cc(C(=O)NC2CCCC2)n([C@@H](C)c2ccccc2)n1] (S)-$N^5$-Cyclopentyl-$N^3$-methyl-1-(1-phenylethyl)-1H-pyrazole-3,5-dicarboxamide | 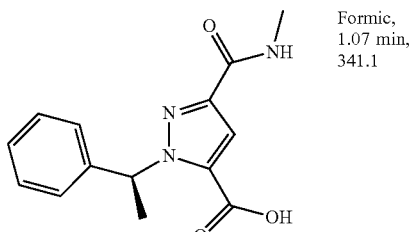 Intermediate 5 | Formic, 1.07 min, 341.1 |
| 29 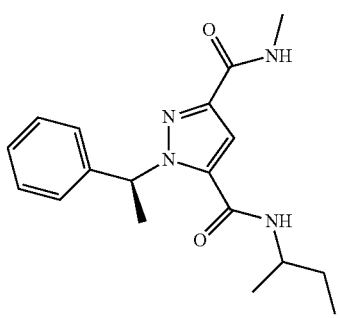 [SMILES: CCC(C)NC(=O)c1cc(C(=O)NC)nn1[C@@H](C)c1ccccc1] $N^5$-(sec-Butyl)-$N^3$-methyl-1-((S)-1-phenylethyl)-1H-pyrazole-3,5-dicarboxamide, mixture of diastereomers | 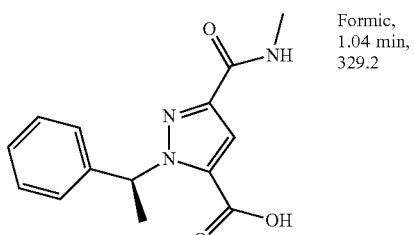 Intermediate 5 | Formic, 1.04 min, 329.2 |

| Example | Intermediate used | LCMS: (System, $t_{RET}$, MH+) |
|---|---|---|
| 30 | (S)-N⁵-Isobutyl-N³-methyl-1-(1-phenylethyl)-1H-pyrazole-3,5-dicarboxamide | Intermediate 5 | Formic, 1.06 min, 329.1 |
| 31 | N³-Methyl-1-((S)-1-phenylethyl)-N⁵-(tetrahydro-2H-pyran-3-yl)-1H-pyrazole-3,5-dicarboxamide, mixture of diastereomers | Intermediate 5 | Formic, 0.91 min, 357.1 |
| 32 | (S)-N⁵-Cyclobutyl-N³-methyl-1-(1-phenylethyl)-1H-pyrazole-3,5-dicarboxamide | Intermediate 5 | Formic, 1.02 min, 327.1 |

| Example | | Intermediate used | LCMS: (System, $t_{RET}$, MH+) |
|---|---|---|---|
| 33 | (S)-N³-Methyl-N⁵-(oxazol-2-yl)-1-(1-phenylethyl)-1H-pyrazole-3,5-dicarboxamide | Intermediate 5 | Formic, 0.85 min, 340.1 |
| 34 | (S)-N⁵-(3-Methoxypropyl)-N³-methyl-1-(1-phenylethyl)-1H-pyrazole-3,5-dicarboxamide | Intermediate 5 | Formic, 0.90 min, 345.1 |
| 35 | (S)-N³-Methyl-N⁵-(1-methyl-1H-pyrazol-4-yl)-1-(1-phenylethyl)-1H-pyrazole-3,5-dicarboxamide | Intermediate 5 | Formic, 0.89 min, 353.1 |
| 36 | N⁵-(2-Hydroxypropyl)-N³-methyl-1-((S)-1-phenylethyl)-1H-pyrazole-3,5-dicarboxamide, mixture of diastereomers | Intermediate 5 | Formic, 0.80 min, 331.1 |

| Example | | Intermediate used | LCMS: (System, $t_{RET}$, MH+) |
|---|---|---|---|
| 37 | 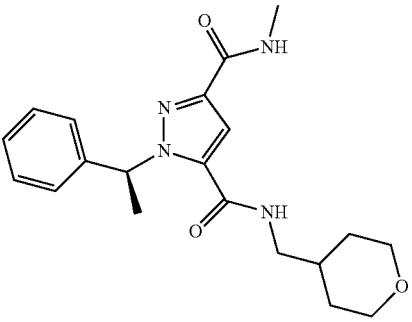 [SMILES: CNC(=O)c1cc(C(=O)NCC2CCOCC2)n([C@@H](C)c2ccccc2)n1]<br>(S)-N³-Methyl-1-(1-phenylethyl)-N⁵-((tetrahydro-2H-pyran-4-yl)methyl)-1H-pyrazole-3,5-dicarboxamide | 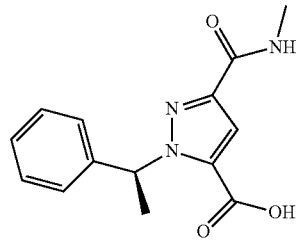 [SMILES: CNC(=O)c1cc(C(=O)O)n([C@@H](C)c2ccccc2)n1]<br>Intermediate 5 | Formic, 0.90 min, 371.1 |
| 38 | 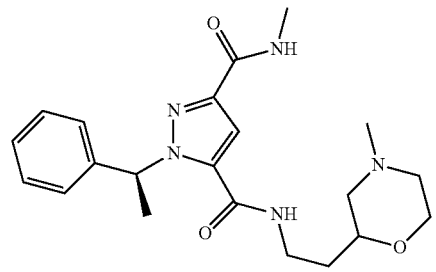 [SMILES: CNC(=O)c1cc(C(=O)NCCC2CN(C)CCO2)n([C@@H](C)c2ccccc2)n1]<br>N³-Methyl-N⁵-(2-(4-methylmorpholin-2-yl)ethyl)-1-((S)-1-phenylethyl)-1H-pyrazole-3,5-dicarboxamide, mixture of diastereomers | 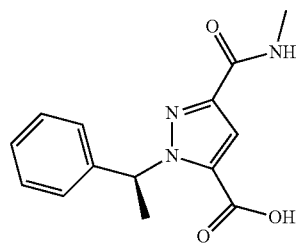 [SMILES: CNC(=O)c1cc(C(=O)O)n([C@@H](C)c2ccccc2)n1]<br>Intermediate 5 | Formic, 0.55 min, 400.2 |
| 39 | 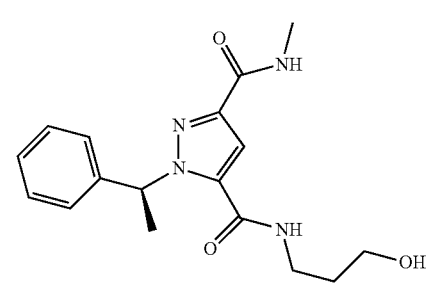 [SMILES: CNC(=O)c1cc(C(=O)NCCCO)n([C@@H](C)c2ccccc2)n1]<br>(S)-N⁵-(3-Hydroxypropyl)-N³-methyl-1-(1-phenylethyl)-1H-pyrazole-3,5-dicarboxamide | 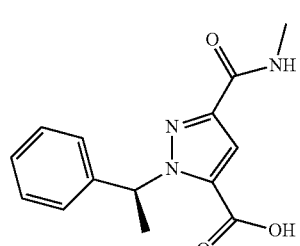<br>Intermediate 5 | Formic, 0.77 min, 331.1 |
| 40 | 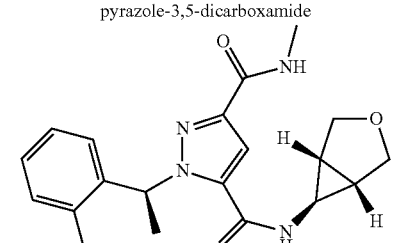<br>N⁵-((1R,5S,6r)-3-Oxabicyclo[3.1.0]hexan-6-yl)-1-((S)-1-(2-chlorophenyl)ethyl)-N³-methyl-1H-pyrazole-3,5-dicarboxamide | 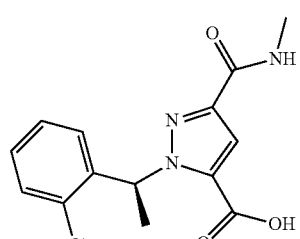<br>Intermediate 63 | Formic, 0.90 min, 389.5 |

| Example | Intermediate used | LCMS: (System, $t_{RET}$, MH+) |
|---|---|---|
| 41 | 1-((S)-1-(2-Chlorophenyl)ethyl)-N⁵-((1r,4S)-4-hydroxycyclohexyl)-N³-methyl-1H-pyrazole-3,5-dicarboxamide | Intermediate 63 | Formic, 0.87 min, 449.4 |
| 42 | N⁵-((1r,4S)-4-Hydroxy-4-methylcyclohexyl)-N³-methyl-1-((S)-1-phenylethyl)-1H-pyrazole-3,5-dicarboxamide | Intermediate 5 | Formic, 0.82 min, 385.2 |
| 43 | N⁵-((1R,5S,6r)-3-Oxabicyclo[3.1.0]hexan-6-yl)-1-((S)-1-(3-methoxyphenyl)ethyl)-N³-methyl-1H-pyrazole-3,5-dicarboxamide | Intermediate 64 | Formic, 0.86 min, 385.3 |

Examples 44-49 were prepared via an array with the following method:—

To a 20 mL vial was weighed (S)-3-(methylcarbamoyl)-1-(1-phenylethyl)-1H-pyrazole-5-carboxylic acid (0.027 g, 0.1 mmol)×14=383 mg and HATU (0.042 g, 0.110 mmol)×14=586 mg. To this vial was added DMF (0.5 mL)×14=7 mL and DIPEA (0.050 mL, 0.286 mmol)×14=700 µL. The mixture was stirred for 5 min and then aliquoted into vials (550 µL) each containing the appropriate pre-weighed amine (0.120 mmol). (NOTE: additional DIPEA (0.050 mL, 0.286 mmol) was added to amines which were HCl salts). The mixture was allowed to react for 66 h. T₃P (100 µL, 50 wt % in EtOAc) and DIPEA (0.050 mL, 0.286 mmol) were added and after 5 min additional amine (0.120 mmol) was added. The mixtures were reacted for a further 24 h. The reactions were purified by MDAP (High pH) and concentrated to give:—

| Ex No. | Name | Structure | Mass (mg) | Yield (%) | [MH]⁺ | Rt (min) Formic |
|---|---|---|---|---|---|---|
| 44 | (S)-N³-Methyl-1-(1-phenylethyl)-N⁵-(2-(tetrahydro-2H-pyran-4-yl)ethyl)-1H-pyrazole-3,5-dicarboxamide | 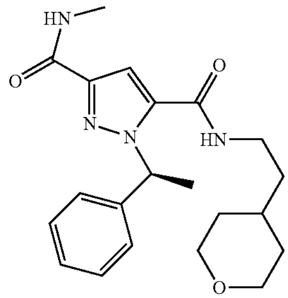 [SMILES: CNC(=O)c1cc(C(=O)NCCC2CCOCC2)n([C@@H](C)c2ccccc2)n1] | 6.8 | 16 | 385 | 0.96 |
| 45 | (S)-N⁵-(Cyclopropylmethyl)-N³-methyl-1-(1-phenylethyl)-1H-pyrazole-3,5-dicarboxamide | 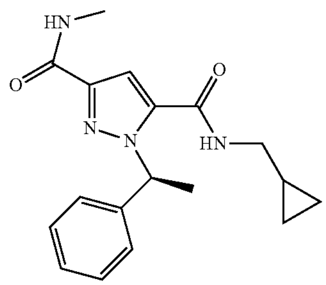 [SMILES: CNC(=O)c1cc(C(=O)NCC2CC2)n([C@@H](C)c2ccccc2)n1] | 6.6 | 18 | 327 | 1.01 |
| 46 | (S)-N⁵-Isopropyl-N³-methyl-1-(1-phenylethyl)-1H-pyrazole-3,5-dicarboxamide | 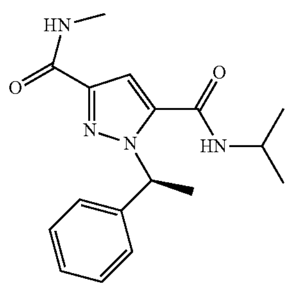 [SMILES: CNC(=O)c1cc(C(=O)NC(C)C)n([C@@H](C)c2ccccc2)n1] | 21 | 61 | 315 | 0.97 |
| 47 | (S)-N⁵-(4-Hydroxybicyclo[2.2.2]octan-1-yl)-N³-methyl-1-(1-phenylethyl)-1H-pyrazole-3,5-dicarboxamide | 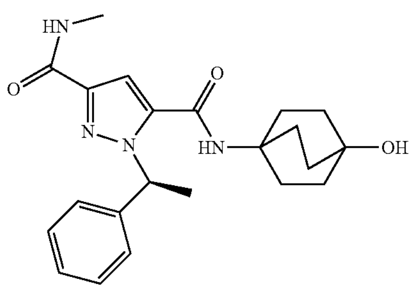 [SMILES: CNC(=O)c1cc(C(=O)NC23CCC(O)(CC2)CC3)n([C@@H](C)c2ccccc2)n1] | 13 | 29 | 397 | 0.87 |
| 48 | N⁵-((1s,4R)-4-Hydroxycyclohexyl)-N³-methyl-1-((S)-1-phenylethyl)-1H-pyrazole-3,5-dicarboxamide | 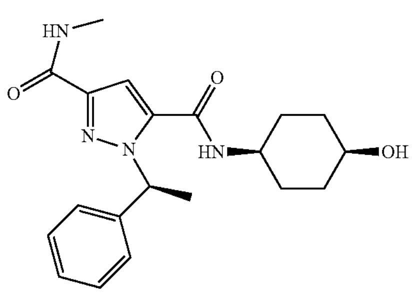 [SMILES: CNC(=O)c1cc(C(=O)N[C@H]2CC[C@@H](O)CC2)n([C@@H](C)c2ccccc2)n1] | 8 | 19 | 371 | 0.87 |

-continued

| Ex No. | Name | Structure | Mass (mg) | Yield (%) | [MH]+ | Rt (min) Formic |
|---|---|---|---|---|---|---|
| 49 | N5-((1s,4R)-4-Hydroxy-4-methylcyclohexyl)-N3-methyl-1-((S)-1-phenylethyl)-1H-pyrazole-3,5-dicarboxamide | 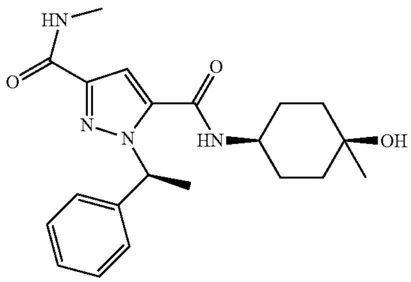 [SMILES: CNC(=O)c1cc(C(=O)N[C@H]2CC[C@@](C)(O)CC2)n([C@@H](C)c2ccccc2)n1] | 19 | 44 | 385 | 0.94 |

Examples 50-64 were prepared as part of an amide array using the following commercial amines,

| Reagent Name | Structure | MW | Reagent Mass (g) | mmol |
|---|---|---|---|---|
| Ethanamine | 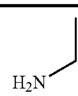 | 45 | 0.005 | 0.120 |
| Propan-1-amine | 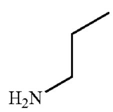 | 59 | 0.007 | 0.120 |
| (+/−)-4-Aminobutan-2-ol | 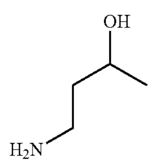 | 89 | 0.011 | 0.120 |
| Tetrahydro-2H-pyran-4-amine | 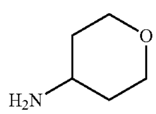 | 101 | 0.012 | 0.120 |
| (+/−)-Tetrahydrofuran-3-amine | 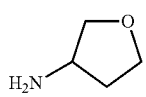 | 87 | 0.010 | 0.120 |
| (+/−)-2-(Tetrahydro-2H-pyran-2-yl)ethanamine | 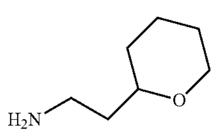 | 129 | 0.016 | 0.120 |
| (+/−)-(Tetrahydrofuran-3-yl)methanamine hydrochloride | 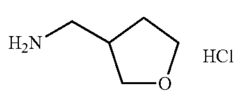 | 137 | 0.017 | 0.120 |
| (+/−)-2-(Tetrahydro-2H-pyran-3-yl)ethanamine | 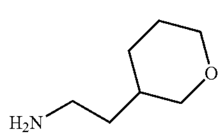 | 129 | 0.016 | 0.120 |
| Oxetan-3-ylmethanamine | 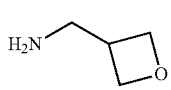 | 87 | 0.010 | 0.120 |

-continued

| Reagent Name | Structure | MW | Reagent Mass (g) | mmol |
|---|---|---|---|---|
| 3-Fluorocyclobutanamine, mixture of diastereomers | 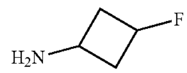 | 89 | 0.011 | 0.120 |
| tert-Butyl ((1r,4r)-4-(2-aminoethyl)cyclohexyl) carbamate | 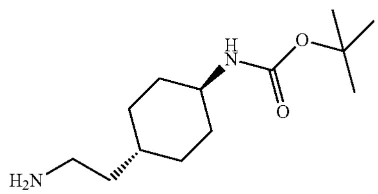 [SMILES: CC(C)(C)OC(=O)N[C@H]1CC[C@H](CCN)CC1] | 242 | 0.029 | 0.120 |
| Oxetan-3-amine | 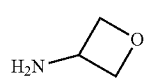 | 73 | 0.009 | 0.120 |
| 2-Cyclopropylethanamine | 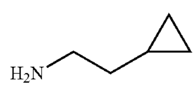 | 85 | 0.010 | 0.120 |
| 2-(1H-Pyrazol-3-yl)ethanamine | 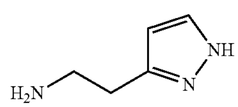 | 111 | 0.013 | 0.120 |
| (1s,3R,4r,5S,7s)-4-Aminoadamantan-1-ol hydrochloride | 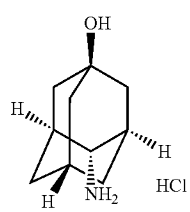 [SMILES: N[C@H]1[C@@H]2C[C@@H]3C[C@H]1C[C@@](O)(C3)C2 ; Cl] | 203 | 0.024 | 0.120 |

Method: A stock solution of (5)-3-(methylcarbamoyl)-1-(1-phenylethyl)-1H-pyrazole-5-carboxylic acid (0.027 g, 0.100 mmol)*18=492 mg and HATU (0.038 g, 0.100 mmol)*18=684 mg was dissolved in DMF (0.5 mL)*18=9.0 mL. To this stock solution was added DIPEA (0.052 mL, 0.300 mmol)×18. The vials were capped and shaken at rt to allow full dissolution. After 2 min an aliquot (0.5 mL) of the above stock solution was added to a set of pre-weighed amines*18 (0.120 mmol, for amounts see table) in 1 mL plastic matrix vials. Each vial was capped and shaken to aid dissolution and left to stand overnight for 18 h at rt. T$_3$P (50% by wt. EtOAc) 120 µL and DIPEA (0.052 mL, 0.300 mmol) was added to each reaction mixture and left for >48 h at rt. The reactions were purified by MDAP (high pH) to give final compounds (for amounts see table)

Boc deprotection of the reaction intermediate, corresponding to the coupling of tert-butyl ((1r,4r)-4-(2-aminoethyl)cyclohexyl)carbamate was carried out in DCM (0.5 mL) using 3M HCl in CPME (0.5 mL). A glass microwave vial was used as the reaction vessel. The reaction was left to stir overnight for 22 h at 35° C. Further DCM (0.5 mL) and 3M HCl in CPME (0.5 mL) were added to the reaction mixture and it was left to stir overnight for 18 h at 35° C. The solvent was then removed to dryness under a stream of nitrogen to afford the HCl salt of the free amine. Further DCM (0.5 mL) and 3M HCl in CPME (0.5 mL) were added to the solid material. The solution was left to stand at rt over the weekend. The solvent was removed to dryness to afford the HCl salt of the free amine (example 60) as shown in the table below.

| Ex No. | Name | Structure | Mass (mg) | Yield (%) | [MH]+ | Rt (min) Formic |
|---|---|---|---|---|---|---|
| 50 | (S)-N5-Ethyl-N3-methyl-1-(1-phenylethyl)-1H-pyrazole-3,5-dicarboxamide | 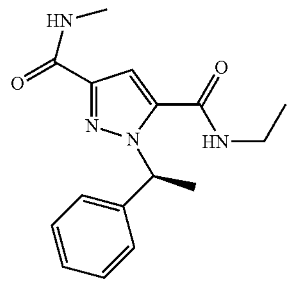 [SMILES: CCNC(=O)c1cc(C(=O)NC)nn1[C@@H](C)c1ccccc1] | 18 | 54 | 301 | 0.90 |
| 51 | (S)-N3-Methyl-1-(1-phenylethyl)-N5-propyl-1H-pyrazole-3,5-dicarboxamide | 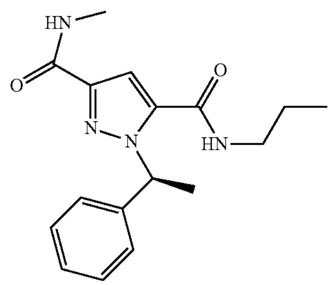 [SMILES: CCCNC(=O)c1cc(C(=O)NC)nn1[C@@H](C)c1ccccc1] | 14 | 40 | 315 | 0.98 |
| 52 | N5-(3-Hydroxybutyl)-N3-methyl-1-((S)-1-phenylethyl)-1H-pyrazole-3,5-dicarboxamide | 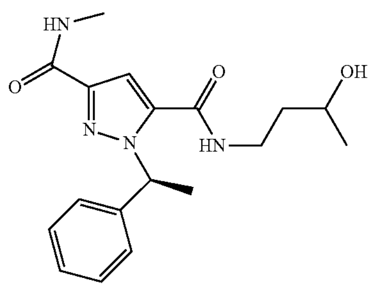 [SMILES: CNC(=O)c1cc(C(=O)NCCC(C)O)n([C@@H](C)c2ccccc2)n1] | 19 | 49 | 345 | 0.82 |
| 53 | (S)-N3-Methyl-1-(1-phenylethyl)-N5-(tetrahydro-2H-pyran-4-yl)-1H-pyrazole-3,5-dicarboxamide | 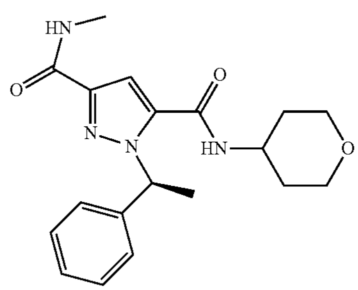 [SMILES: CNC(=O)c1cc(C(=O)NC2CCOCC2)n([C@@H](C)c2ccccc2)n1] | 12 | 31 | 357 | 0.89 |
| 54 | N3-Methyl-1-((S)-1-phenylethyl)-N5-(tetrahydrofuran-3-yl)-1H-pyrazole-3,5-dicarboxamide | 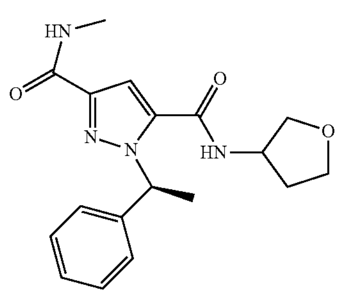 [SMILES: CNC(=O)c1cc(C(=O)NC2CCOC2)n([C@@H](C)c2ccccc2)n1] | 18 | 48 | 343 | 0.86 |

| Ex No. | Name | Structure | Mass (mg) | Yield (%) | [MH]+ | Rt (min) Formic |
|---|---|---|---|---|---|---|
| 55 | N³-Methyl-1-((S)-1-phenylethyl)-N⁵-(2-(tetrahydro-2H-pyran-2-yl)ethyl)-1H-pyrazole-3,5-dicarboxamide | 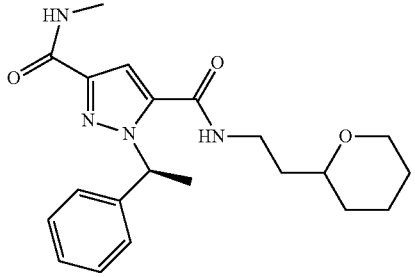 [SMILES: CNC(=O)c1cc(C(=O)NCCC2CCCCO2)n([C@@H](C)c2ccccc2)n1] | 18 | 43 | 385 | 1.05 |
| 56 | N³-Methyl-1-((S)-1-phenylethyl)-N⁵-((tetrahydrofuran-3-yl)methyl)-1H-pyrazole-3,5-dicarboxamide | 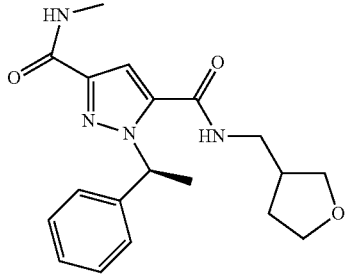 [SMILES: CNC(=O)c1cc(C(=O)NCC2CCOC2)n([C@@H](C)c2ccccc2)n1] | 18 | 44 | 357 | 0.87 |
| 57 | N³-Methyl-1-((S)-1-phenylethyl)-N⁵-(2-(tetrahydro-2H-pyran-3-yl)ethyl)-1H-pyrazole-3,5-dicarboxamide | 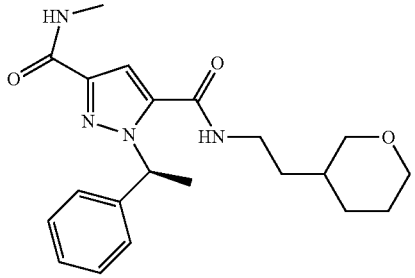 [SMILES: CNC(=O)c1cc(C(=O)NCCC2CCCOC2)n([C@@H](C)c2ccccc2)n1] | 21 | 49 | 385 | 0.99 |
| 58 | (S)-N³-Methyl-N⁵-(oxetan-3-ylmethyl)-1-(1-phenylethyl)-1H-pyrazole-3,5-dicarboxamide | 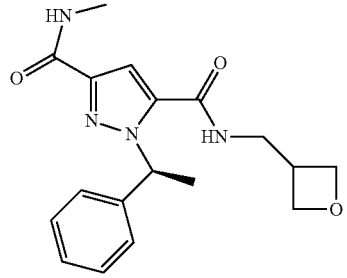 [SMILES: CNC(=O)c1cc(C(=O)NCC2COC2)n([C@@H](C)c2ccccc2)n1] | 17 | 43 | 343 | 0.82 |
| 59 | (S)-N⁵-(3-Fluorocyclobutyl)-N³-methyl-1-(1-phenylethyl)-1H-pyrazole-3,5-dicarboxamide | 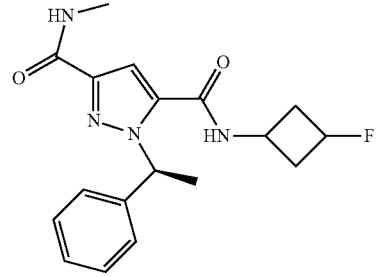 [SMILES: CNC(=O)c1cc(C(=O)NC2CC(F)C2)n([C@@H](C)c2ccccc2)n1] | 7 | 19 | 345 | 0.98 |

| Ex No. | Name | Structure | Mass (mg) | Yield (%) | [MH]+ | Rt (min) Formic |
|---|---|---|---|---|---|---|
| 60 | $N^5$-(2-((1r,4S)-4-Aminocyclohexyl)ethyl)-$N^3$-methyl-1-((S)-1-phenylethyl)-1H-pyrazole-3,5-dicarboxamide hydrochloride | 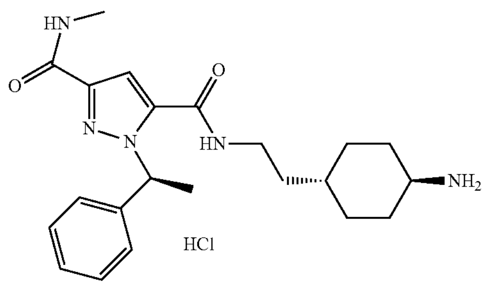 [SMILES: CNC(=O)c1cc(C(=O)NCC[C@H]2CC[C@H](N)CC2)n([C@@H](C)c2ccccc2)n1 ; Cl] | 23 | 47 | 398 | 0.60 |
| 61 | (S)-$N^3$-Methyl-$N^5$-(oxetan-3-yl)-1-(1-phenylethyl)-1H-pyrazole-3,5-dicarboxamide | 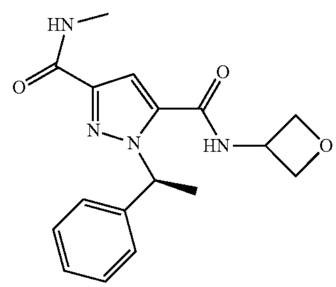 [SMILES: CNC(=O)c1cc(C(=O)NC2COC2)n([C@@H](C)c2ccccc2)n1] | 14 | 38 | 329 | 0.83 |
| 62 | (S)-$N^5$-(2-Cyclopropylethyl)-$N^3$-methyl-1-(1-phenylethyl)-1H-pyrazole-3,5-dicarboxamide | 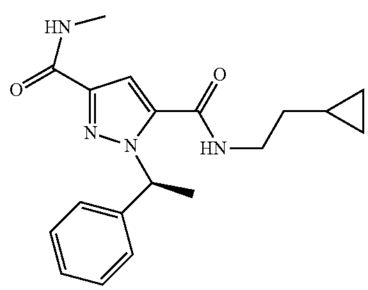 [SMILES: CNC(=O)c1cc(C(=O)NCCC2CC2)n([C@@H](C)c2ccccc2)n1] | 16 | 43 | 341 | 1.07 |
| 63 | (S)-$N^5$-(2-(1H-Pyrazol-3-yl)ethyl)-$N^3$-methyl-1-(1-phenylethyl)-1H-pyrazole-3,5-dicarboxamide | 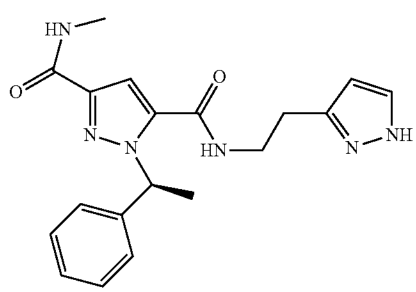 [SMILES: CNC(=O)c1cc(C(=O)NCCc2cc[nH]n2)n([C@@H](C)c2ccccc2)n1] | 22 | 54 | 367 | 0.82 |
| 64 | $N^5$-((1S,3S,5R,7R)-5-Hydroxyadamantan-2-yl)-$N^3$-methyl-1-((S)-1-phenylethyl)-1H-pyrazole-3,5-dicarboxamide | 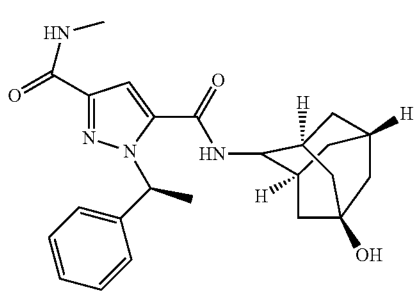 [SMILES: CNC(=O)c1cc(C(=O)NC2[C@H]3C[C@H]4C[C@H]2C[C@](O)(C3)C4)n([C@@H](C)c2ccccc2)n1] | 19 | 41 | 423 | 0.89 |

Example 65: (S)—$N^3,N^5$-Dimethyl-1-(1-phenyl-ethyl)-1H-pyrazole-3,5-dicarboxamide

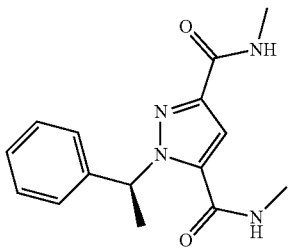 [SMILES: CNC(=O)c1cc(C(=O)NC)n([C@@H](C)c2ccccc2)n1]

To a suspension of $N^3,N^5$-dimethyl-1H-pyrazole-3,5-dicarboxamide (39 mg, 0.214 mmol) in THF (1 mL) was added (R)-1-phenylethanol (40 mg, 0.327 mmol) and triphenylphosphine (90 mg, 0.343 mmol) and the reaction mixture was stirred at rt for 15 min. The reaction mixture was cooled to 0° C. and DIAD (0.067 mL, 0.343 mmol) was added. The vial was then heated in the microwave at 140° C. for 15 min. The reaction mixture was then heated at 140° C. for a further 20 min. Further portions of (R)-1-phenylethanol (40 mg, 0.327 mmol), triphenylphosphine (90 mg, 0.343 mmol) and DIAD (0.067 mL, 0.343 mmol) were added and the reaction mixture heated at 140° C. for 15 min. The solvent was removed in vacuo to give 770 mg of a crude yellow oil. This was purified by chromatography on $SiO_2$ (Biotage SNAP 25 g cartridge, eluting with 0-100% ethyl acetate/cyclohexane) to give 50 mg of a colourless oil. This was further purified by MDAP (high pH). The fractions containing desired product were concentrated in vacuo to give (S)—$N^3,N^5$-dimethyl-1-(1-phenylethyl)-1H-pyrazole-3,5-dicarboxamide (17 mg, 0.053 mmol, 25% yield) as a white solid.

LCMS (2 min Formic): Rt=0.82 min, $[MH]^+$=287.2.

Example 66: 1-Benzyl-$N^3$-((1r,4r)-4-hydroxycyclohexyl)-$N^3$-methyl-1H-pyrazole-3,5-dicarboxamide

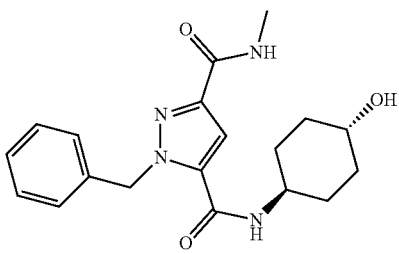 [SMILES: CNC(=O)c1cc(C(=O)N[C@H]2CC[C@H](O)CC2)n(Cc2ccccc2)n1]

To a solution of 1-benzyl-3-(methylcarbamoyl)-1H-pyrazole-5-carboxylic acid (150 mg, 0.509 mmol) and DIPEA (0.267 mL, 1.527 mmol) in DMF (1 mL) stirred under nitrogen at rt was added HATU (290 mg, 0.764 mmol) followed by the addition of (1r,4r)-4-aminocyclohexanol (70.4 mg, 0.611 mmol) in one charge. The reaction mixture was stirred at rt for 16 h. The reaction mass was poured into ice water, then extracted with EtOAc (3×20 mL). The combined organic layer was washed with water (2×15 mL), brine solution, dried over sodium sulphate, filtered and the filtrate was concentrated under vaccum to afford the crude product. The crude product was triturated with 50% DCM+ diethyl ether (3×1 mL), to give solid product, which was filtered and dried under vaccum for 15 min to give, 1-benzyl-$N^3$-((1r,4r)-4-hydroxycyclohexyl)-$N^3$-methyl-1H-pyrazole-3,5-dicarboxamide (160 mg, 0.447 mmol, 88% yield) as an off-white solid.

LCMS (4.5 min Method A): Rt=1.61 min, $[MH]^+$=357.1.

Example 67: 1-Benzyl-$N^3$-cyclobutyl-$N^3$-methyl-1H-pyrazole-3,5-dicarboxamide

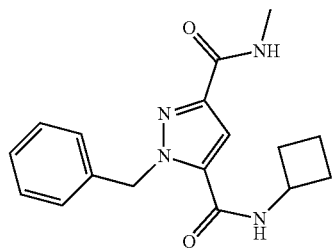 [SMILES: CNC(=O)c1cc(C(=O)NC2CCC2)n(Cc2ccccc2)n1]

To a solution of 1-benzyl-3-(methylcarbamoyl)-1H-pyrazole-5-carboxylic acid (200 mg, 0.733 mmol) and DIPEA (0.384 mL, 2.199 mmol) in DMF (1 mL) stirred under nitrogen at rt was added HATU (418 mg, 1.099 mmol) followed by the addition of cyclobutanamine (104 mg, 1.466 mmol, commercially available from, for example, Sigma Aldrich) in one charge. The reaction mixture was stirred at rt for 16 h. The reaction was poured into ice water, then extracted with EtOAc (3×20 mL). The combined organic layer was washed with brine solution, dried over sodium sulphate, filtered and the filtrate was concentrated under vaccum to give the crude product. The crude product was added to a silica gel 60-120 column and was eluted with 65% EtOAc in n-hexane. The collected pure fractions were concentrated under vaccum to give 1-benzyl-$N^3$-cyclobutyl-$N^3$-methyl-1H-pyrazole-3,5-dicarboxamide (84 mg, 0.255 mmol, 35% yield) as a white solid.

LCMS (10 min Method D): Rt=4.26 min, $[MH]^+$=313.2.

Example 68: (S*)—$N^5$-Cyclopropyl-$N^3$-methyl-1-(1-phenylethyl)-1H-pyrazole-3,5-dicarboxamide

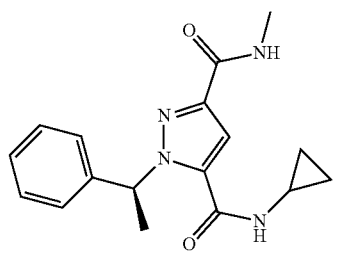 [SMILES: CNC(=O)c1cc(C(=O)NC2CC2)n([C@@H](C)c2ccccc2)n1]

Intermediate 11 was purified by chiral HPLC. Preparative NP-HPLC conditions were as follows:—

Column/dimensions: Chiralpak IC (250×30 mm), 5 μm

Mobile Phase: n-hexane: ethanol (70:30)

Flow: 38 mL/min

Temperature: ambient

Wave length: 249 nm

Run time: 18 min

Solubility: THF+n-hexane+ethanol

Load ability/Inj: 33.0 mg/Inj

Total No of injections: 10 The pure fractions corresponding to peak 1 were concentrated under vaccum to give (S*)—$N^3$-cyclopropyl-$N^3$-methyl-1-(1-phenylethyl)-1H-pyrazole-3,5-dicarboxamide (36 mg, 0.105 mmol, 15% yield) as a white solid.

LCMS (4.5 min Method B): Rt=1.89 min, [MH]$^+$=313.2.

Example 69: $N^5$-Cyclopropyl-$N^3$-methyl-1-(3-methylbenzyl)-1H-pyrazole-3,5-dicarboxamide

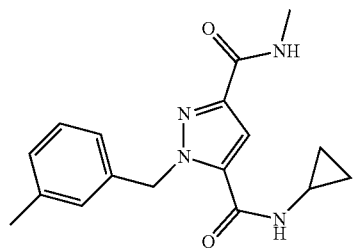 [SMILES: CNC(=O)c1cc(C(=O)NC2CC2)n(Cc2cccc(C)c2)n1]

To a solution of $N^5$-cyclopropyl-$N^3$-methylpyrazole-3,5-dicarboxamide (300 mg, 1.366 mmol) in DMF (2 mL) stirred under nitrogen at rt was added $K_2CO_3$ (566 mg, 4.10 mmol) followed by the addition of 1-(bromomethyl)-3-methylbenzene (0.211 mL, 1.640 mmol, commercially available from, for example, Sigma Aldrich) in one charge. The reaction mixture was stirred at rt for 16 h. The reaction was poured into ice water, then extracted with EtOAc (3×25 mL). The combined organic layer was washed with water (3×15 mL), brine solution, dried over sodium sulphate, filtered and the filtrate was concentrated under vaccum to give the crude product which was a mixture of 2 regioisomers. These were purified by SFC chiral HPLC. Preparative SFC conditions were as follows:—

Column/dimensions: LuxCellulose-2 (250×30 mm), 5 µm

% $CO_2$: 60.0%

% co-solvent: 40.0% (MeOH)

Total Flow: 90.0 g/min

Back Pressure: 100.0 bar

UV: 211 nm

Stack time: 3.8 min

Load/Inj: 16.0 mg

Solubility: methanol

Total No of injections: 20

Instrument details: Make/Model: Thar SFC-200-005

The pure fractions corresponding to peak 1 were concentrated under vaccum to give $N^5$-cyclopropyl-M-methyl-1-(3-methylbenzyl)-1H-pyrazole-3,5-dicarboxamide (76 mg, 0.238 mmol, 63% yield) as a white solid.

LCMS (4.5 min Method B): Rt=1.90 min, [MH]$^+$=313.2.

Example 70: 1-((1H-Indol-5-yl)methyl)-$N^3$-cyclopropyl-$N^3$-methyl-1H-pyrazole-3,5-dicarboxamide

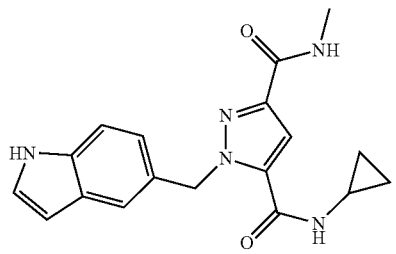 [SMILES: CNC(=O)c1cc(C(=O)NC2CC2)n(Cc2ccc3[nH]ccc3c2)n1]

To a solution of $N^5$-cyclopropyl-$N^3$-methyl-1-((1-tosyl-1H-indol-5-yl)methyl)-1H-pyrazole-3,5-dicarboxamide (420 mg, 0.666 mmol) in methanol (1 mL) stirred under nitrogen at rt was added NaOH (80 mg, 1.999 mmol) in one charge. The reaction mixture was stirred at 70° C. for 16 h. The reaction mass was cooled to rt, then diluted with water (20 mL), then the aqueous layer was extracted with EtOAc (3×15 mL). The combined organic layer was washed with water (3×10 mL), brine solution, dried over sodium sulphate, filtered and the filtrate was concentrated under vaccum to give the crude product as a mixture of regioisomers. These were purified by SFC, chiral HPLC. Preparative SFC conditions were as follows:—

Column/dimensions: Chiralpak IC (250×30 mm), 5 µm

% $CO_2$: 50.0%

% co-solvent: 50.0% (MeOH)

Total Flow: 60.0 g/min

Back Pressure: 100.0 bar

UV: 215 nm

Stack time: 6.5 min

Load/Inj: 8.0 mg

Solubility: MeOH

Total No of injections: 40 The pure fractions corresponding to peak 1 were concentrated under vaccum to give 1-((1H-indol-5-yl)methyl)-$N^3$-cyclopropyl-$N^3$-methyl-1H-pyrazole-3,5-dicarboxamide (95 mg, 0.272 mmol, 85% yield) as an off-white solid.

LCMS (4.5 min Method B): Rt=1.68 min, [MH]$^+$=338.2.

Example 71: 1-((1H-Indol-4-yl)methyl)-$N^3$-cyclopropyl-$N^3$-methyl-1H-pyrazole-3,5-dicarboxamide

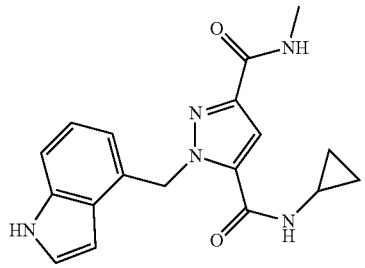 [SMILES: CNC(=O)c1cc(C(=O)NC2CC2)n(Cc2cccc3[nH]ccc23)n1]

To a solution of $N^5$-cyclopropyl-$N^3$-methyl-1-((1-tosyl-1H-indol-4-yl)methyl)-1H-pyrazole-3,5-dicarboxamide (400 mg, 0.745 mmol) in methanol (1 mL) stirred under nitrogen at rt was added NaOH (29.8 mg, 0.745 mmol). The reaction mixture was stirred at 70° C. for 16 h. The reaction was diluted with water, then extracted with DCM (3×15 mL). The combined organic layer was washed with brine solution, dried over sodium sulphate, filtered and the filtrate was concentrated under vaccum to give a crude mixture of regioisomers (410 mg) which were purified by SFC. Preparative SFC conditions were as follows:—
Column/dimensions: Chiralpak AD-H (250×21 mm), 5 μm
% $CO_2$: 60.0%
% co-solvent: 40.0% (MeOH)
Total Flow: 60.0 g/min
Back Pressure: 100.0 bar
UV: 215 nm
Stack time: 3.6 min
Load/Inj: 2.6 mg
Solubility: Methanol+DCM
Total No of injections: 34

The pure fractions corresponding to peak 1 were concentrated under vaccum to give $N^5$-cyclopropyl-$N^3$-methyl-1-((1-tosyl-1H-indol-4-yl)methyl)-1H-pyrazole-3,5-dicarboxamide (400 mg, 0.745 mmol) as an off-white solid.

LCMS (4.5 min Method B): Rt=1.65 min, $[MH]^+$=338.2.

Example 72: $N^5$-((1R,3S,5S,6r)-3-Hydroxybicyclo[3.1.0]hexan-6-yl)-$N^3$-methyl-1-((S)-1-phenylethyl)-1H-pyrazole-3,5-dicarboxamide

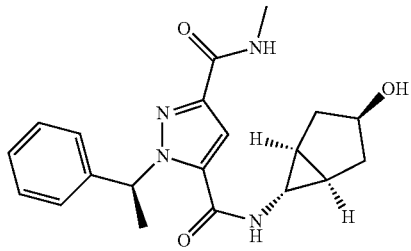 [SMILES: CNC(=O)c1cc(C(=O)N[C@H]2[C@@H]3C[C@H](O)C[C@@H]32)n([C@@H](C)c2ccccc2)n1]

3-Hydroxybicyclo[3.1.0]hexane-6-carboxylic acid (720 mg, 5.06 mmol) was dissolved in toluene (10 mL) and tert-butanol (10 mL), then $Et_3N$ (1.412 mL, 10.13 mmol) and diphenyl phosphorazidate (1.637 mL, 7.60 mmol) were added and the mixture was heated at 80° C. overnight. The mixture was diluted with EtOAc (20 mL) and washed with water (20 mL), the solvent dried and evaporated to give a pale yellow gum. This was dissolved in DCM (10 mL) and loaded onto a 50 g silica column, then eluted with 0-100% EtOAc/cyclohexane and the ninhydrin active fractions were evaporated in vacuo to give a mixture of diastereomers of tert-butyl (3-hydroxybicyclo[3.1.0]hexan-6-yl)carbamate which was used crude in the following step. tert-Butyl (3-hydroxybicyclo[3.1.0]hexan-6-yl)carbamate (55 mg, 0.258 mmol) (crude) was dissolved in DCM (10 mL) and TFA (1 mL) was added, then the mixture was stirred for 2 h at rt. The solvent was evaporated in vacuo and the residue was dissolved in fresh DCM (10 mL) and $Et_3N$ (0.072 mL, 0.516 mmol), HATU (147 mg, 0.387 mmol) and (S)-3-(methylcarbamoyl)-1-(1-phenylethyl)-1H-pyrazole-5-carboxylic acid (70.5 mg, 0.258 mmol) were added, then the mixture stirred for 2 h at rt. The reaction mixture was washed with water (10 mL), dried and evaporated in vacuo to give a pale yellow gum. This was purified by MDAP (high pH) to give $N^5$-((1R,3S,5S,6r)-3-hydroxybicyclo[3.1.0]hexan-6-yl)-$N^3$-methyl-1-((S)-1-phenylethyl)-1H-pyrazole-3,5-dicarboxamide (16 mg, 0.043 mmol, 17% yield) as a colourless solid.

LCMS (2 min High pH): Rt=0.84 min, $[MH]^+$=369.3.

Example 73: $N^5$-(2-((2r,5S)-5-Amino-1,3-dioxan-2-yl)ethyl)-$N^3$-methyl-1-((S)-1-phenylethyl)-1H-pyrazole-3,5-dicarboxamide

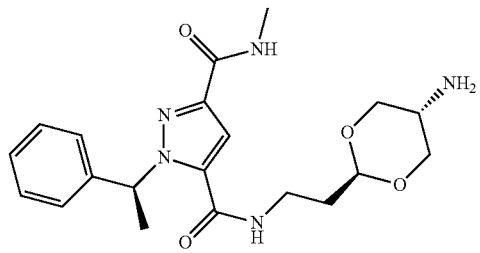 [SMILES: CNC(=O)c1cc(C(=O)NCC[C@H]2OC[C@H](N)CO2)n([C@@H](C)c2ccccc2)n1]

To a suspension of $N^5$-(2-((2r,5S)-5-(1,3-dioxoisoindolin-2-yl)-1,3-dioxan-2-yl)ethyl)-$N^3$-methyl-1-((S)-1-phenylethyl)-1H-pyrazole-3,5-dicarboxamide (102 mg, 0.192 mmol) in ethanol (3 mL) was added hydrazine hydrate (90 μL, 1.836 mmol). The reaction was stirred at 40° C. for 4 h. The crude product was filtered, and purified by MDAP (high pH). The fractions containing the desired product were concentrated in vacuo to give $N^5$-(2-((2r,5S)-5-amino-1,3-dioxan-2-yl)ethyl)-$N^3$-methyl-1-((S)-1-phenylethyl)-1H-pyrazole-3,5-dicarboxamide (61 mg, 0.137 mmol, 71% yield).

LCMS (2 min High pH): Rt=0.78 min, $[MH]^+$=402.2.

Example 74: $N^5$-(3-((2r,5S)-5-Amino-1,3-dioxan-2-yl)propyl)-$N^3$-methyl-1-((S)-1-phenylethyl)-1H-pyrazole-3,5-dicarboxamide

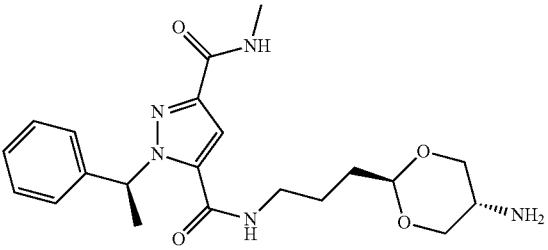 [SMILES: CNC(=O)c1cc(C(=O)NCCC[C@H]2OC[C@H](N)CO2)n([C@@H](C)c2ccccc2)n1]

To a suspension of $N^5$-(3-((2r,5S)-5-(1,3-dioxoisoindolin-2-yl)-1,3-dioxan-2-yl)propyl)-$N^3$-methyl-1-((S)-1-phenylethyl)-1H-pyrazole-3,5-dicarboxamide (81 mg, 0.148 mmol) in ethanol (3 mL) was added hydrazine hydrate (90 μL, 1.836 mmol). The reaction was stirred at 40° C. for 19 h. The crude product was filtered, and purified by MDAP (high pH). The fractions containing desired product were concentrated in vacuo to give $N^5$-(3-((2r,5S)-5-amino-1,3-dioxan-2-yl)propyl)-$N^3$-methyl-1-((5)-1-phenylethyl)-1H-pyrazole-3,5-dicarboxamide (42 mg, 0.091 mmol, 61% yield).

LCMS (2 min High pH): Rt=0.80 min, $[MH]^+$=416.3.

Example 75: N⁵-((1R,5S,6r)-3-oxabicyclo[3.1.0]hexan-6-yl)-1-((R)-2-hydroxy-1-phenylethyl)-N³-methyl-1H-pyrazole-3,5-dicarboxamide

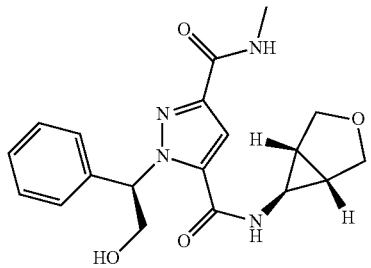 [SMILES: CNC(=O)c1cc(C(=O)N[C@H]2[C@@H]3COC[C@@H]32)n([C@@H](CO)c2ccccc2)n1]

N⁵-((1R,5S,6r)-3-Oxabicyclo[3.1.0]hexan-6-yl)-1-((R)-2-((tert-butyldimethylsilyl)oxy)-1-phenylethyl)-N⁵-methylpyrazole-3,5-dicarboxamide (214 mg, 0.442 mmol) was taken up in 4M hydrochloric acid in dioxane (500 μL, 2.000 mmol) and left to stir for 1.5 h. The sample was dissolved in 1:1 MeOH:DMSO (2×1 mL) and purified by MDAP (high pH). The relevant fractions were combined and concentrated in vacuo to give N⁵-((1R,5S,6r)-3-oxabicyclo[3.1.0]hexan-6-yl)-1-((R)-2-hydroxy-1-phenylethyl)-N³-methyl-1H-pyrazole-3,5-dicarboxamide (68.4 mg, 0.166 mmol, 38% yield) as the second eluting regioisomer.

LCMS (2 min Formic): Rt=0.71 min, [MH]⁺=371.2.

Example 76: N⁵-((1R,5S,6s)-3-Azabicyclo[3.1.0]hexan-6-yl)-N³-methyl-1-((S)-1-phenylethyl)-1H-pyrazole-3,5-dicarboxamide

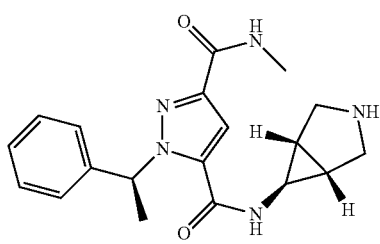 [SMILES: CNC(=O)c1cc(C(=O)N[C@H]2[C@@H]3CNC[C@@H]32)n([C@@H](C)c2ccccc2)n1]

To a part suspension of tert-butyl (1R,5S,6s)-6-(3-(methylcarbamoyl)-1-((S)-1-phenylethyl)-1H-pyrazole-5-carboxamido)-3-azabicyclo[3.1.0]hexane-3-carboxylate (95 mg, 0.209 mmol) in DCM (2 mL) was added TFA (0.5 mL, 6.49 mmol) and the reaction mixture was stirred at rt for 6 h. The reaction mixture was concentrated and loaded onto a 2 g SCX cartridge (pre-conditioned with MeOH). This was eluted with MeOH (30 mL) followed by 2M NH₃ in MeOH (30 mL). The ammonia fractions containing product were combined and concentrated to give the title compound (57 mg, 0.145 mmol, 69% yield) as a pale yellow oil.

LCMS (2 min Formic): Rt=0.51 min, [MH]⁺=354.4

Example 77: N⁵-((1R,5S,6s)-3-Acetyl-3-azabicyclo[3.1.0]hexan-6-yl)-N³-methyl-1-((S)-1-phenylethyl)-1H-pyrazole-3,5-dicarboxamide

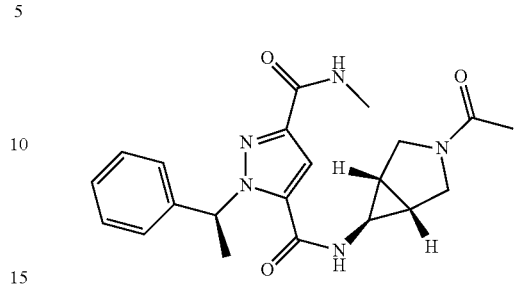

N⁵-((1R,5S,6r)-3-Azabicyclo[3.1.0]hexan-6-yl)-N³-methyl-1-((S)-1-phenylethyl)-1H-pyrazole-3,5-dicarboxamide (49 mg, 0.139 mmol) was stirred in acetic anhydride (300 μL, 3.18 mmol) at rt for 2 h. The reaction was diluted with sat NaHCO₃ (aq.) and extracted with EtOAc, the organic phase was washed with water, dried using a hydrophobic frit and concentrated to give the title compound (46 mg, 0.105 mmol, 76% yield) as a colourless oil.

LCMS (2 min Formic): Rt=0.77 min, [MH]⁺=396.4

Example 78: 1-((1H-Indol-4-yl)methyl)-N⁵-((1R,5S,6r)-3-oxabicyclo[3.1.0]hexan-6-yl)-M-methyl-1H-pyrazole-3,5-dicarboxamide

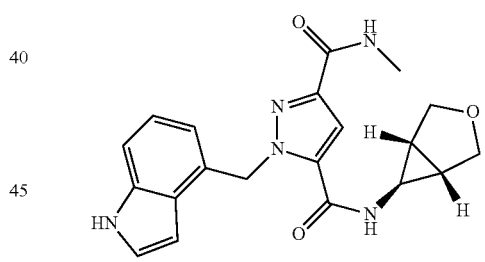

N⁵-((1R,5S,6r)-3-Oxabicyclo[3.1.0]hexan-6-yl)-N³-methyl-1-((1-tosyl-1H-indol-4-yl)methyl)-1H-pyrazole-3,5-dicarboxamide (99.7 mg, 0.187 mmol) was taken up in THF (4 mL) and methanol (2 mL). Cesium carbonate (304 mg, 0.934 mmol) was added and the reaction was heated to 73° C. and left to stir overnight. The reaction was concentrated in vacuo. Water (10 mL) was added to the residue, which was then acidified with 2N HCl, and then extracted with ethyl acetate (2×10 mL). The combined organics were dried with Na₂SO₄, filtered and concentrated in vacuo to yield the title compound (63.8 mg, 0.160 mmol, 85% yield) as a purple solid.

LCMS (2 min Formic): Rt=0.74 min, [MH]⁺=380.3

Example 79: 1-(1H-Indol-4-yl)methyl)-N$^5$-((1R,5S,6s)-3-azabicyclo[3.1.0]hexan-6-yl)-N$^5$-methyl-1H-pyrazole-3,5-dicarboxamide

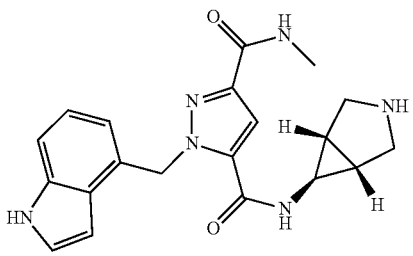 [SMILES: CNC(=O)c1cc(C(=O)N[C@H]2[C@@H]3CNC[C@@H]32)n(Cc2cccc3[nH]ccc23)n1]

tert-Butyl (1R,5S,6s)-6-(1-((1H-indol-4-yl)methyl)-3-(methylcarbamoyl)-1H-pyrazole-5-carboxamido)-3-azabicyclo[3.1.0]hexane-3-carboxylate (86.5 mg, 0.181 mmol) was taken up in DCM (4 mL). TFA (1 mL, 12.98 mmol) was added and the mixture was left to stir at rt for 2 h. The reaction was concentrated in vacuo. The sample was then loaded in methanol and purified by solid phase extraction using a 1 g SCX cartridge, washing with methanol then eluting with 2M ammonia/methanol. The appropriate fractions were combined and evaporated in vacuo to yield the crude product as a cream solid. The crude product was taken up in 1:2 MeOH:DCM (30 mL) and free flow silica added (1 g). The solvent was removed in vacuo and the silica loaded onto a 10 g ULTRA SNAP cartridge in the minimum of DCM and eluted with 0% (2M NH$_3$ in methanol) in DCM for 2CV then 0-20% (2M NH$_3$ in Methanol)/DCM. The appropriate fractions were combined and concentrated in vacuo to yield the desired product, 1-((1H-indol-4-yl)methyl)-N$^3$-((1R,5S,6s)-3-azabicyclo[3.1.0]hexan-6-yl)-N$^3$-methyl-1H-pyrazole-3,5-dicarboxamide (29.4 mg, 0.070 mmol, 39% yield) as a green solid.

LCMS (2 min Formic): Rt=0.46 min, [MH]$^+$=379.4

Example 80: 1-(1-(1H-Indol-4-yl)ethyl)-N$^5$-((1r,4r)-4-hydroxycyclohexyl)-N$^3$-methyl-1H-pyrazole-3,5-dicarboxamide

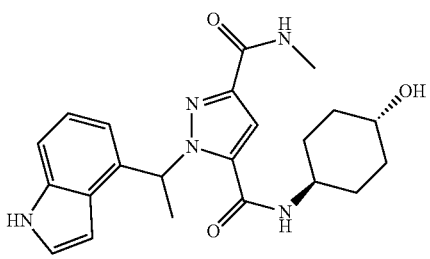 [SMILES: CNC(=O)c1cc(C(=O)N[C@H]2CC[C@H](O)CC2)n(C(C)c2cccc3[nH]ccc23)n1]

To a solution of N$^5$-((1r,4r)-4-hydroxycyclohexyl)-N$^3$-methyl-1-(1-(1-tosyl-1H-indol-4-yl)ethyl)-1H-pyrazole-3,5-dicarboxamide (330 mg, 0.585 mmol) in methanol (2 mL) and THF (4 mL) was added Cs$_2$CO$_3$ (1546 mg, 4.74 mmol) and the reaction mixture was stirred at 70° C. for 2.5 h. The reaction mixture was concentrated in vacuo and partitioned between ethyl acetate and water, and washed with brine. The layers were separated and the aqueous layer was further extracted with ethyl acetate (2×15 mL). The organic layers were combined, dried with a hydrophobic frit and concentrated in vacuo to give 153 mg of crude residue. The crude product was dissolved in 1:1 DMSO:methanol (2 mL) and was purified by MDAP (Formic). The fractions containing desired product were partitioned between sat. NaHCO$_3$ solution and DCM. The layers were separated and the aqueous layer was further extracted with two further portions of DCM (2×15 mL). The organic layers were combined, dried (hydrophobic frit) and concentrated in vacuo to give the title compound (79 mg, 0.193 mmol, 33% yield).

LCMS (2 min Formic): Rt=0.76 min, [M−H]$^−$=408

Example 81: 1-((S*)-1-(1H-Indol-4-yl)ethyl)-N$^3$-((1r,4S)-4-hydroxycyclohexyl)-N$^3$-methyl-1H-pyrazole-3,5-dicarboxamide (single enantiomer of unknown configuration at methyl centre)

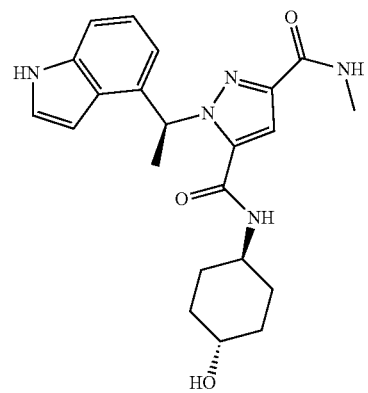 [SMILES: CNC(=O)c1cc(C(=O)N[C@H]2CC[C@H](O)CC2)n([C@@H](C)c2cccc3[nH]ccc23)n1]

69 mg of 1-(1-(1H-indol-4-yl)ethyl)-N$^3$-((1r,4r)-4-hydroxycyclohexyl)-N$^3$-methyl-1H-pyrazole-3,5-dicarboxamide (For a preparation see Example 80) was separated by chiral column chromatography using the following conditions:

The crude sample was dissolved in EtOH (4 mL) with heating.
Injection: 2 mL of the solution was injected onto the column.
Solvent: 20% EtOH (+0.2% isopropylamine)/heptane, flow rate=30 mL/min. Wavelength 215 nm
Column: 30 mm×25 cm Chiralpak AD-H (5 µm)
Total number of injections: 2

The fractions corresponding to the first eluting peak were combined and evaporated to give the desired product (30 mg).

LCMS (2 min Formic): Rt=0.74 min, [M−H]$^−$=408

Example 82: 1-(1-(1H-Pyrrolo[2,3-b]pyridin-4-yl)ethyl)-N$^3$-methyl-N$^3$-((1S,2S)-2-methylcyclopropyl)-1H-pyrazole-3,5-dicarboxamide

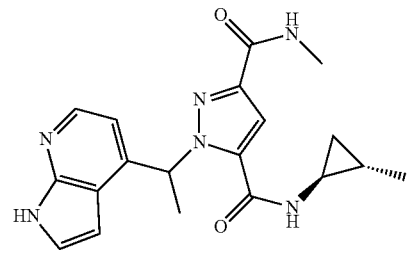 [SMILES: CNC(=O)c1cc(C(=O)N[C@H]2C[C@@H]2C)n(C(C)c2ccnc3[nH]ccc23)n1]

To a solution of N³-methyl-N³-((1S,2S)-2-methylcyclopropyl)-1-(1-(1-tosyl-1H-pyrrolo[2,3-b]pyridin-4-yl)ethyl)-1H-pyrazole-3,5-dicarboxamide (300 mg, 0.576 mmol) in methanol (2 mL) and THF (4 mL) was added Cs₂CO₃ (1502 mg, 4.61 mmol) and the reaction mixture (suspension) was stirred at 70° C. for 1.5 h. The reaction mixture was concentrated in vacuo and partitioned between ethyl acetate and water. The organic layer was separated and the aqueous layer further extracted with ethyl acetate (2×20 mL). The combined organic layers were dried with a hydrophobic frit and concentrated in vacuo to give 152 mg of a crude residue. This was purified by chromatography on silica gel, eluting with 0-100% ethyl acetate/cyclohexane followed by a gradient of 100% ethyl acetate to 25% EtOH/ethyl acetate. The fractions containing desired product were concentrated in vacuo to give the desired product as a pale yellow solid (74 mg, 28% yield).

LCMS (2 min Formic): Rt=0.65 min, [MH]⁺=367.1

Example 83: 1-((S*)-1-(1H-Pyrrolo[2,3-b]pyridin-4-yl)ethyl)-N³-methyl-N³-((1S,2S)-2-methylcyclopropyl)-1H-pyrazole-3,5-dicarboxamide

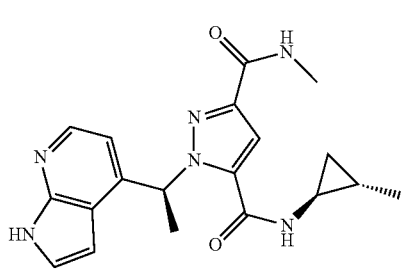 [SMILES: CNC(=O)c1cc(C(=O)N[C@H]2C[C@@H]2C)n([C@@H](C)c2ccnc3[nH]ccc23)n1]

Example 82 (62 mg) was purified by chiral HPLC. The racemate was dissolved in EtOH (4 mL) with heating. Injection: 2 mL of the solution was injected onto the column 20% EtOH (+0.2% isopropylamine)/heptane(+0.2% isopropylamine), flow rate=30 mL/min, detection wavelength=215 nm, 4. Ref 550, 100, Column 30 mm×25 cm Chiralpak AD-H (5 μm), lot no. ADH13231). Total number of injections=2. Fractions from 10-11 min were bulked and labelled peak 1. Fractions from 14-16 min were bulked labelled peak 2. The bulked pure fractions were concentrated in vacuo and then transferred to weighed flasks.

The fractions corresponding to peak 1 were collected to afford example 83 (23 mg)

LCMS (2 min Formic): Rt=0.67 min, [MH]⁺=367.2.

Example 84: 1-((1H-Indol-5-yl)methyl)-N³-((1R,5S,6r)-3-oxabicyclo[3.1.0]hexan-6-yl)-N⁵-methyl-1H-pyrazole-3,5-dicarboxamide

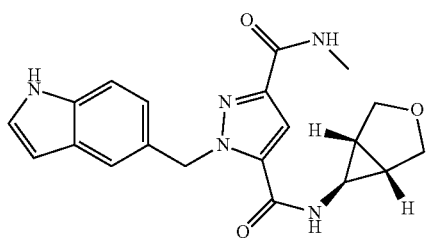 [SMILES: CNC(=O)c1cc(C(=O)N[C@H]2[C@@H]3COC[C@@H]32)n(Cc2ccc3[nH]ccc3c2)n1]

N⁵-((1R,5S,6r)-3-Oxabicyclo[3.1.0]hexan-6-yl)-N³-methyl-1-((1-tosyl-1H-indol-5-yl)methyl)-1H-pyrazole-3,5-dicarboxamide (135 mg, 0.253 mmol) was suspended in THF (2 mL) and methanol (1 mL). Cesium carbonate (412 mg, 1.265 mmol) was added, and the reaction was left to stir at 70° C. for 1 h. The reaction was concentrated in vacuo. Water (20 mL) was added to the residue and this was extracted with ethyl acetate (2×15 mL). The combined organics were dried with Na₂SO₄, filtered and concentrated in vacuo to yield the desired product (67.4 mg, 0.169 mmol, 67% yield) as a pale brown solid.

LCMS (2 min High pH): Rt=0.76 min, [MH]⁺=380.5

Example 85: 1-(1-(1H-Indol-5-yl)ethyl)-N³-((1R,5S,6r)-3-oxabicyclo[3.1.0]hexan-6-yl)-N³-methyl-1H-pyrazole-3,5-dicarboxamide

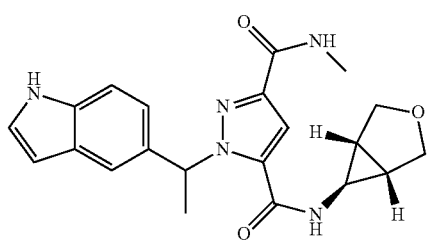 [SMILES: CNC(=O)c1cc(C(=O)N[C@H]2[C@@H]3COC[C@@H]32)n(C(C)c2ccc3[nH]ccc3c2)n1]

N⁵-((1R,5S,6r)-3-oxabicyclo[3.1.0]hexan-6-yl)-N³-methyl-1-(1-(1-tosyl-1H-indol-5-yl)ethyl)-1H-pyrazole-3,5-dicarboxamide (117 mg, 0.214 mmol) was taken up in THF (2 mL) and methanol (1 mL). Cesium carbonate (348 mg, 1.068 mmol) was added, and the reaction left to stir at 70° C. for 2 h. Water (15 mL) was added to the residue, and this was extracted with ethyl acetate (2×15 mL). The combined organics were dried with Na₂SO₄, filtered and concentrated in vacuo to yield a colourless solid. The crude product was purified by MDAP (Formic). The MDAP did not collect the product, so the waste was concentrated in vacuo and the residue was purified by MDAP (Formic). The MDAP did not collect the product, so the waste was concentrated in vacuo and the residue was purified by MDAP (Formic). The appropriate fractions were dried under a stream of nitrogen to give 1-(1-(1H-indol-5-yl)ethyl)-N³-((1R,5S,6r)-3-oxabicyclo[3.1.0]hexan-6-yl)-N³-methyl-1H-pyrazole-3,5-dicarboxamide (12.2 mg, 0.028 mmol, 13% yield) as a white solid.

LCMS (2 min Formic): Rt=0.82 min, [M−H]⁻=392.

Example 86: 1-(1-(1H-Indol-4-yl)ethyl)-N³-((1R,5S,6r)-3-oxabicyclo[3.1.0]hexan-6-yl)-N⁵-methyl-1H-pyrazole-3,5-dicarboxamide

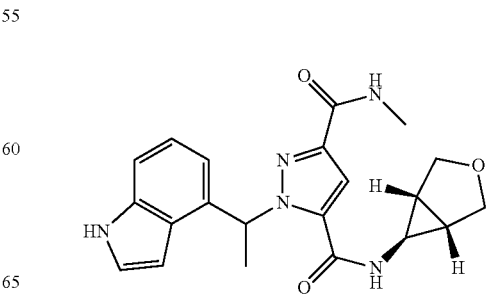

To a solution of $N^5$-((1R,5S)-3-oxabicyclo[3.1.0]hexan-6-yl)-$N^3$-methyl-1-(1-(1-tosyl-1H-indol-4-yl)ethyl)-1H-pyrazole-3,5-dicarboxamide (278 mg, 0.508 mmol) in methanol (2 mL) and THF (4 mL) was added $Cs_2CO_3$ (1323 mg, 4.06 mmol) and the reaction mixture was stirred at 70° C. for 2.5 h. The reaction mixture was concentrated in vacuo and partitioned between ethyl acetate and water. The organic layer was separated and aqueous layer further extracted with ethyl acetate (2×20 mL). The combined organic layers were dried with a hydrophobic frit and concentrated in vacuo to give 152 mg of crude residue which was purified by MDAP (Formic). The fractions containing desired product were partitioned between saturated $NaHCO_3$ solution and DCM. The organic layer was separated and aqueous layer further extracted with DCM (2×20 mL). Combined organic layers were dried (hydrophobic frit) and concentrated in vacuo to give the desired product (44 mg, 0.101 mmol, 20% yield) as a light brown solid.

LCMS (High pH): Rt=0.80 min, [M−H]⁻=392

Example 87: 1-((S*)-1-(1H-Indol-4-yl)ethyl)-$N^3$-((1R,5S,6r)-3-oxabicyclo[3.1.0]hexan-6-yl)-$N^3$-methyl-1H-pyrazole-3,5-dicarboxamide

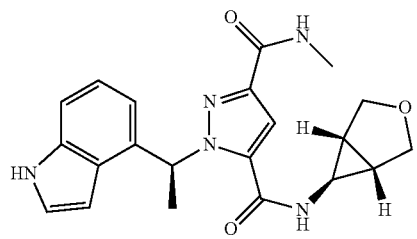 [SMILES: CNC(=O)c1cc(C(=O)N[C@H]2[C@@H]3COC[C@@H]32)n([C@@H](C)c2cccc3[nH]ccc23)n1]

36 mg of 1-(1-(1H-indol-4-yl)ethyl)-$N^3$-((1R,5S,6r)-3-oxabicyclo[3.1.0]hexan-6-yl)-$N^3$-methyl-1 pyrazole-3,5-dicarboxamide (for a preparation see Example 86) was separated by chiral column chromatography using the following conditions:

The crude sample was dissolved in EtOH (4 mL) with heating.

Injection: 2 mL of the solution was injected onto the column.
Solvent: 20% EtOH/heptane, flow rate=30 mL/min. Wavelength 215 nm
Column: 30 mm×25 cm Chiralpak AD-H (5 μm)
Total number of injections: 2

The fractions corresponding to the first eluting peak were combined and evaporated to give the desired product (13 mg).

LCMS (Formic): Rt=0.80 min, [M−H]⁻=392

Example 88: 1-((S)-1-(3-Chlorophenyl)ethyl)-$N^5$-((1R,3R,5S,6r)-3-hydroxybicyclo[3.1.0]hexan-6-yl)-$N^3$-methyl-1H-pyrazole-3,5-dicarboxamide

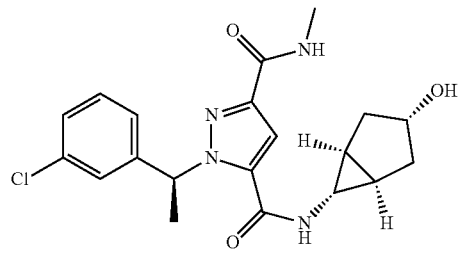 [SMILES: CNC(=O)c1cc(C(=O)N[C@H]2[C@@H]3C[C@@H](O)C[C@@H]32)n([C@@H](C)c2cccc(Cl)c2)n1]

$N^5$-((1R,5S,6r)-3-((tert-Butyldimethylsilyl)oxy)bicyclo[3.1.0]hexan-6-yl)-1-((S)-1-(3-chlorophenyl)ethyl)-$N^3$-methyl-1H-pyrazole-3,5-dicarboxamide (257 mg, 0.497 mmol) was taken up in 4M hydrochloric acid in dioxane (5 mL, 20.00 mmol) and left to stir at rt for 30 min. The reaction was concentrated in vacuo to yield a brown gum. The crude product was purified by MDAP (high pH). The appropriate fractions were concentrated in vacuo to yield 1-((S)-1-(3-chlorophenyl)ethyl)-$N^3$-((1R,3R,5S,6r)-3-hydroxybicyclo[3.1.0]hexan-6-yl)-$N^3$-methyl-1H-pyrazole-3,5-dicarboxamide (35 mg, 0.083 mmol, 17% yield) as a yellow solid.

LCMS (2 min Formic): Rt=0.89 min, [MH]⁺=403.6.

The following example was prepared in a similar manner to Example 88:

| Example | Structure and name | Intermediate used | LCMS: (System, $t_{RET}$, MH⁺) |
|---|---|---|---|
| 89 | $N^5$-((1R,3R,5S,6r)-3-Hydroxybicyclo[3.1.0]hexan-6-yl)-$N^3$-methyl-1-((S)-1-phenylpropyl)-1H-pyrazole-3,5-dicarboxamide | Intermediate 82 | Formic, 0.88 min, 383.3 |

Example 90: 1-((S)-1-(3-Chlorophenyl)ethyl)-N³-((1R,3S,5S,6r)-3-hydroxybicyclo[3.1.0]hexan-6-yl)-N³-methyl-1H-pyrazole-3,5-dicarboxamide

Example 92: 1-Benzyl-N³-cyclopropyl-N³-methyl-1H-Pyrazole-3,5-dicarboxamide

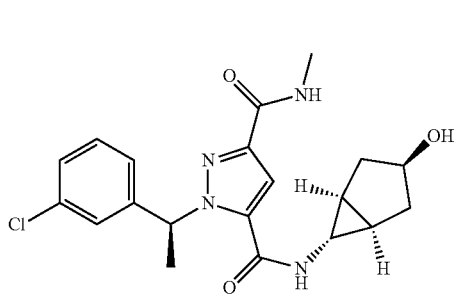 [SMILES: CNC(=O)c1cc(C(=O)N[C@H]2[C@@H]3C[C@H](O)C[C@@H]32)n([C@@H](C)c2cccc(Cl)c2)n1]

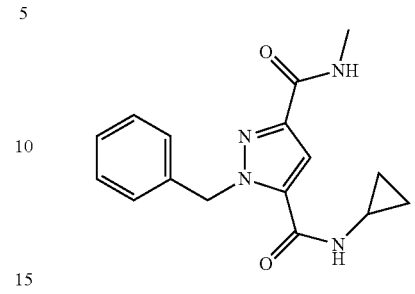

N⁵-((1R,5S,6r)-3-((tert-Butyldimethylsilypoxy)bicyclo[3.1.0]hexan-6-yl)-1-((S)-1-(3-chlorophenyl)ethyl)-N³-methyl-1H-pyrazole-3,5-dicarboxamide (257 mg, 0.497 mmol) was taken up in 4M hydrochloric acid in dioxane (5 mL, 20.00 mmol) and left to stir at rt for 30 min. The reaction was concentrated in vacuo to yield a brown gum. The crude product was purified by MDAP (High pH). The desired fractions were concentrated in vacuo to yield 1-((S)-1-(3-chlorophenyl)ethyl)-N⁵-((1R,3S,5S,6r)-3-hydroxybicyclo[3.1.0]hexan-6-yl)-N³-methyl-1H-pyrazole-3,5-dicarboxamide (52.5 mg, 0.124 mmol, 24.91% yield) as a cream solid.

LCMS (2 min Formic): Rt=0.92 min, [MH]⁺=403.6.

The following example was prepared in a similar manner to Example 90:

To a solution of 1-benzyl-3-(methylcarbamoyl)-1H-pyrazole-5-carboxylic acid (1 g, 3.66 mmol) and DIPEA (3.84 mL, 21.99 mmol) in DMF (1 mL) stirred under nitrogen at rt was added oxalyl chloride (0.642 mL, 7.33 mmol) followed by the addition of cyclopropanamine (0.418 g, 7.33 mmol) in one charge. The reaction mixture was stirred at rt for 16 h. The reaction was poured into ice water, then extracted with EtOAc (3×20 mL), combined organic layer was washed with brine solution, dried over sodium sulphate, filtered and the filtrate was concentrated under vacuum to afford the crude product. The crude product was added to a silica gel 60-120 column and was eluted with 65% EtOAc in n-hexane and collected pure fractions were concentrated under vacuum to get 1-benzyl-N³-cyclopropyl-M-methylpyrazole-3,5-dicarboxamide (901 mg, 2.75 mmol, 75% yield) as an off-white solid. LCMS (5.5 min Method E): Rt=2.47 min, [MH]⁺=299.3.

Examples 93-138

Examples 93-138 were prepared in an analogous manner to examples described above.

| Example | Structure and name | Intermediate used | LCMS: (System, $t_{RET}$, MH⁺) |
|---|---|---|---|
| 91 | N⁵-((1R,3S,5S,6r)-3-Hydroxybicyclo[3.1.0]hexan-6-yl)-N³-methyl-1-((S)-1-phenylpropyl)-1H-pyrazole-3,5-dicarboxamide | Intermediate 82 | Formic, 0.91 min, 383.3 |

| Ex No. | Name | Structure | [MH]+ | Rt (min), Method |
|---|---|---|---|---|
| 93 | 1-Benzyl-$N^3$-methyl-$N^5$-(tetrahydro-2H-pyran-4-yl)-1H-pyrazole-3,5-dicarboxamide | 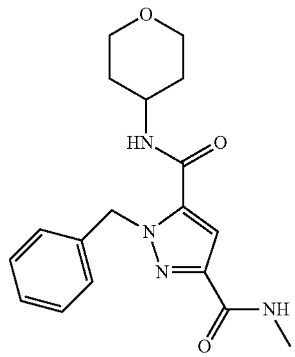 [SMILES: CNC(=O)c1cc(C(=O)NC2CCOCC2)n(Cc2ccccc2)n1] | 343.1 | 1.72 (Method A) |
| 94 | 1-Benzyl-$N^3$,$N^5$-dimethyl-1H-pyrazole-3,5-dicarboxamide | 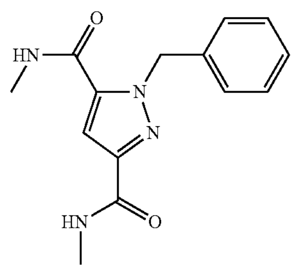 [SMILES: CNC(=O)c1cc(C(=O)NC)n(Cc2ccccc2)n1] | 273.1 | 1.63 (Method A) |
| 95 | 1-Benzyl-$N^3$-methyl-$N^5$-(2-(piperidin-4-yl)ethyl)-1H-pyrazole-3,5-dicarboxamide | 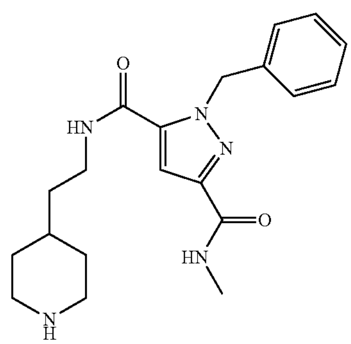 [SMILES: CNC(=O)c1cc(C(=O)NCCC2CCNCC2)n(Cc2ccccc2)n1] | 370.2 | 1.34 (Method A) |
| 96 | 1-Benzyl-$N^5$-isopropyl-$N^3$-methyl-1H-pyrazole-3,5-dicarboxamide | 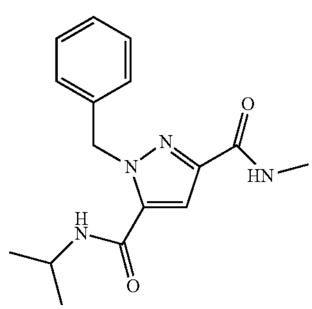 [SMILES: CNC(=O)c1cc(C(=O)NC(C)C)n(Cc2ccccc2)n1] | 301.2 | 1.91 (Method B) |
| 97 | 1-Benzyl-$N^3$-methyl-$N^5$-propyl-1H-pyrazole-3,5-dicarboxamide | 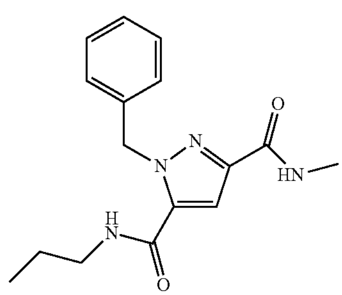 [SMILES: CCCNC(=O)c1cc(C(=O)NC)nn1Cc1ccccc1] | 301.2 | 1.93 (Method B) |

-continued

| Ex No. | Name | Structure | [MH]+ | Rt (min), Method |
|---|---|---|---|---|
| 98 | 1-Benzyl-$N^5$-ethyl-$N^3$-methyl-1H-pyrazole-3,5-dicarboxamide | 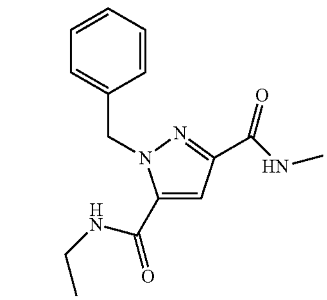 [SMILES: CCNC(=O)c1cc(C(=O)NC)nn1Cc1ccccc1] | 287.4 | 1.77 (Method D) |
| 99 | 1-Benzyl-$N^3$-methyl-$N^5$-(tetrahydrofuran-3-yl)-1H-pyrazole-3,5-dicarboxamide | 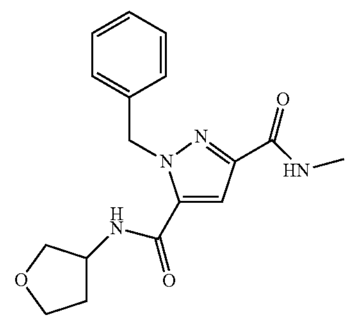 [SMILES: CNC(=O)c1cc(C(=O)NC2CCOC2)n(Cc2ccccc2)n1] | 329.3 | 1.69 (Method B) |
| 100 | $N^5$-Cyclopropyl-1-(4-fluorobenzyl)-$N^3$-methyl-1H-pyrazole-3,5-dicarboxamide | 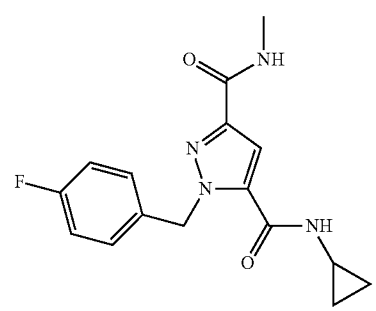 [SMILES: CNC(=O)c1cc(C(=O)NC2CC2)n(Cc2ccc(F)cc2)n1] | 317.1 | 1.82 (Method B) |
| 101 | $N^5$-Cyclopropyl-1-(2-fluorobenzyl)-$N^3$-methyl-1H-pyrazole-3,5-dicarboxamide | 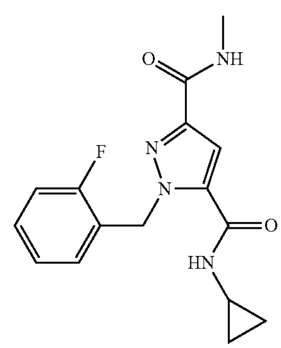 [SMILES: CNC(=O)c1cc(C(=O)NC2CC2)n(Cc2ccccc2F)n1] | 317.1 | 1.78 (Method E) |

| Ex No. | Name | Structure | [MH]⁺ | Rt (min), Method |
|---|---|---|---|---|
| 102 | 1-(4-Cyanobenzyl)-$N^5$-cyclopropyl-$N^3$-methyl-1H-pyrazole-3,5-dicarboxamide | 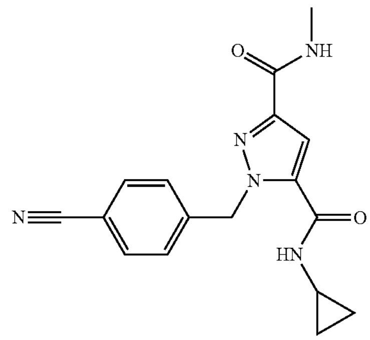 [SMILES: CNC(=O)c1cc(C(=O)NC2CC2)n(Cc2ccc(C#N)cc2)n1] | 324.1 | 1.67 (Method B) |
| 103 | $N^5$-Cyclopropyl-1-(3-methoxybenzyl)-$N^3$-methyl-1H-pyrazole-3,5-dicarboxamide | 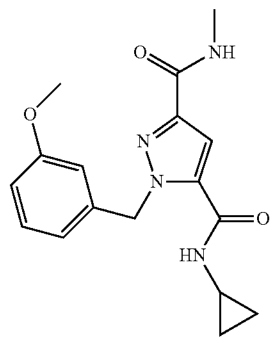 [SMILES: CNC(=O)c1cc(C(=O)NC2CC2)n(Cc2cccc(OC)c2)n1] | 329.1 | 6.28 (Method C) |
| 104 | $N^5$-Cyclopropyl-1-(4-methoxybenzyl)-$N^3$-methyl-1H-pyrazole-3,5-dicarboxamide | 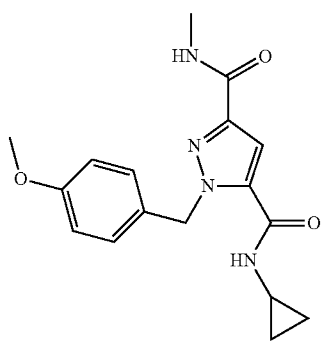 [SMILES: CNC(=O)c1cc(C(=O)NC2CC2)n(Cc2ccc(OC)cc2)n1] | 329.2 | 1.82 (Method B) |
| 105 | $N^5$-Cyclopropyl-$N^3$-methyl-1-(4-methylbenzyl)-1H-pyrazole-3,5-dicarboxamide | 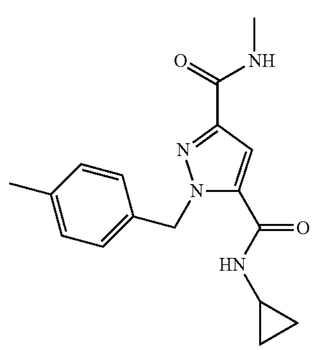 [SMILES: CNC(=O)c1cc(C(=O)NC2CC2)n(Cc2ccc(C)cc2)n1] | 313.1 | 6.63 (Method C) |

-continued

| Ex No. | Name | Structure | [MH]+ | Rt (min), Method |
|---|---|---|---|---|
| 106 | N5-Cyclopropyl-1-(2-methoxybenzyl)-N3-methyl-1H-pyrazole-3,5-dicarboxamide | 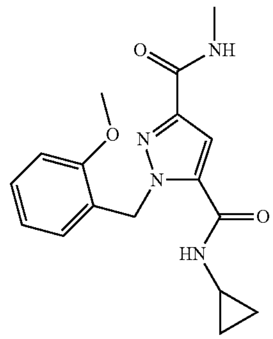 [SMILES: CNC(=O)c1cc(C(=O)NC2CC2)n(Cc2ccccc2OC)n1] | 329.2 | 1.76 (Method B) |
| 107 | 1-((1H-Indol-4-yl)methyl)-N5-((1R,5S,6s)-3-acetyl-3-azabicyclo[3.1.0]hexan-6-yl)-N3-methyl-1H-pyrazole-3,5-dicarboxamide | 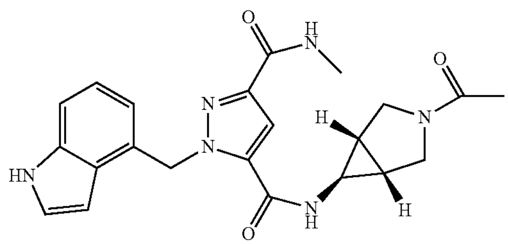 [SMILES: CNC(=O)c1cc(C(=O)N[C@H]2[C@@H]3CN(C(C)=O)C[C@@H]32)n(Cc2cccc3[nH]ccc23)n1] | 421.3 | 0.69 (Formic) |
| 108 | N3-Ethyl-N5-((1r,4S)-4-hydroxycyclohexyl)-1-((S)-1-phenylethyl)-1H-pyrazole-3,5-dicarboxamide | 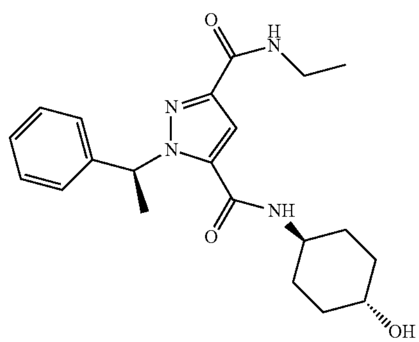 [SMILES: CCNC(=O)c1cc(C(=O)N[C@H]2CC[C@H](O)CC2)n([C@@H](C)c2ccccc2)n1] | 385.3 | 0.88 (Formic) |
| 109 | N5-((1R,5S,6r)-3-Oxabicyclo[3.1.0]hexan-6-yl)-N3-methyl-1-((R)-1-phenylethyl)-1H-pyrazole-3,5-dicarboxamide | 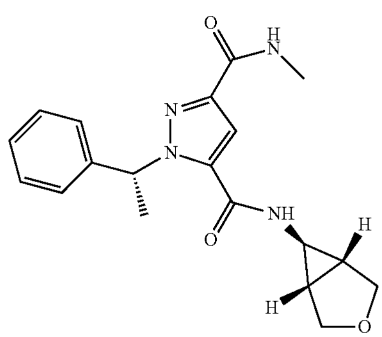 [SMILES: CNC(=O)c1cc(C(=O)N[C@H]2[C@@H]3COC[C@@H]32)n([C@H](C)c2ccccc2)n1] | 355.3 | 0.85 (Formic) |

-continued

| Ex No. | Name | [MH]+ | Rt (min), Method |
|---|---|---|---|
| 110 | N5-((1r,4R)-4-Hydroxycyclohexyl)-N3-methyl-1-((R)-1-phenylethyl)-1H-pyrazole-3,5-dicarboxamide | 371.3 | 0.82 (Formic) |
| 111 | N5-(1-Hydroxypropan-2-yl)-N3-methyl-1-((S)-1-phenylethyl)-1H-pyrazole-3,5-dicarboxamide, mixture of diastereomers | 331.1 | 0.79 (Formic) |
| 112 | (S)-N5-(tert-Butyl)-N3-methyl-1-(1-phenylethyl)-1H-pyrazole-3,5-dicarboxamide | 329.1 | 1.08 (Formic) |
| 113 | N5-((S)-sec-Butyl)-N3-methyl-1-((S)-1-phenylethyl)-1H-pyrazole-3,5-dicarboxamide | 329.2 | 1.04 (Formic) |
| 114 | N5-((1R,3R,5S,6s)-3-Hydroxybicyclo[3.1.0]hexan-6-yl)-N3-methyl-1-((S)-1-phenylethyl)-1H-pyrazole-3,5-dicarboxamide | 369.4 | 0.79 (High pH) |

-continued

| Ex No. | Name | Structure | [MH]+ | Rt (min), Method |
|---|---|---|---|---|
| 115 | (S)-N5-(2-Hydroxyethyl)-N3-methyl-1-(1-phenylethyl)-1H-pyrazole-3,5-dicarboxamide | 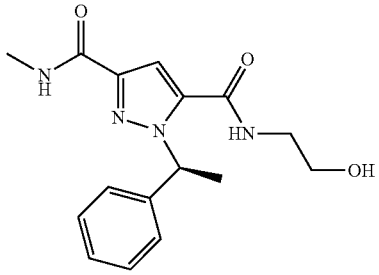 [SMILES: CNC(=O)c1cc(C(=O)NCCO)n([C@@H](C)c2ccccc2)n1] | 317.1 | 0.75 (Formic) |
| 116 | (S)-N5-(2-Cyanoethyl)-N3-methyl-1-(1-phenylethyl)-1H-pyrazole-3,5-dicarboxamide | 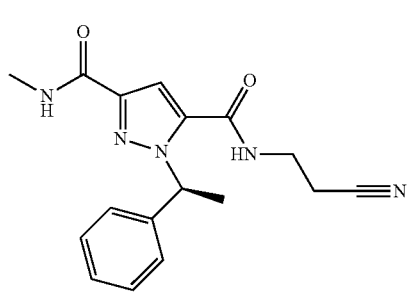 [SMILES: CNC(=O)c1cc(C(=O)NCCC#N)n([C@@H](C)c2ccccc2)n1] | 326.1 | 0.86 (Formic) |
| 117 | (S)-N5-(2-(1H-Imidazol-4-yl)ethyl)-N3-methyl-1-(1-phenylethyl)-1H-pyrazole-3,5-dicarboxamide | 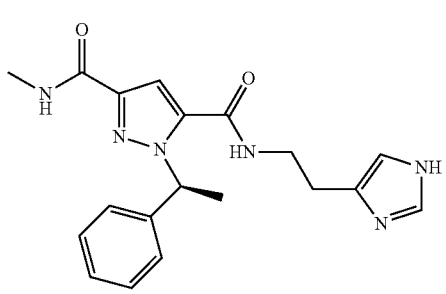 [SMILES: CNC(=O)c1cc(C(=O)NCCc2c[nH]cn2)n([C@@H](C)c2ccccc2)n1] | 367.1 | 0.53 (Formic) |
| 118 | (S)-N3-Methyl-N5-(3-morpholinopropyl)-1-(1-phenylethyl)-1H-pyrazole-3,5-dicarboxamide | 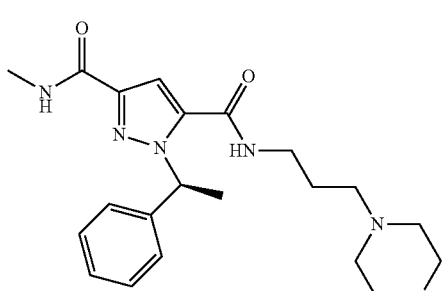 | 400.2 | 0.54 (Formic) |
| 119 | (S)-N3-Methyl-1-(1-phenylethyl)-N5-(2-(pyridin-4-yl)ethyl)-1H-pyrazole-3,5-dicarboxamide | 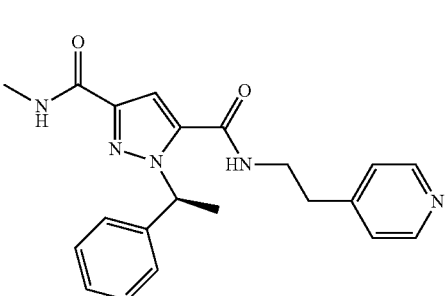 | 378.1 | 0.56 (Formic) |

-continued

| Ex No. | Name | Structure | [MH]+ | Rt (min), Method |
|---|---|---|---|---|
| 120 | (S)-N$^5$-(3-(Dimethylamino)propyl)-N$^3$-methyl-1-(1-phenylethyl)-1H-pyrazole-3,5-dicarboxamide | 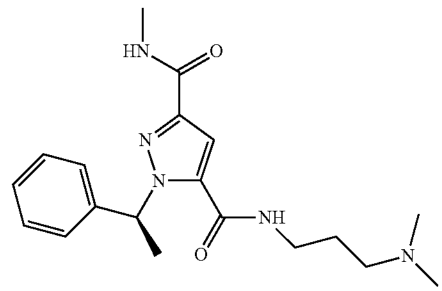 [SMILES: CNC(=O)c1cc(C(=O)NCCCN(C)C)n([C@@H](C)c2ccccc2)n1] | 358.1 | 0.53 (Formic) |
| 121 | (S)-N$^5$-(2-Methoxyethyl)-N$^3$-methyl-1-(1-phenylethyl)-1H-pyrazole-3,5-dicarboxamide | 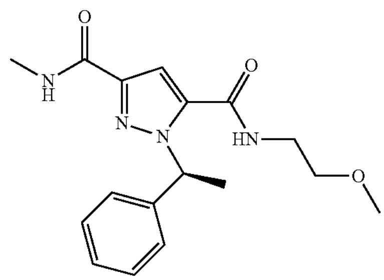 | 331.1 | 0.87 (Formic) |
| 122 | (S)-N$^5$-(2-(1H-Imidazol-2-yl)ethyl)-N$^3$-methyl-1-(1-phenylethyl)-1H-pyrazole-3,5-dicarboxamide | 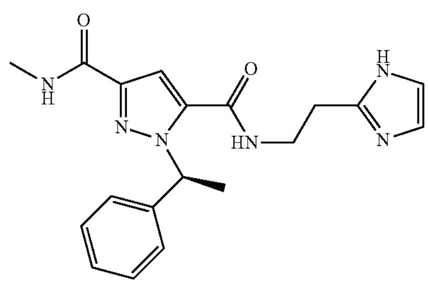 [SMILES: CNC(=O)c1cc(C(=O)NCCc2ncc[nH]2)n([C@@H](C)c2ccccc2)n1] | 367.1 | 0.52 (Formic) |
| 123 | (S)-N$^3$-Methyl-1-(1-phenylethyl)-N$^5$-(pyridin-4-ylmethyl)-1H-pyrazole-3,5-dicarboxamide | 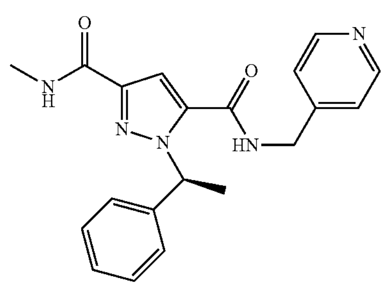 [SMILES: CNC(=O)c1cc(C(=O)NCc2ccncc2)n([C@@H](C)c2ccccc2)n1] | 364.1 | 0.56 (Formic) |
| 124 | (S)-N$^3$-Methyl-1-(1-phenylethyl)-N$^5$-(2-(pyridin-3-yl)ethyl)-1H-pyrazole-3,5-dicarboxamide | 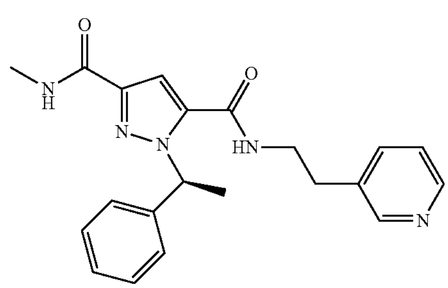 [SMILES: CNC(=O)c1cc(C(=O)NCCc2cccnc2)n([C@@H](C)c2ccccc2)n1] | 378.1 | 0.58 (Formic) |

-continued

| Ex No. | Name | Structure | [MH]+ | Rt (min), Method |
|---|---|---|---|---|
| 125 | (S)-N³-Methyl-1-(1-phenylethyl)-N⁵-(2-(pyridin-2-yl)ethyl)-1H-pyrazole-3,5-dicarboxamide | 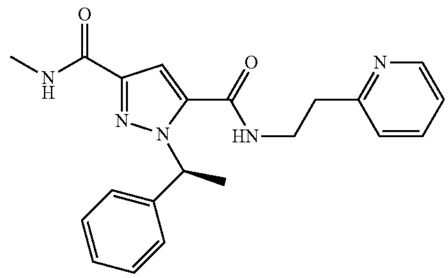 [SMILES: CNC(=O)c1cc(C(=O)NCCc2ccccn2)n([C@@H](C)c2ccccc2)n1] | 378.1 | 0.59 (Formic) |
| 126 | (S)-N⁵-(2,2-Difluoroethyl)-N³-methyl-1-(1-phenylethyl)-1H-pyrazole-3,5-dicarboxamide | 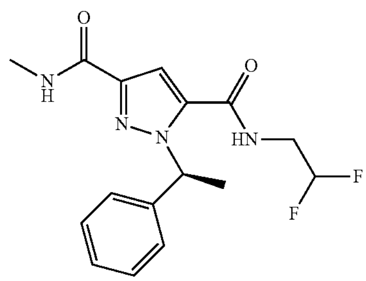 [SMILES: CNC(=O)c1cc(C(=O)NCC(F)F)n([C@@H](C)c2ccccc2)n1] | 337.1 | 0.95 (Formic) |
| 127 | N⁵-(2-(4-Acetylmorpholin-2-yl)ethyl)-N³-methyl-1-((S)-1-phenylethyl)-1H-pyrazole-3,5-dicarboxamide, mixture of diastereomers | 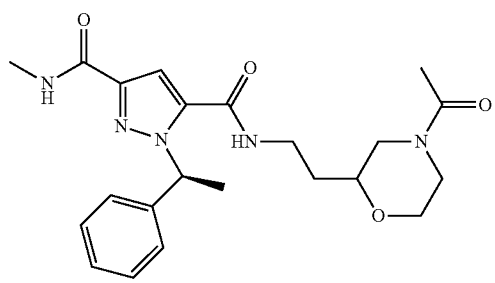 [SMILES: CNC(=O)c1cc(C(=O)NCCC2CN(C(C)=O)CCO2)n([C@@H](C)c2ccccc2)n1] | 428.2 | 0.81 (Formic) |
| 128 | N⁵-((1s,3R)-3-Hydroxycyclobutyl)-N³-methyl 1-((S)-1-phenylethyl)-1H-pyrazole-3,5-dicarboxamide | 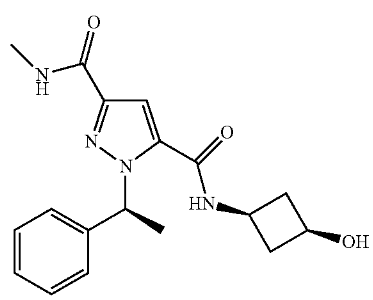 [SMILES: CNC(=O)c1cc(C(=O)N[C@H]2C[C@@H](O)C2)n([C@@H](C)c2ccccc2)n1] | 343.1 | 0.80 (Formic) |
| 129 | N³-Methyl-1-((S)-1-phenylethyl)-N⁵-((tetrahydro-2H-pyran-2-yl)methyl)-1H-pyrazole-3,5-dicarboxamide, mixture of diastereomers | 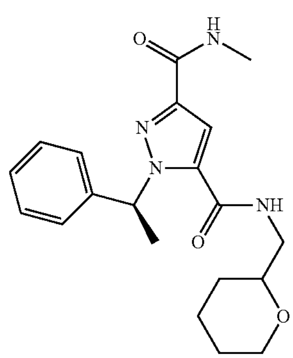 [SMILES: CNC(=O)c1cc(C(=O)NCC2CCCCO2)n([C@@H](C)c2ccccc2)n1] | 371.1 | 1.01 (Formic) |

-continued

| Ex No. | Name | Structure | [MH]+ | Rt (min), Method |
|---|---|---|---|---|
| 130 | N⁵-((1R,2R)-2-Hydroxycyclobutyl)-N³-methyl-1-((S)-1-phenylethyl)-1H-pyrazole-3,5-dicarboxamide | 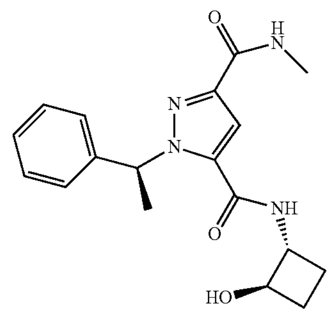 [SMILES: CNC(=O)c1cc(C(=O)N[C@@H]2CC[C@H]2O)n([C@@H](C)c2ccccc2)n1] | 343.1 | 0.82 (Formic) |
| 131 | 1-((R*)-1-(1H-Indol-4-yl)ethyl)-N⁵-(1r,4R)-4-hydroxycyclohexyl)-N³-methyl-1H-pyrazole-3,5-dicarboxamide | 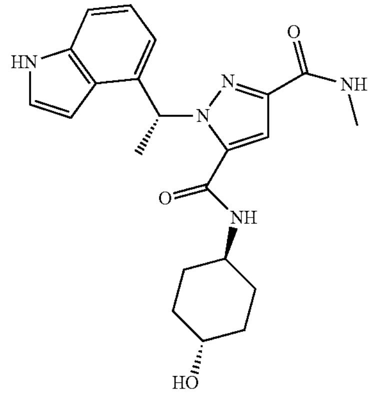 [SMILES: CNC(=O)c1cc(C(=O)N[C@H]2CC[C@H](O)CC2)n([C@H](C)c2cccc3[nH]ccc23)n1] | MH– 408.3 | 0.74 (Formic) |
| 132 | 1-((R)-1-(1H-Indol-4-yl)ethyl)-N⁵-((1R,5S,6r)-3-oxabicyclo[3.1.0]hexan-6-yl)-N³-methyl-1H-pyrazole-3,5-dicarboxamide | 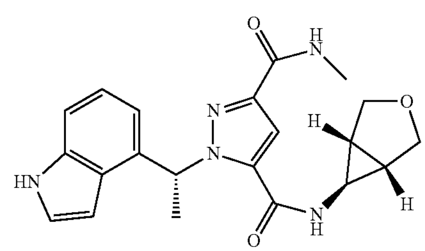 [SMILES: CNC(=O)c1cc(C(=O)N[C@H]2[C@@H]3COC[C@@H]32)n([C@H](C)c2cccc3[nH]ccc23)n1] | MH– 392.3 | 0.77 (Formic) |
| 133 | N⁵-((1R,5S,6r)-3-Oxabicyclo[3.1.0]hexan-6-yl)-N³-methyl-1-((S)-1-(pyridin-2-yl)ethyl)-1H-pyrazole-3,5-dicarboxamide | 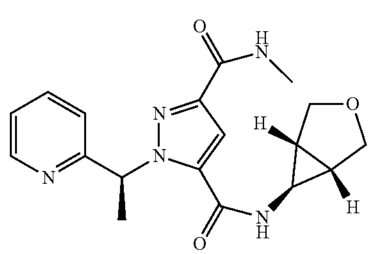 [SMILES: CNC(=O)c1cc(C(=O)N[C@H]2[C@@H]3COC[C@@H]32)n([C@@H](C)c2ccccn2)n1] | 356.5 | 0.67 (High pH) |
| 134 | (S)-N³-Methyl-N⁵-(1H-pyrazol-4-yl)-1-(1-(pyridin-2-yl)ethyl)-1H-pyrazole-3,5-dicarboxamide | 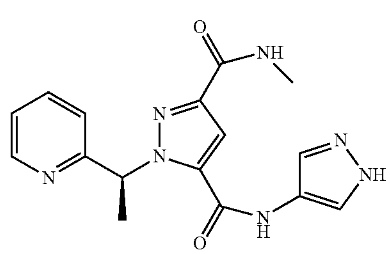 [SMILES: CNC(=O)c1cc(C(=O)Nc2cn[nH]c2)n([C@@H](C)c2ccccn2)n1] | 340.5 | 0.53 (Formic) |

| Ex No. | Name | Structure | [MH]+ | Rt (min), Method |
|---|---|---|---|---|
| 135 | N³-Methyl-N⁵-((1S,2S)-2-methylcyclopropyl)-1-(1-(1-tosyl-1H-pyrrolo[2,3-b]pyridin-4-yl)ethyl)-1H-pyrazole-3,5-dicarboxamide, mixture of diasatereomers | 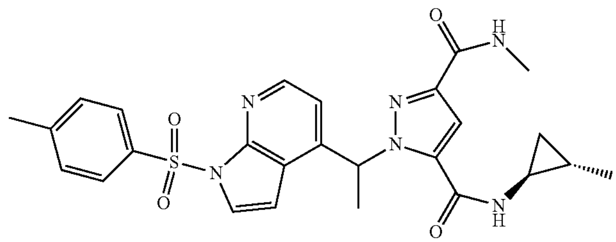 | 521.1 | 1.11 (Formic) |
| 136 | N⁵-((1R,5S,6r)-3-Oxabicyclo[3.1.0]hexan-6-yl)-1-((S)-1-(2-methoxyphenyl)ethyl)-N³-methyl-1H-pyrazole-3,5-dicarboxamide | 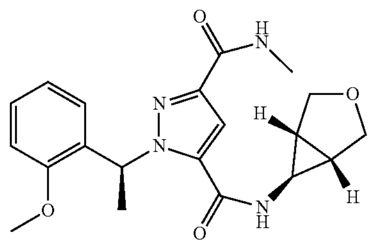 [SMILES: CNC(=O)c1cc(C(=O)N[C@H]2[C@@H]3COC[C@@H]32)n([C@@H](C)c2ccccc2OC)n1] | 385.2 | 0.84 (Formic) |
| 137 | 1-((R)-1-(1H-Pyrrolo[2,3-b]pyridin-4-yl)ethyl)-N³-methyl-N⁵-((1S,2S)-2-methylcyclopropyl)-1H-pyrazole-3,5-dicarboxamide | 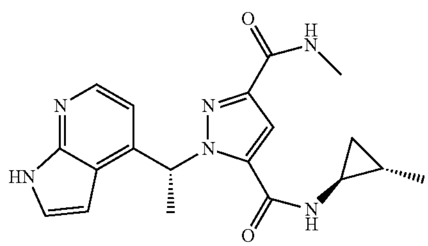 [SMILES: CNC(=O)c1cc(C(=O)N[C@H]2C[C@@H]2C)n([C@H](C)c2ccnc3[nH]ccc23)n1] | 367.2 | 0.66 (Formic) |
| 138 | 1-((S)-1-(3-Chlorophenyl)ethyl)-N⁵-((1R,3R,5S,6s)-3-hydroxybicyclo[3.1.0]hexan-6-yl)-N³-methyl-1H-pyrazole-3,5-dicarboxamide | 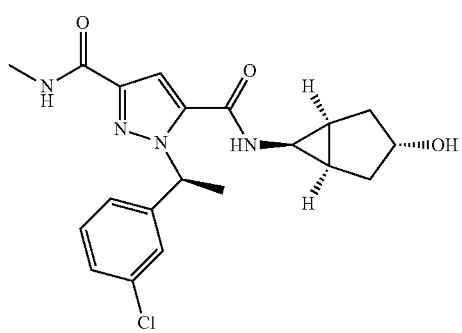 [SMILES: CNC(=O)c1cc(C(=O)N[C@@H]2[C@@H]3C[C@@H](O)C[C@@H]32)n([C@@H](C)c2cccc(Cl)c2)n1] | 403.6 | 0.87 (Formic) |

Example 139: N⁵-((1r,4S)-4-Methoxycyclohexyl)-N³-methyl-1-((S)-1-phenylethyl)-1H-pyrazole-3,5-dicarboxamide

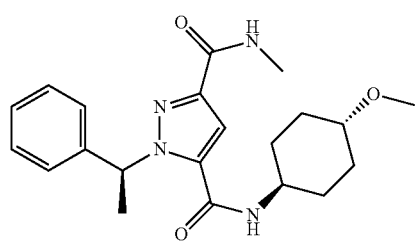 [SMILES: CNC(=O)c1cc(C(=O)N[C@H]2CC[C@H](OC)CC2)n([C@@H](C)c2ccccc2)n1]

(S)-3-(Methylcarbamoyl)-1-(1-phenylethyl)-1H-pyrazole-5-carboxylic acid (For a preparation, see Intermediate 5, 112 mg, 0.410 mmol) was dissolved in DMF (1 mL) before the addition of HATU (234 mg, 0.615 mmol). (1r,4r)-4-Methoxycyclohexan-1-amine hydrochloride (82 mg, 0.445 mmol) was then added followed by DIPEA (0.358 mL, 2.049 mmol) and the reaction stirred at rt for 2 h. The sample was purified directly by MDAP (high pH). The relevant fractions were combined and concentrated in vacuo to give N⁵-((1r,4S)-4-methoxycyclohexyl)-N³-methyl-1-((S)-1-phenylethyl)-1H-pyrazole-3,5-dicarboxamide (135 mg, 0.316 mmol, 77% yield).

LCMS (2 min Formic): Rt=0.96 min, [MH]+=385.2.

¹H NMR (400 MHz, DMSO-d₆) δ ppm 8.32 (d, J=7.83 Hz, 1H) 8.09-8.17 (m, 1H) 7.20-7.34 (m, 6H) 6.67 (q, J=7.01 Hz, 1H) 3.60-3.74 (m, 1H) 3.23 (s, 3H) 3.03-3.14 (m, 1H) 2.78 (d, J=4.65 Hz, 3H) 1.94-2.05 (m, 2H) 1.84 (d, J=7.09 Hz, 4H) 1.71-1.79 (m, 1H) 1.13-1.40 (m, 4H)

Example 140: N⁵-((1R,5S,6r)-3-Oxabicyclo[3.1.0]hexan-6-yl)-1-(indolin-4-ylmethyl)-N³-methyl-1H-pyrazole-3,5-dicarboxamide

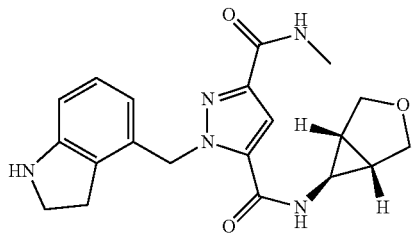 [SMILES: CNC(=O)c1cc(C(=O)N[C@H]2[C@@H]3COC[C@@H]32)n(Cc2cccc3c2CCN3)n1]

1-((1H-Indol-4-yl)methyl-N⁵-((1R,5S,6r)-3-oxabicyclo[3.1.0]hexan-6-yl)-N³-methyl-1H pyrazole-3,5-dicarboxamide (For a preparation, see Example 78, 10 mg, 0.026 mmol) was taken up in glacial acetic acid (1 mL). Sodium cyanoborohydride (3.31 mg, 0.053 mmol) was added, and the reaction left to stir at rt for 2 h. The reaction was diluted with water and extracted with 10% MeOH in DCM. The aqueous layer was concentrated in vacuo and extracted with 10% MeOH in DCM. The combined organics were passed through a hydrophobic frit and concentrated in vacuo to give a crude residue which was purified by MDAP (High pH). The appropriate fractions were concentrated in vacuo to give N⁵-((1R,5S,6r)-3-oxabicyclo[3.1.0]hexan-6-yl)-1-(indolin-4-ylmethyl)-N³-methyl-1H-pyrazole-3,5-dicarboxamide (3.8 mg, 8.47 μmol, 32% yield) as a white solid.

LCMS (2 min HpH): Rt=0.69 min, [MH]⁺=382.2

Example 141: 1-(1-(3-(2-Hydroxyethoxy)phenyl)ethyl)-N³-methyl-N⁵-((1S,2S)-2-methylcyclopropyl)-1H-pyrazole-3,5-dicarboxamide, Mixture of Diastereomers

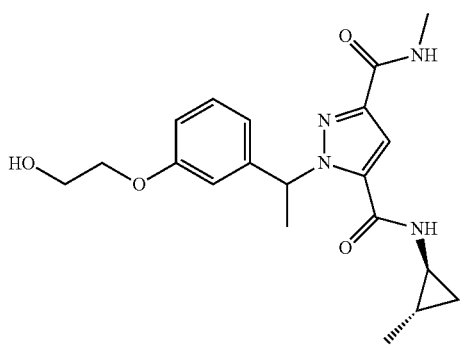 [SMILES: CNC(=O)c1cc(C(=O)N[C@H]2C[C@@H]2C)n(C(C)c2cccc(OCCO)c2)n1]

1-(1-(3-(2-((tert-Butyldimethylsilypoxy)ethoxy)phenyl)ethyl)-N³-methyl-N⁵-((1S,2S)-2-methylcyclopropyl)-1H-pyrazole-3,5-dicarboxamide (For a preparation, see Intermediate 132, 1.1 g, 2.197 mmol, mixture of diastereomers) was dissolved in DCM (20 mL) and HCl (5 mL, 5.00 mmol, 1M in ether) was added, then the mixture was stirred at rt for 2 h. The solvent was evaporated in vacuo and the residue was dissolved in DCM (10 mL) and loaded onto a 25 g SNAP Ultra silica column, which was eluted with 0-100% (25% EtOH/EtOAc)/cyclohexane and the product-containing fractions were evaporated in vacuo to give 1-(1-(3-(2-hydroxyethoxy)phenyl)ethyl)-N³-methyl-N⁵-((1S,2S)-2-methylcyclopropyl)-1H-pyrazole-3,5-dicarboxamide (0.71 g, 1.837 mmol, 84% yield, mixture of diastereomers) as a colourless solid.

LCMS (2 min Formic): Rt=0.81 min, [M+Na]⁺=409.3.

Example 142: (+/−)-N⁵-((1R,5S,6r)-3-Oxabicyclo[3.1.0]hexan-6-yl)-1-(1-(3-(2-hydroxyethoxy)phenyl)ethyl)-N³-methyl-1H-pyrazole-3,5-dicarboxamide

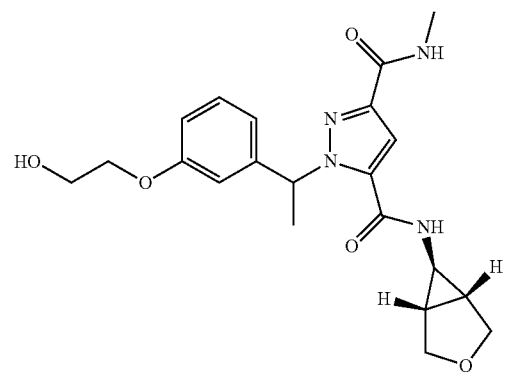 [SMILES: CNC(=O)c1cc(C(=O)N[C@H]2[C@@H]3COC[C@@H]32)n(C(C)c2cccc(OCCO)c2)n1]

(+/−)-1-(1-(3-(2-((tert-Butyldimethylsilypoxy)ethoxy)phenyl)ethyl)-3-(methylcarbamoyl)-1H-pyrazole-5-carboxylic acid (For a preparation, see Intermediate 131, 0.27 g, 0.603 mmol), (1R,5S,6r)-3-oxabicyclo[3.1.0]hexan-6-amine, hydrochloride (0.106 g, 0.784 mmol), HATU (0.298 g, 0.784 mmol) and Et₃N (0.252 mL, 1.810 mmol) were dissolved in DCM (20 mL) and the mixture was stirred for 2 h, then allowed to stand over the weekend at rt. The resulting mixture was stirred with water (50 mL) for 1 h, then the organic layer was separated, dried and evaporated in vacuo to give a pale yellow gum. This was dissolved in DCM and loaded onto a 100 g SNAP ultra silica column and eluted with 0-100% EtOAc/cyclohexane. The product-containing fractions were evaporated in vacuo to give (+/−)-N⁵-((1R,5S,6r)-3-oxabicyclo[3.1.0]hexan-6-yl)-1-(1-(3-(2-((tert-butyldimethylsilyl)oxy)ethoxy)phenyl)ethyl)-N³-methyl-1H-pyrazole-3,5-dicarboxamide (0.14 g, 0.265 mmol, 44% yield) as a colourless solid. This solid was dissolved in DCM (5 mL) and HCl (2 mL, 2.0 mmol, 1M in ether) was added, then the mixture was stirred for 2 h at rt. The solvent was evaporated in vacuo and the crude product was dissolved in DCM and loaded onto a 10 g silica column and purified by flash chromatography eluting with 0-100% (25% EtOH/EtOAc)/cyclohexane. The product-containing fractions were evaporated in vacuo to give (+/−)-N⁵-((1R,5S,6r)-3-oxabicyclo[3.1.0]hexan-6-yl)-1-(1-(3-(2-hydroxyethoxy)phenyl)ethyl)-N³-methyl-1H-pyrazole-3,5-dicarboxamide (81 mg, 0.195 mmol, 32% yield) as a colourless foam.

LCMS (2 min Formic): Rt=0.71 min, [MH]⁺=415.4.

The following examples were prepared in a similar manner to Example 1:

| Example number | Structure and name | [MH+] | Rt (min) |
|---|---|---|---|
| 143 | (S)-N³-Methyl-N⁵-(3-methylisothiazol-5-yl)-1-(1-phenylethyl)-1H-pyrazole-3,5-dicarboxamide | 370.0 | 1.00 (Formic) |
| 144 | N⁵-((1R,3R,5S,6r)-3-Methoxybicyclo[3.1.0]hexan-6-yl)-N³-methyl-1-((S)-1-phenylethyl)-1H-pyrazole-3,5-dicarboxamide | 493.1 | 1.30 (High pH) |
| 145 | (S)-N⁵-(6-Hydroxyspiro[3.3]heptan-2-yl)-N³-methyl-1-(1-phenylethyl)-1H-pyrazole-3,5-dicarboxamide, mixture of diastereomers | 383.4 | 0.86 (Formic) |
| 146 | N⁵-((1r,4S)-4-(Hydroxymethyl)cyclohexyl)-N³-methyl-1-((S)-1-phenylethyl)-1H-pyrazole-3,5-dicarboxamide | 385.3 | 0.89 (High pH) |

-continued

| Example number | Structure and name | [MH+] | Rt (min) |
|---|---|---|---|
| 147 | (S)-N³-Methyl-1-(1-phenylethyl)-N⁵-(pyridazin-4-yl)-1H-pyrazole-3,5-dicarboxamide | 351.0 | 0.81 (Formic) |
| 148 | N⁵-((1S*,4S*)-4-Hydroxy-3,3-dimethylcyclohexyl)-N³-methyl-1-((S)-1-phenylethyl)-1H-pyrazole-3,5-dicarboxamide | 399.1 | 0.94 (High pH) |
| 149 | N⁵-((1R,5S,6r)-3-Oxabicyclo[3.1.0]hexan-6-yl)-N³-methyl-1-((S)-1-(m-tolyl)ethyl)-1H-pyrazole-3,5-dicarboxamide | 369.5 | 0.94 (High pH) |
| 150 | (+/−)-N⁵-((1R,5S,6r)-3-Oxabicyclo[3.1.0]hexan-6-yl)-1-(1-(3-chloro-5-fluorophenyl)ethyl)-N³-methyl-1H-pyrazole-3,5-dicarboxamide | 407.2 | 1.00 (Formic) |

| Example number | Structure and name | [MH+] | Rt (min) |
|---|---|---|---|
| 151 | 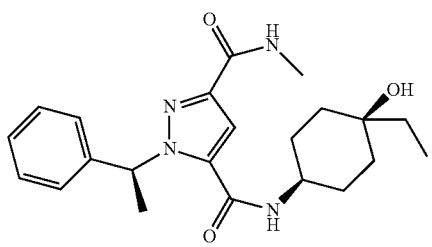 [SMILES: CC[C@]1(O)CC[C@@H](NC(=O)c2cc(C(=O)NC)nn2[C@@H](C)c2ccccc2)CC1]<br>N5-((1s*,4R*)-4-Ethyl-4-hydroxycyclohexyl)-N3-methyl-1-((S)-1-phenylethyl)-1H-pyrazole-3,5-dicarboxamide | 399.2 | 1.01 (High pH) |
| 152 | 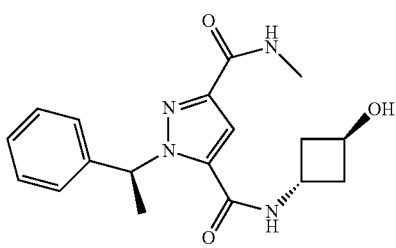 [SMILES: CNC(=O)c1cc(C(=O)N[C@H]2C[C@H](O)C2)n([C@@H](C)c2ccccc2)n1]<br>N5-((1r*,3S*)-3-Hydroxycyclobutyl)-N3-methyl-1-((S)-1-phenylethyl)-1H-pyrazole-3,5-dicarboxamide | 343.0 | 0.75 (Formic) |
| 153 | 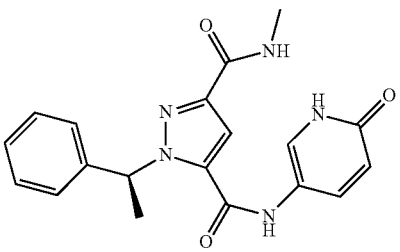 [SMILES: CNC(=O)c1cc(C(=O)Nc2ccc(=O)[nH]c2)n([C@@H](C)c2ccccc2)n1]<br>(S)-N3-Methyl-N5-(6-oxo-1,6-dihydropyridin-3-yl)-1-(1-phenylethyl)-1H-pyrazole-3,5-dicarboxamide | 366.0 | 0.75 (Formic) |
| 154 | 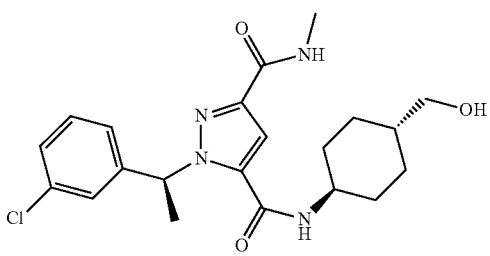 [SMILES: CNC(=O)c1cc(C(=O)N[C@H]2CC[C@H](CO)CC2)n([C@@H](C)c2cccc(Cl)c2)n1]<br>1-((S)-1-(3-Chlorophenyl)ethyl)-N5-((1r,4S)-4-(hydroxymethyl)cyclohexyl)-N3-methyl-1H-pyrazole-3,5-dicarboxamide | 419.3 | 0.98 (High pH) |

| Example number | Structure and name | [MH+] | Rt (min) |
|---|---|---|---|
| 155 | 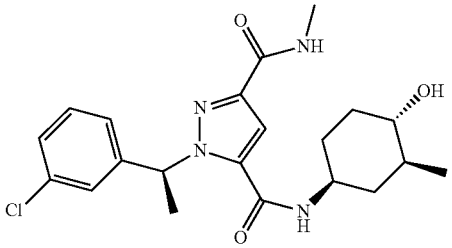 [SMILES: CNC(=O)c1cc(C(=O)N[C@H]2CC[C@H](O)[C@@H](C)C2)n([C@@H](C)c2cccc(Cl)c2)n1]<br>1-((S)-1-(3-Chlorophenyl)ethyl)-N⁵-((1S,3S,4S)-4-hydroxy-3-methylcyclohexyl)-N³-methyl-1H-pyrazole-3,5-dicarboxamide | 419.3 | 0.98 (Formic) |
| 156 | 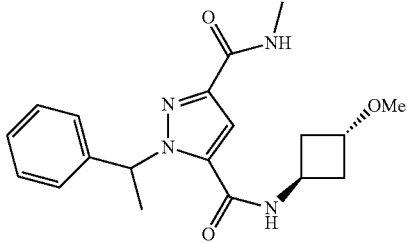 [SMILES: CNC(=O)c1cc(C(=O)N[C@H]2C[C@H](OC)C2)n(C(C)c2ccccc2)n1]<br>(+/−)-N⁵-(1r,3S)-3-Methoxycyclobutyl)-N³-methyl-1-(1-phenylethyl)-1H-pyrazole-3,5-dicarboxamide | 357.2 | 0.91 (High pH) |
| 157 | 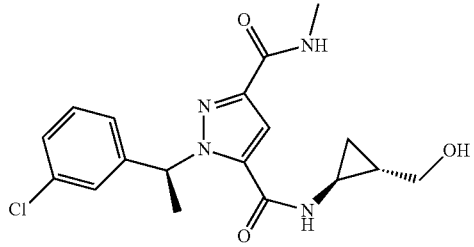 [SMILES: CNC(=O)c1cc(C(=O)N[C@H]2C[C@@H]2CO)n([C@@H](C)c2cccc(Cl)c2)n1]<br>1-((S)-1-(3-Chlorophenyl)ethyl)-N⁵-((trans)-2-(hydroxymethyl)cyclopropyl)-N³-methyl-1H-pyrazole-3,5-dicarboxamide, mixture of diastereomers | 377.1 | 0.87 (High pH) |
| 158 | 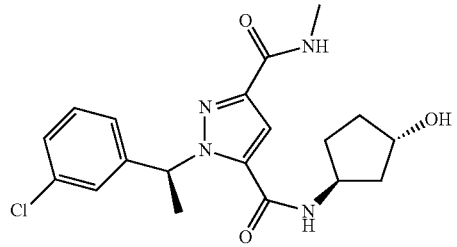 [SMILES: CNC(=O)c1cc(C(=O)N[C@H]2CC[C@H](O)C2)n([C@@H](C)c2cccc(Cl)c2)n1]<br>1-((S)-1-(3-Chlorophenyl)ethyl)-N⁵-((trans)-3-hydroxycyclopentyl)-N³-methyl-1H-pyrazole-3,5-dicarboxamide, mixture of diastereomers | 391.3 | 0.89 (Formic) |

-continued
| Example number | Structure and name | [MH+] | Rt (min) |
|---|---|---|---|
| 159 | 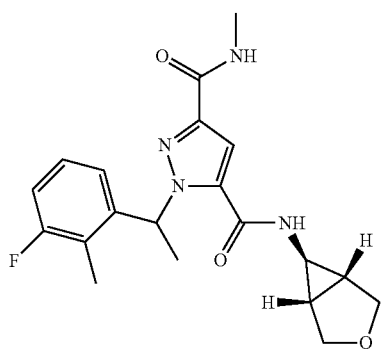 [SMILES: CNC(=O)c1cc(C(=O)N[C@H]2[C@@H]3COC[C@@H]32)n(C(C)c2cccc(F)c2C)n1]<br>(+/−)-N5-((1R,5S,6r)-3-Oxabicyclo[3.1.0]hexan-6-yl)-1-(1-(3-fluoro-2-methylphenyl)ethyl)-N3-methyl-1H-pyrazole-3,5-dicarboxamide | 387.3 | 0.93 (Formic) |
| 160 | 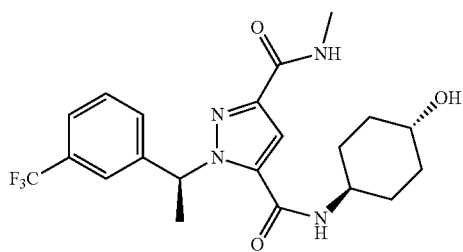 [SMILES: CNC(=O)c1cc(C(=O)N[C@H]2CC[C@H](O)CC2)n([C@@H](C)c2cccc(C(F)(F)F)c2)n1]<br>N5-((1s,4R)-4-Hydroxycyclohexyl)-N3-methyl-1-((S*)-1-(3-(trifluoromethyl)phenyl)ethyl)-1H-pyrazole-3,5-dicarboxamide | 387.3 | 0.93 (Formic) |
| 161 | 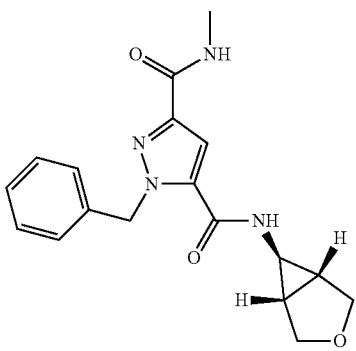 [SMILES: CNC(=O)c1cc(C(=O)N[C@H]2[C@@H]3COC[C@@H]32)n(Cc2ccccc2)n1]<br>1-Benzyl-N5-((1R,5S,6r)-3-oxabicyclo[3.1.0]hexan-6-yl)-N3-methyl-1H-pyrazole-3,5-dicarboxamide | 341.2 | 0.80 (Formic) |

-continued

| Example number | Structure and name | [MH+] | Rt (min) |
|---|---|---|---|
| 162 | N5-((1R*,3S*,5S*,6s*)-3-(Benzyloxy)bicyclo[3.1.0]hexan-6-yl)-1-((S)-1-(3-chlorophenyl)ethyl)-N3-methyl-1H-pyrazole-3,5-dicarboxamide | 493.5 | 1.30 (High pH) |
| 163 | (S)-1-(1-(3-Chlorophenyl)ethyl)-N5-(6-hydroxyspiro[3.3]heptan-2-yl)-N3-methyl-1H-pyrazole-3,5-dicarboxamide, mixture of diastereomers | 417.4 | 0.97 (Formic) |
| 164 | N5-((1S,3S,4S)-4-Hydroxy-3-methylcyclohexyl)-N3-methyl-1-((S)-1-phenylethyl)-1H-pyrazole-3,5-dicarboxamide | 385.3 | 0.86 (Formic) |
| 165 | (S)-N5-(2-Ethyl-2H-1,2,3-triazol-4-yl)-N3-methyl-1-(1-phenylethyl)-1H-pyrazole-3,5-dicarboxamide | 368.1 | 1.00 (Formic) |

| Example number | Structure and name | [MH+] | Rt (min) |
|---|---|---|---|
| 166 | 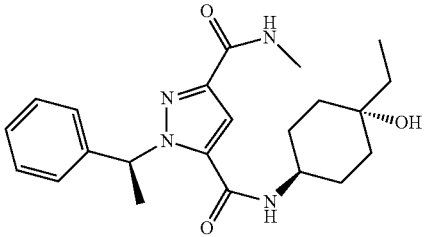 [SMILES: CC[C@]1(O)CC[C@H](NC(=O)c2cc(C(=O)NC)nn2[C@@H](C)c2ccccc2)CC1]<br>N5-((1r*,4S*)-4-Ethyl-4-hydroxycyclohexyl)-N3-methyl-1-((S)-1-phenylethyl)-1H-pyrazole-3,5-dicarboxamide | 399.2 | 0.91 (HpH) |
| 167 | 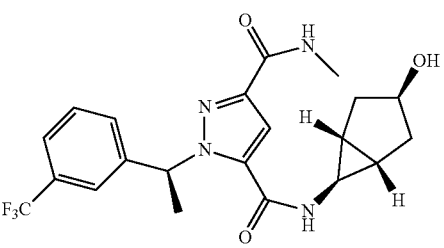 [SMILES: CNC(=O)c1cc(C(=O)N[C@H]2[C@@H]3C[C@@H](O)C[C@@H]32)n([C@@H](C)c2cccc(C(F)(F)F)c2)n1]<br>N5-((1R*,3R*,5S*,6r*)-3-Hydroxybicyclo[3.1.0]hexan-6-yl)-N3-methyl-1-((S*)-1-(3-(trifluoromethyl)phenyl)ethyl)-1H-pyrazole-3,5-dicarboxamide | 437.2 | 0.92 (Formic) |
| 168 | 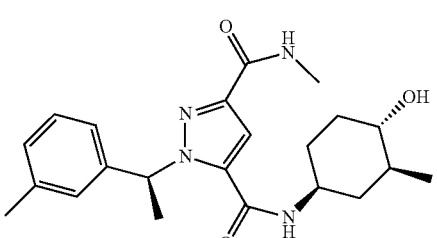<br>N5-((1S,3S,4S)-4-Hydroxy-3-methylcyclohexyl)-N3-methyl-1-((S)-1-(m-tolyl)ethyl)-1H-pyrazole-3,5-dicarboxamide | 399.6 | 0.95 (HpH) |
| 169 | 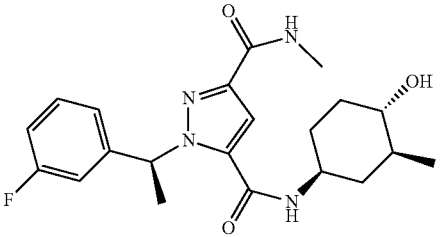 [SMILES: CNC(=O)c1cc(C(=O)N[C@H]2CC[C@H](O)[C@@H](C)C2)n([C@@H](C)c2cccc(F)c2)n1]<br>1-((S)-1-(3-Fluorophenyl)ethyl)-N5-((1S,3S,4S)-4-hydroxy-3-methylcyclohexyl)-N3-methyl-1H-pyrazole-3,5-dicarboxamide | 403.6 | 0.93 (HpH) |

| Example number | Structure and name | [MH+] | Rt (min) |
|---|---|---|---|
| 170 | 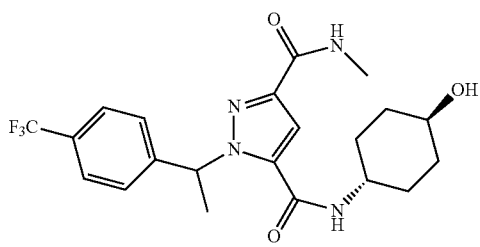 [SMILES: CNC(=O)c1cc(C(=O)N[C@H]2CC[C@H](O)CC2)n(C(C)c2ccc(C(F)(F)F)cc2)n1]<br>(+/−)-N⁵-((1r,4r)-4-Hydroxycyclohexyl)-N³-methyl-1-(1-(4-(trifluoromethyl)phenyl)ethyl)-1H-pyrazole-3,5-dicarboxamide | 439.1 | 0.96 (Formic) |
| 171 | 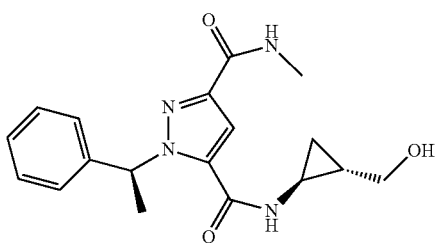 [SMILES: CNC(=O)c1cc(C(=O)N[C@H]2C[C@@H]2CO)n([C@@H](C)c2ccccc2)n1]<br>N⁵-((1S*,2S*)-2-(Hydroxymethyl)cyclopropyl)-N³-methyl-1-((S)-1-phenylethyl)-1H-pyrazole-3,5-dicarboxamide | 343.1 | 0.78 (HpH) |
| 172 | 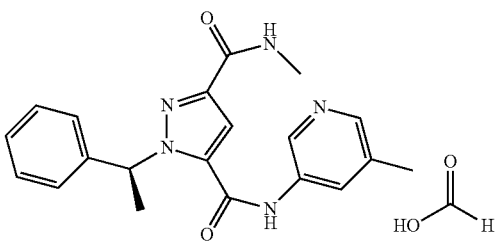<br>(S)-N³-Methyl-N⁵-(5-methylpyridin-3-yl)-1-(1-phenylethyl)-1H-pyrazole-3,5-dicarboxamide, formate salt | 364.0 | 0.75 (Formic) |
| 173 | 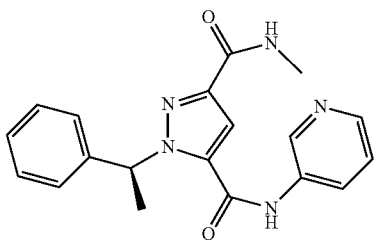 [SMILES: CNC(=O)c1cc(C(=O)Nc2cccnc2)n([C@@H](C)c2ccccc2)n1]<br>(S)-N³-Methyl-1-(1-phenylethyl)-N⁵-(pyridin-3-yl)-1H-pyrazole-3,5-dicarboxamide | 350.0 | 0.75 (Formic) |

| Example number | Structure and name | [MH+] | Rt (min) |
|---|---|---|---|
| 174 | 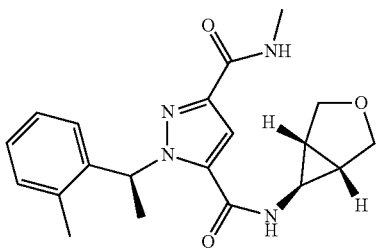 [SMILES: CNC(=O)c1cc(C(=O)N[C@H]2[C@@H]3COC[C@@H]32)n([C@@H](C)c2ccccc2C)n1]<br>N⁵-((1R,5S,6r)-3-Oxabicyclo[3.1.0]hexan-6-yl)-N³-methyl-1-((S)-1-(o-tolyl)ethyl)-1H-pyrazole-3,5-dicarboxamide | 369.3 | 0.90 (Formic) |
| 175 | 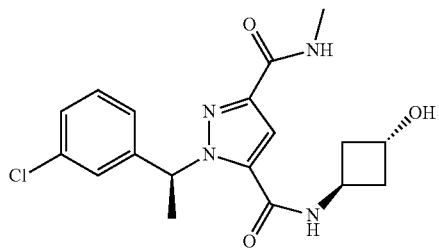 [SMILES: CNC(=O)c1cc(C(=O)N[C@H]2C[C@H](O)C2)n([C@@H](C)c2cccc(Cl)c2)n1]<br>1-((S)-1-(3-Chlorophenyl)ethyl)-N⁵-((1r,3S)-3-hydroxycyclobutyl)-N³-methyl-1H-pyrazole-3,5-dicarboxamide | 377.2 | 0.87 (High pH) |
| 176 | 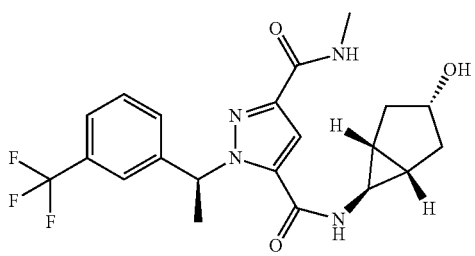 [SMILES: CNC(=O)c1cc(C(=O)N[C@H]2[C@@H]3C[C@H](O)C[C@@H]32)n([C@@H](C)c2cccc(C(F)(F)F)c2)n1]<br>N⁵-((1R*,3S*,5S*,6r*)-3-Hydroxybicyclo[3.1.0]hexan-6-yl)-N³-methyl-1-((S*)-1-(3-(trifluoromethyl)phenyl)ethyl)-1H-pyrazole-3,5-dicarboxamide | 437.2 | 0.95 (Formic) |
| 177 | 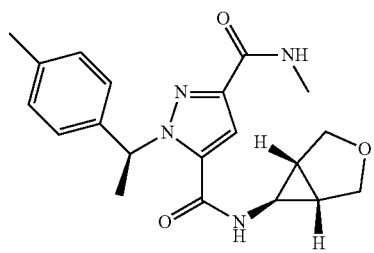 [SMILES: CNC(=O)c1cc(C(=O)N[C@H]2[C@@H]3COC[C@@H]32)n([C@@H](C)c2ccc(C)cc2)n1]<br>N⁵-((1R,5S,6r)-3-Oxabicyclo[3.1.0]hexan-6-yl)-N³-methyl-1-((S)-1-(p-tolyl)ethyl)-1H-pyrazole-3,5-dicarboxamide | 369.6 | 0.95 (High pH) |

| Example number | Structure and name | [MH+] | Rt (min) |
|---|---|---|---|
| 178 | 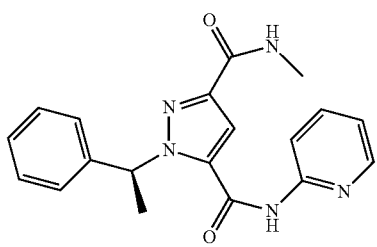 [SMILES: CNC(=O)c1cc(C(=O)Nc2ccccn2)n([C@@H](C)c2ccccc2)n1]<br>(S)-N³-Methyl-1-(1-phenylethyl)-N⁵-(pyridin-2-yl)-1H-pyrazole-3,5-dicarboxamide formate salt | 350.0 | 0.98 (Formic) |
| 179 | 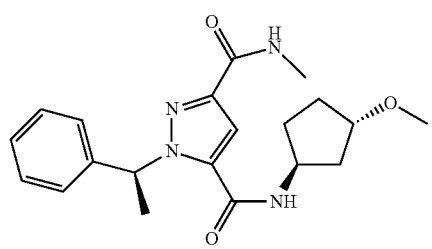 [SMILES: CNC(=O)c1cc(C(=O)N[C@H]2CC[C@H](OC)C2)n([C@@H](C)c2ccccc2)n1]<br>N⁵-((1S,3S)-3-Methoxycyclopentyl)-N³-methyl-1-((S)-1-phenylethyl)-1H-pyrazole-3,5-dicarboxamide | 371.6 | 0.98 (High pH) |
| 180 | 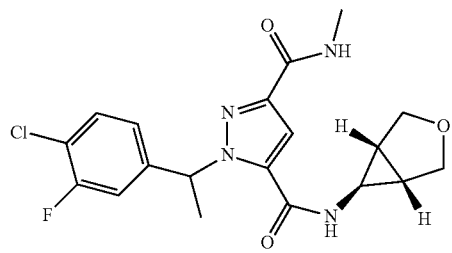 [SMILES: CNC(=O)c1cc(C(=O)N[C@H]2[C@@H]3COC[C@@H]32)n(C(C)c2ccc(Cl)c(F)c2)n1]<br>(+/−)-N⁵-((1R,5S,6r)-3-Oxabicyclo[3.1.0]hexan-6-yl)-1-(1-(4-chloro-3-fluorophenyl)ethyl)-N³-methyl-1H-pyrazole-3,5-dicarboxamide | 407.3 | 0.98 (Formic) |
| 181 | 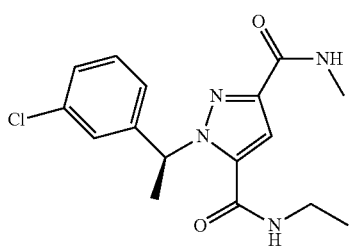 [SMILES: CCNC(=O)c1cc(C(=O)NC)nn1[C@@H](C)c1cccc(Cl)c1]<br>(S)-1-(1-(3-Chlorophenyl)ethyl)-N⁵-ethyl-N³-methyl-1H-pyrazole-3,5-dicarboxamide | 335.2 | 1.00 (Formic) |

| Example number | Structure and name | [MH+] | Rt (min) |
|---|---|---|---|
| 182 | 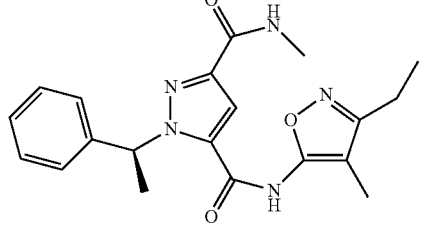<br>(S)-N$^5$-(3-Ethyl-4-methylisoxazol-5-yl)-<br>N$^3$-methyl-1-(1-phenylethyl)-1H-<br>pyrazole-3,5-dicarboxamide | 382.0 | 1.06 (Formic) |
| 183 | 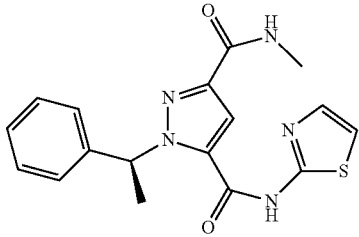 [SMILES: CNC(=O)c1cc(C(=O)Nc2nccs2)n([C@@H](C)c2ccccc2)n1]<br>(S)-N$^3$-Methyl-1-(1-phenylethyl)-N$^5$-<br>(thiazol-2-yl)-1H-pyrazole-3,5-<br>dicarboxamide | 356.0 | 1.00 (Formic) |

The following examples were prepared in a similar manner to Example 81:

| Example number | Structure and name | [MH+] | Rt (min) |
|---|---|---|---|
| 184 | 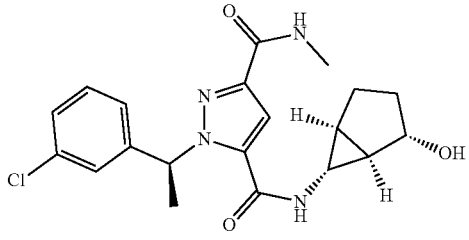<br>1-((S)-1-(3-Chlorophenyl)ethyl)-N$^5$-<br>((1R*,2S*,5S*,6R*)-2-<br>hydroxybicyclo[3.1.0]hexan-6-yl)-N$^3$-<br>methyl-1H-pyrazole-3,5-dicarboxamide | 403.5 | 0.94 (High pH) |
| 185 | 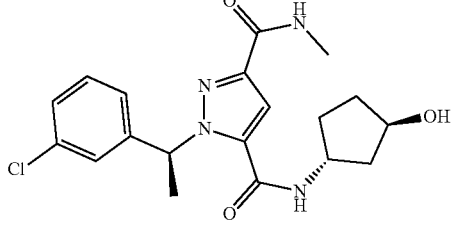<br>1-((S)-1-(3-Chlorophenyl)ethyl)-N$^5$-<br>((1R*,3R*)-3-hydroxycyclopentyl)-N$^3$-<br>methyl-1H-pyrazole-3,5-dicarboxamide | 391.3 | 0.90 (Formic) |

| Example number | Structure and name | [MH⁺] | Rt (min) |
|---|---|---|---|
| 186 | 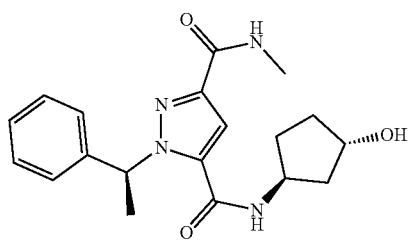<br>N⁵-((1S*,3S*)-3-Hydroxycyclopentyl)-N³-methyl-1-((S)-1-phenylethyl)-1H-pyrazole-3,5-dicarboxamide | 357.4 | 0.80 (Formic) |
| 187 | 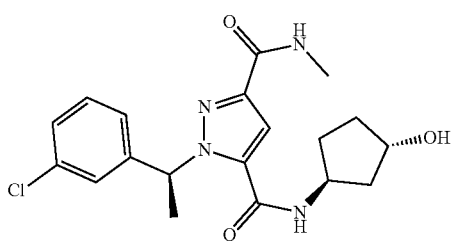<br>1-((S)-1-(3-Chlorophenyl)ethyl)-N⁵-((1S*,3S*)-3-hydroxycyclopentyl)-N³-methyl-1H-pyrazole-3,5-dicarboxamide | 391.3 | 0.89 (Formic) |
| 188 | 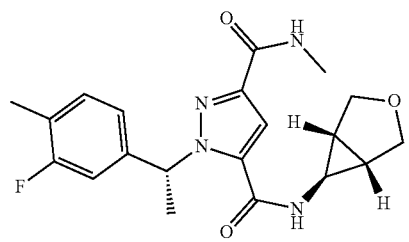<br>N⁵-((1R,5S,6r)-3-Oxabicyclo[3.1.0]hexan-6-yl)-1-((R)-1-(3-fluoro-4-methylphenyl)ethyl)-N³-methyl-1H-pyrazole-3,5-dicarboxamide | 387.2 | 0.95 (Formic) |
| 189 | 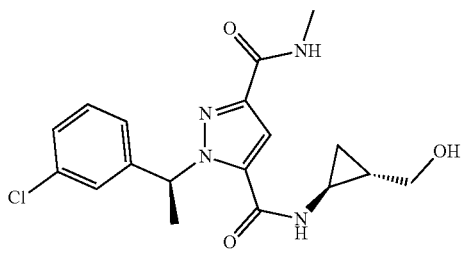<br>1-((S)-1-(3-Chlorophenyl)ethyl)-N⁵-((1S*,2S*)-2-(hydroxymethyl)cyclopropyl)-N³-methyl-1H-pyrazole-3,5-dicarboxamide | 439.3 | 0.95 (Formic) |

| Example number | Structure and name | [MH+] | Rt (min) |
|---|---|---|---|
| 190 | 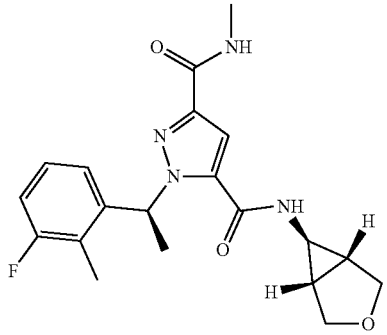<br>N5-((1R,5S,6r)-3-Oxabicyclo[3.1.0]hexan-6-yl)-1-((S*)-1-(3-fluoro-2-methylphenyl)ethyl)-N3-methyl-1H-pyrazole-3,5-dicarboxamide | 387.2 | 0.92 (Formic) |
| 191 | 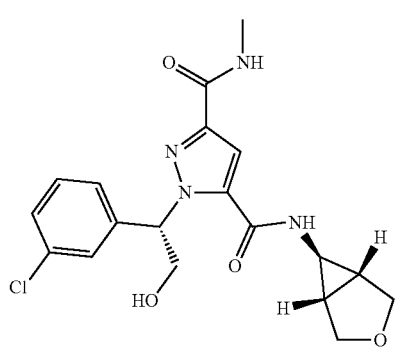<br>N5-((1R,5S,6r)-3-Oxabicyclo[3.1.0]hexan-6-yl)-1-((S*)-1-(3-chlorophenyl)-2-hydroxyethyl)-N3-methyl-1H-pyrazole-3,5-dicarboxamide | 405.5 | 0.83 (High pH) |
| 192 | 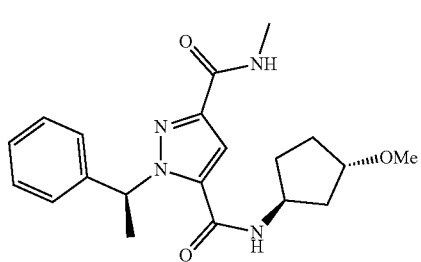<br>N5-((1S*,3S*)-3-Methoxycyclopentyl)-N3-methyl-1-((S)-1-phenylethyl)-1H-pyrazole-3,5-dicarboxamide | 371.6 | 0.97 (High pH) |

-continued

| Example number | Structure and name | [MH+] | Rt (min) |
|---|---|---|---|
| 193 | 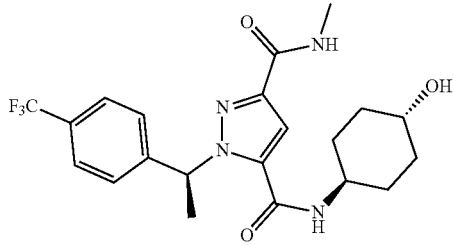<br>N5-((1r,4S)-4-Hydroxycyclohexyl)-N3-methyl-1-((S*)-1-(4-(trifluoromethyl)phenyl)ethyl)-1H-pyrazole-3,5-dicarboxamide | 439.3 | 0.95 (Formic) |
| 194 | 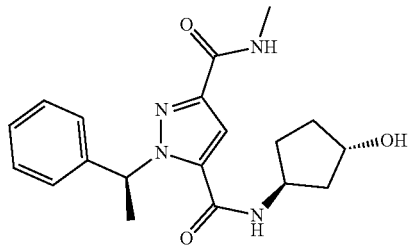<br>N5-((1S*,3S*)-3-Hydroxycyclopentyl)-N3-methyl-1-((S)-1-phenylethyl)-1H-pyrazole-3,5-dicarboxamide | 357.4 | 0.79 (Formic) |
| 195 | 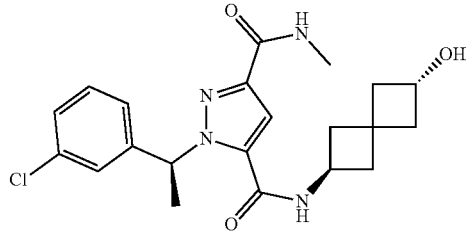<br>(S)-1-(1-(3-chlorophenyl)ethyl)-N5-(6-hydroxyspiro[3.3]heptan-2-yl)-N3-methyl-1H-pyrazole-3,5-dicarboxamide | 417.3 | 1.01 (Formic) |
| 196 | 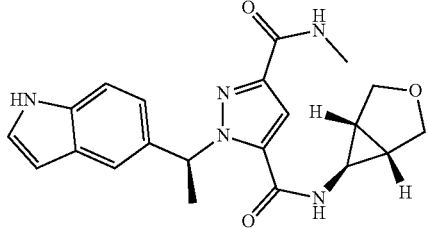<br>1-((S*)-1-(1H-Indol-5-yl)ethyl)-N5-((1R,5S,6r)-3-oxabicyclo[3.1.0]hexan-6-yl)-N3-methyl-1H-pyrazole-3,5-dicarboxamide | 394.2 [MH+] | 0.80 (Formic) |

-continued

| Example number | Structure and name | [MH+] | Rt (min) |
|---|---|---|---|
| 197 | 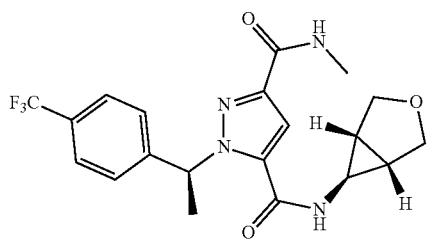<br>$N^5$-((1R,5S,6r)-3-Oxabicyclo[3.1.0]hexan-6-yl)-$N^3$-methyl-1-((S*)-1-(4-(trifluoromethyl)phenyl)ethyl)-1H-pyrazole-3,5-dicarboxamide | 437.3 [MH+] | 0.94 (Formic) |
| 198 | 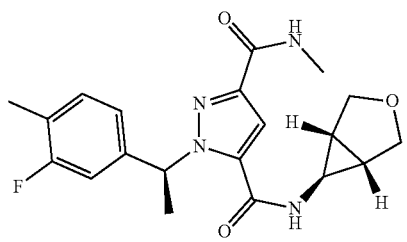<br>$N^5$-((1R,5S,6r)-3-Oxabicyclo[3.1.0]hexan-6-yl)-1-((S)-1-(3-fluoro-4-methylphenyl)ethyl)-$N^3$-methyl-1H-pyrazole-3,5-dicarboxamide | 387.1 [MH+] | 0.95 (Formic) |
| 199 | 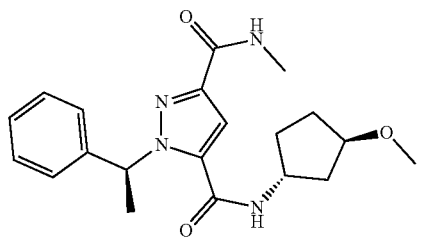<br>N5-((1R*,3R*)-3-Methoxycyclopentyl)-N3-methyl-1-((S)-1-phenylethyl)-1H-pyrazole-3,5-dicarboxamide | 371.6 [MH+] | 0.97 (HpH) |
| 200 | 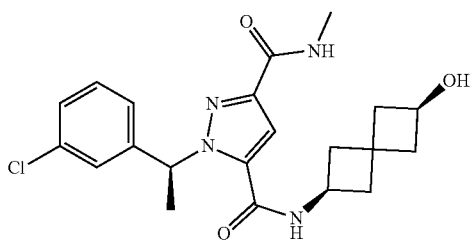<br>(S)-1-(1-(3-Chlorophenyl)ethyl)-$N^5$-(6-hydroxyspiro[3.3]heptan-2-yl)-$N^3$-methyl-1H-pyrazole-3,5-dicarboxamide - single isomer with unknown stereochemistry on spirocycle | 417.3 | 1.01 (Formic) |

-continued

| Example number | Structure and name | [MH+] | Rt (min) |
|---|---|---|---|
| 201 | 1-((S)-1-(3-Chlorophenyl)ethyl)-N5-((1S*,2R*,5R*,6S*)-2-hydroxybicyclo[3.1.0]hexan-6-yl)-N3-methyl-1H-pyrazole-3,5-dicarboxamide, diastereomer 1 | 403.5 | 0.94 (High pH) |
| 202 | (S)-N5-(6-Hydroxyspiro[3.3]heptan-2-yl)-N3-methyl-1-(1-phenylethyl)-1H-pyrazole-3,5-dicarboxamide - single isomer with unknown stereochemistry on spirocycle | 383.3 | 0.85 (Formic) |
| 203 | N5-((1S*,2S*)-2-(Hydroxymethyl)cyclopropyl)-N3-methyl-1-((S)-1-phenylethyl)-1H-pyrazole-3,5-dicarboxamide, diasteromer 1 | 343.3 | 0.78 (High pH) |
| 204 | N5-((1R,5S,6r)-3-Oxabicyclo[3.1.0]hexan-6-yl)-1-((S*)-1-(3-chloro-5-fluorophenyl)ethyl)-N3-methyl-1H-pyrazole-3,5-dicarboxamide | 407.3 | 1.00 (Formic) |

-continued

| Example number | Structure and name | [MH⁺] | Rt (min) |
|---|---|---|---|
| 205 | 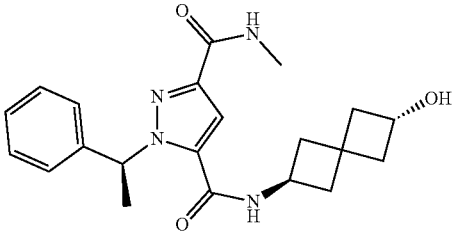<br>(S)-N⁵-(6-Hydroxyspiro[3.3]heptan-2-yl)-N³-methyl-1-(1-phenylethyl)-1H-pyrazole-3,5-dicarboxamide - single isomer with unknown stereochemistry on spirocycle | 383.3 | 0.85 (Formic) |
| 206 | 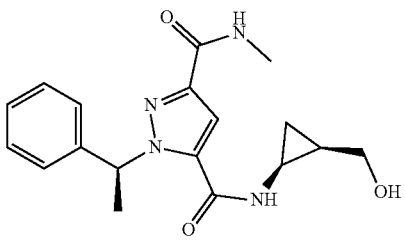<br>N⁵-((1R*,2R*)-2-(Hydroxymethyl)cyclopropyl)-N³-methyl-1-((S)-1-phenylethyl)-1H-pyrazole-3,5-dicarboxamide | 343.2 | 0.78 (High pH) |

The following examples were prepared in a similar manner to Example 88:

| Example number | Name and structure | [MH⁺] | Rt (min) |
|---|---|---|---|
| 207 | 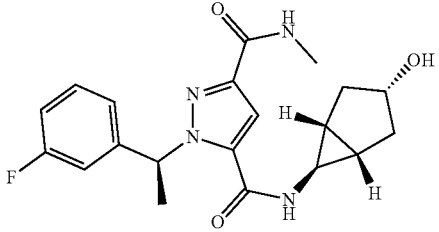<br>1-((S)-1-(3-Fluorophenyl)ethyl)-N⁵-((1R,3S,5S,6r)-3-hydroxybicyclo[3.1.0]hexan-6-yl)-N³-methyl-1H-pyrazole-3,5-dicarboxamide | 387.6 | 0.89 (high pH) |

| Example number | Name and structure | [MH+] | Rt (min) |
|---|---|---|---|
| 208 | 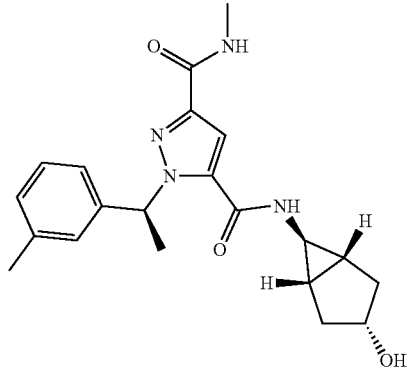<br>N5-((1R,3S,5S,6r)-3-Hydroxybicyclo[3.1.0]hexan-6-yl)-N3-methyl-1-((S)-1-(m-tolyl)ethyl)-1H-pyrazole-3,5-dicarboxamide | 383.6 | 0.92 (High pH) |
| 209 | 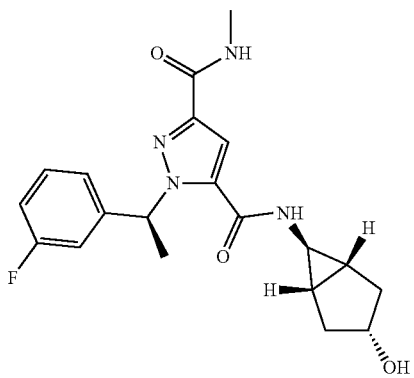<br>1-((S)-1-(3-Fluorophenyl)ethyl)-N5-((1R,3R,5S,6r)-3-hydroxybicyclo[3.1.0]hexan-6-yl)-N3-methyl-1H-pyrazole-3,5-dicarboxamide | 387.6 | 0.86 (High pH) |
| 210 | 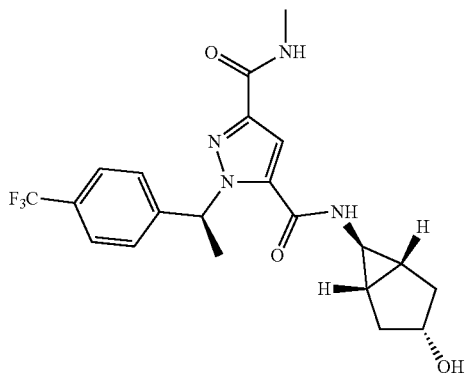<br>N5-((1R,3S,5S,6r)-3-Hydroxybicyclo[3.1.0]hexan-6-yl)-N3-methyl-1-((S*)-1-(4-(trifluoromethyl)phenyl)ethyl)-1H-pyrazole-3,5-dicarboxamide | 437.2 | 0.99 (Formic) |

-continued

| Example number | Name and structure | [MH+] | Rt (min) |
|---|---|---|---|
| 211 | 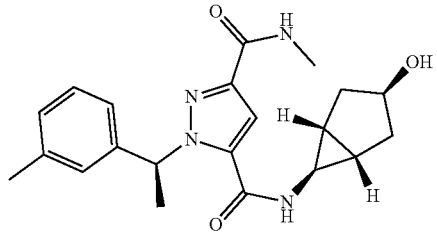<br>N5-((1R,3R,5S,6r)-3-Hydroxybicyclo[3.1.0]hexan-6-yl)-N3-methyl-1-(S)-1-(m-tolyl)ethyl)-1H-pyrazole-3,5-dicarboxamide | 383.5 | 0.89 (HpH) |
| 212 | 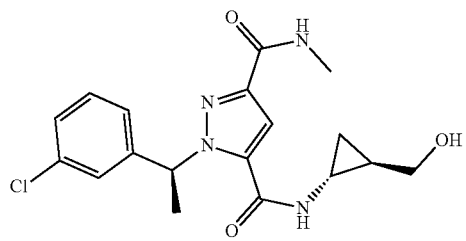<br>1-((S)-1-(3-Chlorophenyl)ethyl)-N5-((1R*,2R*)-2-(hydroxymethyl)cyclopropyl)-N3-methyl-1H-pyrazole-3,5-dicarboxamide | 377.1 | 0.87 (HpH) |

The following example was prepared in a similar manner to Example 74:

| Example number | Structure and name | [MH+] | Rt (min) |
|---|---|---|---|
| 213 | 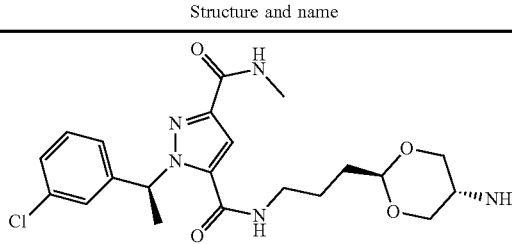<br>N5-(3-((2r,5S)-5-Amino-1,3-dioxan-2-yl)propyl)-1-((S)-1-(3-chlorophenyl)ethyl)-N3-methyl-1H-pyrazole-3,5-dicarboxamide | 450.6 | 0.91 (High pH) |

The following examples were prepared in a similar manner to Example 75:

| Example number | Structure and name | [MH+] | Rt (min) |
|---|---|---|---|
| 214 | 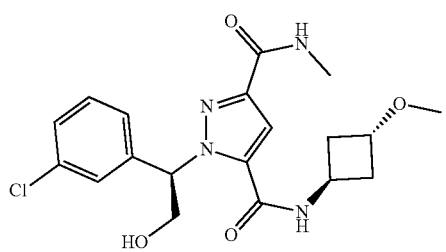<br>1-((R)-1-(3-Chlorophenyl)-2-hydroxyethyl)-N$^5$-((1r,3R)-3-methoxycyclobutyl)-N$^3$-methyl-1H-pyrazole-3,5-dicarboxamide | 407.2 | 0.85 (High pH) |
| 215 | 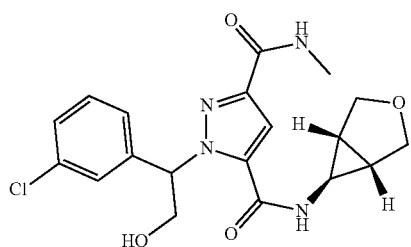<br>(+/-)-N$^5$-((1R,5S,6r)-3-Oxabicyclo[3.1.0]hexan-6-yl)-1-(1-(3-chlorophenyl)-2-hydroxyethyl)-N$^3$-methyl-1H-pyrazole-3,5-dicarboxamide | 405.5 | 0.84 (High pH) |
| 216 | 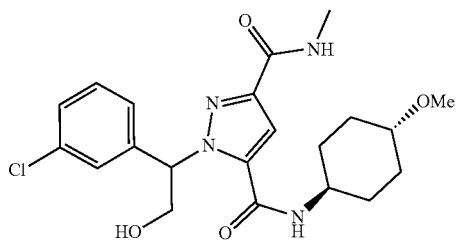<br>(+/-)-1-(1-(3-Chlorophenyl)-2-hydroxyethyl)-N$^5$-((1r,4r)-4-methoxycyclohexyl)-N$^3$-methyl-1H-pyrazole-3,5-dicarboxamide | 435.2 | 0.90 (High pH) |
| 217 | 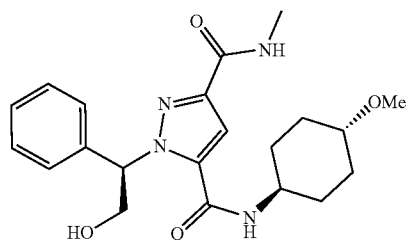<br>1-((R)-2-Hydroxy-1-phenylethyl)-N$^5$-((1r,4R)-4-methoxycyclohexyl)-N$^3$-methyl-1H-pyrazole-3,5-dicarboxamide | 401.4 | 0.79 (Formic) |

The following examples were prepared in a similar manner to Example 86:

| Example number | Structure and Name | [MH+] | Rt (min) |
|---|---|---|---|
| 218 | 1-((1H-Indol-7-yl)methyl)-N⁵-((1R,5S,6r)-3-oxabicyclo[3.1.0]hexan-6-yl)-N³-methyl-1H-pyrazole-3,5-dicarboxamide | 380.3 | 0.89 (Formic) |
| 219 | 1-((1H-Indazol-4-yl)methyl)-N⁵-((1R,5S,6r)-3-oxabicyclo[3.1.0]hexan-6-yl)-N³-methyl-1H-pyrazole-3,5-dicarboxamide | 381.3 | 0.66 (Formic) |

Examples 220-261 were prepared in an analogous manner to examples described above.

| Example number | Structure and name | [MH+] | Rt (min) |
|---|---|---|---|
| 220 | 1-((R*)-1-(1H-Indol-5-yl)ethyl)-N⁵-((1R,5S,6r)-3-oxabicyclo[3.1.0]hexan-6-yl)-N³-methyl-1H-pyrazole-3,5-dicarboxamide | 416.2 [M + Na] | 0.80 (Formic) |
| 221 | N⁵-((1R,5S,6r)-3-Oxabicyclo[3.1.0]hexan-6-yl)-1-((S*)-1-(4-chloro-3-fluorophenyl)ethyl-N³-methyl-1H-pyrazole-3,5-dicarboxamide | 407.3 | 0.98 (Formic) |

-continued

| Example number | Structure and name | [MH+] | Rt (min) |
|---|---|---|---|
| 222 | 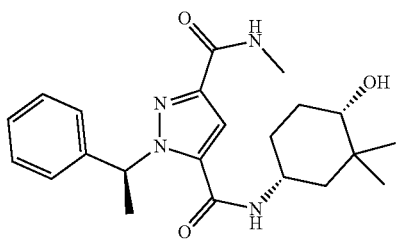<br>N5-((1R*,4S*)-4-Hydroxy-3,3-dimethylcyclohexyl)-N3-methyl-1-((S)-1-phenylethyl)-1H-pyrazole-3,5-dicarboxamide | 399.1 | 1.01 (High pH) |
| 223 | 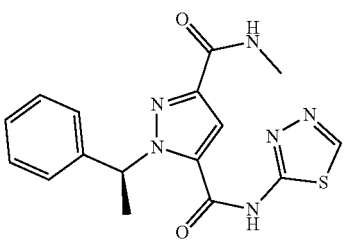<br>(S)-N3-Methyl-1-(1-phenylethyl)-N5-(1,3,4-thiadiazol-2-yl)-1H-pyrazole-3,5-dicarboxamide | 357.0 | 0.90 (Formic) |
| 224 | 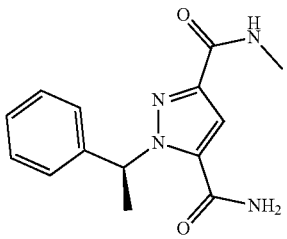<br>(S)-N3-Methyl-1-(1-phenylethyl)-1H-pyrazole-3,5-dicarboxamide | 273.2 | 0.77 (Formic) |
| 225 | 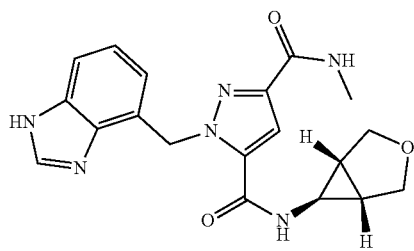<br>1-((1H-Benzo[d]imidazol-4-yl)methyl)-N5-((1R,5S,6r)-3-oxabicyclo[3.1.0]hexan-6-yl)-N3-methyl-1H-pyrazole-3,5-dicarboxamide | 365.4 | 0.67 (High pH) |

| Example number | Structure and name | [MH+] | Rt (min) |
|---|---|---|---|
| 226 | 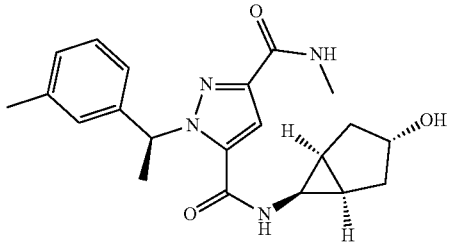<br>N5-((1R,3R,5S,6s)-3-Hydroxybicyclo[3.1.0]hexan-6-yl)-N3-methyl-1-((S)-1-(m-tolyl)ethyl)-1H-pyrazole-3,5-dicarboxamide | 383.6 | 0.98 (High pH) |
| 227 | 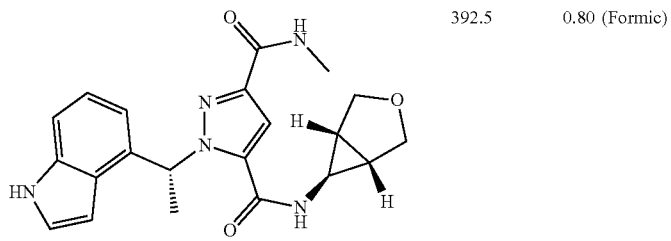<br>1-((R)-1-(1H-Indol-4-yl)ethyl)-N5-((1R,5S,6r)-3-oxabicyclo[3.1.0]hexan-6-yl)-N3-methyl-1H-pyrazole-3,5-dicarboxamide | 392.5 | 0.80 (Formic) |
| 228 | 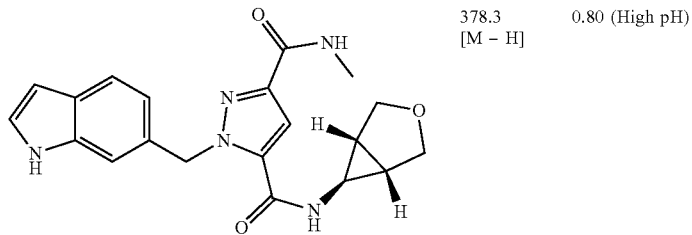<br>1-((1H-Indol-6-yl)methyl)-N5-((1R,5S,6r)-3-oxabicyclo[3.1.0]hexan-6-yl)-N3-methyl-1H-pyrazole-3,5-dicarboxamide | 378.3 [M − H] | 0.80 (High pH) |
| 229 | 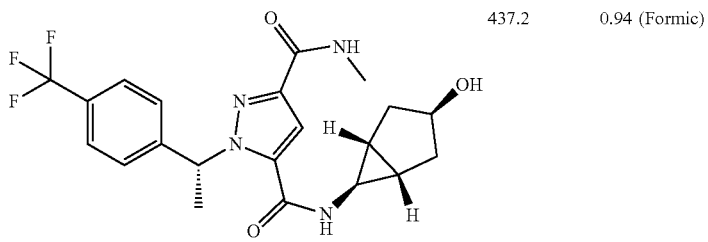<br>N5-((1R,3S,5S,6r)-3-Hydroxybicyclo[3.1.0]hexan-6-yl)-N3-methyl-1-((R*)-1-(4-(trifluoromethyl)phenyl)ethyl)-1H-pyrazole-3,5-dicarboxamide | 437.2 | 0.94 (Formic) |

-continued

| Example number | Structure and name | [MH⁺] | Rt (min) |
|---|---|---|---|
| 230 | 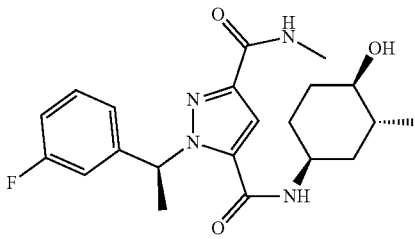<br>1-((S)-1-(3-Fluorophenyl)ethyl)-$N^5$-((1S,3R,4R)-4-hydroxy-3-methylcyclohexyl)-$N^3$-methyl-1H-pyrazole-3,5-dicarboxamide | 403.6 | 0.97 (High pH) |
| 231 | 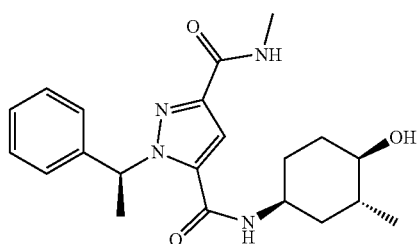<br>$N^5$-((1S,3R,4R)-4-Hydroxy-3-methylcyclohexyl)-$N^3$-methyl-1-((S)-1-phenylethyl)-1H-pyrazole-3,5-dicarboxamide | 385.3 | 0.91 (Formic) |
| 232 | 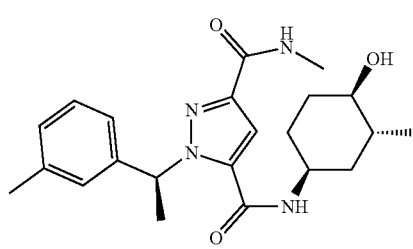<br>$N^5$-((1S,3R,4R)-4-Hydroxy-3-methylcyclohexyl)-$N^3$-methyl-1-((S)-1-(m-tolyl)ethyl)-1H-pyrazole-3,5-dicarboxamide | 399.6 | 1.00 (High pH) |
| 233 | 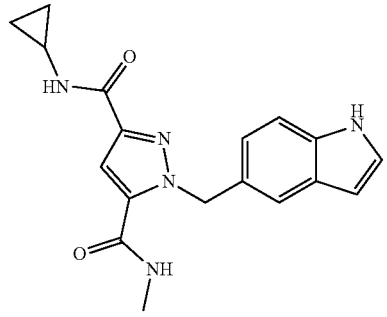<br>1-((1H-Indol-5-yl)methyl)-$N^3$-cyclopropyl-$N^5$-methyl-1H-pyrazole-3,5-dicarboxamide | 338.2 | 1.70 (Formic) |

| Example number | Structure and name | [MH+] | Rt (min) |
|---|---|---|---|
| 234 | 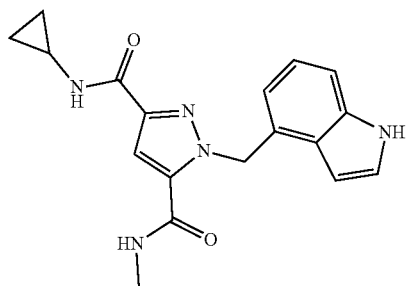<br>1-((1H-Indol-4-yl)methyl)-N$^3$-cyclopropyl-N$^5$-methyl-1H-pyrazole-3,5-dicarboxamide | 338.2 | 1.67 (Formic) |
| 235 | 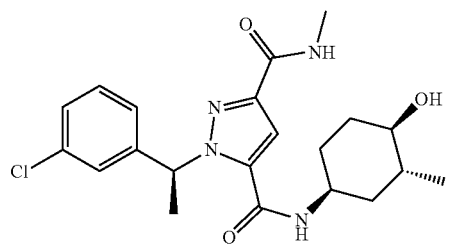<br>1-((S)-1-(3-Chlorophenyl)ethyl)-N$^5$-((1S,3R,4R)-4-hydroxy-3-methylcyclohexyl)-N$^3$-methyl-1H-pyrazole-3,5-dicarboxamide | 419.3/420.4 | 1.02 (Formic) |
| 236 | 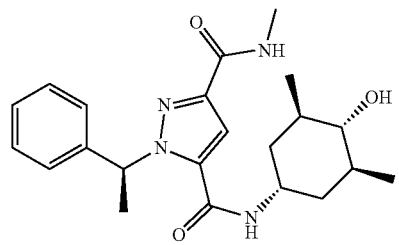<br>N$^5$-((1s,3R,4S,5S)-4-Hydroxy-3,5-dimethylcyclohexyl)-N$^3$-methyl-1-((S)-1-phenylethyl)-1H-pyrazole-3,5-dicarboxamide | 399.6 | 1.02 (High pH) |

-continued
| Example number | Structure and name | [MH+] | Rt (min) |
|---|---|---|---|
| 237 | 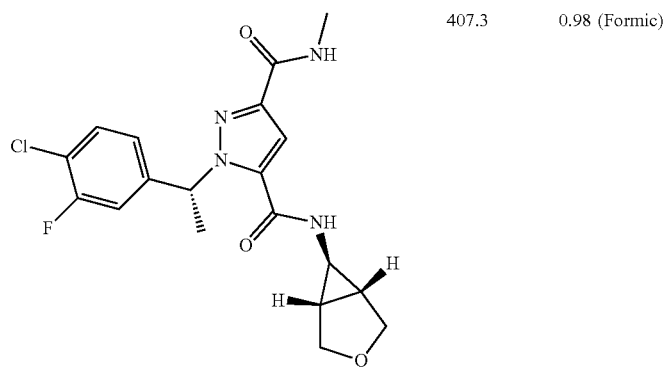<br>N5-((1R,5S,6r)-3-Oxabicyclo[3.1.0]hexan-6-yl)-1-((R*)-1-(4-chloro-3-fluorophenyl)ethyl)-N3-methyl-1H-pyrazole-3,5-dicarboxamide | 407.3 | 0.98 (Formic) |
| 238 | 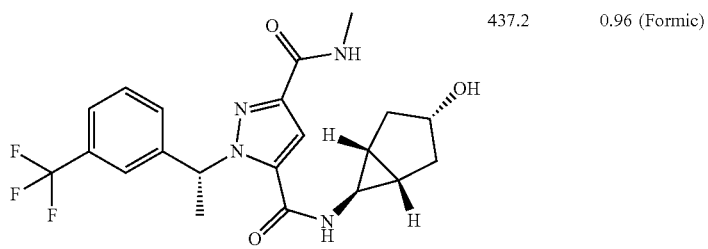<br>N5-((1R,3R,5S,6r)-3-Hydroxybicyclo[3.1.0]hexan-6-yl)-N3-methyl-1-((R*)-1-(3-(trifluoromethyl)phenyl)ethyl)-1H-pyrazole-3,5-dicarboxamide | 437.2 | 0.96 (Formic) |
| 239 | 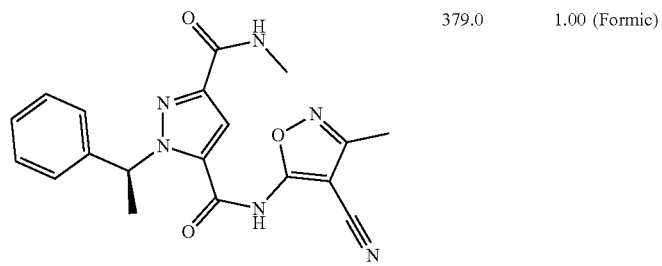<br>(S)-N5-(4-Cyano-3-methylisoxazol-5-yl)-N3-methyl-1-(1-phenylethyl)-1H-pyrazole-3,5-dicarboxamide | 379.0 | 1.00 (Formic) |

-continued

| Example number | Structure and name | [MH+] | Rt (min) |
|---|---|---|---|
| 240 | (S)-N³-Methyl-1-(1-phenylethyl)-N⁵-(5-(trifluoromethyl)-1,3,4-thiadiazol-2-yl)-1H-pyrazole-3,5-dicarboxamide | 425.0 | 1.20 (Formic) |
| 241 | N⁵-((1R,3S,5S,6r)-3-hydroxybicyclo[3.1.0]hexan-6-yl)-N³-methyl-1-((R*)-1-(3-(trifluoromethyl)phenyl)ethyl)-1H-pyrazole-3,5-dicarboxamide | 437.2 | 0.93 (Formic) |
| 242 | N⁵-((1R,5S,6r)-3-Oxabicyclo[3.1.0]hexan-6-yl)-1-((R*)-1-(3-chloro-5-fluorophenyl)ethyl)-N³-methyl-1H-pyrazole-3,5-dicarboxamide | 407.3 | 1.00 (Formic) |
| 243 | (S)-N⁵-(2,4-Dimethylpyridin-3-yl)-N³-methyl-1-(1-phenylethyl)-1H-pyrazole-3,5-dicarboxamide | 378.1 | 0.62 (Formic) |

| Example number | Structure and name | [MH+] | Rt (min) |
|---|---|---|---|
| 244 | 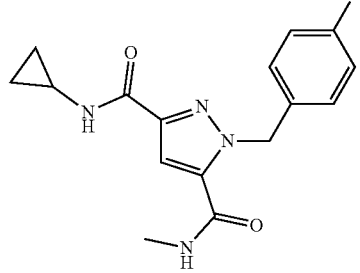<br>N³-Cyclopropyl-1-(4-methoxybenzyl)-N⁵-methyl-1H-pyrazole-3,5-dicarboxamide | 329.2 | 1.84 (Formic) |
| 245 | 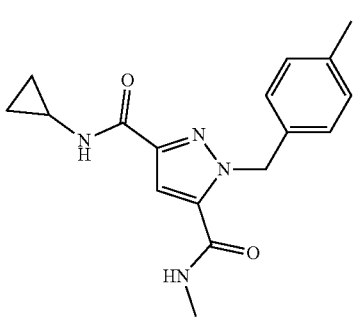<br>N³-Cyclopropyl-N⁵-methyl-1-(4-methylbenzyl)-1H-pyrazole-3,5-dicarboxamide | 313.1 | 6.68 (TFA 15 min method) |
| 246 | 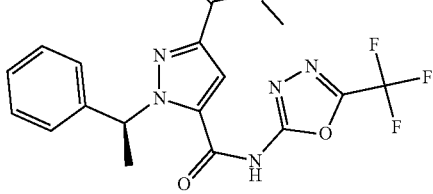<br>(S)-N³-Methyl-1-(1-phenylethyl)-N⁵-(5-(trifluoromethyl)-1,3,4-oxadiazol-2-yl)-1H-pyrazole-3,5-dicarboxamide | 409.0 | 1.05 (Formic) |
| 247 | 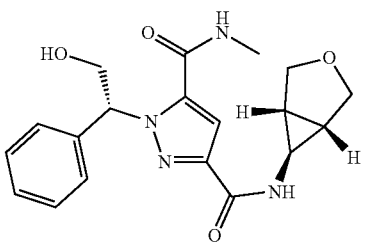<br>N³-((1R,5S,6r)-3-Oxabicyclo[3.1.0]hexan-6-yl)-1-((R)-2-hydroxy-1-phenylethyl)-N⁵-methyl-1H-pyrazole-3,5-dicarboxamide | 371.3 | 0.68 (Formic) |

| Example number | Structure and name | [MH+] | Rt (min) |
|---|---|---|---|
| 248 | (S)-N⁵-(3,5-Dimethylisoxazol-4-yl)-N³-methyl-1-(1-phenylethyl)-1H-pyrazole-3,5-dicarboxamide | 368.0 | 0.95 (Formic) |
| 249 | N⁵-((1r,4R)-4-Hydroxycyclohexyl)-N³-methyl-1-((R*)-1-(3-(trifluoromethyl)phenyl)ethyl)-1H-pyrazole-3,5-dicarboxamide | 439.3 | 0.95 (Formic) |
| 250 | N⁵-((1r,4R)-4-Hydroxycyclohexyl)-N³-methyl-1-((R*)-1-(4-(trifluoromethyl)phenyl)ethyl)-1H-pyrazole-3,5-dicarboxamide | 439.3 | 0.95 (Formic) |
| 251 | N⁵-((1R,5S,6r)-3-Oxabicyclo[3.1.0]hexan-6-yl)-1-((R*)-1-(3-chlorophenyl)-2-hydroxyethyl)-N³-methyl-1H-pyrazole-3,5-dicarboxamide | 405.5 | 0.83 (High pH) |

-continued

| Example number | Structure and name | [MH+] | Rt (min) |
|---|---|---|---|
| 252 | 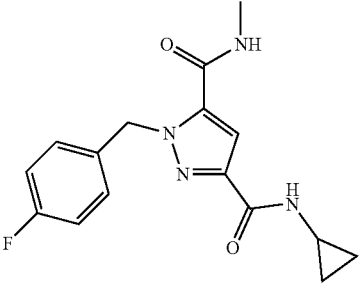<br>N3-Cyclopropyl-1-(4-fluorobenzyl)-N5-methyl-1H-pyrazole-3,5-dicarboxamide | 317.2 | 1.86 (Formic) |
| 253 | 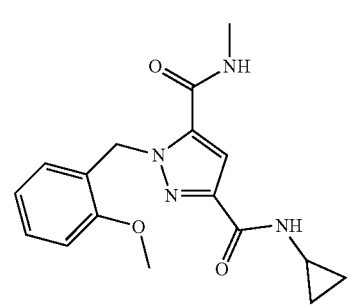<br>N3-Cyclopropyl-1-(2-methoxybenzyl)-N5-methyl-1H-pyrazole-3,5-dicarboxamide | 329.2 | 1.78 (Formic) |
| 254 | 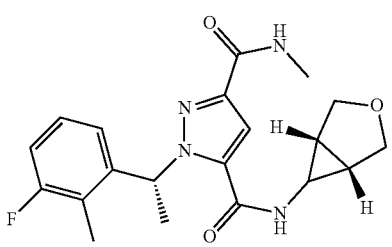<br>N5-((1R,5S,6r)-3-Oxabicyclo[3.1.0]hexan-6-yl)-1-((R*)-1-(3-fluoro-2-methylphenyl)ethyl)-N3-methyl-1H-pyrazole-3,5-dicarboxamide | 387.2 | 0.92 (Formic) |
| 255 | 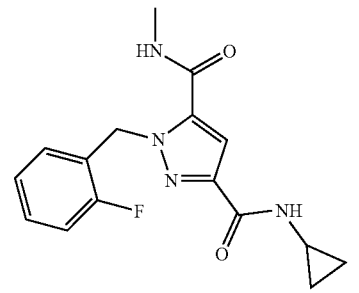<br>N3-Cyclopropyl-1-(2-fluorobenzyl)-N5-methyl-1H-pyrazole-3,5-dicarboxamide | 317.1 | 1.80 (Formic) |

| Example number | Structure and name | [MH⁺] | Rt (min) |
|---|---|---|---|
| 256 | 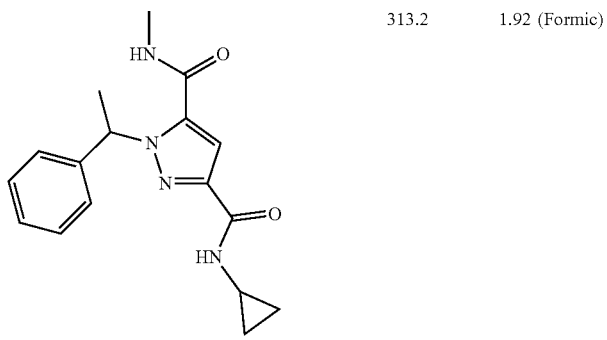<br>(+/-)-N³-Cyclopropyl-N⁵-methyl-1-(1-phenylethyl)-1H-pyrazole-3,5-dicarboxamide | 313.2 | 1.92 (Formic) |
| 257 | 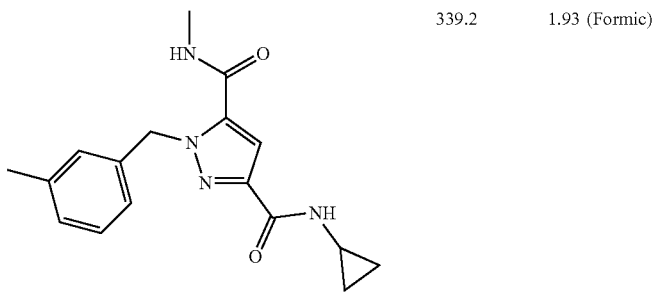<br>N³-Cyclopropyl-N⁵-methyl-1-(3-methylbenzyl)-1H-pyrazole-3,5-dicarboxamide | 339.2 | 1.93 (Formic) |
| 258 | 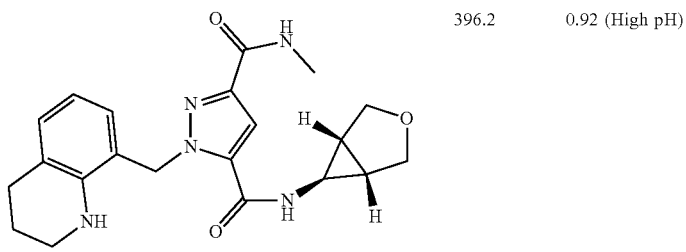<br>N⁵-((1R,5S,6r)-3-Oxabicyclo[3.1.0]hexan-6-yl)-N³-methyl-1-((1,2,3,4-tetrahydroquinolin-8-yl)methyl)-1H-pyrazole-3,5-dicarboxamide | 396.2 | 0.92 (High pH) |

-continued

| Example number | Structure and name | [MH+] | Rt (min) |
|---|---|---|---|
| 259 | 1-Benzyl-$N^3$-cyclopropyl-$N^5$-methyl-1H-pyrazole-3,5-dicarboxamide | 395.3 | 3.83 (Formic 10 min method) |
| 260 | 1-(4-Cyanobenzyl)-$N^3$-cyclopropyl-$N^5$-methyl-1H-pyrazole-3,5-dicarboxamide | 324.1 | 1.71 (Formic) |
| 261 | $N^3$-Cyclopropyl-1-(3-methoxybenzyl)-$N^5$-methyl-1H-pyrazole-3,5-dicarboxamide | 329.1 | 6.35 (TFA 15 min method) |

Biological Data

The compounds of formula (I) may be tested in one or more of the following assays:

Time Resolved Fluorescence Resonance Energy Transfer (TR-FRET) assay

Bromodomain binding was assessed utilising a time resolved fluorescent resonance energy transfer (TR-FRET) competition assay. To enable this approach a known, high affinity, pan-BET interacting small molecule was labelled with Alexa Fluor® 647, which is a far-red-fluorescent dye (Reference Compound X). Reference Compound X acts as a reporter of bromodomain binding and is the acceptor fluorophore component of the TR-FRET pair. Europium chelate, conjugated to an anti-6*His antibody, was utilised as the donor fluorophore in the TR-FRET pair. The anti-6*His antibody binds selectively to a six Histidine purification epitope added to the amino-terminus of each of the BET tandem bromodomain protein constructs used in this study. A TR-FRET signal is generated when the donor and acceptor fluorophores are in close proximity, between 20-80 Å, which is enabled in this assay by binding of Reference Compound X to the bromodomain protein.

Reference Compound X: 4-((Z)-3-(6-((5-(2-((4.5)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

mass of 1320.984 which is $N^5$-29. This is a standard occurrence with the Alexa Fluor 647 dye and represents a theoretical loss of two methylene groups under the conditions of the mass spectrometer.

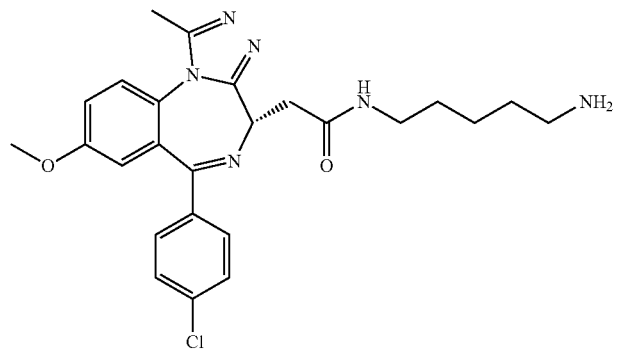

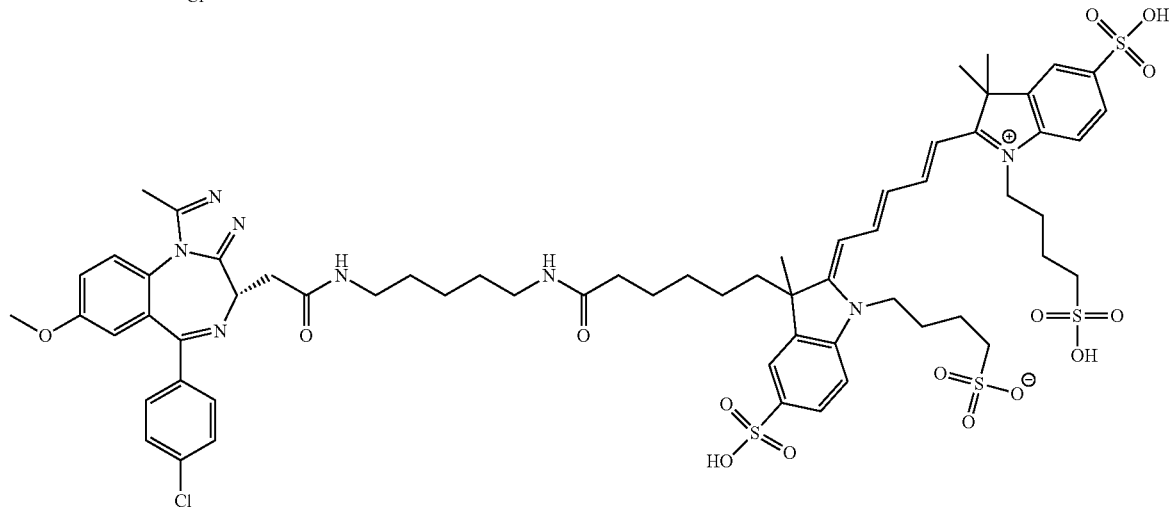

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 µmol) in DMF (40 µL) was added a solution of AlexaFluor647-ONSu (2.16 mg, 1.966 µmol) also in DMF (100 µL). The mixture was basified with DIPEA (1 µl, 5.73 µmol) and agitated overnight on a vortex mixer.

The reaction mixture was evaporated to dryness. The solid was dissolved in MeCN/water/AcOH (5/4/1, <1 mL) filtered and was applied to a Phenomenex Jupiter C18 preparative column and eluted with the following gradient (A=0.1% trifluoroacetic acid in water, B=0.1% TFA/90% MeCN/10% water): Flow rate=10 mL/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B.

Fractions F1.25/26&27 were combined and evaporated to dryness. Transferred with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: [M+H]⁺ (obs): 661.8/– corresponding with $N^5$-29. This equates to [(M+2H)/2]⁺ for a calculated Assay Principle: In order to generate a TR-FRET signal, donor fluorophore is excited by a laser at λ337 nm, which subsequently leads to emission at λ618 nm. If the acceptor fluorophore is in close proximity then energy transfer can occur, which leads to emission of Alexa Fluor® 647 at λ665 nm. In the presence of competitor compound, Reference Compound X can be displaced from binding to the bromodomain. If displacement occurs, the acceptor fluorophore is no longer in proximity to the donor fluorophore, which prevents fluorescent energy transfer and, subsequently, a loss of Alexa Fluor® 647 emission at λ665 nm.

The competition of the compounds of formula (I) with Reference Compound X for binding to the BET family (BRD2, BRD3, BRD4 and BRDT) was assessed using protein truncates spanning both bromodomain 1 (BD1) and bromodomain 2 (BD2). In order to monitor differential binding to either BD1 or BD2, single residue mutations of key tyrosines to alanine were made in the acetyl lysine binding pockets. To validate this approach, a double residue mutant tandem domain protein was produced for each of the BET family members. Utilising a Fluorescence Polarisation approach, binding affinities for each of the single and double mutants for Reference Compound X were determined. The affinities of the double mutant tandem proteins for Reference Compound X were greatly greatly reduced in comparison to the non mutated, wild type tandem BET proteins (>1000 fold reduction in Kd). The affinities of the single mutated bromdomain tandem proteins for Reference Compound X were equi-potent with the corresponding non-mutated BET protein. These data demonstrated that single mutations of Tyrosine to Alanine reduce the Kd of the interaction between the mutated bromodomain and Reference Compound X by >1000 fold. In the TR-FRET competition assay, Reference Compound X is used at a concentration that is equivalent to the Kd for the non-mutated bromodomain, which ensures that no binding at the mutated bromodomain is detected.

Protein production: Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in E. coli cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 µL/mL protease inhibitor cocktail and extracted from the E. coli cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry. Protocol for Bromodomain BRD2, 3, 4 and T, BD1+BD2 mutant TR-FRET competition assays:

All assay components were dissolved in an assay buffer composing of 50 mM HEPES pH7.4, 50 mM NaCl, 5% Glycerol, 1 mM DTT and 1 mM CHAPS. Reference Compound X was diluted, in assay buffer containing 20 nM single mutant, tandem bromodomain protein, to a concentration equivalent to 2*Kd for this bromodomain. The solution containing bromodomain and Reference Compound X was added to dose response dilutions of test compound or DMSO vehicle (a maximum of 0.5% DMSO is used in this assay) in Greiner 384 well black low volume microtitre plates and subsequently incubated for 30 minutes at rt. An equal volume of 3 nM of anti-6*His Europium chelate was added to all wells, followed by a further 30 minute incubation at rt. TR-FRET was detected using a Perkin Elmer Multimode plate reader, by exciting the donor fluorophore at λ337 nm and subsequently, after a delay of 50 µsecs, measuring emission of the donor and acceptor fluorophores at λ615 nm and λ665 nm, respectively. In order to control these assays, 16 replicates each of uninhibited (DMSO vehicle) and inhibited (10*IC$_{50}$ concentrations of Example 11 of WO 2011/054846A1) TR-FRET assays were included on every microtitre plate.

cA four parameter curve fit of the following form was then applied:

$$y=a+((b-a)/(1+(10\hat{}x/10\hat{}c)\hat{}d)$$

Where 'a' is the minimum, 'H' is the Hill slope, 'c' is the pIC$_{50}$ and 'd' is the maximum.

All compounds (Examples) were each tested in the BRD4 BD1 and the BRD4 BD2 TR-FRET assays essentially as described above. Those of skill in the art will recognise that in vitro binding assays and cell-based assays for functional activity are subject to experimental variability. Accordingly, it is to be understood that the pIC$_{50}$ values given below are exemplary only. pIC$_{50}$ values are expressed as log$_{10}$ units.

All Examples, with the exception of Examples 131, 242-247 and 249-261, were found to have a pIC$_{50}$≥5.0 in at least one assay described above.

Examples 94, 96, 102, 106, 108-110, 112, 114, 132, 135, 135, 136, 137, 229, 233, 234, 236-241 and 248. were found to have a pIC$_{50}$≥ 5.0 and <6.0 in the BRD4 BD2 assay.

All other compounds were found to have a pIC$_{50}$≥6.0 and <8.0 in the BRD4 BD2 assay. In particular, Example 1 was found to have a pIC$_{50}$ of 7.2 in the BRD4 BD2 assay; Example 2 was found to have a pIC$_{50}$ of 7.1 in the BRD4 BD2 assay; Example 3 was found to have a pIC$_{50}$ of 7.5 in the BRD4 BD2 assay; and Example 139 was found to have a pIC$_{50}$ of 7.4 in the BRD4 BD2 assay.

Calculation of Selectivity for BRD4 BD2 Over BRD4 BD1

Selectivity for BRD4 BD2 over BRD4 BD1 was calculated as follows:

Selectivity=BRD4 BD2 pIC$_{50}$−BRD4 BD1 pIC$_{50}$
pIC$_{50}$

All Examples, with the exemption of Examples 114, 116, 131, 134, 136-138 and 238-261, were found to have selectivity for BRD4 BD2 over BRD4 BD1 of ≥1 log unit in at least one of the TR-FRET assays described above, and hence are at least 10 fold selective for BRD4 BD2 over BRD4 BD1.

Examples 1-91, 139-219 were found to have selectivity for BRD4 BD2 over BRD4 BD1 of ≥2 log unit in at least one of the TR-FRET assays described above, and hence are at least 100 fold selective for BRD4 BD2 over BRD4 BD1.

Example 1 was found to have a selectivity for BRD4 BD2 over BRD4 BD1 of 2.8 log units in at least one of the TR-FRET assays described above.

Example 2 was found to have a selectivity for BRD4 BD2 over BRD4 BD1 of 3.0 log units in at least one of the TR-FRET assays described above.

Example 3 was found to have a selectivity for BRD4 BD2 over BRD4 BD1 of 3.0 log units in at least one of the TR-FRET assays described above.

Example 139 was found to have a selectivity for BRD4 BD2 over BRD4 BD1 of 3.0 log units in at least one of the TR-FRET assays described above.

The invention claimed is:

1. A compound of formula (I)

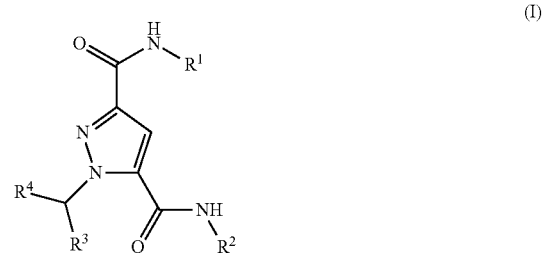

(I)

or a pharmaceutically acceptable salt thereof
wherein:
R$^1$ is —C$_{1-3}$alkyl or cyclopropyl;
R$^2$ is —C$_{0-3}$alkyl-cycloalkyl, wherein the cycloalkyl group is optionally substituted with one, two, or three R$^5$ groups which may be the same or different;
or R$^2$ is —C$_{0-4}$alkyl-heterocyclyl or —(CH$_2$)$_p$O-heterocyclyl, wherein each heterocyclyl is optionally substituted by one or two R$^9$ groups which may be the same or different; or R² is H, —CH₃, —C₂₋₆alkyl optionally substituted by one, two, three, four or five fluoro, —C₂₋₆alkylOR⁶, —C₂₋₆alkylNR¹⁰ᵃR¹¹ᵃ, —(CH₂)$_m$SO₂C₁₋₃alkyl, —(CH₂)$_m$SO₂NR¹⁰R¹¹, —(CH₂)$_m$C(O)NR¹⁰R¹¹, —(CH₂)$_m$CN, —(CH₂)$_m$CO₂R⁶, —(CH₂)$_m$NHCO₂C₁₋₄alkyl, —(CH₂)$_m$NHC(O)C₁₋₄alkyl, or —(CH₂)$_n$heteroaryl, wherein the heteroaryl is optionally substituted by one or two R⁷ groups which may be the same or different;

R³ is H, —C₁₋₄alkyl, cyclopropyl, —CH₂F, —C₁₋₃alkylOR⁶, or —C₁₋₃alkylCN;

R⁴ is phenyl or a heteroaryl group, wherein each are optionally substituted by one, two, or three R⁷ groups which may be the same or different;

each R⁵ is independently halo, —C₀₋₆alkyl-R⁸, —OCH₂phenyl, —CN, or —SO₂C₁₋₃alkyl;

R⁶ is H or —C₁₋₄alkyl;

each R⁷ is independently oxo, halo, —C₁₋₄alkyl optionally substituted by one, two or three fluoro, —C₀₋₃alkylOR⁶, —OC₂₋₃alkylOR⁶, —C₀₋₃alkylNR¹⁰R¹¹, —C₀₋₃alkyl-CONR₁₀R¹¹, —SO₂—C₁₋₃alkyl, —SO₂NR¹⁰R¹¹, or —SO₂phenyl optionally substituted by —C₁₋₄alkyl;

R⁸ is H, —OR⁶, —NR¹⁰R¹¹ heteroaryl;

each R⁹ is independently halo, —C₁₋₄alkyl, cyclopropyl, cyclobutyl, —CH₂CF₃, —CH₂CHF₂, —CH₂CH₂F, —OCH₂CH₂OR⁶, —C₀₋₃alkylOR⁶, —C₀₋₃alkylNR¹⁰R¹¹, —NHCH₂CH₂OR⁶, —NHCO₂C₁₋₄alkyl, oxo, —C(O)R⁶, —C(O)OR⁶, or —C(O)NR¹⁰R¹¹, R¹⁰ and R¹¹ are each independently selected from H and —C₁₋₃alkyl; or R¹⁰ and R¹¹ may join together with the nitrogen to which they are attached, to form a 4 to 7-membered heterocyclyl optionally substituted by one or two substituents independently selected from —C₁₋₃alkyl optionally substituted with one, two, or three fluorine atoms, —C₂₋₄alkylOH, —OH, and F;

R¹⁰ᵃ and R¹¹ᵃ are each independently selected from H and —C₁₋₃alkyl;

m is an integer selected from 2, 3, or 4;
n is an integer selected from 0, 1, 2, 3, or 4; and
p is an integer selected from 2, 3, or 4.

2. The compound or pharmaceutically acceptable salt thereof according to claim 1, wherein R¹ is methyl.

3. The compound or pharmaceutically acceptable salt thereof according to claim 1, wherein R² is a —C₀₋₃alkyl-C₃₋₇cycloalkyl group, wherein the C₃₋₇cycloalkyl group is selected from cyclopropyl, cyclobutyl, cyclohexyl, and bicyclo[3.1.0]hexanyl, wherein said cyclopropyl, cyclobutyl, cyclohexyl, or bicyclo[3.1.0]hexanyl is optionally substituted with one, two, or three R⁵ groups which may be the same or different.

4. The compound or pharmaceutically acceptable salt thereof according to claim 1, wherein R² is —C₀₋₄alkyl-heterocyclyl wherein the heterocyclyl is selected from oxetanyl, tetrahydrofuranyl, tetrahydro-2H-pyranyl, morpholinyl, piperidinyl, piperazinyl, (1r,5s)-3-oxabicyclo[3.1.0]hexanyl and (1r,5s)-3-azabicyclo[3.1.0]hexanyl, wherein said oxetanyl, tetrahydrofuranyl, tetrahydro-2H-pyranyl, morpholinyl, piperidinyl, piperazinyl, (1r,5s)-3-oxabicyclo[3.1.0]hexanyl or (1r,5s)-3-azabicyclo[3.1.0]hexanyl is optionally substituted by one or two R⁹ groups which may be the same or different.

5. The compound or pharmaceutically acceptable salt thereof according to claim 1, wherein R² is methyl, ethyl, propyl, iso-propyl, butyl, —CH₂CH₂CH(CH₃)₂, —CH₂CH(CH₃)₂, —CH₂CH₂OR⁶, —CH₂CH₂CH₂OR⁶, —CH₂CH(CH₃)OR⁶, —CH₂CH₂CH(CH₃)OR⁶, —CH₂CH₂CH(CH₃)NR¹⁰R¹¹, —CH₂CH₂CH₂NR¹⁰R¹¹, —(CH₂)$_m$SO₂CH₃, —(CH₂)$_m$C(O)NHCH₃, —(CH₂)$_m$CN, —(CH₂)$_m$CO₂R⁶, —(CH₂)$_m$CF₃, and —(CH₂)$_m$NHCO₂C(CH₃)₃.

6. The compound or pharmaceutically acceptable salt thereof according to claim 1, wherein R² is —(CH₂)$_n$C₅₋₆heteroaryl, wherein the C₅₋₆heteroaryl group is selected from furanyl, thienyl, pyrrolyl, triazolyl, thiazolyl, oxazolyl, isoxazolyl, oxadiazolyl, imidazolyl, pyrazolyl, triazolyl, tetrazolyl, isoxazolyl, pyridinyl, pyridazinyl, pyrazinyl, and pyrimidinyl, wherein said furanyl, thienyl, pyrrolyl, triazolyl, thiazolyl, oxazolyl, isoxazolyl, oxadiazolyl, imidazolyl, pyrazolyl, triazolyl, tetrazolyl, isoxazolyl, pyridinyl, pyridazinyl, pyrazinyl or pyrimidinyl is optionally substituted by one or two substituents independently selected from halo, C₁₋₄alkyl, C₃₋₄cycloalkyl, and —C₀₋₃alkylOR⁶.

7. The compound or pharmaceutically acceptable salt thereof according to claim 1, wherein R³ is H, methyl, ethyl, —CH₂F, —CH₂OH, —CH(OH)CH₃, —CH₂OMe, or —CH₂CN.

8. The compound or pharmaceutically acceptable salt thereof according to claim 1, wherein R⁴ is unsubstituted phenyl or is phenyl substituted by one or two R⁷ groups which may be the same or different selected from halo, —C₁₋₄alkyl, —C₀₋₃alkylOR⁶, and CN.

9. The compound or salt thereof according to claim 1, wherein R⁴ is a heteroaryl group selected from the group consisting of pyridyl, indolyl, and pyrrolopyridinyl, wherein said pyridyl, indolyl, and pyrrolopyridinyl is optionally substituted by one, two, or three R⁷ groups which may be the same or different.

10. A compound which is selected from
N⁵-((1r,4S)-4-hydroxycyclohexyl)-N³-methyl-1-((S)-1-phenylethyl)-1H-pyrazole-3,5-dicarboxamide;
N⁵-((1R,3R,5S,6r)-3-hydroxybicyclo[3.1.0]hexan-6-yl)-N³-methyl-1-((S)-1-phenylethyl)-1H-pyrazole-3,5-dicarboxamide;
N⁵-((1R,5S,6r)-3-oxabicyclo[3.1.0]hexan-6-yl)-1-((S)-1-(4-chlorophenyl)ethyl)-N³-methyl-1H-pyrazole-3,5-dicarboxamide;
(S)—N³-methyl-1-(1-phenylethyl)-N⁵-(1H-pyrazol-4-yl)-1H-pyrazole-3,5-dicarboxamide;
1-((S)-1-(4-chlorophenyl)ethyl)-N⁵-((1R,3R,5S,6r)-3-hydroxybicyclo[3.1.0]hexan-6-yl)-N³-methyl-1H-pyrazole-3,5-dicarboxamide;
1-((S)-1-(3-chlorophenyl)ethyl)-N⁵-((1R,3R,5S,6r)-3-hydroxybicyclo[3.1.0]hexan-6-yl)-N³-methyl-1H-pyrazole-3,5-dicarboxamide;
N⁵-((1R,3R,5S,6r)-3-hydroxybicyclo[3.1.0]hexan-6-yl)-N³-methyl-1-((S)-1-phenylpropyl)-1H-pyrazole-3,5-dicarboxamide; and
N⁵-((1r,4S)-4-methoxycyclohexyl)-N³-methyl-1-((S)-1-phenylethyl)-1H-pyrazole-3,5-dicarboxamide
or a pharmaceutically acceptable salt thereof.

11. A compound which is N⁵-((1R,5S,6r)-3-oxabicyclo[3.1.0]hexan-6-yl)-N³-methyl-1-((S)-1-phenylethyl)-1H-pyrazole-3,5-dicarboxamide represented by the formula

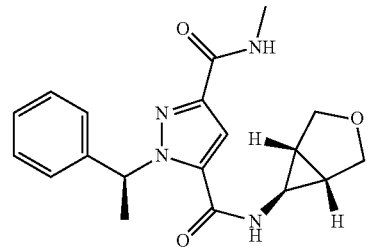 [SMILES: CNC(=O)c1cc(C(=O)N[C@H]2[C@@H]3COC[C@@H]32)n([C@@H](C)c2ccccc2)n1]

or a pharmaceutically acceptable salt thereof.

12. A pharmaceutical composition comprising the compound or pharmaceutically acceptable salt thereof according to claim 1 and one or more pharmaceutically acceptable excipients.

13. A combination comprising the compound or pharmaceutically acceptable salt thereof according to claim 1 together with one or more other therapeutically active agents.

14. A method of treatment of a disease or condition in a human for which a bromodomain inhibitor is indicated, the method comprising administering to the human in need thereof a therapeutically effective amount of the compound or pharmaceutically acceptable salt thereof according to claim 1, wherein the disease or condition is an acute or chronic autoimmune and/or inflammatory condition.

15. A method of treatment according to claim 14, wherein the disease or condition involves an inflammatory response to an infection with bacteria, a virus, fungi, a parasite, or their toxins.

16. A method of treatment according to claim 14, wherein the disease or condition is a viral infection.

17. A method of treatment according to claim 14, wherein the disease or condition is rheumatoid arthritis.

\* \* \* \* \*